US007955805B2

(12) United States Patent
Karumanchi et al.

(10) Patent No.: US 7,955,805 B2
(45) Date of Patent: Jun. 7, 2011

(54) NUCLEIC ACIDS AND POLYPEPTIDES USEFUL FOR DIAGNOSING COMPLICATIONS OF PREGNANCY

(75) Inventors: S. Ananth Karumanchi, Chestnut Hill, MA (US); Vikas P. Sukhatme, Newton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1055 days.

(21) Appl. No.: 11/300,928

(22) Filed: Dec. 15, 2005

(65) Prior Publication Data

US 2006/0166277 A1 Jul. 27, 2006

Related U.S. Application Data

(60) Provisional application No. 60/636,275, filed on Dec. 15, 2004.

(51) Int. Cl.
*G01N 33/53* (2006.01)

(52) U.S. Cl. ........................................ 435/7.1; 436/518

(58) Field of Classification Search ........................ None
See application file for complete search history.

(56) References Cited

U.S. PATENT DOCUMENTS

| | | | |
|---|---|---|---|
| 5,194,596 | A | 3/1993 | Tischer et al. |
| 5,219,739 | A | 6/1993 | Tischer et al. |
| 5,238,819 | A | 8/1993 | Roberts et al. |
| 5,240,848 | A | 8/1993 | Keck et al. |
| 5,332,671 | A | 7/1994 | Ferrara et al. |
| 5,543,138 | A | 8/1996 | Keith |
| 5,660,827 | A | 8/1997 | Thorpe et al. |
| 5,712,395 | A | 1/1998 | App et al. |
| 5,763,441 | A | 6/1998 | App et al. |
| 5,830,879 | A | 11/1998 | Isner |
| 5,928,641 | A | 7/1999 | Seon |
| 5,958,715 | A | 9/1999 | Muller |
| 6,100,071 | A | 8/2000 | Davis-Smyth et al. |
| 6,258,787 | B1 | 7/2001 | Isner |
| 6,361,946 | B1 | 3/2002 | Alitalo et al. |
| 6,365,157 | B2 | 4/2002 | Rockwell et al. |
| 6,376,199 | B1 | 4/2002 | Caniggia et al. |
| 6,399,585 | B1 | 6/2002 | Larson et al. |
| 6,410,322 | B1 | 6/2002 | Robinson |
| 6,447,768 | B1 | 9/2002 | Van Zonneveld et al. |
| 6,620,590 | B2 | 9/2003 | Groome et al. |
| 6,660,534 | B2 | 12/2003 | McVicker et al. |
| 6,677,300 | B1 | 1/2004 | Schreiner et al. |
| 7,191,068 | B2 | 3/2007 | Rosenfeld et al. |
| 7,323,346 | B2 | 1/2008 | Thadhani et al. |
| 7,344,892 | B2 | 3/2008 | Thadhani et al. |
| 2001/0055781 | A1 | 12/2001 | Groome et al. |
| 2003/0114412 | A1 | 6/2003 | Ward et al. |
| 2003/0144298 | A1 | 7/2003 | Curwen et al. |
| 2003/0220262 | A1 | 11/2003 | Schreiner et al. |
| 2004/0038305 | A1 | 2/2004 | Poston et al. |
| 2004/0126828 | A1 | 7/2004 | Karumanchi et al. |
| 2005/0025762 | A1 | 2/2005 | Karumanchi et al. |
| 2005/0148040 | A1 | 7/2005 | Thadhani et al. |
| 2005/0170444 | A1 | 8/2005 | Karumanchi et al. |
| 2005/0266409 | A1 | 12/2005 | Brown et al. |
| 2006/0067937 | A1 | 3/2006 | Karumanchi et al. |
| 2006/0183175 | A1 | 8/2006 | Buhimschi et al. |
| 2007/0104707 | A1 | 5/2007 | Karumanchi et al. |

FOREIGN PATENT DOCUMENTS

| | | |
|---|---|---|
| EP | 0 359 274 | 3/1990 |
| EP | 1 417 971 | 5/2004 |
| WO | WO 98/28006 | 7/1998 |
| WO | WO 02/37120 | 5/2002 |
| WO | WO 2004/008946 | 1/2004 |
| WO | WO 2005/077007 | 8/2005 |
| WO | WO 2006/034507 | 3/2006 |
| WO | WO 2006/069373 | 6/2006 |
| WO | WO 2008/030283 | 3/2008 |

OTHER PUBLICATIONS

Milkiewicz et al. J. Physiology 2006, vol. 577, p. 671-678.*
Schedel et al. Ann Rheum Dis 2004 vol. 63, p. 1205-1211.*
Nishizawa et al. Molecular Human Reproduction 2008, vol. 14, p. 595-602.*
Velzing-Aarts et al. Am J Rep Immu 2002 vol. 48, p. 319-322).*
Baker et al., "Elevated Serum Levels of Vascular Endothelial Growth Factor in Patients with Preeclampsia," *Obstet. Gynecol.* 86: 815-821 (1995). Davis-Smyth et al., "The Second Immunoglobulin-Like Domain of the VEGF Tyrosine Kinase Recpetor Flt-1 Determines Ligand Binding and May Initiate a Signal Transduction Cascade," *EMBO J.* 15: 4919-4927 (1996).
Davis-Smyth et al., "Mapping the Charged Residues in the Second Immunoglobulin-Like Domain of the Vascular Endothelial Growth Factor/Placenta Growth Factor Receptor Flt-1 Required for Binding and Structural Stability," *J. Biol. Chem.* 273: 3216-3222 (1998).

(Continued)

*Primary Examiner* — Jacob Cheu

(74) *Attorney, Agent, or Firm* — Kristina Bieker-Brady; Kimya F. Harris; Clark & Elbing LLP

(57) ABSTRACT

Disclosed herein are methods for diagnosing or treating pregnancy related hypertensive disorders that include the use of a polypeptide or a nucleic acid encoding a polypeptide selected from the following: follistatin related protein, interleukin 8, inhibin A, VEGF-C, angiogenin, beta fertilin, hypothetical protein, leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, alpha defensin, ADAM-TS3, cholecystokinin precursor, interferon stimulated T-cell alpha chemoattractant precursor, azurocidin, sperminine oxidase, UDP glycosyltransferase 2 family polypeptide B28, neurotrophic tyrosine kinase receptor 2, neutral endopeptidase, CDC28 protein kinase regulatory subunit 2, beta glucosidase, lanosterol synthase, calcium/calmodulin-dependent serine protein kinase, estrogen receptor-alternatively spliced transcript H, chemokine (CX3C motif) receptor 1, tyrosinase-related protein 1, hydoxy-delta-5-steroid dehyrogenase, dihydropyramidinase-like-4, and cytochrome P450-family 11.

29 Claims, 84 Drawing Sheets

OTHER PUBLICATIONS

Dvorak, "Vascular Permeability Factor/Vascular Endothelial Growth Factor: A Critical Cytokine in Tumor Angiogenesis and a Potential Target for Diagnosis and Therapy," *J. Clin. Oncol.* 20: 4368-4380 (2002).
Errico et al., "Identification of Placenta Growth Factor Determinants for Binding and Activation of Flt-1 Receptor," *J. Biol. Chem.* 279: 43929-43939 (2004).
Ferrara, "Role of Vascular Endothelial Growth Factor in Regulation of Physiological Angiogenesis," *Am. J. Physiol. Cell Physiol.* 280: C1358-C1366 (2001).
Florio et al., "Inhibins and Activins in Pregnancy," *Mol. Cell. Endocrinol.* 225: 93-100 (2004).
Hsieh, "Maternal Serum Placenta Growth Factor and Vascular Endothelial Growth Factor in Pregnancies Complicated by Preeclampsia (Abstract)," *Am. J. Obstet. Gynecol.* 184: S70 (2001).
Iyer et al., "The Crystal Structure of Human Placenta Growth Factor-1 (PIGF-1), an Angiogenic Protein, at 2.0 Å Resolution," *J. Biol. Chem.* 276: 12153-12161 (2001).
Keyt et al., "Identification of Vascular Endothelial Growth Factor Determinants for Binding KDR and FLT-1 Receptors," *J. Biol. Chem.* 271: 5638-5646 (1996).
Krauss et al, "Circulating Endothelial Cell Adhesion Molecules as Diagnostic Markers for the Early Identification of Pregnant Women at Risk for Development of Preeclampsia," *Am. J. Obstet. Gynecol.* 177: 443-449 (1997).
Krussel et al., "Expression of mRNA for Vascular Endothelial Growth Factor Transmembraneous Recpetors Flt1 and KDR, and the Soluble Receptor sflt in Cycling Human Endometrium," *Mol. Hum. Reprod.* 5: 452-458 (1999).
Li et al., "Recombinant VEGF121 Attenuates Hypertension and Improves Kidney Damage in a Rat Model of Preeclampsia," *Hypertension* 092098 (2007).
Lyall et al., "Suppression of Serum Vascular Endothelial Growth Factor Immunoreactivity in Normal Pregnancy and in Pre-Eclampsia," *BJOG* 104: 223-228 (1997).
Maynard et al., "Sflt-1, a Circulating VEGF Antagonist, is Up-Regulated in Preeclampsia and Contributes to Endothelial Dysfunction," *J. Am. Soc. Nephrol.* 13: SU-FC280 (2002).
Moran et al., "Glomerular Ultrafiltration in Normal and Preeclamptic Pregnancy," *J. Am. Soc. Nephrol.* 14: 648-652 (2003).
Muller et al., "The Crystal Structure of Vascular Endothelial Growth Factor (VEGF) Refined to 1.93 Å Resolution: Multiple Copy Flexibility and Receptor Binding," *Structure* 5: 1325-1338 (1997).
Muller et al., "Vascular Endothelial Growth Factor: Crystal Structure and Functional Mapping of the Kinase Domain Receptor Binding Site," *Proc. Natl. Acad. Sci. USA* 94: 7192-7197 (1997).
Nishizawa et al., "Increased Levels of Pregnancy-Associated Plasma Protein-A2 in the Serum of Pre-Eclamptic Patients," *Mol. Hum. Reprod.* 14: 595-602 (2008).
Oswald et al., "Mesanchymal Stem Cells Can Be Differentiated into Endothelial Cells In Vitro," *Stem Cells* 22: 377-384 (2004).
Olofsson et al., "Vascular Endothelial Growth Factor B (VEGF-B) Binds to VEGF Receptor-1 and Regulates Plasminogen Activator Activity in Endothelial Cells," *Proc. Natl. Acad. Sci. USA* 95: 11709-11714 (1998).
Park et al., "Placenta Growth Factor: Potentiation of Vascular Endothelial Growth Factor Bioactivity, In Vitro and In Vivo, and High Affinity Binding to Flt-1 but not to Flk-1/KDR," *J. Biol. Chem.* 269: 25646-25654 (1994).
Park et al., "An Elevated Maternal Plasma, but not Amniotic Fluid, Soluble fms-Like Tyrosine Kinase-1 (sFlt-1) at the Time of Mid-Trimester Genetic Amniocentesis is a Risk Factor for Preeclampsia," *Am. J. Obstet. Gynecol.* 193: 984-989 (2005).
Powers et al., "Maternal Serum Soluble fms-like Tyrosine Kinase 1 Concentrations are not Increased in Early Pregnancy and Decrease More Slowly Postpartum in Women Who Develop Preeclampsia," *Am. J. Obstet. Gynecol.* 193: 185-191 (2005).
Pryor-Koishi et al., "Overproduction of the Follistatin-Related Gene Protein in the Placenta and Maternal Serum of Women with Pre-Eclampsia," *BJOG* 114: 1128-1137 (2007).
Reuvekamp et al., "Selective Deficit of Angiogenic Growth Factors Characterises Pregnancies Complicated by Pre-eclampsia," *BJOG* 106: 1019-1022 (1999).
Sawano et al., "Flt-1 but not KDR/Flk-1 Tyrosine Kinase is a Receptor for Placenta Growth Factor, Which is Related to Vascular Endothelial Growth Factor," *Cell Growth Differ.* 7: 213-221 (1996).
Schultze-Mosgau et al., "Improved Free Vascular Grat Survival in an Irradiated Surgical SIte Following Topical Application of rVEGF," *Int. J. Radiat. Oncol. Biol. Phys.* 57: 803-812 (2003).
Takahashi et al., "Antiangiogenic Therapy of Established Tumors in Human Skin/Severe Combined Immunodeficiency Mouse Chimeras by Anti-Endoglin (CD105) Monoclonal Antibodies, and Synergy between Anti-Endoglin Antibody and Cyclophosphamide," *Cancer Res.* 61: 7846-7854 (2001).
Wald et al., "Multiple Marker Second Trimester Serum Screening for Pre-Eclampsia," *J. Med. Screen* 8: 65-68 (2001).
Walsh et al., "Computer Modelling of the Receptor-Binding Domains of VEGF and PIGF," *Protein Eng.* 10: 389-398 (1997).
Wiesmann et al., "Crystal Structure at 1.7 Å Resolution of VEGF in Complex with Domain 2 of the Flt-1 Receptor," *Cell* 91: 695-704 (1997).
European Search Report for EP 0359274, completed on Sep. 13, 1990.
Office Action for U.S. Appl. No. 10/624,809, mailed on Jun. 30, 2006.
International Search Report for PCT/US2003/022892, mailed on Nov. 16, 2005.
Reply to Office Action for U.S. Appl. No. 11/019,559, filed Dec. 5, 2006.
Reply to Office Action for U.S. Appl. No. 10/624,809, filed Dec. 7, 2006.
Reply to Office Action for U.S. Appl. No. 10/771,518, filed Dec. 13, 2006.
Office Action for U.S. Appl. No. 10/771,518, mailed on Mar. 8, 2007.
Office Action for U.S. Appl. No. 11/019,559, mailed Mar. 22, 2007.
International Search Report for PCT/US2005/034483, mailed on Apr. 5, 2007.
Office Action for U.S. Appl. No. 10/624,809, mailed on May 1, 2007.
Reply to Office Action for U.S. Appl. No. 10/771,518, filed Sep. 10, 2007.
Reply to Office Action for U.S. Appl. No. 11/019,559, filed Sep. 24, 2007.
Reply to Office Action for U.S. Appl. No. 10/624,809, filed Oct. 24, 2007.
Office Action for U.S. Appl. No. 11/019,559, mailed on Dec. 13, 2007.
Office Action for U.S. Appl. No. 10/624,809, mailed on Dec. 31, 2007.
Reply to Office Action for U.S. Appl. No. 11/019,559, filed Feb. 4, 2008.
Reply to Office Action for U.S. Appl. No. 10/624,809, filed Feb. 14, 2008.
Written Opinion for Singapore Patent Application No. 0704479-5, mailed on Jun. 27, 2008.
Office Action for U.S. Appl. No. 11/235,577, mailed on Jul. 25, 2008.
Written Opinion for Singapore Patent Application No. 0702085-2, dated Sep. 11, 2008.
Reply to Office Action for U.S. Appl. No. 11/235,577, filed Nov. 25, 2008.
European Search Report for EP 05858653, dated Nov. 27, 2008.
Office Action for U.S. Appl. No. 11/443,920, mailed on Jan. 21, 2009.
Office Action for U.S. Appl. No. 11/235,577, mailed on Feb. 18, 2009.
European Examination Report for EP 05815390, dated Mar. 20, 2009.
Ahmed et al., "Regulation of Placental Vascular Endothelial Growth Factor (VEGF) and Placenta Growth Factor (PIGF) and Soluble Flt-1 by Oxygen- A Review," *Placenta* 21:S16-S24 (2000).
Baek et al., "Hypoxia-Induced VEGF Enhances Tumor Survivability Via Suppression of Serum Deprivation-Induced Apoptosis," *Oncogene* 19:4621-4631 (2000).

Barleon et al., "Soluble VEGFR-1 Secreted by Endothelial Cells and Monocytes is Present in Human Serum and Plasma From Healthy Donors," *Angiogenesis* 4:143-154.
Baumgartner et al., "Constitutive Expression of phVEGF$_{165}$After Intramuscular Gene Transfer Promotes Collateral Vessel Development in Patients with Critical Limb Ischemia," *Circulation* 97:1114-1123 (1998).
Belgore et al., "Measurement of Free and Complexed Soluble Vascular Endothelial Growth Factor Receptor, Flt-1, in Fluid Samples: Development and Application of Two New Immunoassays," *Clin. Sci.* 100:567-575 (2001).
Belgore et al., "Plasma Levels of Vascular Endothelial Growth Factor and Its Soluble Receptor (SFlt-1) in Essential Hypertension," *Am. J. Cardiol.* 87:805-807 (2001).
Belgore et al., "sFlt-1, a Potential Antagonist for Exogenous VEGF," *Circulation* 102:E108-E109 (2000).
Belgore et al., "Successful Therapy Reduces Levels of Vascular Endothelial Growth Factor (VEGF) in Patients with Hypertension and Patients with Hypercholesterolemia," *Atherosclerosis* 151:599 (2000).
Belgore et al., "Vascular Endothelial Growth Factor and its Receptor, Flt-1, in Smokers and Non-Smokers," *Br. J. Biomed. Sci.* 57: 207-213 (2000).
Blann et al., "Plasma Vascular Endothelial Growth Factor and Its Receptor Flt-1 in Patients with Hyperlipidemia and Atherosclerosis and the Effects of Fluvastatin or Fenofibrate," *Am. J. Cardiol.* 87:1160-1163 (2001).
Brockelsby et al., "VEGF Via VEGF Receptor-1 (Flt-1) Mimics Preeclamptic Plasma in Inhibiting Uterine Blood Vessel Relaxation in Pregnancy: Implications in the Pathogenesis of Preeclampsia," *Lab Invest.* 79:1101-1111 (1999).
Brown et al., "Vascular Permeability Factor mRNA and Protein Expression in Human Kidney," *Kidney Int.* 42: 1457-1461 (1992).
Bouletreau et al., "Hypoxia and VEGF Up-Regulate BMP-2 mRNA and Protein Expression in Microvascular Endothelial Cells: Implications for Fracture Healing," *Plast. Reconstr. Surg.* 109:2384-2397 (2002).
Celletti et al., "Effect of Human Recombinant Vascular Endothelial Growth Factor $_{165}$ on Progression of Atherosclerotic Plaque," *J. Am. Coll. Cardiol.* 37:2126-2130 (2001).
Charnock-Jones et al., "Determination of the Circulating Levels of the Soluble Form of the VEGF-R1 (sFlt-1) in Women at High Risk of Developing Pre-Eclampsia," *J. Soc. Gynecol. Investig.* 10:166A Abstract No. 230 (2003).
Charnock-Jones et al., "Identification and Localization of Alternately Spliced mRNAs for Vascular Endothelial Growth Factor in Human Uterus and Estrogen Regulation in Endometrial Carcinoma Cell Lines," *Biol. Reprod.* 48:1120-1128 (1993).
Chong et al., "Structure and Expression of a Membrane Component of the Inhibin Receptor System," *Endocrinology* 141:2600-2607 (2000).
Clark et al., "A Vascular Endothelila Growth Factor Antagonist is Produced by the Human Placenta and Released into the Maternal Circulation," *Biol. Reprod.* 59:1540-1548 (1998).
Cockell et al., "Human Placental Syncytiotrophoblast Microvillous Membranes Impaired Maternal Vascular Endothelial Function," *Br. J. Obstet. Gynaecol.* 104:235-240 (1997).
Cohen et al., "Amelioration of Diabetic Nephropathy by Treatment with Monoclonal Antibodies Against Glycated Albumin," *Kidney Int.* 45:1673-1679 (1994).
Del Sorbo et al., "The Synthesis of Platelet-Activating Factors Modulates Chemotaxis of Monocytes Induced by HIV-1 Tat," *Eur. J. Immunol.* 29:1513-1521 (1999).
Deodato et al., "Recombinant AAV Vector Encoding Human VEGF 165 Enhances Wound Healing," *Gene Ther.* 9:777-785 (2002).
Eddahibi et al., "Imbalance Between Platelet Vascular Endothelial Growth Factor and Platelet-Derived Growth Factor in Pulmonary Hypertension," *Am. J. Respir. Crit. Care Med.* 162:1493-1499 (2000).
Eremina et al., "Glomerular-Specific Alterations of VEGF-A Expression Lead to Distinct Congenital and Acquired Renal Diseases," *J. Clin. Invest.* 111:707-716 (2003).
Evans et al., "Characterization of the Binding of Recombinant Mouse Sperm Fertilin α Subunit to Mouse Eggs: Evidence for Function as a Cell Adhesion Molecule in Sperm-Egg Binding," *Dev. Biol.* 187:94-106 (1997).
Ferguson, "Meeting Highlights: Highlights of the $48^{th}$ Scientific Sessions of the American College of Cardiology," *Circulation* 100:570-575 (1999).
Ferrara et al., "The Role of Vascular Endothelial Growth Factor in Angiogenesis," *Acta. Haematol.* 106:148-156 (2001).
Freedman et al., "Therapeutic Angiogenesis for Coronary Artery Disease," *Ann. Intern. Med.* 136:54-71 (2002).
Gille et al., "Analysis of Biological Effects and Signaling Properties of Flt-1 (VEGFR-1) and KDR (VEGFR-2)," *J. Biol. Chem.* 276:3222-3230 (2001).
Gordon et al., "Phase I Safety and Pharmacokinetic Study of Recombinant Human Anti-Vascular Endothelial Growth Factor in Patients with Advanced Cancer," *J. Clin. Oncol.* 19:843-850 (2001).
Graubert et al., "Vascular Repair After Menstruation Involves Regulation of Vascular Endothelial Growth Factor-Receptor Phosphorylation by sFLT-1," *Am. J. Pathol.* 158:1399-1410 (2001).
Hayashi et al., "Changes in Urinary Excretion of Six Biochemical Parameters in Normotensive Pregnancy and Preeclampsia," *Am. J. Kidney Dis.* 39:392-400 (2002).
He et al., "Alternative Splicing of Vascular Endothelial Growth Factor (VEGF)-R1 (FLT-1) Pre-mRNA is Important for the Regulation of VEGF Activity," *Mol. Endocrinol.* 13:537-545 (1999).
He et al., "Vascular Endothelial Growth Factor Signals Endothelial Cell Production of Nitric Oxide and Prostacyclin Through Flk-1/KDR Activation of c-Src," *J. Biol. Chem.* 274:25130-24135 (1999).
Heeschen et al., "Nicotine Stimulates Angiogenesis and Promotes Tumor Growth and Atherosclerosis," *Nat. Med.* 7:833-839 (2001).
Helske et al., "Expression of Vascular Endothelial Growth Factor Receptors 1, 2,and 3 in Placentas From Normal and Complicated Pregnancies," *Mol. Hum. Reprod.* 7:205-210 (2001).
Henry et al., "Intracoronary Admimistration of Recombinant Human Vascular Endothelial Growth Factor to Patients with Coronary Artery Disease," *Am. Heart J.* 142:872-880 (2001).
Holzgreve et al., "Disturbed Feto-Maternal Cell Traffic in Preeclampsia," *Obstet. Gynecol.* 91:669-672 (1998).
Hornig et al., "Release and Complex Formation of Soluble VEGFR-1 from Endothelial Cells and Biological Fluids," *Invest.* 80:443-454 (2000).
Hunter et al., "Serum Levels of Vascular Endothelial Growth Factor in Preeclamptic and Normotensive Pregnancy," *Hypertension* 36:965-969 (2000).
Ikawa et al., "Calmegin is Required for Fertilin α/β Heterodimerization and Sperm Fertility," *Dev. Biol.* 240:254-261 (2001).
Isner et al., "VEGF Gene Transfer for Diabetic Neuropathy," *Hum. Gene Ther.* 12:1593-1594 (2001).
Isner et al., "Myocardial Gene Therapy," *Nature* 415:234-239 (2002).
Kabbinavar et al., "Phase II, Randomized Trial Comparing Bevacizumab Plus Flurouracil (FU)/Leucovorin (LV) with FU/LV Alone in Patients with Metastatic Colorectal Cancer," *J. Clin. Oncol.* 21:60-65 (2003).
Kaku et al., "Effects of Vascular Endothelial Growth Factor on Osteoclast Induction During Tooth Movement in Mice," *J. Dent. Res.* 80:1880-1883 (2001).
Kendall et al., "Identification of a Natural Soluble Form of the Vascular Endothelial Growth Factor Receptor, FLT-1, and Its Heterodimerization with KDR," *Biochem. Biophys. Res. Commun.* 226:324-328 (1996).
Kendall et al., "Inhibition of Vascular Endothelial Cell Growth Factor Activity by an Endogenously Encoded Soluble Recpetor," *Proc. Natl. Acad. Sci.* 90:10705-10709 (1993).
Kincaid-Smith "The Renal Lesion of Preeclampsia Revisted," *Am. J. Kidney Dis.* 17:144-148 (1991).
Knebelmann et al., "Transforming Growth Factor α is a Target for the Von Hippel-Lindau Tumor Suppressor," *Cancer Res.* 58:226-231 (1998).
Koga et al., "Elevated Serum Soluble Vascular Endothelial Growth Factor Receptor1 (sVEGFR-1) Levels in Women with Preeclampsia," *J. Clin. Endocrinol. Metab.* 88:2348-2351 (2003).

Koransky, "VEGF Gene Delivery for Treatment of Ischemic Cardiovascular Disease." *Trends Cardiovasc. Med.* 12:108-114 (2002).
Kuo et al., "Comparative Evaluation of the Antitumor Activity of Antiangiogenic Proteins Delivered by Gene Transfer," *Proc. Natl. Acad. Sci. U.S.A.* 98:4605-4610 (2001).
Lai et al., "Inhibition of Angiogenesis by Adenovirus-Mediated sFlt-1 Expression in a Rat Model of Corneal Neovascularization," *Hum. Gene Ther.* 12:1299-1310 (2001).
Lai et al., "Potential Long-Term Inhibition of Ocular Neovascularisation by Recombinant Adeno-Associated Virus-Mediated Secretion Gene Therapy," *Gene Ther.* 9:804-813 (2002).
Lain et al., "Contemporary Concepts of the Pathogenesis and Management of Preeclampsia," *JAMA* 287:3183-3186 (2002).
LeCouter et al., "Identification of an Angiogenic Mitogen Selective for Endocrine Gland Endothelium," *Nature* 412:877-884 (2001).
Leong et al., "Adapting Pharmacokinetic Properties of a Humanized Anti-interleukin-8 Antibody For Therapeutic Applications Using Site-specific Pegylation," *Cytokine* 16:106-119 (2001).
Levine et al., "Circulating Angiogenic Factors and the Risk of Preeclampsia," *N. Engl. J. Med.* 350:672-683 (2004).
Levine et al., "Trial of Calcium for Preeclampsia Prevention (CPEP): Rationale, Design, and Methods," *Control Clin. Trials* 17:442-469 (1996).
Levine et al., "Trial of Calcium to Prevent Preeclampsia," *N. Engl. J. Med.* 337:69-76 (1997).
Levine et al., "Two-Stage Elevation of Cell-Free Fetal DNA in Maternal Sera Before Onset of Preeclampsia," *Am. J. Obstet. Gynecol.* 190:707-713 (2004).
Levine et al., "Urinary Placental Growth Factor and Risk of Preeclampsia," *JAMA* 293:77-85 (2005).
Lip et al., "Plasma VEGF and Soluble VEGF Receptor FLT-1 in Proliferative Retinopathy: Relationship to Endothelial Dysfunction and Laser Treatment," *Invest. Ophthalmol. Vis. Sci.* 41:2115-2119 (2000).
Livingston et al., "Placenta Growth Factor is not an Early Marker for the Development of Severe Preeclampsia," *Am. J. Obstet. Gynecol.* 184:1218-1220 (2001).
Livingston et al., "Reductions of Vascular Endothelial Growth Factor and Placental Growth Factor Concentrations in Severe Preeclampsia," *Am. J. Obstet. Gynecol.* 183:1554-1557 (2000).
Luttun et al., "Soluble VEGF Receptor Flt1: The Elusive Preclampsia Factor Discovered?" *J. Clin. Invest.* 111: 600-602 (2003).
Margolin et al., "Phase Ib Trial of Intravenous Recombinant Humanized Monoclonal Antibody to Vascular Endothelial Growth Factor in Combination with Chemotherapy in Patients with Advanced Cancer: Pharmacologic and Long-Term Safety Data," *J. Clin. Oncol.* 19:851-856 (2001).
Masuda et al., "Vascular Endothelial Growth Factor Enhances Glomerular Capillary Repair and Accelerates Resolution of Experimentally Induced Glomerulonephritis," *Am. J. Pathol.* 159:599-608 (2001).
Maynard et al., "Excess Placental Soluble fms-Like Tyrosine Kinase 1 (sFlt1) May Contribute to Endothelial Dysfunction, Hypertension, and Proteinuria in Preeclampsia," *J. Clinical Invest.* 111:649-658 (2003).
Mian et al., "Fully Human Anti-Interleukin 8 Antibody Inhibits Tumor Growth in Orthotopic Bladder Cancer Xenografts Via Down-Regulation of Matrix Metalloproteases and Nuclear Factor-κB," *Clin. Cancer Res.* 9:3167-3175 (2003).
Mills et al., "Prostacyclin and Thromboxane Changes Predating Clinical Onset of Preeclampsia," *JAMA* 281: 356-362 (1999).
Morbidelli et al., "Nitric Oxide Mediates Mitogenic Effect of VEGF on Coronary Venular Endothelium," *Am. J. Physiol.* 270:H411-H415 (1996).
Mortensen et al., "Smoking, Sex of the Offspring, and Risk of Placental Abruption, Placenta Previa, and Preeclampsia : A Population-Based Cohort Study," *Acta. Obstet. Gynecol. Scand.* 80:894-898 (2001).
Myers et al., "Hypertensive Diseases and Eclampsia,"*Curr. Opin. Obstet. Gynecol.* 14:119-125 (2002).
Neufeld et al., "Similarities and Differences Between the Vascular Endothelial Growth Factor (VEGF) Splice Variants," *Cancer Metastasis Rev.* 15:153-158 (1996).
Newman et al., "Cigarette Smoking and Pre-Eclampsia : Their Association and Effects on Clinical Outcomes," *J. Matern. Fetal Med.* 10:166-170. (2001).
Nishimoto et al., "Glomerular Hypertrophy in Preeclamptic Patients with Focal Segmental Glomerulosclerosis: A Morphometric Analysis," *Clin. Nephrol.* 51:209-219 (1999).
Ong et al., "First-Trimester Maternal Serum Levels of Placenta Growth Factor as Predictor of Preeclampsia and Fetal Growth Restriction," *Obstet. Gynecol.* 98:608-611 (2001).
Ostendorf et al., "VEGF $_{165}$Mediates Glomerular Endothelial Repair," *J. Clin. Invest.* 104:913-923 (1999).
Page et al., "Excessive Placental Secretion of Neurokinin B During the Third Trimester Causes Pre-Eclampsia," *Nature* 405:797-800 (2000).
Parry et al., "Dinucleotide Repeat Polymorphisms within the Flt-1 Gene in Minimal Change Nephropathy," *Eur. J. Immunogenet.* 26:321-323 (1999).
Paternoster et al., "Markers of Tubular Damage in Pre-Eclampsia," *Minerva Ginecol.* 51:373-377 (1999).
Polliotti et al., "Second-Trimester Maternal Serum Placental Growth Factor and Vascular Endothelial Growth Factor for Predicting Severe, Early-Onset Preeclampsia," *Obstet. Gynecol.* 101:1266-1274 (2003).
Quirici et al., "Differentiation and Expansion of Endothelial Cells from Human Bone Marrow CD 133$^+$ Cells, " *Br. J. Haematol.* 115:186-194 (2001).
Regnault et al., "Placental Expression of VEGF, PIGF and their Receptors in a Model of Placental Insufficiency-Intrauterine Growth Restriction (PI-IUGR)," *Placenta* 23:132-144 (2002).
Reimer et al., "Microarray Analysis of Differentially Epxressed Genes in Placental Tissue of Pre-eclampsia: Up-regulation of Obesity-related Genes," *Mol. Hum. Reprod.* 8:674-680 (2002).
Rishi et al., "Use of Monoclonal Antibody Against Human Inhibin as a Marker For Sex Cord-stromal Tumors of the Ovary," *Am. J. Surg. Pathol.* 21:583-589 (1997).
Roberts, "Endothelial Dysfunction in Preeclampsia," *Semin Reprod. Endocrinol.* 16:5-15 (1998).
Roberts et al., "Pathogenesis and Genetics of Pre-Eclampsia," *Lancet.* 357:53-56 (2001).
Roes et al., "High Levels of Urinary Vascular Endothelial Growth Factor in Women with Severe Preclampsia," *Int. J. Biol. Markers* 19:72-75 (2004).
Sato et al., "Increased Pulmonary Vascular Contraction to Serotonin after Cardiopulmonary Bypass: Role of Cyclooxygenase," *J. Surg. Res.* 90:138-143 (2000).
Sibai, "Diagnosis and Management of Gestational Hypertension and Preeclampsia," *Obstet. Gynecol.* 102:181-192 (2003).
Sibai et al., "What We Have Learned About Preeclampsia," *Semin. Perinatol.* 27:239-246 (2003).
Simon et al., "Expression of Vascular Endothelial Growth Factor and its Receptors in Human Renal Ontogenesis and in Adult Kidney," *Am. J. Physiol.* 268:F240-F250 (1995).
Sood et al., "Gene Expression Patterns in Human Placenta," *Proc. Natl. Acad. Sci. USA* 103:5478-5483 (2006).
Spencer et al., "First Timester Maternal Serum Placenta Growth Factor (PIGF) Concentrations in Pregnancies with Fetal Trisomy 21 or Trisomy 18," *Prenat. Diagn.* 21:718-722 (2001).
Strevens et al., "Glomerular Endotheliosis in Normal Pregnancy and Pre-Eclampsia," *Br. J. Obstet. Gynecol.* 110: 831-836 (2003).
Su et al., "Decreased Maternal Serum Placenta Growth Factor in Early Second Trimester and Preeclampsia," *Obstet. Gynecol.* 97:898-904 (2001).
Sugimoto et al., "Neutralization of Circulating Vascular Endothelial Growth Factor (VEGF) by Anti-VEGF Antibodies and Soluble VEGF Receptor 1 (sFlt-1) Induces Proteinuria," *J. Biol. Chem.* 278:12605-12608 (2003).
Taylor et al., "Longitudinal Serum Concentyrations of Placental Growth Factor: Evidence for Abnormal Placental Angiogenesis in Pathologic Pregnancies," *Am. J. Obstet. Gynecol.* 188:177-182 (2003.
Thadhani et al., "First Trimester Placental Growth Factor and Soluble FMS-like Tyrosine Kinase 1 and Risk for Preeclampsia," *J. Clin. Endocrinol. Metab.* 89:770-775 (2004).

Tidwell et al., "Low Maternal Serum Levels of Placenta Growth Fctor as an Antecedent of Clinical Preeclampsia," *Am. J. Obstet. Gynecol.* 184:1267-1272 (2001).
Tischer et al., "The Human Gene for Vascular Endothelial Growth Factor Multiple Protein Forms are Encoded Through Alternative Exon Splicing," *J. Biol. Chem.* 266:11947-11954 (1991).
Tjoa et al., "Plasma Placenta Growth Factor Levels in Midtrimester Pregnancies," *Obstet. Gynecol.* 98:600-607 (2001).
Tonner et al., "Hormonal Control of Plasmin and Tissue-type Plasminogen Activator Activity in Rat Milk During Involution of the Mammary Gland," *J. Endocrinol.* 167:265-273 (2000).
Tonner et al., "Insulin-like Growth Factor Binding Protein-5 (IGFBP-5) Induces Premature Cell Death in the Mammary Glands of Transgenic Mice," *Development* 129:4547-4557 (2000).
Tonner et al., "Insulin-like Growth Factor Binding Protein-5 (IGFBP-5) Potentially Regulates Programmed Cell Death and Plasminogen Activation in the Mammary Gland," *Adv. Exp. Med. Biol.* 480:45-53 (2000).
Tortoriello et al., "Human Follistatin-Related Protein: A Structural Homologue of Follistatin with Nuclear Localization," *Endocrinology* 142:3426-3434 (2001).
Torry et al., "Expression and Function of Placenta Growth Factor: Implications for Abnormal Placentation," *J. Soc. Gynecol. Investig.* 10:178-188 (2003).
Torry et al., "Preeclampsia is Associated with Reduced Serum Levels of Placenta Growth Factor," *Am. J. Obstet. Gynecol.* 179:1539-1544 (1998).
Traver et al., "Walking the Walk: Migration and Other Common Themes in Blood and Vascular Development," *Cell* 108:731-734 (2002).
Tsatsaris et al., "Overexpression of the Soluble Vascular Endothelial Growth Factor Receptor in Preeclamptic Patients: Pathophysiological Consequences," *J. Clin. Endocrinol. Metab.* 88:5555-5563 (2003).
Tucci et al., "rhVEGF and Experimental Rat Skin Flaps: Systemic or Local Administration and Morphological Characteristics," *Int. J. Artif. Organs* 24:743-751 (2001).
Vale et al., "Activins and Inhibins and Their Signaling," *Ann. N.Y. Acad. Sci.* 1038:142-147 (2004).
Vuorela et al., "Amniotic Fluid-Soluble Vascular Endothelial Growth Factor Receptor-1 in Preeclampsia," *Obstet. Gynecol.* 95:353-357 (2000).
Walker, "Pre-Eclampsia," *Lancet* 356:1260-1265 (2000).
Wankell et al., "The Activin Binding Proteins Follistatin and Follistatin-related Protein are Differentially Regulated In Vitro and During Cutaneous Wound Repair," *J. Endocrin.* 171:385-395 (2001).
Yang et al., "A Randomized Trial of Bevacizumab, an Anti-Vascular Endothelial Growth Factor Antibody, for Metastatic Renal Cancer," *N. Engl. J. Med.* 349:427-434 (2003).
Yang et al., "sFlt-1 Gene-Transfected Fibroblasts: A Wound-Specific Gene Therapy Inhibits Local Cancer Recurrence," *Cancer Res.* 61:7840-7845 (2001).
Zhang et al., "Birth-Weight-for-Gestational-Age-Patterns By Race, Sex, and Parity in the United States Population," *Obstet. Gynecol.* 86:200-208 (1995).
Zhou et al., "Preeclampsia is Associated With Failure of Human Cytotrophoblasts to Mimic a Vascular Adhesion Phenotype. One Cause of Defective Endovascular Invasion in This Syndrome?" *J. Clin. Invest.* 99:2152-2164 (1997).
Zhou et al., "Vascular Endothelial Growth Factor Ligands and Receptors That Regulate Human Cytotrophoblast Survival Are Dysregulated in Severe Preeclampsia and Hemolysis, Elevated Liver Enzymes, and Low Platelets Syndrome," *Am. J. Pathol.* 160:1405-1423 (2002).
Foreign Search Report Application No. SG 200500265-4, 2005.
International Search Report Application No. PCT/US03/22892, 2003.
International Search Report Application No. PCT/US2005/003884, 2005.
European Supplementary Search Report for EP 05858653.8, dated Nov. 19, 2008.

* cited by examiner

Normal placenta

Preeclamptic placenta

Figure 6A

MRPGAPGPLWPLPWGALAWAVGFVSSMGSGNPAPGGVCWLQQGQEATCSLVLQTDVTRAEC
CASGNIDTAWSNLTHPGNKINLLGFLGLVHCLPCKDSCDGVECGPGKACRMLGGRPRCECAPD
CSGLPARLQVCGSDGATYRDECELRAARCRGHPDLSVMYRGRCRKSCEHVVCPRPQSCVVDQ
TGSAHCVVCRAAPCPVPSSPGQELCGNNNVTYISSCHMRQATCFLGRSIGVRHAGSCAGTPEE
PPGGESAEEEENFV

Figure 6B gttcgccatg cgtcccgggg cgccagggcc actctggcct ctgccctggg gggccctggc ttgggccgtg ggcttcgtga gctccatggg
ctcggggaac cccgcgcccg gtggtgtttg ctggctccag cagggccagg aggccacctg cagcctggtg ctccagactg atgtcacccg
ggccgagtgc tgtgcctccg gcaacattga caccgcctgg tccaacctca cccacccggg gaacaagatc aacctcctcg gcttcttggg
ccttgtccac tgccttccct gcaaagattc gtgcgacggc gtggagtgcg gcccgggcaa ggcgtgccgc atgctggggg gccgcccgcg
ctgcgagtgc gcgcccgact gctcggggct cccggcgcgg ctgcaggtct gcggctcaga cggcgccacc taccgcgacg agtgcgagct
gcgcgccgcg cgctgccgcg gccacccgga cctgagcgtc atgtaccggg gccgctgccg caagtcctgt gagcacgtgg tgtgcccgcg
gccacagtcg tgcgtcgtgg accagacggg cagcgcccac tgcgtggtgt gtcgagcggc gccctgccct gtgccctcca gccccggcca
ggagctttgc ggcaacaaca acgtcaccta catctcctcg tgccacatgc gccaggccac ctgcttcctg ggccgctcca tcggcgtgcg
ccacgcgggc agctgcgcag gcacccctga ggagccgcca ggtggtgagt ctgcagaaga ggaagagaac ttcgtgtgag cctgcaggac
aggcctgggc ctggtgcccg aggcccccca tcatcccctg ttatttattg ccacagcaga gtctaattta tatgccacgg acactcctta
gagcccggat tcggaccact tggggatccc agaacctccc tgacgatatc ctggaaggac tgaggaaggg aggcctgggg gccggctggt
gggtgggata gacctgcgtt ccggacactg agcgcctgat ttagggccct tctctaggat gccccagccc ctaccctaag acctattgcc
ggggaggatt ccacacttcc gctcctttgg ggataaacct attaattatt gctactatca agagggctgg gcattctctg ctggtaattc
ctgaagaggc atgactgctt ttctcagccc caagcctcta gtctgggtgt gtacggaggg tctagcctgg gtgtgtacgg agggtctagc
ctgggtgagt acggagggtc tagcctgggt gagtacggag ggtctagcct gggtgagtac ggagagtcta gcctgggtgt gtatggagga
tctagcctgg gtgagtatgg agggtctagc ctgggtgagt atggagggtc tagcctgggt gtgtatggag ggtctagcct gggtgagtat
ggagggtcta gcctgggtgt gtatggaggg tctagcctgg gtgagtatgg agggtctagc ctgggtgtgt acggagggtc tagtctgagt
gcgtgtgggg acctcagaac actgtgacct tagcccagca agccaggccc ttcatgaagg ccaagaaggc tgccaccatt ccctgccagc
ccaagaactc cagcttcccc actgcctctg tgtgcccctt tgcgtcctgt gaaggccatt gagaaatgcc cagtgtgccc cctgggaaag
ggcacggcct gtgctcctga cacgggctgt gcttggccac agaaccaccc agcgtctccc ctgctgctgt ccacgtcagt tcatgaggca
acgtcgcgtg gtctcagacg tggagcagcc agcggcagct cagagcaggg cactgtgtcc ggcggagcca agtccactct gggggagctc
tggcggggac cacgggccac tgctcaccca ctggccccga ggggggtgta gacgccaaga ctcacgcatg tgtgacatcc ggagtcctgg
agccgggtgt cccagtggca ccactaggtg cctgctgcct ccacagtggg gttcacaccc agggctcctt ggtcccccac aacctgcccc
ggccaggcct gcagacccag actccagcca gacctgcctc acccaccaat gcagccgggg ctggcgacac cagccaggtg ctggtcttgg
gccagttctc ccacgacggc tcaccctccc ctccatctgc gttgatgctc agaatcgcct acctgtgcct gcgtgtaaac cacagcctca
gaccagctat ggggagagga caacacggag gatatccagc ttccccggtc tggggtgagg agtgtgggga gcttgggcat cctcctccag
cctcctccag cccccaggca gtgccttacc tgtggtgccc agaaaagtgc ccctaggttg gtgggtctac aggagcctca gccaggcagc
ccaccccacc ctggggccct gcctcaccaa ggaaataaag actcaaagaa gccttttttt ttttttttt

Figure 7A

MTSKLAVALLAAFLISAALCEGAVLPRSAKELRCQCIKTYSKPFHPKFIKELRVIESGPHCANTEIIV
KLSDGRELCLDPKENWVQRVVEKFLKRAENS

Figure 7B gaattcagta acccaggcat tattttatcc tcaagtctta ggttggttgg agaaagataa caaaaagaaa catgattgtg cagaaacaga
caaacctttt tggaaagcat ttgaaaatgg cattccccct ccacagtgtg ttcacagtgt gggcaaattc actgctctgt cgtactttct
gaaaatgaag aactgttaca ccaaggtgaa ttatttataa attatgtact tgcccagaag cgaacagact tttactatca taagaaccct
tccttggtgt gctctttatc tacagaatcc aagacctttc aagaaaggtc ttggattctt ttcttcagga cactaggaca taaagccacc tttttatgat
ttgttgaaat ttctcactcc atcccttttg ctgatgatca tgggtcctca gaggtcagac ttggtgtcct tggataaaga gcatgaagca
acagtggctg aaccagagtt ggaacccaga tgctctttcc actaagcata caactttcca ttagataaca cctccctccc accccaacca
agcagctcca gtgcaccact ttctggagca taaacatacc ttaactttac aacttgagtg gccttgaata ctgttcctat ctggaatgtg ctgttctctt
tcatcttcct ctattgaagc cctcctattc ctcaatgcct tgctccaact gcctttggaa gattctgctc ttatgcctcc actggaatta atgtcttagt
accacttgtc tattctgcta tatagtcagt ccttacattg ctttcttctt ctgatagacc aaactcttta aggacaagta cctagtctta tctatttcta
gatcccccac attactcaga aagttactcc ataaatgttt gtggaactga tttctatgtg aagacatgtg ccccttcact ctgttaacta
gcattagaaa aacaaatctt ttgaaaagtt gtagtatgcc cctaagagca gtaacagttc ctagaaactc tctaaaatgc ttagaaaaag
atttatttta aattacctcc ccaataaaat gattggctgg cttatcttca ccatcatgat agcatctgta attaactgaa aaaaaataat tatgccatta
aaagaaaatc atccatgatc ttgttctaac acctgccact ctagtactat atctgtcaca tggtctatga taaagttatc tagaaataaa
aaagcataca attgataatt caccaaattg tggagcttca gtattttaaa tgtatattaa aattaaatta ttttaaagat caaagaaaac tttcgtcata
ctccgtattt gataaggaac aaataggaag tgtgatgact caggtttgcc ctgaggggat gggccatcag ttgcaaatcg tggaatttcc
tctgacataa tgaaaagatg agggtgcata agttctctag tagggtgatg atataaaaag ccaccggagc actccataag gcacaaactt
tcagagacag cagagcacac aagcttctag gacaagagcc aggaagaaac caccggaagg aaccattctc actgtgtgta aacatgactt
ccaagctggc cgtggctctc ttggcagcct tcctgatttc tgcagctctg tgtgaaggta agcacatctt tctgacctac agcgttttcc tatgtctaaa
tgtgatcctt agatagcaaa gctattcttg atgctttggt aacaaacatc ctttttattc agaaacagaa tataatctta gcagtcaatt aatgttaaat
tgaagattta gaaaaaacta tatataacac ttaggaaata taaaggtttg atcaatatag atattctgct tttataattt ataccaggta gcatgcatat
atttaacgta aataagtaat ttatagtatg tcctattgag aaccacggtt acctatatta tgtattaata ttgagttgag caaggtaact cagacaattc
cactccttgt agtatttcat tgacaagcct cagatttgtc attaattcct gtctggttta aagataccct gattatagac caggcatgta taacttattt
atatatttct gttaattctt tctgaaggca atttctatgc tggagagtct tagcttgcct actataaata acactgtggt atcacagagg attatgcaat
attgaccaga taaaaatacc atgaagatgt tgatattgta caaaaagaac tctaactctt atataggaag ttgttcaatg ttgtcagtta tgactgtttt
ttaaaacaaa gaactaactg aggtcaaggg ctaggagata ttcaggaatg agttcactag aaacatgatg ccttccatag tctccaaata
atcatattgg aattagaagg aagtagctgg cagagctgtg cctgttgata aaatcaatcc ttaatcactt tttcccccaa caggtgcagt
tttgccaagg agtgctaaag aacttagatg tcagtgcata aagacatact ccaaaccttt ccaccccaaa tttatcaaag aactgagagt
gattgagagt ggaccacact gcgccaacac agaaattatg taagtacttt aaaaaagatt agatattttg ttttagcaaa cttaaaatta
aggaaggtgg aaatatttag gaaagttcca ggtgttagga ttacagtagt aaatgaaaca aaacaaaata aaaatatttg tctacatgac
atttaaatat ggtagcttcc acaactacta taaatgttat tttggactta gactttatgc ctgacttaag gaatcatgat ttgaatgcaa aaactaaata
ttaatctgaa ccatttcttt cttatttcag tgtaaagctt tctgatggaa gagagctctg tctggacccc aaggaaaact gggtgcagag
ggttgtggag aagtttttga agaggtaagt tatatatttt ttaatttaaa tttttcattt atcctgagac atataatcca aagtcagcct ataaatttct
ttctgttgct aaaaatcgtc attaggtatc tgcctttttg gttaaaaaaa aaggaatagc atcaatagtg agtttgttgt acttatgacc
agaaagacca tacatagttt gcccaggaaa ttctgggttt aagcttgtgt cctatactct tagtaaagtt ctttgtcact cccagtagtg tcctatttta
gatgataatt tctttgatct ccctatttat agttgagaat atagagcatt tctaacacat gaatgtcaaa gactatattg acttttcaag aaccctactt
tccttcttat taaacatagc tcatctttat atttttaatt ttattttagg gctgagaatt cataaaaaaa ttcattctct gtggtatcca agaatcagtg
aagatgccag tgaaacttca agcaaatcta cttcaacact tcatgtattg tgtgggtctg ttgtagggtt gccagatgca atacaagatt
cctggttaaa tttgaatttc agtaaacaat gaatagtttt tcattgtacc atgaaatatc cagaacatac ttatatgtaa agtattattt atttgaatct

Figure 7B (Continued)

acaaaaaaca acaaataatt tttaaatata aggattttcc tagatattgc acgggagaat atacaaatag caaaattggg ccaagggcca
agagaatatc cgaactttaa tttcaggaat tgaatgggtt tgctagaatg tgatatttga agcatcacat aaaaatgatg ggacaataaa
ttttgccata aagtcaaatt tagctggaaa tcctggattt ttttctgtta aatctggcaa ccctagtctg ctagccagga tccacaagtc cttgttccac
tgtgccttgg tttctccttt atttctaagt ggaaaaagta ttagccacca tcttacctca cagtgatgtt gtgaggacat gtggaagcac tttaagtttt
ttcatcataa cataaattat tttcaagtgt aacttattaa cctatttatt atttatgtat ttatttaagc atcaaatatt tgtgcaagaa tttggaaaaa
tagaagatga atcattgatt gaatagttat aaagatgtta tagtaaattt attttatttt agatattaaa tgatgtttta ttagataaat ttcaatcagg
gtttttagat taaacaaaca aacaattggg tacccagtta aattttcatt tcagatatac aacaaataat tttttagtat aagtacatta ttgtttatct
gaaattttaa ttgaactaac aatcctagtt tgatactccc agtcttgtca ttgccagctg tgttggtagt gctgtgttga attacggaat aatgagttag
aactattaaa acagccaaaa ctccacagtc aatattagta atttcttgct ggttgaaact tgtttattat gtacaaatag attcttataa tattatttaa
atgactgcat ttttaaatac aaggctttat atttttaact ttagtgtttt tatgtgctct ccaaattttt tttactgttt ctgattgtat ggaaatataa
aagtaaatat gaaacattta aaatataatt tgttgtcaaa gtaatcaagt gtttgtcttt tttttagttt tagcttattg ggattctctt tgtttatatt
taaaattata ctttgattta gaaaacataa atgcttcccc ttagcatttt gttatggaaa attacaaact tttattttta gaaaacagaa ctcctttcca
gaaataggtt acaaacagta gtgtcctcca cagaatgttg gaaatgtttt caactcccca ctgtatacta tcttgctaat aagtctgtct tcagatttcg
attaaccggt ttgtatgtct gtgcacttta gcatagctgg acattaaaga ggaaagagag tacatattat aagttgctta tcagtaactg
aggagtaaaa ctgataaatg tgaggcaaag aagtttaaaa tatggttaaa gcctaagcat atttgcaaac aaatcaaaca atactctgag
aagtaaaaac ataattattt aattaacaaa tttcagtgga taaattttat aacaaattag acacagttga aaataaaatt agaaaactag
aaaatagaac aaaagaaact tctggaattc a

Figure 8A

MVLHLLLFLLLTPQGGHSCQGLELARELVLAKVRALFLDALGPPAVTREGGDPGVRRLPRRHAL
GGFTHRGSEPEEEEDVSQAILFPATDASCEDKSAARGLAQEAEEGLFRYMFRPSQHTRSRQVT
SAQLWFHTGLDRQGTAASNSSEPLLGLLALSPGGPVAVPMSLGHAPPHWAVLHLATSALSLLTH
PVLVLLLRCPLCTCSARPEATPFLVAHTRTRPPSGGERARRSTPLMSWPWSPSALRLLQRPPEE
PAAHANCHRVALNISFQELGWERWIVYPPSFIFHYCHGGCGLHIPPNLSLPVPGAPPTPAQPYSL
LPGAQPCCAALPGTMRPLHVRTTSDGGYSFKYETVPNLLTQHCACI

Figure 8B gaaggactgg ggaagactgg atgagaaggg tagaagaggg tgggtgtggg atggggaggg gagagtggaa aggccctggg
cagaccctgg cagaaggggc acggggcagg gtgtgagttc cccactagca gggccaggtg agctatggtg ctgcacctac tgctcttctt
gctgctgacc ccacagggtg ggcacagctg ccaggggctg gagctggccc gggaacttgt tctggccaag gtgagggccc tgttcttgga
tgccttgggg ccccccgcgg tgaccaggga aggtggggac cctggagtca ggcggctgcc ccgaagacat gccctggggg gcttcacaca
caggggctct gagcccgagg aagaggagga tgtctcccaa gccatccttt tcccagccac agatgccagc tgtgaggaca agtcagctgc
cagagggctg gcccaggagg ctgaggaggg cctcttcaga tacatgttcc ggccatccca gcatacacgc agccgccagg tgacttcagc
ccagctgtgg ttccacaccg ggctggacag gcagggcaca gcagcctcca atagctctga gcccctgcta ggcctgctgg cactgtcacc
gggaggaccc gtggctgtgc ccatgtcttt gggccatgct ccccctcact gggccgtgct gcacctggcc acctctgctc tctctctgct
gacccacccc gtcctggtgc tgctgctgcg ctgtcccctc tgtacctgct cagcccggcc tgaggccacg cccttcctgg tggcccacac
tcggaccaga ccacccagtg gaggggagag agcccgacgc tcaactcccc tgatgtcctg gccttggtct ccctctgctc tgcgcctgct
gcagaggcct ccggaggaac cggctgccca tgccaactgc cacagagtag cactgaacat ctccttccag gagctgggct gggaacggtg
gatcgtgtac cctcccagtt tcatcttcca ctactgtcat ggtggttgtg ggctgcacat cccaccaaac ctgtcccttc cagtccctgg
ggctcccccct accccagccc agccctactc cttgctgcca ggggcccagc cctgctgtgc tgctctccca gggaccatga ggcccctaca
tgtccgcacc acctcggatg gaggttactc tttcaagtat gagacagtgc ccaaccttct cacgcagcac tgtgcttgta tctaagggtg
gggggtcttc cttcttaatc ccatggctgg tggccacgcc cccaccatca tcagctggga ggaaaggcag agttgggaaa tagatggc

Figure 9A

MHLLGFFSVACSLLAAALLPGPREAPAAAAAFESGLDLSDAEPDAGEATAYASKDLEEQLRSVSS
VDELMTVLYPEYWKMYKCQLRKGGWQHNREQANLNSRTEETIKFAAAHYNTEILKSIDNEWRKT
QCMPREVCIDVGKEFGVATNTFFKPPCVSVYRCGGCCNSEGLQCMNTSTSYLSKTLFEITVPLS
QGPKPVTISFANHTSCRCMSKLDVYRQVHSIIRRSLPATLPQCQAANKTCPTNYMWNNHICRCL
AQEDFMFSSDAGDDSTDGFHDICGPNKELDEETCQCVCRAGLRPASCGPHKELDRNSCQCVC
KNKLFPSQCGANREFDENTCQCVCKRTCPRNQPLNPGKCACECTESPQKCLLKGKKFHHQTC
SCYRRPCTNRQKACEPGFSYSEEVCRCVPSYWKRPQMS

Figure 9B cgcggggtgt tctggtgtcc cccgccccgc ctctccaaaa agctacaccg acgcggaccg cggcggcgtc ctccctcgcc ctcgcttcac
ctcgcgggct ccgaatgcgg ggagctcgga tgtccggttt cctgtgaggc ttttacctga cacccgccgc ctttccccgg cactggctgg
gagggcgccc tgcaaagttg ggaacgcgga gccccggacc cgctcccgcc gcctccggct cgcccagggg gggtcgccgg
gaggagcccg ggggagaggg accaggaggg gcccgcggcc tcgcaggggc gcccgcgccc ccaccccctgc ccccgccagc
ggaccggtcc cccaccccccg gtccttccac catgcacttg ctgggcttct tctctgtggc gtgttctctg ctcgccgctg cgctgctccc
gggtcctcgc gaggcgcccg ccgccgccgc cgccttcgag tccggactcg acctctcgga cgcggagccc gacgcgggcg aggccacggc
ttatgcaagc aaagatctgg aggagcagtt acggtctgtg tccagtgtag atgaactcat gactgtactc tacccagaat attggaaaat
gtacaagtgt cagctaagga aaggaggctg gcaacataac agagaacagg ccaacctcaa ctcaaggaca gaagagacta taaaatttgc
tgcagcacat tataatacag agatcttgaa aagtattgat aatgagtgga gaaagactca atgcatgcca cgggaggtgt gtatagatgt
ggggaaggag tttggagtcg cgacaaacac cttctttaaa cctccatgtg tgtccgtcta cagatgtggg ggttgctgca atagtgaggg
gctgcagtgc atgaacacca gcacgagcta cctcagcaag acgttatttg aaattacagt gcctctctct caaggcccca aaccagtaac
aatcagtttt gccaatcaca cttcctgccg atgcatgtct aaactggatg tttacagaca agttcattcc attattagac gttccctgcc
agcaacacta ccacagtgtc aggcagcgaa caagacctgc ccccaccaatt acatgtggaa taatcacatc tgcagatgcc tggctcagga
agattttatg ttttcctcgg atgctggaga tgactcaaca gatggattcc atgacatctg tggaccaaac aaggagctgg atgaagagac
ctgtcagtgt gtctgcagag cggggcttcg gcctgccagc tgtggacccc acaaagaact agacagaaac tcatgccagt gtgtctgtaa
aaacaaactc ttccccagcc aatgtggggc caaccgagaa tttgatgaaa acacatgcca gtgtgtatgt aaaagaacct gccccagaaa
tcaacccccta aatcctggaa aatgtgcctg tgaatgtaca gaaagtccac agaaatgctt gttaaaagga aagaagttcc accaccaaac
atgcagctgt tacagacggc catgtacgaa ccgccagaag gcttgtgagc caggattttc atatagtgaa gaagtgtgtc gttgtgtccc
ttcatattgg aaaagaccac aaatgagcta agattgtact gttttccagt tcatcgattt tctattatgg aaaactgtgt tgccacagta gaactgtctg
tgaacagaga gacccttgtg ggtccatgct aacaaagaca aaagtctgtc tttcctgaac catgtggata actttacaga aatggactgg
agctcatctg caaaaggcct cttgtaaaga ctggttttct gccaatgacc aaacagccaa gattttcctc ttgtgatttc tttaaaagaa
tgactatata atttatttcc actaaaaata ttgtttctgc attcattttt atagcaacaa caattggtaa aactcactgt gatcaatatt tttatatcat
gcaaaatatg tttaaaataa aatgaaaatt gtatt

Figure 10A

MVMGLGVLLLVFVLGLGLTPPTLAQDNSRYTHFLTQHYDAKPQGRDDRYCESIMRRRGLTSPCK
DINTFIHGNKRSIKAICENKNGNPHRENLRISKSSFQVTTCKLHGGSPWPPCQYRATAGFRNVVV
ACENGLPVHLDQSIFRRP

Figure 10B tgtttgcatt aagttcatag attataattt gtaatggaat caacaccaaa tgcaaattag aaagagagcc cactttgctc acccagtcac
gtcttcccat gtaaccatag aacgttgggg tcctgtgtct ttctagatcc acagtcttgc tctcagaaca ggctagccac accacaggcc
tagtgccagg acccatggcc tttttttaag ctcagactcc cttctgtgaa cagcaatatc cccacaactt gtacaacatt ggtgcttcct
gcaagggcta cagaactatt tgatacgaaa atgttcattg acttacacac aagagaagca caaaataaaa aattaataat taatttaatg
tctttgaaaa tgtaccattt atttttacat ttggggtcat aagaattgta ttacacttaa gaatgcaata caatttgaag atcagatttt tctccctttg
tgagaatttc tcagtatgtg tgatgactac caagaaatca tagccagtca taaattcagt gagttactca taaacgaaca agaaccacct
acttcttggg gaggtaggtc tgcttccctt caactcagga tacaactgct ttcaactgct ttcttcacat tagctgacta attagctaga agcctgtcgt
aaacaatttt atggttgact ccttccctgg gctcagggtt ccctagaaca gagaggtccc caaatcccgg tctgtggcct gtccgcctaa
gctctgcctc ctgccagatc agcaggcagc attagattct cataggagct ggacgcctat tgtgaactgc gcatgtgcgg gatccagatt
gtgcactctt tatgagaatc taactaatgc ttgatgatct atctgaacca gaacaatttc atcctgaaac catcccccac caatccatag
aaatactgtc ttccacaaaa atgatccctg gtgccaaaaa tgttagagac cactccccta aaactctctt cttagctctc acctcctgta
ttactatctc atctcagtac attgaagccc ccatcttttc cccatggatg cctcatttcc tattagggag gcattttttt attttttgtt tttatttttt
tccgagacgg agtctcgctc tgtcgccaag gctggagtgc agtggcgcga tctcggctca ctgcaagctc cgcctcccgg gttcacgcca
ttctcctgcc tcagcctccc aagtagctgg gactacaggc gcccgcacta cgcccggcta attttttgta tttttagtag agacggggtt
tcaccgtggt agccaggatg gtctcgatct cctgacctcg tgatccgccc gccttggcct cccaaagtgc tgggattaca ggcgtgagac
cgcgcccggc cgtcatttgg tatgtcttaa tgtgcctcag gacctagcac agtccctggt acccagtaga gacctatgta atgttcgtta
ttcaataata aatacatgaa ttaaagagtg agagtggatt ttgtaatgtt acgactgata gagaaatact cagtgattct aagggatggg
gaagaacggt tggagctaga ggttgtgctc aggaaactat taaatagacg ttccgcagga agggattgac gaagtgtgag gttaatgagg
aagggaaaat agaatataaa atttggtggt ggaaaagatc tgattcatga tgccgtgtca gagagcaaag ctcctgtcct tttggcctaa
tttggtgatg ctgttcttgg gtctaccaca cctccttttg ccctccgcag gagcctgtgt tggaagagat ggtgatgggc ctgggcgttt tgttgttggt
cttcgtgctg ggtctgggtc tgaccccacc gaccctggct caggataact ccaggtacac acacttcctg acccagcact atgatgccaa
accacagggc cgggatgaca gatactgtga aagcatcatg aggagacggg gcctgacctc accctgcaaa gacatcaaca catttattca
tggcaacaag cgcagcatca aggccatctg tgaaaacaag aatggaaacc ctcacagaga aaacctaaga ataagcaagt cttctttcca
ggtcaccact tgcaagctac atggaggttc cccctggcct ccatgccagt accgagccac agcggggttc agaaacgttg ttgttgcttg
tgaaaatggc ttacctgtcc acttggatca gtcaattttc cgtcgtccgt aaccagcggg cccctggtca agtgctggct ctgctgtcct
tgccttccat ttcccctctg cacccagaac agtggtggca acattcattg ccaagggccc aaagaaagag ctacctggac cttttgtttt
ctgtttgaca acatgtttaa taaataaaaa tgtcttgata tcagtaagaa tcagagtctt ctcactgatt ctgggcatat tgatctttcc cccattttct
ctacttggct gctccctgag aggactgcat aggatagaaa tgccttttc ttttctttc gttttttttt ttttttttt ttgagatgga gtctcactct
gtcgcccagg cttaagtgca atggcacaat ctcggctcac tgcaacctct ctctcctggg ttcaagtgat tctcctgcct cagcctccca
aatagctgag attacaggca tgcaccacca cacctggcta atttttgtgt ttttagtaga gacagggttt caccgttttg gccaggttgg
tcttgaactc ctgacctcgg gagatccgcc caccttggcc tctctttgtg ctgggattac aggcatgagc cactgagccg ggccactttt
tccttatcag tcagttttta caagtcatta gggaggtaga ctttacctct ctgtgaagga aagtatggta tgttgatcta cagagagaga
tggaaaaatt ccagggctcg tagctactaa gcagaatttc caagataggc aaattgtttt ttctgtcaaa taataagcta atattacttc
tacaaatatg agaccttgga gagaagtttc caaggaccaa gtaccaacat accaacagat tattatagtt tctctcactc ttacacacac
acacacacat atacacatat gtaatccagc atgaatacca aaattcattc agggtagcca ccttttgtct taatcgagag ataattttga
tgtttgaatg gaatgctccc aggatattct cttgtcatgg ttattttata taaaattcaa aaaccaatta cattatttcc tctgtaatct tttactttat
caactaatgt ctggcaagtg tgatgttttg gggaagttat agaagattcc ggccaggcgc ttatctcacg cttgtaatcc agcactttgg
gaagctgagg cggacagatc acgaggtcaa gagatcaaga ccatcctgga caacatggtg aaaccttgtc tctactaaaa atgtgaaaat
tagctgggcg tggtggcaca cacctatagt cccagctact cgggaggctg aggcaggaga atcgcttgaa cctaggaggc ggaggttgca

Figure 10B (Continued)

ctgagccgag atcacgccac tgcactccag cctgggcgac agagcgagac tccatctcaa aaaaaaaaaa aaaagaaaga tcccagttta
tcccagttta tcccttattc ttcctcaatt ctcaagattt gtttttaagt taacataact taggttaaca cactctttgt aaaatacact gttcaatcta
cagactcagt ggttagcttc ctgttaacta atttctgttg acaggtactt ggatatttta tttagaaagt ggttgccaat aaattagtta taagtcgcca
gtttcactgc cttgtgaaca cataattatt gtggtctcag tattccctat ggtggcttct cctgctcctg gtattgccct gaaatgggcc aaaagccgtg
gctccccaat gctcaggtta tagaacattg tccaggtacc acctaggaga gcccagcctc actgaaagta ttcaaattta ggaatgggtt
tgagaagtag gtagctggta tgtgcttagc acaagaatct ctcttccttg ggttagtctg tttcaaaact gaaaacactg tcattcctta
agaaaatagg aaaaagtatt ccaaacctct gtcactagaa aatttgccat attaccaaat ctcaaaaacc tctcaggaaa tgagaaagtc
ccagtttctg gtaaactatt tgggcccttt tctcaagttc tccttccagt gctatttcct tgaggtgagg caaagttact caagatcatc gctgccactc
aaggccttga tagggcaagt gaaaggcatg gaccattatt atattgatca cagcataagc tgtgaaaacc cacatcttct ccaaacatct
gcttggagca ttatcatcgc atagtttgct ctggtgttca gggaaatcgc tgtttcatag gaaatcacat ggcagtggga tgggagtgtt
tcctgacctg ccgatggtac tggcacctga gcaagcattc ctagtccttt ttggtctggg cctcttgttc tatcacaacc acaagctgtt
taaaataaaa acgtcaagtc acaggcaggt cattttatcc tgcgtgaatc aattgaag

Figure 11A

MWVLFLLSGLGGLRMDSNFDSLPVQITVPEKIRSIIKEGIESQASYKIVIEGKPYTVNLMQKNFLPH
NFRVYSYSGTGIMKPLDQDFQNFCHYQGYIEGYPKSVVMVSTCTGLRGVLQFENVSYGIEPLES
SVGFEHVIYQVKHKKADVSLYNEKDIESRDLSFKLQSAEPQQDFAKYIEMHVIVEKQLYNHMGSD
TTVVAQKVFQLIGLTNAIFVSFNITIILSSLELWIDENKIATTGEANELLHTFLRWKTSYLVLRPHDVA
FLLVYREKSNYVGATFQGKMCDANYAGGVVLHPRTISLESLAVILAQLLSLSMGITYDDINKCQCS
GAVCIMNPEAIHFSGVKIFSNCSFEDFAHFISKQKSQCLHNQPRLDPFFKQQAVCGNAKLEAGEE
CDCGTEQDCALIGETCCDIATCRFKAGSNCAEGPCCENCLFMSKERMCRPSFEECDLPEYCNG
SSASCPENHYVQTGHPCGLNQWICIDGVCMSGDKQCTDTFGKEVEFGPSECYSHLNSKTDVSG
NCGISDSGYTQCEADNLQCGKLICKYVGKFLLQIPRATIIYANISGHLCIAVEFASDHADSQKMWIK
DGTSCGSNKVCRNQRCVSSSYLGYDCTTDKCNDRGVCNNKKHCHCSASYLPPDCSVQSDLWP
GGSIDSGNFPPVAIPARLPERRYIENIYHSKPMRWPFFLFIPFFIIFCVLIAIMVKVNFQRKKWRTED
YSSDEQPESESEPKG

Figure 11B catctcgcac ttccaactgc cctgtaacca ccaactgccc ttattccggc tgggacccag gacttcaagc catgtgggtc ttgtttctgc
tcagcgggct cggcgggctg cggatggaca gtaattttga tagtttacct gtgcaaatta cagttccgga gaaaatacgg tcaataataa
aggaaggaat tgaatcgcag gcatcctaca aaattgtaat tgaagggaaa ccatatactg tgaatttaat gcaaaaaaac tttttacccc
ataattttag agtttacagt tatagtggca caggaattat gaaaccactt gaccaagatt ttcagaattt ctgccactac caagggtata
ttgaaggtta tccaaaatct gtggtgatgg ttagcacatg tactggactc aggggcgtac tacagtttga aaatgttagt tatggaatag
aacccctgga gtcttcagtt ggctttgaac atgtaattta ccaagtaaaa cataagaaag cagatgtttc cttatataat gagaaggata
ttgaatcaag agatctgtcc tttaaattac aaagcgcaga gccacagcaa gattttgcaa agtatataga aatgcatgtt atagttgaaa
aacaattgta taatcatatg ggtctgata caactgttgt cgctcaaaaa gttttccagt tgattggatt gacgaatgct atttttgttt catttaatat
tacaattatt ctgtcttcat tggagctttg gatagatgaa aataaaattg caaccactgg agaagctaat gagttattac acacattttt
aagatggaaa acatcttatc ttgttttacg tcctcatgat gtggcatttt tacttgttta cagagaaaag tcaaattatg ttggtgcaac ctttcaaggg
aagatgtgtg atgcaaacta tgcaggaggt gttgttctgc accccagaac cataagtctg gaatcacttg cagttatttt agctcaatta
ttgagcctta gtatggggat cacttatgat gacattaaca aatgccagtg ctcaggagct gtctgcatta tgaatccaga agcaattcat
ttcagtggtg tgaagatctt tagtaactgc agcttcgaag actttgcaca ttttatttca aagcagaagt cccagtgtct tcacaatcag cctcgcttag
atcctttttt caaacagcaa gcagtgtgtg gtaatgcaaa gctggaagca ggagaggagt gtgactgtgg gactgaacag gattgtgccc
ttattggaga aacatgctgt gatattgcca catgtagatt taaagccggt tcaaactgtg ctgaaggacc atgctgcgaa aactgtctat
ttatgtcaaa agaaagaatg tgtaggcctt cctttgaaga atgcgacctc cctgaatatt gcaatggatc atctgcatca tgcccagaaa
accactatgt tcagactggg catccgtgtg gactgaatca atggatctgt atagatggag tttgtatgag tggggataaa caatgtacag
acacatttgg caaagaagta gagtttggcc cttcagaatg ttattctcac cttaattcaa agactgatgt atctggaaac tgtggtataa
gtgattcagg atacacacag tgtgaagctg acaatctgca gtgcggaaaa ttaatatgta aatatgtagg taaattttta ttacaaattc
caagagccac tattatttat gccaacataa gtggacatct ctgcattgct gtggaatttg ccagtgatca tgcagacagc caaaagatgt
ggataaaaga tggaacttct tgtggttcaa ataaggtttg caggaatcaa agatgtgtga gttcttcata cttgggttat gattgtacta
ctgacaaatg caatgataga ggtgtatgca ataacaaaaa gcactgtcac tgtagtgctt catatttacc tccagattgc tcagttcaat
cagatctatg gcctggtggg agtattgaca gtggcaattt tccacctgta gctataccag ccagactccc tgaaaggcgc tacattgaga
acatttacca ttccaaacca atgagatggc catttttctt attcattcct ttctttatta ttttctgtgt actgattgct ataatggtga aagttaattt
ccaaaggaaa aaatggagaa ctgaggacta ttcaagcgat gagcaacctg aaagtgagag tgaacctaaa gggtagtctg gacaacagag
atgccatgat atcacttctt ctagagtaat tatctgtgat ggatggacac aaaaaaatgg aaagaaaaga atgtacatta cctggtttcc
tgggattcaa acctgcatat tgtgatttta atttgaccag aaaatatgat atatatgtat aatttcacag ataatttact tatttaaaaa tgcatgataa
tgagttttac attacaaatt tctgtttttt taaagttatc ttacgctatt tctgttggtt agtagacact aattctgtca gtaggggcat ggtataagga
aatatcataa tgtaatgagg tggtactatg attaaaagcc actgttacat ttcaaaaaaa aaaaaaaaaa

FIGURE 12 agagngtcgcccctttttttttttttttttttttttttttttttttttttttgacatttataaatgaacctttattaaagacacttcaatgccatttgttanacacttcaatattttaca
tggttttcaatgtacactgtaccaaaatttctataaataaataactttgtacataaaagtaatactccctctttcacattgcctcncagaagcagcaaattcatatattt
tgtggaagtaagattagtcagttaactgtcaagaacaaaattctaaatgtgcttaccttttgaacagtgatgacacctgacagtaattgttaactattttctcagtaa
ctcccttcagcttttggccaaaggaacatttgaaggaccttgtttcnatttaagttttactaaatgacacattggcactcanaanatggttagctaccagtctcaaa
agtgcaaattatacccanaacccaggtcaagggctgtcctttccaagtcccagctcagtttcatctggtgcgaaggaatggcatggacaggcctgctccggg
tccttaatanaaataaggtanccctgaaaagtcanaacttcctcctttctgtcccccaagggcaatgtaatactcattanattgggcaaaacnaaaacatcngt
atagtaaaaatccacaggtnccaacaccagcagcctttaccttantttnaaaggccncaaaatagca

Figure 13A

MSPHLTALLGLVLCLAQTIHTQEGALPRPSISAEPGTVISPGSHVTFMCRGPVGVQTFRLEREDR
AKYKDSYNVFRLGPSESEARFHIDSVSEGNAGLYRCLYYKPPGWSEHSDFLELLVKGTVPGTEA
SGFDAP

Figure 13B ccacgcgtcc ggggaccggg gccatgtctc cacacctcac tgctctcctg ggcctagtgc tctgcctggc ccagaccatc cacacgcagg
agggggccct tcccagaccc tccatctcgg ctgagccagg cactgtgatc tccccgggga gccatgtgac tttcatgtgc cggggcccgg
ttggggttca aacattccgc ctggagaggg aggatagagc caagtacaaa gatagttata atgtgtttcg actttggtcca tctgagtcag
aggccagatt ccacattgac tcagtaagtg aaggaaatgc cgggctttat cgctgcctct attataagcc ccctggatgg tctgagcaca
gtgacttcct ggagctgctg gtgaaaggga ctgtgccagg cactgaagcc tccggatttg atgcaccatg aatgaggaga aatggcctcc
cgtcttgtga acttcaatgg ggagaaataa ttagaatgag caatagaaat gcacagatgc ctatacatac atatacaaat aaaaagatac
gattcgcaaa aaaaaaaaaa aaaagggc

Figure 14A

MPLLWLRGFLLASCWIIVRSSPTPGSEGHSAAPDCPSCALAALPKDVPNSQPEMVEAVKKHILN
MLHLKKRPDVTQPVPKAALLNAIRKLHVGKVGENGYVEIEDDIGRRAEMNELMEQTSEIITFAESG
TARKTLHFEISKEGSDLSVVERAEVWLFLKVPKANRTRTKVTIRLFQQQKHPQGSLDTGEEAEEV
GLKGERSELLLSEKVVDARKSTWHVFPVSSSIQRLLDQGKSSLDVRIACEQCQESGASLVLLGKK
KKKEEEGEGKKKGGGEGGAGADEEKEQSHRPFLMLQARQSEDHPHRRRRRGLECDGKVNICC
KKQFFVSFKDIGWNDWIIAPSGYHANYCEGECPSHIAGTSGSSLSFHSTVINHYRMRGHSPFANL
KSCCVPTKLRPMSMLYYDDGQNIIKKDIQNMIVEECGCS

Figure 14B tccacacaca caaaaaacct gcgcgtgagg ggggaggaaa agcagggcct ttaaaaaggc aatcacaaca acttttgctg ccaggatgcc
cttgctttgg ctgagaggat ttctgttggc aagttgctgg attatagtga ggagttcccc caccccagga tccgaggggc acagcgcggc
ccccgactgt ccgtcctgtg cgctggccgc cctcccaaag gatgtaccca actctcagcc agagatggtg gaggccgtca agaagcacat
tttaaacatg ctgcacttga agaagagacc cgatgtcacc cagccggtac ccaaggcggc gcttctgaac gcgatcagaa agcttcatgt
gggcaaagtc ggggagaacg ggtatgtgga gatagaggat gacattggaa ggagggcaga aatgaatgaa cttatggagc agacctcgga
gatcatcacg tttgccgagt caggaacagc caggaagacg ctgcacttcg agatttccaa ggaaggcagt gacctgtcag tggtggagcg
tgcagaagtc tggctcttcc taaaagtccc caaggccaac aggaccagga ccaaagtcac catccgcctc ttccagcagc agaagcaccc
gcagggcagc ttggacacag ggaagaggc cgaggaagtg ggcttaaagg gggagaggag tgaactgttg ctctctgaaa aagtagtaga
cgctcggaag agcacctggc atgtcttccc tgtctccagc agcatccagc ggttgctgga ccagggcaag agctccctgg acgttcggat
tgcctgtgag cagtgccagg agagtggcgc cagcttggtt ctcctgggca agaagaagaa gaaagaagag gagggggaag
ggaaaaagaa gggcggaggt gaaggtgggg caggagcaga tgaggaaaag gagcagtcgc acagaccttt cctcatgctg
caggcccggc agtctgaaga ccaccctcat cgccggcgtc ggcggggctt ggagtgtgat ggcaaggtca acatctgctg taagaaacag
ttctttgtca gtttcaagga catcggctgg aatgactgga tcattgctcc ctctggctat catgccaact actgcgaggg tgagtgcccg
agccatatag caggcacgtc cgggtcctca ctgtccttcc actcaacagt catcaaccac taccgcatgc ggggccatag cccctttgcc
aacctcaaat cgtgctgtgt gcccaccaag ctgagaccca tgtccatgtt gtactatgat gatggtcaaa acatcatcaa aaaggacatt
cagaacatga tcgtggagga gtgtgggtgc tcatagagtt gcccagccca gggggaaagg gagcaagagt tgtccagaga agacagtggc
aaaatgaaga aatttttaag gtttctgagt taaccagaaa aatagaaatt aaaaacaaaa caaaacaaaa aaaaaaacaa aaaaaaacaa
aagtaaatta aaaacaaacc tgatgaaaca gatgaaacag atgaaggaag atgtggaaat cttagcctgc cttagccagg gctcagagat
gaagcagtga agagacagat tgggagggaa agggagaatg gtgtaccctt tatttcttct gaaatcacac tgatgacatc agttgtttaa
acggggtatt gtcctttccc cccttgaggt tcccttgtga gcttgaatca accaatctga tctgcagtag tgtggactag aacaacccaa
atagcatcta gaaagccatg agtttgaaag ggcccatcac aggcactttc ctagcctaat

Figure 15A

MNCVCRLVLVVLSLWPDTAVAPGPPPGPPRVSPDPRAELDSTVLLTRSLLADTRQLAAQLRDKF
PADGDHNLDSLPTLAMSAGALGALQLPGVLTRLRADLLSYLRHVQWLRRAGGSSLKTLEPELGT
LQARLDRLLRRLQLLMSRLALPQPPPDPPAPPLAPPSSAWGGIRAAHAILGGLHLTLDWAVRGLL
LLKTRL

Figure 15B gaagggttaa aggcccccgg ctccctgccc cctgccctgg ggaacccctg gccctgtggg gacatgaact gtgtttgccg cctggtcctg
gtcgtgctga gcctgtggcc agatacagct gtcgcccctg ggccaccacc tggcccccct cgagtttccc cagaccctcg ggccgagctg
gacagcaccg tgctcctgac ccgctctctc ctggcggaca cgcggcagct ggctgcacag ctgagggaca aattcccagc tgacggggac
cacaacctgg attccctgcc caccctggcc atgagtgcgg gggcactggg agctctacag ctcccaggtg tgctgacaag gctgcgagcg
gacctactgt cctacctgcg gcacgtgcag tggctgcgcc gggcaggtgg ctcttccctg aagaccctgg agcccgagct gggcaccctg
caggcccgac tggaccggct gctgcgccgg ctgcagctcc tgatgtcccg cctggccctg ccccagccac ccccggaccc gccggcgccc
ccgctggcgc ccccctcctc agcctggggg ggcatcaggg ccgcccacgc catcctgggg gggctgcacc tgacacttga ctgggccgtg
aggggactgc tgctgctgaa gactcggctg tgacccgggg cccaaagcca ccaccgtcct tccaaagcca gatcttattt atttatttat
ttcagtactg ggggcgaaac agccaggtga tcccccgcc attatctccc cctagttaga gacagtcctt ccgtgaggcc tgggggacat
ctgtgcctta tttatactta tttatttcag gagcaggggt gggaggcagg tggactcctg ggtccccgag gaggagggga ctggggtccc
ggattcttgg gtctccaaga agtctgtcca cagacttctg ccctggctct tccccatcta ggcctgggca ggaacatata ttatttattt -
aagcaattac ttttcatgtt ggggtgggga cggaggggaa agggaagcct gggtttttgt acaaaaatgt gagaaacctt tgtgagacag
agaacaggga attaaatgtg tcatacatat ccacttgagg gcgatttgtc tgagagctgg ggctggatgc ttgggtaact ggggcagggc
aggtggaggg gagacctcca ttcaggtgga ggtcccgagt gggcggggca gcgactggga gatgggtcgg tcacccagac agctctgtgg
aggcagggtc tgagccttgc ctggggcccc gcactgcata gggccgtttg tttgtttttt gagatggagt ctcgctctgt tgcctaggct
ggagtgcagt gaggcaatct aaggtcactg caagctccac ctcccgggtt caagcaattc tcctgcctca gcctcccgat tagctgggat
cacaggtgtg caccaccatg cccagctaat tatttatttc ttttgtattt ttagtagaga cagggtttca ccatgttggc caggctggtt tcgaactcct
gacctcaggt gatcctcctg cctcggcctc ccaaagtgct gggattacag gtgtgagcca ccacacctga cccataggtc ttcaataaat
atttaatgga aggttccaca agtcaccctg tgatcaacag tacccgtatg ggacaaagct gcaaggtcaa gatggttcat tatggctgtg
ttcaccatag caaactggaa agaatctaga tatccaacag tgagggttaa gcaacatggt gcatctgtgg atagaacacc acccagccgc
ccggagcagg gactgtcatt cagggaggct aaggagagag gcttgcttgg gatatagaaa gatatcctga cattggccag gcatggtggc
tcacgcctgt aatcctggca ctttgggagg acgaagcgag tggatcactg aagtccaaga gtttgagacc ggcctgcgag acatggcaaa
accctgtctc aaaaaagaaa gaatgatgtc ctgacatgaa acagcaggct acaaaaccac tgcatgctgt gatcccaatt ttgtgttttt
ctttctatat atggattaaa acaaaaatcc taaagggaaa tacgccaaaa tgttgacaat gactgtctcc aggtcaaagg agagaggtgg
gattgtgggt gacttttaat gtgtatgatt gtctgtattt tacagaattt ctgccatgac tgtgtatttt gcatgacaca ttttaaaaat aataaacact
atttttagaa t

Figure 16A

MSPNFKLQCHFILIFLTALRGESRYLELREAADYDPFLLFSANLKRDVAGEQPYRRALRCLDMLSL
QGQFTFTADRPQLHCAAFFISEPEEFITIHYDQVSIDCQGGDFLKVFDGWILKGEKFPSSQDHPLP
SAERYIDFCESGLSRRSIRSSQNVAMIFFRVHEPGNGFTLTIKTDPNLFPCNVISQTPNGKFTLVV
PHQHRNCSFSIIYPVVIKISDLTLGHVNGLQLKKSSAGCEGIGDFVELLEGTGLDPSKMTPLADLC
YPFHGPAQMKVGCDNTVVRMVSSGKHVNRVTFEYRQLEPYELENPNGNSIGEFCLSGL

Figure 16B ggacctccgg agcagacagc acagcagctg cagaggcaag gccagcatgt cgcccaactt caaacttcag tgtcacttca ttctcatctt
cctgacggct ctaagagggg aaagccggta cctagagctg agggaagcgg cggactacga tcctttcctg ctcttcagcg ccaacctgaa
gcgggacgtg gctggggagc agccgtaccg ccgcgctctg cggtgcctgg acatgctgag cctccagggc cagttcacct tcaccgccga
ccggccgcag ctgcactgcg cagccttctt catcagcgag cccgaggagt tcattaccat ccactacgac caggtctcca tcgactgtca
gggcggcgac ttcctgaagg tatttgatgg ttggattctc aagggggaga agttccccag ttcccaggat catcctctcc cctcagctga
gcggtacata gatttctgtg agagtggtct tagcaggagg agcatcagat cttcccagaa tgtggccatg atcttcttcc gagtccatga
accaggaaat ggattcacat taaccataaa gacagacccc aacctctttc cttgcaatgt catttctcag actccaaatg gaaagtttac
cctggtagtt ccacaccagc atcgaaactg cagcttctcc ataatttatc ctgtggtgat caaaatatct gatcttaccc tgggacacgt
aaatggtctt cagttaaaga aatcctcagc aggttgcgag ggaataggag actttgtgga gctgctggag ggaactggat tggacccttc
caagatgacg cctttagctg atctctgcta ccccttcat ggcccggccc agatgaaagt tggctgtgac aacactgtgg tgcgcatggt
ctccagtgga aaacacgtaa atcgtgtgac ttttgagtat cgtcagctgg agccgtacga gctggaaaac ccaaatggaa acagtatcgg
ggaattctgt ttgtctggtc tttgaataac caacccagtg atttacatgc tgatagctaa gtgagttttt aatggccatt gtgtatgatt ttgatgcaca
actagttaaa agcctttcat accagtcagt atttcccagc cttgagcgca cgcacacacc acacacatac acacacgcat tatttttgtt
actttgcttc tttttatgtt tgtaatctgt aaatgaacac atggcagaaa ataaccctga ttggtagg

Figure 17A

TTPDRRLWNPPATSSSLRQMERMLPLLTLGLLAAGFCPAVLCHPNSPLDEENLTQENQDRGTH
VDLGLASANVDFAFSLYKQLVLKAPDKNVIFSPLSISTALAFLSLGAHNTTLTEILKGLKFNLTETSE
AEIHQSFQHLLRTLNQSSDELQLSMGNAMFVKEQLSLLDRFTEDAKRLYGSEAFATDFQDSAAA
KKLINDYVKNGTRGKITDLIKDLDSQTMMVLVNYIFFKAKWEMPFDPQDTHQSRFYLSKKKWVM
VPMMSLHHLTIPYFRDEELSCTVVELKYTGNASALFILPDQDKMEEVEAMLLPETLKRWRDSLEF
REIGELYLPKFSISRDYNLNDILLQLGIEEAFTSKADLSGITGARNLAVSQVVHKAVLDVFEEGTEA
SAATAVKITLLSALVETRTIVRFNRPFLMIIVPTDTQNIFFMSKVTNPKQA

Figure 17B ctgtctcaaa ataaaaataa aaaataaaaa gaaataaaaa agaaatatac caaaatgtta gctggggtct tctctgggta gtaaagtgct
gggggatatt ttccaaagtc cttctttaca ttctctgagt ttttccatgt tcttcaatga gtatttaata agcagataaa aactaataca acaaaggatt
ttttctgtgt gcttttttga cctttggagg aagagattag agctagtccc ataaccaggt tatttgagta ggtctaataa gcccgtatta ccagaaatta
tcatctggtc atttccagtc cgagaacaga acacttggtt gtcctggcat ttcccaagca gtgggaggag ttctctgcag gaataaataa
gcctcagcat tcatgaaaat ccactactcc agacagacgg ctttggaatc caccagctac atccagctcc ctgaggcagg taatccatga
tgttttacat cctgggagcg gaggaatctg tttttccagg agagttttag gcagcagcct ggagtgtgtg gagtgtgagg ggtaagcaga g

Figure 18A

MVLLTAVLLLLAAYAGPAQSLGSFVHCEPCDEKALSMCPPSPLGCELVKEPGCGCCMTCALAEG
QSCGVYTERCAQGLRCLPRQDEEKPLHALLHGRGVCLNEKSYREQVKIERDSREHEEPTTSEM
AEETYSPKIFRPKHTRISELKAEAVKKDRRKKLTQSKFVGGAENTAHPRIISAPEMRQESEQGPC
RRHMEASLQELKASPRMVPRAVYLPNCDRKGFYKRKQCKPSRGRKRGICWCVDKYGMKLPGM
EYVDGDFQCHTFDSSNVE

Figure 18B tgaaaaaaaa aaaaggaaag aaagggattg aaggagcttg ccaagggtag gctgcctaaa ttcacatttt ccctgggtct ttccgtgaaa
tggggacacc agaaacccaa gggtcgggtc tagtgccctc aactctctgg ggatgagagt cttgccttgg ggtagacaag aggcagggca
gggaggagca gagccctggg gtgcggccgt cctcaccgcc tgttgctcta ctcaccccag tgcaaacctt cccgtggccg caagcgtggc
atctgctggt gcgtggacaa gtacgggatg aagctgccag gcatggagta cgttgacggg gactttcagt gccacacctt cgacagcagc
aacgttgagt gatgcgtccc cccccaacct ttccctcacc ccctcccacc cccagccccg actccagcca gcgcctccct ccacccccagg
acgccactca tttcatctca tttaagggaa aaatatatat ctatctattt gaggaaactg aggacctcgg aatctctagc aagggctcaa
cttcgaaaat ggcaacaaca gagatgcaaa aagctaaaaa gacacccccc ccctttaaat ggttttcttt ttgaggcaag ttggatgaac
agagaaggga agagaggaag aacgagagga agagaaggga aggaagtgtt tgtgtagaag agagagaaag acgaatagag
ttaggaaaag gaagacaagc aggtgggcag gaaggacatg caccgagacc aggcaggggc ccaactttca cgtccagccc
tggcctgggg tcgggagagg tgggcgctag aagatgcagc ccaggatgtg gcaatcaatg acactattgg ggtttcccag gatggattgg
tcagggggag aaaggaaaag gcaaaacact ccaggacctc tcccggatct gtctcctcct ctagccagca gtatggacag ctggacccct
gaacttcctc tcctcttacc tgggcagagt gttgtctctc cccaaattta taaaaactaa aatgcattcc attcctctga aagcaaaaca
aattcataat tgagtgatat taaatagaga ggttttcgga agcagatctg tgaatatgaa atacatgtgc atatttcatt ccccaggcag acatttttta
gaaatcaata catgccccaa tattggaaag acttgttctt ccacggtgac tacagtacat gctgaagcgt gccgtttcag ccctcattta
attcaatttg taagtagcgc acgagcctct gtgggggagg ataggctgaa aaa

Figure 19

MVLIQIPMYN EKEVCQLSIG AACRLSWPLD RMIVQVLDDS TDPASKELVN AECDKWARKG
INIMSEIRDN RIGYKAGALK AGMMHNYVKQ CEFVAIFDAD FQPDPDFLER TIPFLIHNHE
ISLVQCRWKF VNANECLMTR MQEMSLNYHF VAEQESGSSI HAFFGFNGTA GVWRIAALNE
AGGWKDRTTV EDMDLAVRAC LHGWKFVYVH DVEVKNELPS TFKAYRFQQH
RWSCGPANLW RKMTMEILQN KKVSAWKKLY LIYNFFFIRK IVVHIFTFVF YCLILPTTVL
FPELQVPKWA TVYFPTTITI LNAIATPRMI KSLTYIVYCR SLHLLVFWIL FENVMSMHRT
KATFIGLLEA GRVNEWVVTE KLGDTLKSKL IGKATTKLYT RFGQRLNWRE LVVGLYIFFC
GCYDFAYGGS YFYVYLFLQS CAFFVAGVGY IGTFVPTV

Figure 20A

MPAGRRGPAAQSARRPPPLLPLLLLLCVLGAPRAGSGAHTAVISPQDPTLLIGSSLLATCSVHGD
PPGATAEGLYWTLNGRRLPPELSRVLNASTLALALANLNGSRQRSGDNLVCHARDGSILAGSCL
YVGLPPEKPVNISCWSKNMKDLTCRWTPGAHGETFLHTNYSLKYKLRWYGQDNTCEEYHTVGP
HSCHIPKDLALFTPYEIWVEATNRLGSARSDVLTLDILDVVTTDPPPDVHVSRVGGLEDQLSVRW
VSPPALKDFLFQAKYQIRYRVEDSVDWKVVDDVSNQTSCRLAGLKPGTVYFVQVRCNPFGIYGS
KKAGIWSEWSHPTAASTPRSERPGPGGGACEPRGGEPSSGPVRRELKQFLGWLKKHAYCSNL
SFRLYDQWRAWMQKSHKTRNQDEGILPSGRRGTARGPAR

Figure 20B cgcccagcga cgtgcgggcg gcctggcccg cgccctcccg cgcccggcct gcgtcccgcg ccctgcgcca ccgccgccga gccgcagccc
gccgcgcgcc cccggcagcg ccggccccat gcccgccggc cgccggggcc ccgccgccca atccgcgcgg cggccgccgc
cgttgctgcc cctgctgctg ctgctctgcg tcctcggggc gccgcgagcc ggatcaggag cccacacagc tgtgatcagt ccccaggatc
ccacgcttct catcggctcc tccctgctgg ccacctgctc agtgcacgga gacccaccag gagccaccgc cgagggcctc tactggaccc
tcaacgggcg ccgcctgccc cctgagctct cccgtgtact caacgcctcc accttggctc tggccctggc caacctcaat gggtccaggc
agcggtcggg ggacaacctc gtgtgccacg cccgtgacgg cagcatcctg gctggctcct gcctctatgt tggcctgccc ccagagaaac
ccgtcaacat cagctgctgg tccaagaaca tgaaggactt gacctgccgc tggacgccag gggcccacgg ggagaccttc ctccacacca
actactccct caagtacaag cttaggtggt atggccagga caacacatgt gaggagtacc acacagtggg gccccactcc tgccacatcc
ccaaggacct ggctctcttt acgccctatg agatctgggt ggaggccacc aaccgcctgg gctctgcccg ctccgatgta ctcacgctgg
atatcctgga tgtggtgacc acggaccccc cgcccgacgt gcacgtgagc cgcgtcgggg gcctggagga ccagctgagc gtgcgctggg
tgtcgccacc cgccctcaag gatttcctct ttcaagccaa ataccagatc cgctaccgag tggaggacag tgtggactgg aaggtggtgg
acgatgtgag caaccagacc tcctgccgcc tggccggcct gaaacccggc accgtgtact tcgtgcaagt gcgctgcaac ccctttggca
tctatggctc caagaaagcc gggatctgga gtgagtggag ccaccccaca gccgcctcca ctcccccgcag tgagcgcccg ggcccgggcg
gcggggcgtg cgaaccgcgg ggcggagagc cgagctcggg gccggtgcgg cgcgagctca agcagttcct gggctggctc
aagaagcacg cgtactgctc caacctcagc ttccgcctct acgaccagtg gcgagcctgg atgcagaagt cgcacaagac ccgcaaccag
gacgagggga tcctgccctc gggcagacgg ggcacggcga gaggtcctgc cagataagct gtaggggctc aggccaccct ccctgccacg
tggagacgca gaggccgaac ccaaactggg gccacctctg taccctcact tcagggcacc tgagccaccc tcagcaggag ctggggtggc
ccctgagctc caacggccat aacagctctg actcccacgt gaggccacct ttgggtgcac cccagtgggt gtgtgtgtgt gtgtgagggt
tggttgagtt gcctagaacc cctgccaggg ctgggggtga gaaggggagt cattactccc cattacctag ggcccctcca aaagagtcct
tttaaataaa tgagctattt aggtgc

Figure 21

MLHVEMLTLV FLVLWMCVFS QDPGSKAVAD RYAVYWNSSN PRFQRGDYHI DVCINDYLDV
FCPHYEDSVP EDKTERYVLY MVNFDGYSAC DHTSKGFKRW ECNRPHSPNG PLKFSEKFQL1
FTPFSLGFEF RPGREYFYIS SAIPDNGRRS CLKLKVFVRP TNSCMKTIGV HDRVFDVNDK
VENSLEPADD TVHESAEPSR GENAAQTPRI PSRLLAILLF LLAMLLTL

Figure 22A

MGGCTVKPQLLLLALVLHPWNPCLGADSEKPSSIPTDKLLVITVATKESDGFHRFMQSAKYFNYT
VKVLGQGEEWRGGDGINSIGGGQKVRLMKEVMEHYADQDDLVVMFTECFDVIFAGGPEEVLKK
FQKANHKVVFAADGILWPDKRLADKYPVVHIGKRYLNSGGFIGYAPYVNRIVQQWNLQDNDDDQ
LFYTKVYIDPLKREAINITLDHKCKIFQTLNGAVDEVVLKFENGKARAKNTFYETLPVAINGNGPTKI
LLNYFGNYVPNSWTQDNGCTLCEFDTVDLSAVDVHPNVSIGVFIEQPTPFLPRFLDILLTLDYPKE
ALKLFIHNKEVYHEKDIKVFFDKAKHEIKTIKIVGPEENLSQAEARNMGMDFCRQDEKCDYYFSVD
ADVVLTNPRTLKILIEQNRKIIAPLVTRHGKLWSNFWGALSPDGYYARSEDYVDIVQGNRVGVWN
VPYMANVYLIKGKTLRSEMNERNYFVRDKLDPDMALCRNAREMGVFMYISNRHEFGRLLSTANY
NTSHYNNDLWQIFENPVDWKEKYINRDYSKIFTENIVEQPCPDVFWFPIFSEKACDELVEEMEHY
GKWSGGKHHDSRISGGYENVPTDDIHMKQVDLENVWLDFIREFIAPVTLKVFAGYYTKGFALLNF
VVKYSPERQRSLRPHHDASTFTINIALNNVGEDFQGGGCKFLRYNCSIESPRKGWSFMHPGRLT
HLHEGLPVKNGTRYIAVSFIDP

Figure 22B atggggggat gcacggtgaa gcctcagctg ctgctcctgg cgctcgtcct ccacccctgg aatccctgtc tgggtgcgga ctcggagaag
ccctcgagca tccccacaga taaattatta gtcataactg tagcaacaaa agaaagtgat ggattccatc gatttatgca gtcagccaaa
tatttcaatt atactgtgaa ggtccttggt caaggagaag aatggagagg tggtgatgga attaatagta ttggaggggg ccagaaagtg
agattaatga aagaagtcat ggaacactat gctgatcaag atgatctggt tgtcatgttt actgaatgct ttgatgtcat atttgctggt
ggtccagaag aagttctaaa aaaattccaa aaggcaaacc acaaagtggt ctttgcagca gatggaattt tgtggccaga taaaagacta
gcagacaagt atcctgttgt gcacattggg aaacgctatc tgaattcagg aggatttatt ggctatgctc catatgtcaa ccgtatagtt
caacaatgga atctccagga taatgatgat gatcagctct tttacactaa agtttacatt gatccactga aaagggaagc tattaacatc
acattggatc acaaatgcaa aattttccag accttaaatg gagctgtaga tgaagttgtt ttaaaatttg aaaatggcaa agccagagct
aagaatacat tttatgaaac attaccagtg gcaattaatg gaaatggacc caccaagatt ctcctgaatt attttggaaa ctatgtaccc
aattcatgga cacaggataa tggctgcact ctttgtgaat tcgatacagt cgacttgtct gcagtagatg tccatccaaa cgtatcaata
ggtgttttta ttgagcaacc aacccctttt ctacctcggt ttctggacat attgttgaca ctggattacc caaaagaagc acttaaactt tttattcata
acaaagaagt ttatcatgaa aaggacatca aggtattttt tgataaagct aagcatgaaa tcaaaactat aaaaatagta ggaccagaag
aaaatctaag tcaagcggaa gccagaaaca tgggaatgga cttttgccgt caggatgaaa agtgtgatta ttactttagt gtggatgcag
atgttgtttt gacaaatcca aggactttaa aaattttgat tgaacaaaac agaaagatca ttgctcctct tgtaactcgt catggaaagc
tgtggtccaa tttctgggga gcattgagtc ctgatggata ctatgcacga tctgaagatt atgtggatat tgttcaaggg aatagagtag
gagtatggaa tgtcccatat atggctaatg tgtacttaat taaaggaaag acactccgat cagagatgaa tgaaaggaac tattttgttc
gtgataaact ggatcctgat atggctcttt gccgaaatgc tagagaaatg ggtgtattta tgtacatttc taatagacat gaatttggaa ggctattatc
cactgctaat tacaatactt cccattataa caatgacctc tggcagattt ttgaaaatcc tgtggactgg aaggaaaagt atataaaccg
tgattattca aagattttca ctgaaaatat agttgaacag ccctgtccag atgtcttttg gttccccata ttttctgaaa aagcctgtga tgaattggta
gaagaaatgg aacattacgg caaatggtct gggggaaaac atcatgatag ccgtatatct ggtggttatg aaaatgtccc aactgatgat
atccacatga agcaagttga tctggagaat gtatggcttg attttatccg ggagttcatt gcaccagtta cactgaaggt ctttgcaggc
tattatacga agggatttgc actactgaat tttgtagtaa aatactcccc tgaacgacag cgttctcttc gtcctcatca tgatgcttct acatttacca
taaacattgc acttaataac gtgggagaag actttcaggg aggtggttgc aaatttctaa ggtacaattg ctctattgag tcaccacgaa
aaggctggag cttcatgcat cctgggagac tcacacattt gcatgaagga cttcctgtta aaaatggaac aagatacatt gcagtgtcat
ttatagatcc ctaagttatt tacttttcat tgaattgaaa tttattttgg gtgaatgact ggcatgaaca cgtctttgaa gttgtggctg agaagatgag
aggaatattt aaataacatc aacagaacaa cttcactttg ggccaaacat ttgaaaaact ttttataaaa aattgtttga tatttcttaa tgtctgctct
gagccttaaa acacagattg aagaagaaaa gaaagaaaaa acttaaatat ttatttctat gctttgttgc ctctgagaat aatgacaatt
tatgaatttg tgtttcaaat tgataaaata tttaggtaca aataacaaga ctaataatat tttcttattt aaaaaaagca tgggaagatt tttatttatc
aaaatataga ggaaatgtag acaaaatgga tataaatgaa aattaccatg ttgtaaaacc ttgaaaatca gattctaact gattgtatgc
aactaagtat ttctgaacac ctatgcaggt cttatttaca gtgttactaa gggaacacac aaagaattac acaacgtttt cctcaagaaa
atggtacaaa acacaaccga ggagcgtata cagttgaaaa catttttgtt ttgattggaa ggcagattat tttatattag tattaaaaat
caaaccctat gtttctttca gatgaatctt ccaaagtgga ttatattaag caggtattag atttagaaaa cctttccatt tcttaaagta ttatcaagtg
tcaagatcag caagtgtcct taagtcaaat aggttttttt ttgttggtgg ttgtgcttgc tttcctttttt tagaaagttc tagaaaatag gaaaacgaaa
aatttcattg agatgagtag tgcatttaat tatttttaa aaaacttttt aagtacttga attttatatc aggaaaacaa agttgttgag ccttgcttct
tccgttttgc cctttgtctc gctccttatt cttttttggg gggagggtta tttgcttttt tatcttcctg gcataatttc cattttattc ttctgagtgt ctatgttaac
ttccctctat cccgcttata aaaaaattct ccaacaaaaa tacttgttga cttgatgttt tatcacttct ctaagtaagg ttgaaatatc cttattgtag
ctactgtttt taatgtaaag gttaaacttg aaaagaaatt cttaatcacg gtgccaaaat tcattttcta acaccatgtg ttagaaaatt ataaaaaata
aaataatttt aaaaaaaaaa aaaaaaaaaa aaa

Figure 23A

MLQNSAVLLVLVISASATHEAEQNDSVSPRKSRVAAQNSAEVVRCLNSALQVGCGAFACLENST
CDTDGMYDICKSFLYSAAKFDTQGKAFVKESLKCIANGVTSKVFLAIRRCSTFQRMIAEVQEECY
SKLNVCSIAKRNPEAITEVVQLPNHFSNRYYNRLVRSLLECDEDTVSTIRDSLMEKIGPNMASLFH
ILQTDHCAQTHPRADFNRRRTNEPQKLKVLLRNLRGEEDSPSHIKRTSHESA

Figure 23B cagtttgcaa aagccagagg tgcaagaagc agcgactgca gcagcagcag cagcagcggc ggtggcagca gcagcagcag
cggcggcagc agcagcagca gcggaggcac cggtggcagc agcagcatca ccagcaacaa caacaaaaaa aaatcctcat
caaatcctca cctaagcttt cagtgtatcc agatccacat cttcactcaa gccaggagag ggaaagagga aagggggca ggaaaaaaaa
aaaacccaac aacttagcgg aaacttctca gagaatgctc caaaactcag cagtgcttct ggtgctggtg atcagtgctt ctgcaaccca
tgaggcggag cagaatgact ctgtgagccc caggaaatcc cgagtggcgg ctcaaaactc agctgaagtg gttcgttgcc tcaacagtgc
tctacaggtc ggctgcgggg cttttgcatg cctggaaaac tccacctgtg acacagatgg gatgtatgac atctgtaaat ccttcttgta
cagcgctgct aaatttgaca ctcagggaaa agcattcgtc aaagagagct taaaatgcat cgccaacggg gtcacctcca aggtcttcct
cgccattcgg aggtgctcca ctttccaaag gatgattgct gaggtgcagg aagagtgcta cagcaagctg aatgtgtgca gcatcgccaa
gcggaaccct gaagccatca ctgaggtcgt ccagctgccc aatcacttct ccaacagata ctataacaga cttgtccgaa gcctgctgga
atgtgatgaa gacacagtca gcacaatcag agacagcctg atggagaaaa ttgggcctaa catggccagc ctcttccaca tcctgcagac
agaccactgt gcccaaacac acccacgagc tgacttcaac aggagacgca ccaatgagcc gcagaagctg aaagtcctcc tcaggaacct
ccgaggtgag gaggactctc cctcccacat caaacgcaca tcccatgaga gtgcataacc agggagaggt tattcacaac ctcaccaaac
tagtatcatt ttaggggtgt tgacacacca attttgagtg tactgtgcct ggtttgattt ttttaaagta gttcctattt tctatccccc ttaaagaaaa
ttgcatgaaa ctaggcttct gtaatcaata tcccaacatt ctgcaatggc agcattccca ccaacaaaat ccatgtgatc attctgcctc
tcctcaggag aaagtaccct cttttaccaa cttcctctgc catgtctttt cccctgctcc cctgagacca cccccaaaca caaaacattc
atgtaactct ccagccattg taatttgaag atgtggatcc ctttagaacg gttgccccag tagagttagc tgataaggaa actttattta
aatgcatgtc ttaaatgctc ataaagatgt taaatggaat tcgtgttatg aatctgtgct ggccatggac gaatatgaat gtcacatttg aattcttgat
ctctaatgag ctagtgtctt atggtcttga tcctccaatg tctaattttc tttccgacac atttaccaaa ttgcttgagc ctggctgtcc aaccagactt
tgagcctgca tcttcttgca tctaatgaaa aacaaaaagc taacatcttt acgtactgta actgctcaga gctttaaaag tatctttaac aattgtctta
aaaccagaga atcttaaggt ctaactgtgg aatataaata gctgaaaact aatgtactgt acataaattc cagaggactc tgcttaaaca
aagcagtata taataacttt attgcatata gatttagttt tgtaacttag ctttattttt cttttcctgg gaatggaata actatctcac ttccagatat
ccacataaat gctccttgtg gcctttttta taactaaggg ggtagaagta gttttaattc aacatcaaaa cttaagatgg gcctgtatga
gacaggaaaa accaacaggt ttatctgaag gaccccaggt aagatgttaa tctcccagcc cacctcaacc cagaggctac tcttgactta
gacctatact gaaagatctc tgtcacatcc aactggaaat tccaggaacc aaaaagagca tccctatggg cttggaccac ttacagtgtg
ataaggccta ctatacatta ggaagtggta gttctttact cgtccccttt catcggtgcc tggtactctg gcaaatgatg atggggtggg
agactttcca ttaaatcaat caggaatgag tcaatcagcc tttaggtctt tagtccgggg gacttggggc tgagagagta taaataaccc
tgggctgtcc agccttaata gacttctctt acattttcgt cctgtagcac gctgcctgcc aaagtagtcc tggcagctgg accatctctg
taggatcgta aaaaaataga aaaaaagaaa aaaaaaagaa agaaagaggg aaaaagagct ggtggtttga tcatttctgc catgatgttt
acaagatggc gaccaccaaa gtcaaacgac taacctatct atgaacaaca gtagtttctc agggtcactg tccttgaacc caacagtccc
ttatgagcgt cactgcccac caaaggtcaa tgtcaagaga ggaagagagg gaggaggggt aggactgcag ggccactcc aaactcgctt
aggtagaaac tattggtgct cgactctcac taggctaaac tcaagatttg accaaatcga gtgataggga tcctggtggg aggagagagg
gcacatctcc agaaaaatga aaagcaatac aactttacca taaagccttt aaaaccagta acgtgctgct caaggaccaa gagcaattgc
agcagaccca gcagcagcag cagcagcaca aacattgctg cctttgtccc cacacagcct ctaagcgtgc tgacatcaga ttgttaaggg
catttttata ctcagaactg tcccatcccc aggtccccaa acttatggac actgccttag cctcttggaa atcaggtaga ccatattcta
agttagactc ttcccctccc tcccacactt cccaccccca ggcaaggctg acttctctga atcagaaaag ctattaaagt ttgtgtgttg tgtccatttt
gcaaacccaa ctaagccagg accccaatgc gacaagtagt tcatgagtat tcctagcaaa tttctctctt tcttcagttc agtagatttc ctttttcttt
ttctttttttt ttttttttt tttttggctg tgacctcttc aaaccgtggt acccccccctt ttctccccac gatgatatct atatatgtat ctacaataca
tatatctaca catacagaaa gaagcagttc tcacatgttg ctagtttttt gcttctcttt cccccaccct actccctcca attcccccct taaacttcca
aagcttcgtc ttgtgtttgc tgcagagtga ttcgggggct gacctagacc agtttgcatg attcttctct tgtgatttgg ttgcacttta gacattttttg

Figure 23B (Continued)

tgccattata tttgcattat gtatttataa tttaaatgat atttaggttt ttggctgagt actggaataa acagtgagca tatctggtat atgtcattat
ttattgttaa attacatttt ttaagctcca tgtgcatata aaggttatga aacatatcat ggtaatgaca gatgcaagtt attttatttg cttatttttt
ataattaaag atgccatagc ataatatgaa gcctttggtg aattccttct aagataaaaa taataataaa gtgttacgtt ttattggttt
caaaaaaaaa aaaaaaaaaa a

Figure 24A

MGIGRSEGGRRGALGVLLALGAALLAVGSASEYDYVSFQSDIGPYQSGRFYTKPPQCVDIPADL
RLCHNVGYKKMVLPNLLEHETMAEVKQQASSWVPLLNKNCHAGTQVFLCSLFAPVCLDRPIYPC
RWLCEAVRDSCEPVMQFFGFYWPEMLKCDKFPEGDVCIAMTPPNATEASKPQGTTVCPPCDN
ELKSEAIIEHLCASEFALRMKIKEVKKENGDKKIVPKKKKPLKLGPIKKKDLKKLVLYLKNGADCPC
HQLDNLSHHFLIMGRKVKSQYLLTAIHKWDKKNKEFKNFMKKMKNHECPTFQSVFK

Figure 24B cctgcagcct ccggagtcag tgccgcgcgc ccgccgcccc gcgccttcct gctcgccgca cctccgggag ccggggcgca cccagcccgc
agcgccgcct ccccgcccgc gccgcctccg accgcaggcc gagggccgcc actggccggg gggaccgggc agcagcttgc
ggccgcggag ccgggcaacg ctggggactg cgccttttgt ccccggaggt ccctggaagt ttgcggcagg acgcgcgcgg ggaggcggcg
gaggcagccc cgacgtcgcg gagaacaggg cgcagagccg gcatgggcat cgggcgcagc gaggggggcc gccgcggggc
cctgggcgtg ctgctggcgc tgggcgcggc gcttctggcc gtgggctcgg ccagcgagta cgactacgtg agcttccagt cggacatcgg
cccgtaccag agcgggcgct tctacaccaa gccacctcag tgcgtggaca tccccgcgga cctgcggctg tgccacaacg tgggctacaa
gaagatggtg ctgcccaacc tgctggagca cgagaccatg gcggaggtga agcagcaggc cagcagctgg gtgcccctgc tcaacaagaa
ctgccacgcc gggacccagg tcttcctctg ctcgctcttc gcgcccgtct gcctggaccg gcccatctac ccgtgtcgct ggctctgcga
ggccgtgcgc gactcgtgcg agccggtcat gcagttcttc ggcttctact ggcccgagat gcttaagtgt gacaagttcc cggaggggga
cgtctgcatc gccatgacgc cgcccaatgc caccgaagcc tccaagcccc aaggcacaac ggtgtgtcct ccctgtgaca acgagttgaa
atctgaggcc atcattgaac atctctgtgc cagcgagttt gcactgagga tgaaaataaa agaagtgaaa aaagaaaatg gcgacaagaa
gattgtcccc aagaagaaga agcccctgaa gttggggccc atcaagaaga aggacctgaa gaagcttgtg ctgtacctga agaatggggc
tgactgtccc tgccaccagc tggacaacct cagccaccac ttcctcatca tgggccgcaa ggtgaagagc cagtacttgc tgacggccat
ccacaagtgg gacaagaaaa acaaggagtt caaaaacttc atgaagaaaa tgaaaaacca tgagtgcccc acctttcagt ccgtgtttaa
gtgattctcc cgggggcagg gtggggaggg agcctcgggt ggggtgggag cggggggggac agtgcccggg aacccgtggt
cacacacacg cactgccctg tcagtagtgg acattgtaat ccagtcggct tgttcttgca gcattcccgc tcccttccc tccatagcca
cgctccaaac cccagggtag ccatggccgg gtaaagcaag ggccatttag attaggaagg tttttaagat ccgcaatgtg gagcagcagc
cactgcacag gaggaggtga caaaccattt ccaacagcaa cacagccact aaaacacaaa aagggggatt gggcggaaag
tgagagccag cagcaaaaac tacattttgc aacttgttgg tgtggatcta ttggctgatc tatgcctttc aactagaaaa ttctaatgat
tggcaagtca cgttgttttc aggtccagag tagtttcttt ctgtctgctt taaatggaaa cagactcata ccacacttac aattaaggtc
aagcccagaa agtgataagt gcagggagga aaagtgcaag tccattatct aatagtgaca gcaaagggac caggggagag gcattgcctt
ctctgcccac agtctttccg tgtgattgtc tttgaatctg aatcagccag tctcagatgc cccaaagttt cggttcctat gagcccgggg
catgatctga tccccaagac atgtggaggg gcagcctgtg cctgcctttg tgtcagaaaa aggaaaccac agtgagcctg agagagacgg
cgattttcgg gctgagaagg cagtagtttt caaaacacat agttaaaaaa gaaacaaatg aaaaaaattt tagaacagtc cagcaaattg
ctagtcaggg tgaattgtga aattgggtga agagcttagg attctaatct catgtttttt ccttttcaca tttttaaaag aacaatgaca aacacccact
tatttttcaa ggttttaaaa cagtctacat tgagcatttg aaaggtgtgc tagaacaagg tctcctgatc cgtccgaggc tgcttcccag
aggagcagct ctccccaggc atttgccaag ggaggcggat ttccctggta gtgtagctgt gtggctttcc ttcctgaaga gtccgtggtt
gccctagaac ctaacacccc ctagcaaaac tcacagagct ttccgttttt ttctttcctg taaagaaaca tttcctttga acttgattgc ctatggatca
aagaaattca gaacagcctg cctgttcccc cgcacttttt acatatattt gtttcatttc tgcagatgga aagttgacat gggtggggtg
tccccatcca gcgagagagt ttcaaaagca aaacatctct gcagtttttc ccaagtaccc tgagatactt cccaaagccc ttatgtttaa
tcagcgatgt atataagcca gttcacttag acaactttac ccttcttgtc caatgtacag gaagtagttc taaaaaaaat gcatattaat ttcttccccc
aaagccggat tcttaattct ctgcaacact ttgaggacat ttatgattgt ccctctgggc caatgcttat acccagtgag gatgctgcag
tgaggctgta aagtggcccc ctgcggccct agcctgaccc ggagaaagga tggtagattc tgttaactct tgaagactcc agtatgaaaa
tcagcatgcc cgcctagtta cctaccggag agttatcctg ataaattaac ctctcacagt tagtgatcct gtccttttaa cacctttttt gtggggttct
ctctgacctt tcatcgtaaa gtgctgggga ccttaagtga tttgcctgta attttggatg attaaaaaat gtgtatatat attagctaat tagaaatatt
ctacttctct gttgtcaaac tgaaattcag agcaagttcc tgagtgcgtg gatctgggtc ttagttctgg ttgattcact caagagttca gtgctcatac
gtatctgctc attttgacaa agtgcctcat gcaaccgggc cctctctctg cggcagagtc cttagtggag gggtttacct ggaacataag
tagttaccac agaatacgga agagcaggtg actgtgctgt gcagctctct aaatgggaat tctcaggtag gaagcaacag cttcagaaag
agctcaaaat aaattggaaa tgtgaatcgc agctgtgggt tttaccaccg tctgtctcag agtcccagga ccttgagtgt cattagttac

Figure 24B (Continued)

tttattgaag gttttagacc catagcagct ttgtctctgt cacatcagca atttcagaac caaaagggag gctctctgta ggcacagagc
tgcactatca cgagcctttg tttttctcca caaagtatct aacaaaacca atgtgcagac tgattggcct ggtcattggt ctccgagaga
ggaggtttgc ctgtgatttg cctgtgattt cctaattatc gctagggcca aggtgggatt tgtaaagctt tacaataatc attctggata gagtcctggg
aggtccttgg cagaactcag ttaaatcttt gaagaatatt tgtagttatc ttagaagata gcatgggagg tgaggattcc aaaaacattt
tatttttaaa atatcctgtg taacacttgg ctcttggtac ctgtgggtta gcatcaagtt ctccccaggg tagaattcaa tcagagctcc agtttgcatt
tggatgtgta aattacagta atcccatttc ccaaacctaa aatctgtttt tctcatcaga ctctgagtaa ctggttgctg tgtcataact tcatagatgc
aggaggctca ggtgatctgt ttgaggagag caccctaggc agcctgcagg gaataacata ctggccgttc tgacctgttg ccagcagata
cacaggacat ggatgaaatt cccgtttcct ctagtttctt cctgtagtac tcctctttta gatcctaagt ctcttacaaa agctttgaat actgtgaaaa
tgttttacat tccatttcat ttgtgttgtt tttttaactg cattttacca gatgttttga tgttatcgct tatgttaata gtaattcccg tacgtgttca ttttattttc
atgctttttc agccatgtat caatattcac ttgactaaaa tcactcaatt aatcaatgaa aaaaaaaaa

Figure 25A

MADNFSLHDALSGSGNPNPQGWPGAWGNQPAGAGGYPGASYPGAYPGQAPPGAYPGQAPP
GAYHGAPGAYPGAPAPGVYPGPPSGPGAYPSSGQPSAPGAYPATGPYGAPAGPLIVPYNLPLP
GGVVPRMLITILGTVKPNANRIALDFQRGNDVAFHFNPRFNENNRRVIVCNTKLDNNWGREERQ
SVFPFESGKPFKIQVLVEPDHFKVAVNDAHLLQYNHRVKKLNEISKLGISGDIDLTSASYTMI

Figure 25B ccagccaacg agcggaaaat ggcagacaat ttttcgctcc atgatgcgtt atctgggtct ggaaacccaa accctcaagg atggcctggc
gcatggggga accagcctgc tggggcaggg ggctacccag gggcttccta tcctggggcc taccccgggc aggcaccccc aggggcttat
cctggacagg cacctccagg cgcctaccat ggagcacctg gagcttatcc cggagcacct gcacctggag tctacccagg gccacccagc
ggccctgggg cctacccatc ttctggacag ccaagtgccc ccggagccta ccctgccact ggcccctatg gcgcccctgc tgggccactg
attgtgcctt ataacctgcc tttgcctggg ggagtggtgc ctcgcatgct gataacaatt ctgggcacgg tgaagcccaa tgcaaacaga
attgctttag atttccaaag agggaatgat gttgccttcc actttaaccc acgcttcaat gagaacaaca ggagagtcat tgtttgcaat
acaaagctgg ataataactg gggaagggaa gaaagacagt cggttttccc atttgaaagt gggaaaccat tcaaaataca agtactggtt
gaacctgacc acttcaaggt tgcagtgaat gatgctcact tgttgcagta caatcatcgg gttaaaaaac tcaatgaaat cagcaaactg
ggaatttctg gtgacataga cctcaccagt gcttcatata ccatgatata atctgaaagg ggcagattaa aaaaaaaaaa aaagaatcta
aaccttacat gtgtaaaggt ttcatgttca ctgtgagtga aaatttttac attcatcaat atccctcttg taagtcatct acttaataaa tattacagtg
aaag

Figure 26A

MRTLAILAAILLVALQAQAEPLQARADEVAAAPEQIAADIPEVVVSLAWDESLAPKHPGSRKNMD
CYCRIPACIAGERRYGTCIYQGRLWAFCC

Figure 26B gaattccctg taagccctgt tacaggggct gcaccccaga tacaacctga cctgtgtcca aggcgggcaa ctcaaccctt agatattgaa
tgggtcccat ggcaccaatg cttaaacacc agcagccctc acaaccacag atcgtgtttt aaggatgagg aggtagttct ctggatgcac
aggcttcaat ccaaatgggc tcatgacgcc gcagcacaca cccagtctgc agcctgaaga gttggagcat tgcattcaca gaaagcatcc
agacatgatc atgggctcag ggatacacct gttctccgat gtgtaccagt gaaggatgga aactcctatg cctcccagaa agcaccactc
aagcttttgc tgaatgcttc tctgaaggcc cacaaggctg agaggctgtg caacaccagc agtaaagtga atgcccagac tcccacctcc
tttcttgggt ggccatctgg aaaggccact cccaccctga tggctaatgc ctcagaccag ttcttggccc agatgatcct agacaattgt
ttaagcttaa actgttcatt ggccaagcaa acaggtgata gtacctctgg ggaaccacat gccgcgtgta catccagatc tcaggagaac
ccaaaaatgt ctgttccaca tagcaacaga agcccaggta gcactcagtc tcacctgggt gttctccaac atcccagctc agccaaatgg
ctttcattag tttttatggt tagaccccag gtcctcggga cactgcttta gaaacacatt ccaaatcctc ctctgtgtgc aggtggcatt cctatcccaa
tctctttgca gggcgtatac tgtgatacgc agccaggctg tcccagaggc cttaaatatt cccttggtgc aggtagttca gcttagccac
agccaatgca tcacagggtc aactgtgtta ggagccattg agaatccata gttggttgct gcctgggcct ggccagggct gaccaaggta
gatgagaggt tcctctgtgg agttctactt taacctcacc ttcccaccaa atttctcaac tgtccttgcc accacaatta tttaatggac
ccaacagaaa gtaaccccgg aaattaggac acctcatccc aaaagacctt taaatagggg aagtccactt gtgcacggct gctccttgct
atagaagacc tgggacagag gactgctgtc tgccctctct ggtcaccctg cctagctaga ggatctgtaa gtactacaaa acttaaactt
tacactgagt tttcatcatt gaagctatgc ctccaatctg acctctgact gtggggccgc cccagaggga cccagcgggt gaatccctgc
taggaacgtc tgtccggacc tctggtgact gctggggacg atggcttcca gctaacttaa tagagaaact caagcagttt ccttctaaat
acacatgtca catgtcctgg ttgacatgtc cagtaagaag actatcacag gtctttggaa cattcttttg agagaaacct atttaggtcc ttggtctgtt
tttcaatcag gttgtttgat ttttgctatt gagttgttgg aattccttat gtattcagat atttgcccct tctgccatgt aggttttgca aatattttct ctcattttct
gggttatctt ttcactcggt tgattgtttc ctttgctgtg cagatgcttt agcgttaaat gaagccacac ttgtctattt tccctttat tgcctgtgcc
tttggtgtca tagccaagaa atcattacct acatcaatgt caaaagcttt atccttctat acacttctag tagtttatgg tttcagttgt tacatttagg
ttttcaattc attctgagtt gatgttccta catggtgtga gataaagatt taaatacata catatataaa atcatgaggt agtgtacact ataaatatac
aattgttaat tgttactcaa gtctaagtag aggtggaaat aataaacttt cttttttta cttaaaccac tctgtgtcac tgagctgatt tcacctttag
cctgataaaa tcattgtcct ctccaccctg attcctacag gagactactc accccataac ctcaaaaacc tcttcatgag gatggtaagt
cacctgaatc ctgaagtgaa ttactcgcta ttccattgga actcatatag gacaccagaa tctagacctc cagagaacag caggacccat
cttcagaaaa taagaagcat ttgttccctg agcctgttga atcaaagtgc aatttctatt ctttttggaa tgttaaaaag tgaatcataa tatttaagca
ggtgaaccca cgagtaacat agcagggtct ttcttgtcat tattagctcc aacctagcac agacattaaa ggtacagatg tatactagca
tgaaactggg agaacaggag cattcgagca accttgagac caatgggcct ctcttataaa atgcacacct cctctcactg agattgagga
aggtttcttg tctccgagcc ttctcccagt agagctataa atccaggctg gctcctccct ccccacacag ctgctcctgc tctccctcct
ccaggtgacc ccagccatga ggaccctcgc catccttgct gccattctcc tggtggccct gcaggcccag gctgagccac tccaggcaag
agctgatgag gttgctgcag ccccggagca gattgcagcg gacatcccag aagtggttgt ttcccttgca tgggacgaaa gcttggctcc
aaagcatcca ggtgagagag gcaggcatgc agagctgcta agtctagagg gaaggacggg agagaggttc cagagttggg tctcagcagt
ctatgtcact gaggtggctt cacttagaat ctctgggcat tgattttctc atctagaaat tgaacagaga gccaaataaa cctgagaaac
tttatttctc caaagacttg attccaagaa acatctgtga aattcactaa gtttaagata tgaagagaca gactagttat ttctggatct
aaacaagtag acttagttgt aaagagaaca ttttactcta tctacagaag agcttttaaa aactgcagcc aagcctgagg gtaagttcag
gtgtgtgtgt gatggggcag gaatgcaaaa atgagagcaa aggagaatga gtctcaaatt ctgtgtgaca agcactgctc tgcgtgttta
ttcctatcga ctgaggttgt tcgtgctacc ggctgcaatg cagccagcat cacctgtcag ctagcatgtg acttccccga gattcttttt cttacccact
gctaactcca tactcaattt ctcatgctct ccctgtccca ggctcaagga aaaacatgga ctgctattgc agaataccag cgtgcattgc
aggagaacgt cgctatggaa cctgcatcta ccagggaaga ctctgggcat tctgctgctg agcttgcaga aaaagaaaaa tgagctcaaa
atttgctttg agagctacag ggaattgcta ttactcctgt accttctgct caatttcctt tcctcatctc aaataaatgc cttgttacaa gatttctgtg
tttccacctc tttaatgtgt gatatgtgtc tgtgtcaaga cacttgggat acacgtacca aaacgcaaaa tcaaattttt gaacaatata

Figure 27 A

SLWLIAAALVEVRTSADGQAGNEEMVQIDLPIKRYREYELVTPVSTNLEGRYLSHTLSASHKKRS
ARDVSSNPEQLFFNITAFGKDFHLRLKPNTQLVAPGAVVEWHETSLVPGNITDPINNHQPGSATY
RIRKTEPLQTNCAYVGDIVDIPGTSVAISNCDGLAGMIKSDNEEYFIEPLERGKQMEEEKGRIHVV
YKRSAVEQAPIDMSKDFHYRESDLEGLDDLGTVYGNIHQQLNETMRRRRHAGENDYNIEVLLGV
DDSVVRFHGKEHVQNYLLTLMNIVNEIYHDESLGVHINVVLVRMIMLGYAKSISLIERGNPSRSLE
NVCRWASQQQRSDLNHSEHHDHAIFLTRQDFGPAGMQGYAPVTGMCHPVRSCTLNHEDGFSS
AFVVAHETGHVLGMEHDGQGNRCGDETAMGSVMAPLVQAAFHRYHWSRCSGQELKRYIHSYD
CLLDDPFDHDWPKLPELPGINYSMDEQCRFDFGVGYKMCTAFRTFDPCKQLWCSHPDNPYFCK
TKKGPPLDGTECAAGKWCYKGHCMWKNANQQKQDGNWGSWTKFGSCSRTCGTGVRFRTRQ
CNNPMPINGGQDCPGVNFEYQLCNTEECQKHFEDFRAQQCQQRNSHFEYQNTKHHWLPYEH
PDPKKRCHLYCQSKETGDVAYMKQLVHDGTHCSYKDPYSICVRGECVKVGCDKEIGSNKVEDK
CGVCGGDNSHCRTVKGTFTRTPRKLGYLKMFDIPPGARHVLIQEDEASPHILAIKNQATGHYILN
GKGEEAKSRTFIDLGVEWDYNIEDDIESLHTDGPLHDPVIVLIIPQENDTRSSLTYKYIIHEDSVPTI
NSNNVIQEELDTFEWALKSWSQVSKPCGGGFQYTKYGCRRKSDNKMVHRSFCEANKKPKPIRR
MCNIQECTHPLWVAEEWEHCTKTCGSSGYQLRTVRCLQPLLDGTNRSVHSKYCMGDRPESRR
PCNRVPCPAQWKTGPWSECSVTCGEGTEVRQVLCRAGDHCDGEKPESVRACQLPPCNDEPC
LGDKSIFCQMEVLARYCSIPGYNKLCCESCSKRSSTLPPPYLLEAAETHDDVISNPSDLPRSLVM
PTSLVPYHSETPAKKMSLSSISSVGGPNAYAAFRPNSKPDGANLRQRSAQQAGSKTVRLVTVPS
SPPTKRVHLSSASQMAAASFFAASDSIGASSQARTSKKDGKIIDNRRPTRSSTLER

Figure 27B gtcactttgg ttgatagcag ccgctctggt agaggttagg acttcagctg atggacaagc tggtaatgaa gaaatggtgc aaatagattt
accaataaag agatatagag agtatgagct ggtgactcca gtcagcacaa atctagaagg acgctatctc tcccatactc tttctgcgag
tcacaaaaag aggtcagcga gggacgtgtc ttccaaccct gagcagttgt tctttaacat cacggcattt ggaaaagatt ttcatctgcg
actaaagccc aacactcaac tagtagctcc tggggctgtt gtggagtggc atgagacatc tctggtgcct gggaatataa ccgatcccat
taacaaccat caaccaggaa gtgctacgta tagaatccgg aaaacagagc ctttgcagac taactgtgct tatgttggtg acatcgtgga
cattccagga acctctgttg ccatcagcaa ctgtgatggt ctggctggaa tgataaaaag tgataatgaa gagtatttca ttgaaccctt
ggaaagaggt aaacagatgg aggaagaaaa aggaaggatt catgttgtct acaagagatc agctgtagaa caggctccca tagacatgtc
caaagacttc cactacagag agtcggacct ggaaggcctt gatgatctag gtactgttta tggcaacatc caccagcagc tgaatgaaac
aatgagacgc cgcagacacg cgggagaaaa cgattacaat atcgaggtac tgctgggagt ggatgactct gtggtccgtt tccatggcaa
agagcacgtc caaaactacc tcctgaccct aatgaacatt gtgaatgaaa tttaccatga tgagtccctc ggagtgcata taaatgtggt
cctggtgcgc atgataatgc tgggatatgc aaagtccatc agcctcatag aaaggggaaa cccatccaga agcttggaga atgtgtgtcg
ctgggcgtcc caacagcaaa gatctgatct caaccactct gaacaccatg accatgcaat tttttaacc aggcaagact ttggacctgc
tggaatgcaa ggatatgctc cagtcaccgg catgtgtcat ccagtgagaa gttgtaccct gaatcatgag gatggttttt catctgcttt
tgtagtagcc catgaaacgg gccatgtgtt gggaatggag catgatggac aaggcaacag gtgtggtgat gagactgcta tgggaagtgt
catggctccc ttggtacaag cagcattcca tcgttaccac tggtcccgat gcagtggtca agaactgaaa agatatatcc attcctatga
ctgtctcctt gatgaccctt ttgatcatga ttggcctaaa ctcccagaac ttcctggaat caattattct atggatgagc aatgtcgttt tgattttggt
gttggctata aaatgtgcac cgcgttccga accttgacc catgtaaaca gctgtggtgt agccatcctg ataatcccta cttttgtaag
actaaaaagg gacctccact tgatgggact gaatgtgctg ctggaaaatg gtgctataag ggtcattgca tgtggaagaa tgctaatcag
caaaaacaag atggcaattg gggtcatgg actaaatttg gctcctgttc tcggacatgt ggaactggtg ttcgtttcag aacacgccag
tgcaataatc ccatgcccat caatggtggt caggattgtc ctggtgttaa ttttgagtac cagctttgta acacagaaga atgccaaaaa
cactttgagg acttcagagc acagcagtgt cagcagcgaa actcccactt tgaataccag aataccaaac accactggtt gccatatgaa
catcctgacc ccaagaaaag atgccacctt tactgtcagt ccaaggagac tggagatgtt gcttacatga aacaactggt gcatgatgga
acgcactgtt cttacaaaga tccatatagc atatgtgtgc gaggagagtg tgtgaaagtg ggctgtgata aagaaattgg ttctaataag
gttgaggata agtgtggtgt ctgtggagga gataattccc actgccgaac cgtgaagggg acatttacca gaactcccag gaagcttggg
taccttaaga tgtttgatat accccctggg gctagacatg tgttaatcca agaagacgag gcttctcctc atattcttgc tattaagaac
caggctacag gccattatat tttaaatggc aaaggggagg aagccaagtc gcggaccttc atagatcttg gtgtggagtg ggattataac
attgaagatg acattgaaag tcttcacacc gatggacctt tacatgatcc tgttattgtt ttgattatac ctcaagaaaa tgatacccgc
tctagcctga catataagta catcatccat gaagactctg tacctacaat caacagcaac aatgtcatcc aggaagaatt agatactttt
gagtgggctt tgaagagctg gtctcaggtt tccaaaccct gtggtggagg tttccagtac actaaatatg gatgccgtag gaaaagtgat
aataaaatgg tccatcgcag cttctgtgag gccaacaaaa agccgaaacc tattagacga atgtgcaata ttcaagagtg tacacatcca
ctctgggtag cagaagaatg ggaacactgc accaaaacct gtggaagttc tggctatcag cttcgcactg tacgctgcct tcagccactc
cttgatggca ccaaccgctc tgtgcacagc aaatactgca tgggtgaccg tcccgagagc cgccggccct gtaacagagt gccctgccct
gcacagtgga aaacaggacc ctggagtgag tgttcagtga cctgcggtga aggaacggag gtgaggcagg tcctctgcag ggctggggac
cactgtgatg gtgaaaagcc tgagtcggtc agagcctgtc aactgcctcc ttgtaatgat gaaccatgtt tgggagacaa gtccatattc
tgtcaaatgg aagtgttggc acgatactgc tccataccag gttataacaa gttatgttgt gagtcctgca gcaagcgcag tagcaccctg
ccaccaccat accttctaga agctgctgaa actcatgatg atgtcatctc taaccctagt gacctcccta gatctctagt gatgcctaca
tctttggttc cttatcattc agagacccct gcaaagaaga tgtctttgag tagcatctct tcagtgggag gtccaaatgc atatgctgct
ttcaggccaa acagtaaacc tgatggtgct aatttacgcc agaggagtgc tcagcaagca ggaagtaaga ctgtgagact ggtcaccgta
ccatcctccc cacccaccaa gagggtccac ctcagttcag cttcacaaat ggctgctgct tccttctttg cagccagtga ttcaataggt

Figure 27B (Continued)

gcttcttctc aggcaagaac ctcaaagaaa gatggaaaga tcattgacaa cagacgtccg acaagatcat ccaccttaga aagatgagaa
agtgaaccaa aaaggctaga aaccagagga aaacctggac aacctctctc ttcccatggt gcatatgctt gtttaaagtg gaaatctcta
tagatcgtca gctcatttta tctgtaattg gaagaacaga aagtgctggc tcactttcta gttgctttca tcctcctttt gttctgcatt gactcattta
ccagaattca ttggaagaaa tcaccaaaga ttattacaaa agaaaaatat gttgctaaga ttgtgttggt cgctctctga agcagaaaag
ggactggaac caattgtgca tatcagctga ctttttgttt gttttagaaa agttacagta aaaattaaaa agagatacca atggtttaca
ctttaacaag aaattttgga tatggaacaa agaattctta gacttgtatt cctatttatc tatattagaa atattgtatg agcaaatttg cagctgttgt
gtaaatactg tatattgcaa aaatcagtat tattttaaga gatgtgttct caaatgattg tttactatat tacatttctg gatgttctag gtgcctgtcg
ttgagtattg ccttgtttga cattctatag gttaattttc aaagcagagt attacaaaag agaagttaga attacagcta ctgacaatat aaagggtttt
gttgaatcaa caatgtgata cgtaaattat agaaaaagaa aagaaacaca aaagctatag atatacagat atcagcttac ctattgcctt
ctatacttat aatttaaagg attggtgtct tagtacactt gtggtcacag ggatcaacga atagtaaata atgaactcgt gcaagacaaa
actgaaaccc tctttccagg acctcagtag gcaccgttga ggtgtccttt gtttttgtgt gtgtgtgttc ttttttaatt ttcgcattgt tgacagatac
aaacagttat actcaatgta ctgtaataat cgcaaaggaa aaagttttgg gataacttat ttgtatgttg gtagctgaga aaaatatcat
cagtctagaa ttgatatttg agtatagtag agctttgggg ctttgaaggc aggttcaaga aagcatatgt cgatggttga gatatttatt ttccatatgg
ttcatgttca aatgttcaca accacaatgc atctgactgc aataatgtgc taataattta tgtcagtagt caccttgctc acagcaaagc
cagaaatgct ctctccaggg agtagatgta aagtacttgt acatagaatt cagaactgaa gatatttatt aaaagttgat tttttttct tgatagtatt
tttatgtact aaatatttac actaatatca attacatatt ttggtaaact agagagacat aattagagat gcatgctttg ttctgtgcat agagaccttt
aagcaaacta ctacagccaa ctcaaaagct aaaactgaac aaatttgatg ttatgcaaac atcttgcatt tttagtagtt gatattaagt
tgatgacttg tttcccttca aggaaacatt aaattgtatg gactcagcta gctgttcaat gaaattgtga attagaaaca tttttaaaag tttttgaaag
agataagtgc atcatgaatt acatgtacat gagaggagat agtgatatca gcataatgat tttgaggtca gtacctgagc tgtctaaaaa
tatattatac aaactaaaat gtagatgaat taacctctca aagcacagaa tgtgcaagaa cttttgcatt ttaatcgttg taaactaaca
gcttaaacta ttgactctat acctctaaag aattgctgct actttgtgca agaactttga aggtcaaatt aggcaaattc cagatagtaa
aacaatccct aagccttaag tcttttttt ttcctaaaaa ttcccataga ataaaattct ctctagttta cttgtgtgtg catacatctc atccacaggg
gaagataaag atggtcacac aaacagtttc cataaagatg tacatattca ttatacttct gacctttggg ctttcttttc tactaagcta aaaattcctt
tttatcaaag tgtacactac tgatgctgtt tgttgtactg agagcacgta ccaataaaaa tgttaacaaa atat

Figure 28 tttttttttcagattgaaatcactttaatagcataacaacattttcagaccaggagtcacagatgaagaaaacattttgtcttccatttgcacaattctggtgaggt
gtgtggttgcactggacaatcttacagacacatttttcacattgagaacttaataaatagatacatacaatgtcaaactccacagacaatgagttatgagtgt
gattgttttcttattctgcctcctctgggttgggaggttgcttcccgttgggctgatggcggctgggtcctctaggaggggtactcatactcctcggcactgcgac
ggccaaaatccatccagcccatgtagtcccggtcacttatcctgtggctggggtccaggttctgcaggttcttaacgatggacattcgtccagaaggagctt
tccgggcctgctggatgtatcttgccagcagggcgcccaggtgcgctcgggactcgccatccgttctctgcgataccctcagctgcctacggggcgcctc
ctctgcccgctgcagcccggagcccgcgggatctgcgggaggcaccggctgcgtcagggcgccagccgccagtaccgncatcagcacgcacagg
cacacgccgctgttcat

Figure 29A

MSVKGMAIALAVILCATVVQGFPMFKRGRCLCIGPGVKAVKVADIEKASIMYPSNNCDKIEVIITLK
ENKGQRCLNPKSKQARLIIKKVERKNF

Figure 29B ctccttccaa gaagagcagc aaagctgaag tagcagcaac agcaccagca gcaacagcaa aaaacaaaca tgagtgtgaa
gggcatggct atagccttgg ctgtgatatt gtgtgctaca gttgttcaag gcttccccat gttcaaaaga ggacgctgtc tttgcatagg
ccctggggta aaagcagtga aagtggcaga tattgagaaa gcctccataa tgtacccaag taacaactgt gacaaaatag aagtgattat
taccctgaaa gaaaataaag gacaacgatg cctaaatccc aaatcgaagc aagcaaggct tataatcaaa aaagttgaaa gaaagaattt
ttaaaaatat caaaacatat gaagtcctgg aaaagggcat ctgaaaaacc tagaacaagt ttaactgtga ctactgaaat gacaagaatt
ctacagtagg aaactgagac ttttctatgg ttttgtgact ttcaactttt gtacagttat gtgaaggatg aaaggtgggt gaaaggacca
aaaacagaaa tacagtcttc ctgaatgaat gacaatcaga attccactgc ccaaaggagt ccagcaatta aatggatttc taggaaaagc
taccttaaga aaggctggtt accatcggag tttacaaagt gctttcacgt tcttacttgt tgtattatac attcatgcat ttctaggcta gagaaccttc
tagatttgat gcttacaact attctgttgt gactatgaga acatttctgt ctctagaagt tatctgtctg tattgatctt tatgctatat tactatctgt
ggttacagtg gagacattga cattattact ggagtcaagc ccttataagt caaaagcatc tatgtgtcgt aaagcattcc tcaaacattt
tttcatgcaa atacacaytt ctttccccaa atatcatgta gcacatcaat atgtagggaa acattcttat gcatcatttg gtttgtttta taaccaattc
attaaatgta attcataaaa tgtactatga aaaaaattat acgctatggg atactggcaa cagtgcacat atttcataac caaattagca
gcaccggtct taatttgatg tttttcaact tttattcatt gagatgtttt gaagcaatta ggatatgtgt gtttactgta ctttttgttt tgatccgttt
gtataaatga tagcaatatc ttggacacat ttgaaataca aaatgttttt gtctaccaaa gaaaaatgtt gaaaaataag caaatgtata
cctagcaatc acttttactt tttgtaattc tgtctcttag aaaaatacat aatctaatca aaaaaaaaaa aaaaaaaaaa a

Figure 30 A

MTRLTVLALLAGLLASSRAGSSPLLDIVGGRKARPRQFPFLASIQNQGRHFCGGALIHARFVMTA
ASCFQSQNPGVSTVVLGAYDLRRRERQSRQTFSISSMSENGYDPQQNLNDLMLLQLDREANLT
SSVTILPLPLQNATVEAGTRCQVAGWGSQRSGGRLSRFPRFVNVTVTPEDQCRPNNVCTGVLT
RRGGICNGDGGTPLVCEGLAHGVASFSLGPCGRGPDFFTRVALFRDWIDGVLNNPGPGPA"

Figure 30B ggatccactg gttcctgaca ccctcacctg cccctggggg tgtggccatc ttctagagag ggaaactgag gatcagtgca gaatgtaggg
ggagcccagg ctggcccagg gagcagttgg cggtggaggc cttgggcaat ttcccgtgtt cccactgagt ggggctgtcc ctgggcctgg
gcggggacgc caccaactgc caaggcctgt gtataagggc agccgccgcc ttagccacag acctgccccg ccatgacccg gctgacagtc
ctggccctgc tggctggtct gctggcatcc tcgagggccg gtgagtgcct ctctgtgccg gtggtccccc atctgtgcta gggcccggct
gccagggcag aactcagact taaagcacag agaaggcaag cggcttggcc tgggtcacac agccagcccg gcctggacga
tcccgcgaaa ggcgtgaggg cggacggtgt gcgggactca ggggccccct gtcctcttag ggagtgggac gatgggggag ggtgggtccc
cccgcagccc cactgggtgg atagagctga ggctgcagct tcacacgccc tcccggccac tgtgtggatt cttggggatc tcagagctgt
ctccccccga cccaggctcc agccccctttt tggacatcgt tggcggccgg aaggcgaggc cccgccagtt cccgttcctg gcctccattc
agaatcaagg caggcacttc tgcgggggtg ccctgatcca tgcccgcttc gtgatgaccg cggccagctg cttccaaagc cagtgagggg
tcctggggag ggggcctagg gggcattggg gctcagagaa ggggcttggg gggcttaggc attcagtggg ggtgcttggt aggtgaggag
gggaggggat tgcaaaagga ggggctcagg gaaaggaggg ggcttggaga gggaaatggg gactgagttg aggagggacc
caaggatatt ggggggctca gatggaggag gcccagagaa gggaaggggg tcagatggag gaggcccaga gaaaggaaga
ggctcagatg gaggaggtgc agtgaaggaa agggggtcag atgggggagg cccagagaag ggaaggggct cagatggagg
agggggccca gagaaaggaa ggggctcaga tggaggaggt gcagagaagg gaagggggtc agatgggggg aggcccagag
aagggaaggg gctcagatgg aggaggtgca gagaagggaa ggggctcaga tggaggaggt gcagagaaga gaagggcctc
agatggagga ggtgcagaga agagaagggc ctcagatgga ggaggtgcag agaagggaag ggcctcagat ggaggaggtg
cggagaaggg aagggggtca gatggaggag gtgcagagaa gggaaggggg tcagatgggg gaggcccagg gaagggaagg
ggctcagatg gaggaggggc agagaaggga agggggtcag atgggggagg cccagggaag ggaaggggct cagatggggg
aggcgcagag aagggaaggg ggtcagatgg aggaggtgca gagaagggaa gggggtcaga tgggggaggc ccagataagg
gaatggggtc agatggggga ggtgcagaga agggaagggg gtcagatggg ggaggcccag ataagggaag gggctcagat
ggaggaggtg cagagaaggg gagggggtca gatggaggag gctcagagaa gggaagggac tcagatggag gagggggcgc
agagaagaga aggggctcag atggaggagg aggcgcagag aagggaaggg gctcaagatg ggaagggggc cctggaaagt
ctcggctctg cttctgtaaa agcgggggag ttttcagggt gaaggattgc agtctgcagg ctgggatccc ccctaatttg caagccggct
tgctctgtgc ccaggcccca gcctggtgtc ctccctctgc cctttcctcc gctactctca ggaacccegg ggttagcacc gtggtgctgg
gtgcctatga cctgaggcgg cgggagaggc agtcccgcca gacgttttcc atcagcagca tgagcgagaa tggctacgac ccccagcaga
acctgaacga cctgatgctg cttcaggtga gaggatggtg ccacctgtga tcccagcacc tcgggaggcc gacgttagcc agggaaacaa
gtccaaactt ggtctctaca aaaaaataca aaaattagcc gggagtggtg gcgcgcacct gtggccccctg tgcttcagga ggccgaggcg
gaaggacggc ttgaggtcag gagttcgaga ccagcctggg caacatggcc aaactcagtc tctacaaaaa tatatatgtg tgtgtgtgtg
tgtgtgtgtg tgtgtgtgtg tgtgtatctt gccgggtgag gtggctcatg cctgtaatcc cagcattttg ggaggccgag gtgggcggat
cacgaggtca ggagattgag accagcctgg ccaacatggt gaaaccccat ctctactaaa aatacaaaaa ttagccaggc atggcagcgg
gcgcctctag tcccagctac tcaggaggct gaggcaggag aatcgcttga acccgggagg cggagcttgc agtgagccga gatcgcgccc
ctgcactcca gcctgggtaa cagagccaga ccctatctca aaaaaaactt ccaaaaacaa tacagcaaca catacagatg taccacggtt
cgcgtatgga gcctcctgtt ggtggagact gacgtcgttt tcaaatgctt ttgctatgac agaatcatgt gaatgttttt catgtttggt ttttttcttt
gagaaaatga taaaattatc tcaaaaatat cattaaaaaa tttaaaaaag tagagacggg ggtttcacct tgttggccag tttggtctcg
aactcctggc ctcaagtgat ccacccacct tggcctcgca acgtgctggg aatacaggcg tgagccaccg cacccggccc ctgccgggaa
ttaaacgcaa accacttaca gactacagtt aatgtcgctg acacttctgc tcccaggggt ccccatgagg ctccagtccc cagggccacc
ctcccctgac tccatttcct tccccagctg gaccgtgagg ccaacctcac cagcagcgtg acgatactgc cactgcctct gcagaacgcc
acggtggaag ccggcaccag atgccaggtg gccggctggg ggagccagcg cagtgggggg cgtctctccc gttttcccag gtttgtcaac
gtgactgtga cccccgagga ccagtgtcgc cccaacaacg tgtgcaccgg tgtgctcacc cgccgcggtg gcatctgcaa tgtgagtgct

Figure 30B (Continued)

ccctgtggcg ggaggagggg tcctgagagg tactgagctc tccgtggcag gagaaagcaa gtgcaggctg agggcggcac
agcagggggg ccccaggatt gagcattttc acggtaggag aaacagtatc tttttttttt tttttgagac agagtctcgc tctgtcgccc
aggctggagt gtagtggcgt gatctcggcg gctcactgca acctccgcct cctgggttca agcgattctc ctgcctcagc ctcctaagta
gctgggatta caggcatgcg ccaccacgcc cggctaattt tgtattttta gtagagacag ggtttctcca tgtgggtcag gctggtctcg
aactcctgac ctcatgatcg acccaccttg gcctcccaaa gtgttaggat aacaggcatg agccaccgtg cctggctgag aaacagtagc
tatcaaacgc cggctgtgag ccacgtctgt gctgggggtt ggggacccag caggcatggt agagccggtc actgagggac tcaggcgtgt
gattgccagg ggaggggcac ctggcccagc ctggaggtgc caggaagctc cagaaagcaa ctgatcccaa agtccactag cagttaacca
gggcagagaa agagaagagc catgcaaagg ccctggggct ggatcaggac ttgtaggttc caggggcagc aagaggcctc tgcagttctg
gggtggcgtg ggagccaggc cctgggacgc cctgacacag ctgctgcctg cccaggggga cgggggcacc cccctcgtct gcgagggcct
ggcccacggc gtggcctcct tttccctggg gccctgtggc cgaggccctg acttcttcac ccgagtggcg ctcttccgag actggatcga
tggtgttctc aacaacccgg gaccggggcc agcctagggg ggcctgtgac ctcccatgga gcccagcccc cgccctccac acctccggcg
ctccgcaccc acctcccacg gccccgcccc tgccccccgct ccggccagag gggccctggc tgtaataaag aagccgatct ctcctctgct
cctggtttct gttcattggt gggggagggg gctgtgggga cgcgtgagtg gcaccttcac cggccttagg ggcacccacc gcaggtgcac
tgcctgtgca gatgtcagat gttcagagat tccctcaaag cccggggaag caggggctgg tgttatctgc acccgacagc ggggtgttgg
ggggaggccc aggttcagag aggttgggtg gctgcccaga ggtcacacag tgaatgccgc ccagcacttt gggaggccga ggtgggcgga
tcacctgagg tcaggagttc aagaccagcc cggccaacct ggtgaaaccc catctctata aaaatacaaa aattagccgg gcatgatggc
gggcgcctgt aatcccagtt acttgggagg ctgaggcagg agaatcacct gaacccggga ggcggaggtt gcagcgaacc gagatggcgc
cactgcactc cagcctgggc gacagcgaga ctccagctca aaaaaaaaca aaaaccacgg gagaaaacgg ggaacattct cctcttggat
cc

Figure 31A

MVSYWDTGVLLCALLSCLLLTGSSSGSKLKDPELSLKGTQHIMQAGQTLHLQCRGEAAHKWSLP
EMVSKESERLSITKSACGRNGKQFCSTLTLNTAQANHTGFYSCKYLAVPTSKKKETESAIYIFISD
TGRPFVEMYSEIPEIIHMTEGRELVIPCRVTSPNITVTLKKFPLDTLIPDGKRIIWDSRKGFIISNATY
KEIGLLTCEATVNGHLYKTNYLTHRQTNTIIDVQISTPRPVKLLRGHTLVLNCTATTPLNTRVQMT
WSYPDEKNKRASVRRRIDQSNSHANIFYSVLTIDKMQNKDKGLYTCRVRSGPSFKSVNTSVHIY
DKAFITVKHRKQQVLETVAGKRSYRLSMKVKAFPSPEVVWLKDGLPATEKSARYLTRGYSLIIKD
VTEEDAGNYTILLSIKQSNVFKNLTATLIVNVKPQIYEKAVSSFPDPALYPLGSRQILTCTAYGIPQP
TIKWFWHPCNHNHSEARCDFCSNNEESFILDADSNMGNRIESITQRMAIIEGKNKMASTLVVADS
RISGIYICIASNKVGTVGRNISFYITDVPNGFHVNLEKMPTEGEDLKLSCTVNKFLYRDVTWILLRT
VNNRTMHYSISKQKMAITKEHSITLNLTIMNVSLQDSGTYACRARNVYTGEEILQKKEITIRGEHCN
KKAVFSRISKFKSTRNDCTTQSNVKH

Figure 31B gcggacactc ctctcggctc ctccccggca gcggcggcgg ctcggagcgg gctccggggc tcgggtgcag cggccagcgg gcctggcggc
gaggattacc cggggaagtg gttgtctcct ggctggagcc gcgagacggg cgctcagggc gcggggccgg cggcggcgaa
cgagaggacg gactctggcg gccgggtcgt tggccggggg agcgcgggca ccgggcgagc aggccgcgtc gcgctcacca tggtcagcta
ctgggacacc ggggtcctgc tgtgcgcgct gctcagctgt ctgcttctca caggatctag ttcaggttca aaattaaaag atcctgaact
gagtttaaaa ggcacccagc acatcatgca agcaggccag acactgcatc tccaatgcag gggggaagca gcccataaat ggtctttgcc
tgaaatggtg agtaaggaaa gcgaaaggct gagcataact aaatctgcct gtggaagaaa tggcaaacaa ttctgcagta ctttaacctt
gaacacagct caagcaaacc acactggctt ctacagctgc aaatatctag ctgtacctac ttcaaagaag aaggaaacag aatctgcaat
ctatatattt attagtgata caggtagacc tttcgtagag atgtacagtg aaatccccga aattatacac atgactgaag gaagggagct
cgtcattccc tgccgggtta cgtcacctaa catcactgtt actttaaaaa agtttccact tgacactttg atccctgatg gaaaacgcat
aatctgggac agtagaaagg gcttcatcat atcaaatgca acgtacaaag aaatagggct tctgacctgt gaagcaacag tcaatgggca
tttgtataag acaaactatc tcacacatcg acaaaccaat acaatcatag atgtccaaat aagcacacca cgcccagtca aattacttag
aggccatact cttgtcctca attgtactgc taccactccc ttgaacacga gagttcaaat gacctggagt taccctgatg aaaaaaataa
gagagcttcc gtaaggcgac gaattgacca aagcaattcc catgccaaca tattctacag tgttcttact attgacaaaa tgcagaacaa
agacaaagga ctttatactt gtcgtgtaag gagtggacca tcattcaaat ctgttaacac ctcagtgcat atatatgata aagcattcat
cactgtgaaa catcgaaaac agcaggtgct tgaaaccgta gctggcaagc ggtcttaccg gctctctatg aaagtgaagg catttccctc
gccggaagtt gtatggttaa aagatgggtt acctgcgact gagaaatctg ctcgctattt gactcgtggc tactcgttaa ttatcaagga
cgtaactgaa gaggatgcag ggaattatac aatcttgctg agcataaaac agtcaaatgt gtttaaaaac ctcactgcca ctctaattgt
caatgtgaaa ccccagattt acgaaaaggc cgtgtcatcg tttccagacc cggctctcta cccactgggc agcagacaaa tcctgacttg
taccgcatat ggtatccctc aacctacaat caagtggttc tggcacccct gtaaccataa tcattccgaa gcaaggtgtg acttttgttc
caataatgaa gagtccttta tcctggatgc tgacagcaac atgggaaaca gaattgagag catcactcag cgcatggcaa taatagaagg
aaagaataag atggctagca ccttggttgt ggctgactct agaatttctg gaatctacat ttgcatagct tccaataaag ttgggactgt
gggaagaaac ataagctttt atatcacaga tgtgccaaat gggtttcatg ttaacttgga aaaaatgccg acggaaggag aggacctgaa
actgtcttgc acagttaaca agttcttata cagagacgtt acttggattt tactgcggac agttaataac agaacaatgc actacagtat
tagcaagcaa aaaatggcca tcactaagga gcactccatc actcttaatc ttaccatcat gaatgtttcc ctgcaagatt caggcaccta
tgcctgcaga gccaggaatg tatacacagg ggaagaaatc ctccagaaga aagaaattac aatcagaggt gagcactgca acaaaaaggc
tgttttctct cggatctcca aatttaaaag cacaaggaat gattgtacca cacaaagtaa tgtaaaacat taaaggactc attaaaaagt
aacagttgtc tcatatcatc ttgatttatt gtcactgttg ctaactttca ggctcggagg agatgctcct cccaaaatga gttcggagat
gatagcagta ataatgagac ccccgggctc cagctctggg ccccccattc aggccgaggg ggctgctccg gggggccgac ttggtgcacg
tttggatttg gaggatccct gcactgcctt ctctgtgttt gttgctcttg ctgttttctc ctgcctgata aacaacaact tgggatgatc ctttccattt
tgatgccaac ctctttttat ttttaagcgg cgccctatag t

Figure 32A

MSDSVILRSIKKFGEENDGFESDKSYNNDKKSRLQDEKKGDGVRVGFFQLFRFSSSTDIWLMFV
GSLCAFLHGIAQPGVLLIFGTMTDVFIDYDVELQELQIPGKACVNNTIVWTNSSLNQNMTNGTRC
GLLNIESEMIKFASYYAGIAVAVLITGYIQICFWVIAAARQIQKMRKFYFRRIMRMEIGWFDCNSVG
ELNTRFSDDINKINDAIADQMALFIQRMTSTICGFLLGFFRGWKLTLVIISVSPLIGIGAATIGLSVSK
FTDYELKAYAKAGVVADEVISSMRTVAAFGGEKREVERYEKNLVFAQRWGIRKGIVMGFFTGFV
WCLIFLCYAVAFWYGSTLVLDEGEYTPGTLVQIFLSVIVGALNLGNASPCLEAFATGRAAATSIFE
TIDRKPIIDCMSEDGYKLDRIKGEIEFHNVTFHYPSRPEVKILNDLNMVIKPGEMTALVGPSGAGKS
TALQLIQRFYDPCEGMVTVDGHDIRSLNIQWLRDQIGIVEQEPVLFSTTIAENIRYGREDATMEDIV
QAAKEANAYNFIMDLPQQFDTLVGEGGGQMSGGQKQRVAIARALIRNPKILLLDMATSALDNES
EAMVQEVLSKIQHGHTIISVAHRLSTVRAADTIIGFEHGTAVERGTHEELLERKGVYFTLVTLQSQ
GNQALNEEDIKDATEDDMLARTFSRGSYQDSLRASIRQRSKSQLSYLVHEPPLAVVDHKSTYEE
DRKDKDIPVQEEVEPAPVRRILKFSAPEWPYMLVGSVGAAVNGTVTPLYAFLFSQILGTFSIPDKE
EQRSQINGVCLLFVAMGCVSLFTQFLQGYAFAKSGELLTKRLRKFGFRAMLGQDIAWFDDLRNS
PGALTTRLATDASQVQGAAGSQIGMIVNSFTNVTVAMIIAFSFSWKLSLVILCFFPFLALSGATQTR
MLTGFASRDKQALEMVGQITNEALSNIRTVAGIGKERRFIEALETELEKPFKTAIQKANIYGFCFAF
AQCIMFIANSASYRYGGYLISNEGLHFSYVFRVISAVVLSATALGRAFSYTPSYAKAKISAARFFQL
LDRQPPISVYNTAGEKWDNFQGKIDFVDCKFTYPSRPDSQVLNGLSVSISPGQTLAFVGSSGCG
KSTSIQLLERFYDPDQGKVMIDGHDSKKVNVQFLRSNIGIVSQEPVLFACSIMDNIKYGDNTKEIP
MERVIAAAKQAQLHDFVMSLPEKYETNVGSQGSQLSRGEKQRIAIARAIVRDPKILLLDEATSALD
TESEKTVQVALDKAREGRTCIVIAHRLSTIQNADIIAVMAQGVVIEKGTHEELMAQKGAYYKLVTT
GSPIS

Figure 32B gaatgatgaa aaccgaggtt ggaaaaggtt gtgaaacctt ttaactctcc acagtggagt ccattatttc ctctggcttc ctcaaattca
tattcacagg gtcgttggct gtgggttgca attaccatgt ctgactcagt aattcttcga agtataaaga aatttggaga ggagaatgat
ggttttgagt cagataaatc atataataat gataagaaat caaggttaca agatgagaag aaaggtgatg gcgttagagt tggcttcttt
caattgtttc ggttttcttc atcaactgac atttggctga tgtttgtggg aagtttgtgt gcatttctcc atggaatagc ccagccaggc gtgctactca
tttttggcac aatgacagat gtttttattg actacgacgt tgagttacaa gaactccaga ttccaggaaa agcatgtgtg aataacacca
ttgtatggac taacagttcc ctcaaccaga acatgacaaa tggaacacgt tgtgggttgc tgaacatcga gagcgaaatg atcaaatttg
ccagttacta tgctggaatt gctgtcgcag tacttatcac aggatatatt caaatatgct tttgggtcat tgccgcagct cgtcagatac
agaaaatgag aaaattttac tttaggagaa taatgagaat ggaaataggg tggtttgact gcaattcagt gggggagctg aatacaagat
tctctgatga tattaataaa atcaatgatg ccatagctga ccaaatggcc cttttcattc agcgcatgac ctcgaccatc tgtggtttcc tgttgggatt
tttcaggggt tggaaactga ccttggttat tatttctgtc agccctctca ttgggattgg agcagccacc attggtctga gtgtgtccaa gtttacggac
tatgagctga aggcctatgc caaagcaggg gtggtggctg atgaagtcat ttcatcaatg agaacagtgg ctgcttttgg tggtgagaaa
agagaggttg aaaggtatga gaaaaatctt gtgttcgccc agcgttgggg aattagaaaa ggaatagtga tgggattctt tactggattc
gtgtggtgtc tcatcttttt gtgttatgca gtggccttct ggtacggctc cacacttgtc ctggatgaag gagaatatac accaggaacc
cttgtccaga ttttcctcag tgtcatagta ggagctttaa atcttggcaa tgcctctcct tgtttggaag cctttgcaac tggacgtgca
gcagccacca gcatttttga gacaatagac aggaaaccca tcattgactg catgtcagaa gatggttaca agttggatcg aatcaagggt
gaaattgaat tccataatgt gaccttccat tatccttcca gaccagaggt gaagattcta aatgacctca acatggtcat taaaccaggg
gaaatgacag ctctggtagg acccagtgga gctggaaaaa gtacagcact gcaactcatt cagcgattct atgacccctg tgaaggaatg
gtgaccgtgg atggccatga cattcgctct cttaacattc agtggcttag agatcagatt gggatagtgg agcaagagcc agttctgttc
tctaccacca ttgcagaaaa tattcgctat ggcagagaag atgcaacaat ggaagacata gtccaagctg ccaaggaggc caatgcctac
aacttcatca tggacctgcc acagcaattt gacacccttg ttggagaagg aggaggccag atgagtggtg gccagaaaca aagggtagct
atcgccagag ccctcatccg aaatcccaag attctgcttt tggacatggc cacctcagct ctggacaatg agagtgaagc catggtgcaa
gaagtgctga gtaagattca gcatgggcac acaatcattt cagttgctca tcgcttgtct acggtcagag ctgcagatac catcattggt
tttgaacatg gcactgcagt ggaaagaggg acccatgaag aattactgga aaggaaaggt gtttacttca ctctagtgac tttgcaaagc
cagggaaatc aagctcttaa tgaagaggac ataaaggatg caactgaaga tgacatgctt gcgaggacct ttagcagagg gagctaccag
gatagtttaa gggcttccat ccggcaacgc tccaagtctc agctttctta cctggtgcac gaacctccat tagctgttgt agatcataag
tctacctatg aagaagatag aaaggacaag gacattcctg tgcaggaaga agttgaacct gccccagtta ggaggattct gaaattcagt
gctccagaat ggccctacat gctggtaggg tctgtgggtg cagctgtgaa cgggacagtc acacccttgt atgccttttt attcagccag
attcttggga ctttttcaat tcctgataaa gaggaacaaa ggtcacagat caatggtgtg tgcctacttt ttgtagcaat gggctgtgta tctcttttca
cccaatttct acagggatat gcctttgcta aatctgggga gctcctaaca aaaaggctac gtaaatttgg tttcagggca atgctggggc
aagatattgc ctggtttgat gacctcagaa atagccctgg agcattgaca acaagacttg ctacagatgc ttcccaagtt caaggggctg
ccggctctca gatcgggatg atagtcaatt ccttcactaa cgtcactgtg gccatgatca ttgccttctc ctttagctgg aagctgagcc tggtcatctt
gtgcttcttc cccttcttgg ctttatcagg agccacacag accaggatgt tgacaggatt tgcctctcga gataagcagg ccctggagat
ggtgggacag attacaaatg aagccctcag taacatccgc actgttgctg gaattggaaa ggagaggcgg ttcattgaag cacttgagac
tgagctggag aagcccttca agacagccat tcagaaagcc aatatttacg gattctgctt tgcctttgcc cagtgcatca tgtttattgc
gaattctgct tcctacagat atggaggtta cttaatctcc aatgaggggc tccatttcag ctatgtgttc agggtgatct ctgcagttgt actgagtgca
acagctcttg gaagagcctt ctcttacacc ccaagttatg caaaagctaa aatatcagct gcacgctttt ttcaactgct ggaccgacaa
cccccaatca gtgtatacaa tactgcaggt gaaaaatggg acaacttcca ggggaagatt gattttgttg attgtaaatt tacatatcct
tctcgacctg actcgcaagt tctgaatggt ctctcagtgt cgattagtcc agggcagaca ctggcgtttg ttgggagcag tggatgtggc
aaaagcacta gcattcagct gttggaacgt ttctatgatc ctgatcaagg gaaggtgatg atagatggtc atgacagcaa aaaagtaaat

Figure 32B (Continued)

gtccagttcc tccgctcaaa cattggaatt gtttcccagg aaccagtgtt gtttgcctgt agcataatgg acaatatcaa gtatggagac
aacaccaaag aaattcccat ggaaagagtc atagcagctg caaaacaggc tcagctgcat gattttgtca tgtcactccc agagaaatat
gaaactaacg ttgggtccca ggggtctcaa ctctctagag gggagaaaca acgcattgct attgctcggg ccattgtacg agatcctaaa
atcttgctac tagatgaagc cacttctgcc ttagacacag aaagtgaaaa gacggtgcag gttgctctag acaaagccag agagggtcgg
acctgcattg tcattgccca tcgcttgtcc accatccaga acgcggatat cattgctgtc atggcacagg gggtggtgat tgaaaagggg
acccatgaag aactgatggc ccaaaaagga gcctactaca aactagtcac cactggatcc cccatcagtt gacccaatgc aagaatctca
gacacacatg acgcaccagt tacaggggtt gtttttaaag aaaaaaacaa tcccagcacg agggattgct gggattgttt tttctttaaa
gaagaatntn nntattttac ttttacnnnc nttttcctac atcggaatcc aanctaattt ctaatggcct tccataataa ttctgcttta gatgtgtata
cagaaaatga aagaaactag ggtccatgtg agggaaaacc caatgtcaag tggcagctca gccaccactc agtgcttctc tgtgcaggag
ccagtcctga ttaatatgtg ggaattagtg agacatcagg gagtaagtga cactttgaac tcctcaagga cagagaactg tctttcattt
ttgaaccctc ggtgtacaca gaggcgggtc tgtaacaggc aatcaacaaa cgtttcttga gctagaccaa ggtcagattt gaaaagaaca
gaaggactga agaccagctg tgtttcttaa ctaaatttgt ctttcaagtg aaaccagctt ccttcatctc taaggctaag gatagggaaa
gggtgggatg ctctcangct gagggaggca naaagggaaa gtattancat gagctttcca nttagggctg ttgatttatg ctttaacttc
anantgagtg tagggtggtg anncta

Figure 33A

MDTQTHSLPITHTQLHSNSQPQSRTCTRHCQTFSQSCRQSHRGSRSQSSSQSPASHRNPTGA
HSSSGHQSQSPNTSPPPKRHKKTMNSHHSPMRPTILHCRCPKNRKNLEGKLKKKKMAKRIQQV
YKTKTRSSGWKSN

Figure 33B agactcagct taatctgacc caagggctcc taccctgaac cagtagctgg gactatcccc agggtacccc tgagagctgc cccagcctgg
ggtgagggta aggggtaggg ggctttgtct tggctgagcc acatctctca cacccctgtg gcctgggcat cataatcagc cccaactata
taaccaggtg ggcctgccag ggcctctgta aagctaggcc tgctgggaga ggatgaggag gaggccctgc cctcaaacgt ggcctcctat
ggacacccag actcacagcc ttcctatcac ccacactcag ctccatagca actctcagcc ccaaagccgc acctgcaccc gccattgcca
aaccttcagc cagagttgca gacagagcca tcgtggcagc cggagccaga gctccagcca gagcccggcc agccaccgca
acccaactgg agcccacagc tcatccggcc accagagcca gagtcccaac actagtccac caccaaagcg ccacaaaaag actatgaact
cccaccactc tcccatgcgg cccaccatcc tgcactgccg ctgccccaag aacagaaaga acttggaagg caagctgaaa aagaaaaaaa
tggccaagag gatccagcag gtgtacaaaa ccaagacgcg gagctcaggt accctttaag gaggtgggga agggccaccg agccacagat
gatggagagc agaccttggg ggcagtgaga ggaaggctgc agccaggtca caaaggaacc acaggcaaga aggaagaggg
agaagagaaa caatggcagt tggctagctg aatgtatgat acgttgacgg aaagtcttct ttgaaattgg atgggttgat taggaggatg
gaaagatgga cagatagcag ataagctaga tgaaagcatg aatggagttg agaggttggg ttgatgactg ggtgggtaaa caataaatag
gttatagaaa ggatagttgg aagaatgcat tggctgaatg ataggaagtt tggatacgat tagctggatg gatggataaa tggatgaatg
cactggctgg ctagttattt ggttggttag gtagatgatc agtttgaaga ttgtggttgg tggatgaatt ggttagaaat agagttaaat agttgtagaa
gttttgatgg gttggtttga ttggttaaat attatcttaa tagagtaata tagagtaatt gaataaacag agagaagaat agatatctag
actaatggga tagaatggga aagaaatgtt gaataaatga atggaatgag tgaactaatg aatgggtgga tgacaaatgg aagggataaa
tggatggata cctggattca cataggtcaa aaggacactg acggtagtct aaactctatc tatgtcccat atcaatcaca aatgagtagt
tgtaagacct tacaggaggt caaggaggtc actgacttca tgaagtgctc agctattaaa ggttcctttc ccactcttat cccttaggat
ggaaatccaa ctaatgagac cgcactcctt ggcttgttcc tgcgtgtttc acccaaagga gaaaatgcta ggatgaagtc aatcttcttg
caggaacatg ttactatggt gatttctacg caacactaat taaagcttgt acctggaaga ctatccctga gtagtcattt tgatttcact
aataaaggtg ttatgtgttt tgggggcctg cacaggggca gaaatgaatg gggtaggat gccaagaagc ctgcag

Figure 34A

MGKSESQMDITDINTPKPKKKQRWTRLEISLSVLVLLLTIIAVRMIALYATYDDGICKSSDCIKSAAR
LIQNMDATTEPCRDFFKYACGGWLKRNVIPETSSRYGNFDILRDELEVVLKDVLQEPKTEDIVAV
QKAKALYRSCINESAIDSRGGEPLLKLLPDIYGWPVATENWEQKYGASWTAEKAIAQLNSKYGKK
VLINLFVGTDDKNSVNHVIHIDQPRLGLPSRDYYECTGIYKEACTAYVDFMISVARLIRQEERLPID
ENQLALEMNKVMELEKEIANATAKPEDRNDPMLLYNKMRLAQIQNNFSLEINGKPFSWLNFTNEI
MSTVNISITNEEDVVVYAPEYLTKLKPILTKYSARDLQNLMSWRFIMDLVSSLSRTYKESRNAFRK
ALYGTTSETATWRRCANYVNGNMENAVGRLYVEAAFAGESKHVVEDLIAQIREVFIQTLDDLTW
MDAETKKRAEEKALAIKERIGYPDDIVSNDNKLNNEYLELNYKEDEYFENIIQNLKFSQSKQLKKL
REKVDKDEWISGAAVVNAFYSSGRNQIVFPAGILQPPFFSAQQSNSLNYGGIGMVIGHEITHGFD
DNGRNFNKDGDLVDWWTQQSASNFKEQSQCMVYQYGNFSWDLAGGQHLNGINTLGENIADN
GGLGQAYRAYQNYIKKNGEEKLLPGLDLNHKQLFFLNFAQVWCGTYRPEYAVNSIKTDVHSPGN
FRIIGTLQNSAEFSEAFHCRKNSYMNPEKKCRVW

Figure 34 B gattttaggt gatgggcaag tcagaaagtc agatggatat aactgatatc aacactccaa agccaaagaa gaaacagcga tggactcgac
tggagatcag cctctcggtc cttgtcctgc tcctcaccat catagctgtg agaatgatcg cactctatgc aacctacgat gatggtattt
gcaagtcatc agactgcata aaatcagctg ctcgactgat ccaaaacatg gatgccacca ctgagccttg tagagacttt ttcaaatatg
cttgcggagg ctggttgaaa cgtaatgtca ttcccgagac cagctcccgt tacggcaact ttgacatttt aagagatgaa ctagaagtcg
ttttgaaaga tgtccttcaa gaacccaaaa ctgaagatat agtagcagtg cagaaagcaa aagcattgta caggtcttgt ataaatgaat
ctgctattga tagcagaggt ggagaacctc tactcaaact gttaccagac atatatgggt ggccagtagc aacagaaaac tgggagcaaa
aatatggtgc ttcttggaca gctgaaaaag ctattgcaca actgaattct aaatatggga aaaaagtcct tattaatttg tttgttggca
ctgatgataa gaattctgtg aatcatgtaa ttcatattga ccaacctcga cttggcctcc cttctagaga ttactatgaa tgcactggaa
tctataaaga ggcttgtaca gcatatgtgg attttatgat ttctgtggcc agattgattc gtcaggaaga aagattgccc atcgatgaaa
accagcttgc tttggaaatg aataaagtta tggaattgga aaaagaaatt gccaatgcta cggctaaacc tgaagatcga aatgatccaa
tgcttctgta taacaagatg agattggccc agatccaaaa taacttttca ctagagatca atgggaagcc attcagctgg ttgaatttca
caaatgaaat catgtcaact gtgaatatta gtattacaaa tgaggaagat gtggttgttt atgctccaga atatttaacc aaacttaagc
ccattcttac caaatattct gccagagatc ttcaaaattt aatgtcctgg agattcataa tggatcttgt aagcagcctc agccgaacct
acaaggagtc cagaaatgct ttccgcaagg ccctttatgg tacaacctca gaaacagcaa cttggagacg ttgtgcaaac tatgtcaatg
ggaatatgga aaatgctgtg gggaggcttt atgtggaagc agcatttgct ggagagagta aacatgtggt cgaggatttg attgcacaga
tccgagaagt ttttattcag actttagatg acctcacttg gatggatgcc gagacaaaaa agagagctga agaaaaggcc ttagcaatta
aagaaaggat cggctatcct gatgacattg tttcaaatga taacaaactg aataatgagt acctcgagtt gaactacaaa gaagatgaat
acttcgagaa cataattcaa aatttgaaat tcagccaaag taaacaactg aagaagctcc gagaaaaggt ggacaaagat gagtggataa
gtggagcagc tgtagtcaat gcattttact cttcaggaag aaatcagata gtcttcccag ccggcattct gcagcccccc ttctttagtg
cccagcagtc caactcattg aactatgggg gcatcggcat ggtcatagga cacgaaatca cccatggctt cgatgacaat ggcagaaact
ttaacaaaga tggagacctc gttgactggt ggactcaaca gtctgcaagt aactttaagg agcaatccca gtgcatggtg tatcagtatg
gaaacttttc ctgggacctg gcaggtggac agcaccttaa tggaattaat acactgggag aaaacattgc tgataatgga ggtcttggtc
aagcatacag agcctatcag aattatatta aaaagaatgg cgaagaaaaa ttacttcctg gacttgacct aaatcacaaa caactatttt
tcttgaactt tgcacaggtg tggtgtggaa cctataggcc agagtatgcg gttaactcca ttaaaacaga tgtgcacagt ccaggcaatt
tcaggattat tgggactttg cagaactctg cagagttttc agaagccttt cactgccgca agaattcata catgaatcca gaaaagaagt
gccgggtttg gtgatcttca aaagaagcat tgcagccctt ggctagactt gccaacacca cagaaatggg gaattctcta atcgaaagaa
aatgggccct aggggtcact gtactgactt gagggtgatt aacagagagg gcaccatcac aatacagata acattaggtt gtcctagaaa
gggtgtggag ggaggaaggg ggtctaaggt ctatcaagtc aatcatttct cactgtgtac ataatgctta atttctaaag ataatattac tgtttatttc
tgtttctcat atggtctacc agtttgctga tgtccctaga aaacaatgca aaacctttga ggtagaccag gatttctaat caaaagggaa
aagaagatgt tgaagaatag agttaggcac cagaagaaga gtaggtgaca ctatagttta aaacacattg cctaactact agtttttact
tttatttgca acatttacag tccttcaaaa tccttccaaa gaattcttat acacattggg gccttggagc ttacatagtt ttaaactcat ttttgccata
catcagttat tcattctgtg atcatttatt ttaagcactc ttaaagcaaa aaatgaatgt ctaaaattgt tttttgttgt acctgctttg actgatgctg
agattcttca ggcttcctgc aattttctaa gcaatttctt gctctatctc tcaaaacttg gtatttttca gagatttata taaatgtaaa aataataatt
tttatattta attattaact acatttatga gtaactatta ttataggtaa tcaatgaata ttgaagtttc agcttaaaat aaacagttgt gaaccaagat
ctataaagcg atatacagat gaaaatttga gactatttaa acttataaat catattgatg aaaagattta agcacaaact ttagggtaaa
aattgcgatt ggacagttgt ctagagatat atatacttgt ggttttcaaa ttggactttc aaaattaaat ctgtccctga gagtgtctct gataaaaggg
caaatctgca cctatgtagc tctgcatctc ctgtcttttc aggtttgtca tcagatggaa atattttgat aataaattga aattgtgaac tcattgctcc
ctaagactgt gacaactgtc taactttaga agtgcatttc tgaatagaaa tgggaggcct ctgatggacc ttctagaatt ataagtcaca
aagagttctg gaaaagaact gtttactgct tgataggaat tcatcttttg aggcttctgt tcctctcttt tcctgttgta ttgactattt tcgttcatta

Figure 34B (Continued)

cttgattaag attttacaaa agaggagcac ttccaaaatt cttatttttc ctaacaaaag atgaaagcag ggaatttcta tctaaatgat
gagtattagt tccctgtctc ttgaaaaatg cccatttgcc tttaaaaaaa aaagttacag aaatactata acatatgtac ataaattgca
taaagcataa gtatacagtt caataaactt aactttaact gaacaatggc cctgtagcca gcacctgtaa gaaacagagc agtaccagcg
ctctaaaagc acctccttgt cactttatta ctcccagaac aacaactatc ctgacttcta atatcattca ctagctttgc ctggttttgt cttttatgca
gatagaatca atcagtatgt attcttttgt gcctggcttc tttctctcag ccttacattt gtgagattcc tctgtattgt gctgattgtg gatcttttca
ttctcattgc agaataatgt tctattgtgg gacttattac aatttgttca tcctattgtt gatgggcact tgagaacttt ccattttggc gctattacaa
atagtgcaac tatgaatgta ctgcatgtta ccatcttact tgagccttta atggacttat ttcttcaaat ccttccaaaa attattataa gcattgaaat
tatagtttca agccaactgt ggataccctt accctttcct cctttatcac aaccaccgtt acaagtatac ttatatttcc ctaaaataca tttaaaactt
acctaagtga catttgtagt tggagtaata ggagcttcca gctctaataa aacagctgtc tctaacttat tttatttcca tcatgtcaga
gcaggtgaag agccagaagt gaagagtgac tagtacaaat tataaaaagc cactagactc ttcactgtta gctttttaaa acattaggct
cccatcccta tggaggaaca actctccagt gcctggatcc cctctgtcta caaatataag attttctggg cctaaaggat agatcaaagt
caaaaatagc aatgcctccc tatccctcac acatccagac atcatgaatt ttacatggta ctcttgttga gttctataga gccttctgat
gtctctaaag cactaccgat tctttggagt tgtcacatca gataagacat atctctaatt ccatccataa atccagttct actatggctg agttctggtc
aaagaaagaa agtttagaag ctgagacaca aagggttggg agctgatgaa actcacaaat gatggtagga agaagctctc gacaataccc
gttggcaagg agtctgcctc catgctgcag tgttcgagtg gattgtaggt gcaagatgga aaggattgta ggtgcaagct gtccagagaa
aagagtcctt gttccagccc tattctgcca ctcctgacag ggtgaccttg ggtatttgca atattccttt gggcctctgc ttctctcacc taaaaaaaga
gaattagatt atattggtgg ttctcagcaa gagaaggagt atgtgtccaa tgctgccttc ccatgaatct gtctcccagt tatgaatcag
tgggcaggat aaactgaaaa ctcccattta agtgtctgaa tcgagtgaga caaaatttta gtccaaataa caagtaccaa agttttatca
agtttgggtc tgtgctgctg ttactgttaa ccatttaagt ggggcaaaac cttgctaatt ttctcaaaag catttatcat tcttgttgcc acagctggag
ctctcaaact aaaagacatt tgttattttg gaaagaagaa agactctatt ctcaaagttt cctaatcaga aatttttatc agtttccagt ctcaaaaata
caaaataaaa acaaacgttt ttaatact

Figure 35A

MAHKQIYYSDKYFDEHYEYRHVMLPRELSKQVPKTHLMSEEEWRRLGVQQSLGWVHYMIHEPE
PHILLFRRPLPKDQQK

Figure 35B agtctccggc gagttgttgc ctgggctgga cgtggttttg tctgctgcgc ccgctcttcg cgctctcgtt tcattttctg cagcgcgcca
cgaggatggc ccacaagcag atctactact cggacaagta cttcgacgaa cactacgagt accggcatgt tatgttaccc agagaacttt
ccaaacaagt acctaaaact catctgatgt ctgaagagga gtggaggaga cttggtgtcc aacagagtct aggctgggtt cattacatga
ttcatgagcc agaaccacat attcttctct ttagacgacc tcttccaaaa gatcaacaaa aatgaagttt atctggggat cgtcaaatct ttttcaaatt
taatgtatat gtgtatataa ggtagtattc agtgaatact tgagaaatgt acaaatcttt catccatacc tgtgcatgag ctgtattctt cacagcaaca
gagctcagtt aaatgcaact gcaagtaggt tactgtaaga tgtttaagat aaaagttctt ccagtcagtt tttctcttaa gtgcctgttt gagtttactg
aaacagttta cttttgttca ataaagtttg tatgttgcat ttaaaaaaaa aaaaaaa

Figure 36 gagctctcca tgcacacctg ttactgtttc tgtttttacc tgtaaatatc tgtctctgac ttccatgtct catgcacctc tatagggcaa agactgtgtc
ttaaacatca cggtagcctc agcatgttgt gcaatcaagg tttttttgtt tttgttcttt gttttttttt tggtattagc tttatttgta tcattttgaa atttttatca
aaaaagcagc gtgcctgctg tggttcccat cctctgggat ttaggaatct ttacccgatt ctccatccaa gtctgtcttt cgtattctag gctcttccta
aagttgtcat tcacatatac cctccagaat tttatagggt gtataatctg taacaactcg gaggaagcca attgcccttt agaaatatgg
ctgcaattgc ctcacttcct gtgtcatgtg actctcctag tcatcacatg acccatccac attgggaagc cagaattact tgcaggagta
acctagtgcc tatagctatg gcaggtacct gcatccttgt ttttgtttag tggatcctct atccttcaga gactctggaa cccctgtgct cttctcctca
tctagtgacc ctgaggtgat ggagttttca agtccttcca gagaggtaag agagagagct cccaatcagc attgtcacag tgcttctgga
atcctggcac tggaatttaa tgaatgacag actctctttg aatccagggc catcatggct ctttgagcaa ggcacagatg gaggggaggg
tcgaagttga aatgggtggg aagagtggtg gggagcatcc tgatttgggg tgggcagaga gttgtcatca gaagggttgc agggagagct
gcacccaggt gtctgtgggc cttgtcctaa tgaatgtggg agaccaggcc atgggcaccc aaaggcagct aagccctgcc cgggagagta
gttgaggggt ggagagggac ttgcttttca gtcattcctc attctgtcct caggaatgtc ccaagccttc gggtagggta agcatcatgg
ctggcagcct cacaggattg cttctacttc aggcagtgtc gtgggcatca gatgagtgag tcaaggcagt ggggaggtag cacagagcct
cccttctgcc tcatagtcct ttggtagcct tccagtaagc tggtggtaga cttttagtag gtgctcaata aatccttttg agtgactgag accaactttg
gggtgaggat ttttgaaacc gtcttcagtc tctccaaaca gctgtgtccg ttctccacat ccttgtcaga cctcacctct gcttgtgctc cctccctccc
aggtggtgcc cctgcatccc taaaagcttc agtacagctc ggtggtctgt gtctgcaatg ccacatactg tgactcttga ccccccgacc
tttcctgccc taggtgcctt cagccgctac aagagcagaa gcagtgggca ttggatggag ctgagtacag gaccatacag gctaattgca
ccggcacagg taaccattac acccttcacc ccccgggcca ggctgggtcc tcctagaggt aaacggtgtc agtgatcacc atggagtttc
tccctgggca ctgataaccc tgtggatgtc ctcaggcctg ctactgatcc tgcagccaga agttccagaa agtgaaggga tttggagggg
ccgtgacaga tgcaggtgcc ctcaacatcc ttgccctgtc accccctgcc cagaatttgc tacttaaatg gtacttctct gaagaagatg
aggaggaagg ggacaggatg acatagagcc actgacactt ttctttgcca attctttgga ccctgacttc tgcccatccc tgacatttgg
ttcctgtctt aatgccagtg aaataagatt tcgccgccta tcatctgcta actgctacgg actcaggctc agaaaggcct gcgcttcacc
caggtgccag cctccacagg ttccaaccca ggagcccaag ttccttttgg ccctgactca gacactatta ggactggcaa gtgataagca
gagtcccata ctctcctatt gactcggact accatatctt gatcatcctt ttctgtagga atcggatata acatcatctg ggtacccatg gccagctgtg
acttctccat ccgcacctac acctatgcag acacccctga tgatttccag ttgcacaact tcagcctccc agaggaagat accaagctca
aggtaggcat tctagctttt tcaggccctg agggccctga tgtctggggg ttgagaaact gtagggtagg tctgcttgta cagacatttt
gtcccctgct gttttgtcct gggggtggga gggtgggggc taatggctga accggatgca ctggttgggc tagtatgtgt tccaactctg
ggtgcttctc tcttcactac ctttgtctct agatacccct gattcaccga gccctgcagt tggcccagcg tcccgtttca ctccttgcca gcccctggac
atcacccact tggctcaaga ccaggggagc ggggaatggg aaggggccac tcaagggaca gcccagagac atctaccacc
agacctgggc cagatacatt gtgaagtaag ggatcaacaa ggatgtggga tcaggactgg cctccccttt ggccatgctg atctgtgtcc
caaccctcaa cctggttcca cttccagatc tgcctgtcct cagctcacct ttctaccttc tgggcctttc aaccttgggc ctgtcagtct tgcccactcc
atcaggcttc ctgttctctc ggtctggccc actttcttgg ctggatcatt catgaccttt ctcttgccag gttcctggat gcctatgctg agcacaagtt
acagttctgg gcagtgacag gtgaaaatga gccttctgct gggctgttga gtggataccc cttccagtgc ctgggcttca cccctgaaca
tcagcgagac ttcattgccc gtgacctagg tcctaccctt gccaacggta ctcaccacaa tgtccgccta ctcatgctgg atgaccaacg
cttgctgctg ccccactggg caaaggtggt aaggcctgga cctccatggt gctccagtga ccttcaaatc cagcatccaa atgattggct
cccaaactta gagggatttt tctacccaac tatggatccc tagagcacca ttccccggga cctccagggt gccatggatc ccacagttgg
gacttgaaac ctctctaggg ctgggggtgg tagctcatgg ctataattcc agcactttgg gaaccaaggt gggtggatca cttgaaccta
aggagttcaa gatgagcctg ggaaacatgg tgaaacccta actctacaaa aaaaaaaata gaaaagttag ccgggtgtgg tggtggcacg
ctatagtccc agtattctgg aggctaaggc gggaggttta gttgagccta ggaatttcag gctgcagtga gctatgattg tgccactgta
ctccagcctg tgtgacagag ggagaccctg tctcaaaaac aaaaacaaaa aatccctccc aaaacctctg tagttgcatt cttcccacca

Figure 36 (Continued)

cctaattcag gattcctaca agaggaacta gaagttccag aagcctgtgg gcagggtcca gggtgacttg ttcttccttt gcaggtactg
acagacccag aagcagctaa gtatgttcat ggtattgctg tacattggta cctggacttt ctggctccag ccaaagccac cctaagggag
acacaccacc tgttccccaa caccatgctc tttgcctcag aggcctgtgt gggttccaag ttctgggagc agagtgtgcg gctaggctcc
tgggatcgag ggatgcagta cagccacagc atcatcacag taagccaccc cagtctccct tcctgcaaag gagacctcag acccattagt
agtctcacca aagactgata gaagcccttc ctgtccagct ttccccaggt agcctgccct tttgcgcaac tctggggaac catgattccc
tgtcttgcct ttccttcaca ggtctgcaca cctcattgcc ccttttgcaa ctactgaggc acttgcagct gcctcagact tctcagctcc ccttgagatg
cctggatctt cacaccccca actccttagc tactaaggaa tgtgccctca cagggctgac ctacccacag ctgcctctcc cacatgtgac
ccttacctac actctctggg gacccccagt gttgagcctt tgtctctttg cctttgtcct taccctagaa cctcctgtac catgtggtcg gctggaccga
ctggaaccca tcattgtaga catcaccaag cacacgtttt acaaacagcc catgttctac caccttggcc acttcaggtg agtggagggc
gggcaccccc attccatacc aggcctatca tctcctacat cggatggctt acatcactct acaccacgag ggagcaggaa ggtgttcagg
gtggaacctc ggaagaggca cacccatccc cttttgcacc atggaggcag gaagtgacta ggtagcaaca gaaaacccca atgcctgagg
ctggactgcg atgcagaaaa gcagggtcag tgcccagcag catggctcca ggcctagaga gccagggcag agcctttgca ggagttatgg
ggtgggtccg tgggtgggcg acttcttaga tgagggtttc atgggaggta ccccgaggga ctctgaccat ctgttcccac attcagcaag
ttcattcctg agggctccca gagagtgggg ctggttgcca gtcagaagaa cgacccggac gcagtggcac tgatgcatcc cgatggctct
cctgttgtgg tcgtcctaaa ccggtgaggg caatggtgag gtctgggaag tgggctgaag acagcgttgg gggccttggc aggatcacac
tctcagcttc tcctccctgc tccctagctc ctctaaggat gtgcctctta ccatcaagga tcctgctgtg ggcttcctgg agacaatctc
acctggctac tccattcaca cctacctgtg gcgtcgccag tgatggagca gatactcaag gaggcactgg gctcagcctg ggcattaaag
ggacagagtc agctcacacg ctgtctgtga ctaaagaggg cacaacaggg ccagtgtgag cttacagcga cgtaagccca ggggcaatgg
tttgggtgac tcactttccc ctctaggtgg tgcccagggc tggaggcccc tagaaaaaga tcagtaagcc ccagtgtccc cccagccccc
atgcttatgt gaacatgcgc tgtgtgctgc ttgctttgga aactggcctg ggtccaggcc tagggtgagc tcactgtccg tacaaacaca
agatcagggc tgagggtaag gaaaagaaga gactaggaaa gctgggccca aaactggaga ctgtttgtct ttcctggaga tnnnnnnctg
ggcccgtgga gcagcagtgt cagcatcagg gcggaagcct taaagcagca gcgggtgtgc ccaggcaccc agatgattcc tatggcacca
gccaggaaaa atggcagctc ttaaaggaga aaatgtttga gcccagtcag tgtgagtggc tttattctgg gtggcagcac ccgtgtccgg
ctgtaccaac aacgaggagc acgggggcct ctggaagtca tgagagtaga aaaaccagtc ttggggagt

Figure 37A

MTEGTCLRRRGGPYKTEPATDLGRWRLNCERGRQTWTYLQDERAGREQTGLEAYALGLDTKN
YFKDLPKAHTAFEGALNGMTFYVGLQAEDGHWTGDYGGPLFLLPGLLITCHVARIPLPAGYREEI
VRYLRSVQLPDGGWGLHIEDKSTVFGTALNYVSLRILGVGPDDPDLVRARNILHKKGGAVAIPSW
GKFWLAVLNVYSWEGLNTLFPEMWLFPDWAPAHPSTLWCHCRQVYLPMSYCYAVRLSAAEDP
LVQSLRQELYVEDFASIDWLAQRNNVAPDELYTPHSWLLRVVYALLNLYEHHHSAHLRQRAVQK
LYEHIVADDRFTKSISIGPISKTINMLVRWYVDGPASTAFQEHVSRIPDYLWMGLDGMKMQGTNG
SQIWDTAFAIQALLEAGGHHRPEFSSCLQKAHEFLRLSQVPDNPPDYQKYYRQMRKGGFSFSTL
DCGWIVSDCTAEALKAVLLLQEKCPHVTEHIPRERLCDAVAVLLNMRNPDGGFATYETKRGGHL
LELLNPSEVFGDIMIDYTYVECTSAVMQALKYFHKRFPEHRAAEIRETLTQGLEFCRRQQRADGS
WEGSWGVCFTYGTWFGLEAFACMGQTYRDGTACAEVSRACDFLLSRQMADGGWGEDFESCE
ERRYLQSAQSQIHNTCWAMMGLMAVRHPDIEAQERGVRCLLEKQLPNGDWPQENIAGVFNKS
CAISYTSYRNIFPIWALGRFSQLYPERALAGHP

Figure 37B ccccttgccta ctgctcatgg gtgtggagac tgatattctg gaagactgat aggcagattt actattaaca aacacatagt ctgtggccca
gcaaagccac cccaatccct gcacaagggt aaaaggccag cattagagca ctgcagcagc aatgacggag ggcacgtgtc tgcggcgccg
agggggcccc tacaagaccg agcccgccac cgacctcggc cgctggcgac tcaactgcga gaggggccgg cagacgtgga
cctacctgca ggacgagcgc gccggccgcg agcagaccgg cctggaagcc tacgccctgg ggctggacac caagaattac tttaaggact
tgcccaaagc-ccacaccgcc tttgaggggg ctctgaacgg gatgacattt tacgtggggc tgcaggctga ggatgggcac tggacgggtg
attatggtgg cccacttttc ctcctgccag gcctcctgat cacttgccac gtggcacgca tccctctgcc agccggatac agagaagaga
ttgtgcggta cctgcggtca gtgcagctcc ctgacggtgg ctggggcctg cacattgagg ataagtccac cgtgtttggg actgcgctca
actatgtgtc tctcagaatt ctgggtgttg ggcctgacga tcctgacctg gtacgagccc ggaacattct tcacaagaaa ggtggtgctg
tggccatccc ctcctggggg aagttctggc tggctgtcct gaatgtttac agctgggaag gcctcaatac cctgttccca gagatgtggc
tgtttcctga ctgggcaccg gcacacccct ccacactctg gtgccactgc cggcaggtgt acctgcccat gagctactgc tacgccgttc
ggctgagtgc cgcggaagac ccgctggtcc agagcctccg ccaggagctc tatgtggagg acttcgccag cattgactgg ctggcgcaga
ggaacaacgt ggcccccgac gagctgtaca cgcccccacag ctggctgctc cgcgtggtat atgcgctcct caacctgtat gagcaccacc
acagtgccca cctgcggcag cgggccgtgc agaagctgta tgaacacatt gtggccgacg accgattcac caagagcatc agcatcggcc
cgatctcgaa aaccatcaac atgcttgtgc gctggtatgt ggacgggccc gcctccactg ccttccagga gcatgtctcc agaatcccgg
actatctctg gatgggcctt gacggcatga aaatgcaggg caccaacggc tcacagatct gggacaccgc attcgccatc caggctctgc
ttgaggcggg cggcaccac aggcccgagt tttcgtcctg cctgcagaag gctcatgagt tcctgaggct ctcacaggtc ccagataacc
ctcccgacta ccagaagtac taccgccaga tgcgcaaggg tggcttctcc ttcagtacgc tggactgcgg ctggatcgtt tctgactgca
cggctgaggc cttgaaggct gtgctgctcc tgcaggagaa gtgtccccat gtcaccgagc acatccccag agaacggctc tgcgatgctg
tggctgtgct gctgaacatg agaaatccag atggagggtt cgccacctat gagaccaagc gtgggggggca cttgctggag ctgctgaacc
cctcggaggt cttcggggac atcatgattg actacaccta tgtggagtgc acctcagccg tgatgcaggc gcttaagtat ttccacaagc
gtttcccgga gcacagggca gcggagatcc gggagaccct cacgcagggc ttagagttct gtcggcggca gcagagggcc gatggctcct
gggaaggctc ctggggagtt tgcttcacct acggcacctg gtttggcctg gaggccttcg cctgtatggg gcagacctac cgagatggga
ctgcctgtgc agaggtctcc cgggcctgtg acttcctgct gtcccggcag atggcagacg gaggctgggg ggaggacttt gagtcctgcg
aggagcggcg ttatttgcag agtgcccagt cccagatcca taacacatgc tgggccatga tggggctgat ggccgttcgg catcctgaca
tcgaggccca ggagagagga gtccggtgtc tacttgagaa acagctcccc aatggcgact ggccgcagga aaacattgct ggggtcttca
acaagtcctg tgccatctcc tacacgagct acaggaacat cttccccatc tgggccctcg gccgcttctc ccagctgtac cctgagagag
cccttgctgg ccacccctga gaacatgcct acctgctggg tgccgtctgt gcgttccagt gaggccaagg ggtcctggcc gggttgggga
gccctcccat aaccctgtct tgggctccaa cccctcaacc tctatctcat agatgtgaat ctgggggcca ggctggaggc agggatgggg
acagggtggg tggcttagac tcttgatttt tactgtaggt tcatttctga aagtagcttg tcgggcttgg gtgaggaagg gggcacagga
gccgtgaccc ctgaggaggc acagcgcctt ctgccacctc tgggcacggc ctcaaggtag tgaggctagg aggtttttc tgaccaatag
ctgagttctt gggagaggag cagctgtgcc tgtgtgattc cttagtgtcg agtgggctct gggctggggt cggccctggg caggcttctc
ctgcaccttt tgtctgctgg gctgagggac acgagggcaa ccctgtgaca atggcaggta gtgtgcatcc gtgaatagcc cagtgcgggg
gttgctcatg gagcatcctg aggccgtgca gcagggagcc ccatgcccct gggtcgtgag cttgcctgcg tatggggtgg tgtcatggag
cctcatgccc ctgggtcgtg agctcgcctg agtatggggt ggtgtcatgg agccgcatac ccctgggttg tgagctcgcc tgcatatgca
gggtctgtca tggaacatcc caagtctgtg cagcagggag ccccatgccc ctgggacatg aacccacctg cgtggaatgc tgtttgtgag
gtgtctacag ggtttatagt agtcttgtgg acacagaaat gcacagggga cacttacgga cacaga

Figure 38 gacgacgact tgctgttcga ggatgtgtac gagctgtgcg aggtgatcgg aaagggtccc ttcagtgttg tacgacgatg
tatcaacaga gaaactgggc aacaatttgc tgtaaaaatt gttgatgtag ccaagttcac atcaagtcca gggttaagta
cagaagatct aaagcgggaa gccagtatct gtcatatgct gaaacatcca cacattgtag agttattgga gacatatagc
tcagatggaa tgctttacat ggttttcgaa ttgtgagtgt gtattttaat tcttaaaggg taaaacttga agcaatgttg
gtgttggata atgctaacac ttttctcttg aaatttagca gtagttgtga acttatctgt tcagaaagac ctaaagtcac
aagaaaaaag gattatgtca tcataaggtt tacagtggca aaggaagcaa aagctgggca tattcagtta ctcttcatgc
tttcagcatg cttcagagaa gagact

Figure 39 gagcctcaaa tatctccaaa atctgatacc aatccttttg attgtgaatt atattctgta gctaccaaag aaggaagaag aaaactagga
aggagtaagc acaaagatct cttcacattc tccgggactg cggtaccaaa tatcagcaca gcacttcttg aaaaaggatg tagattttaa
tctgaacttt gaaccatcac tgaggtggcc cgccggtttc tgagccttc

Figure 40A

MDGKVAVQERGPPAVSWVPEEGEKLDQEDEDQVKDRGQWTNKMEFVLSVAGEIIGLGNVWRF
PYLCYKNGGGAFFIPYFIFFFVCGIPVFFLEVALGQYTSQGSVTAWRKICPLFQGIGLASVVIESYL
NVYYIIILAWALFYLFSSFTSELPWTTCNNFWNTEHCTDFLNHSGAGTVTPFENFTSPVMEFWER
RVLGITSGIHDLGSLRWELALCLLLAWVICYFCIWKGVKSTGKVVYFTATFPYLMLVILLIRGVTLP
GAYQGIIYYLKPDLFRLKDPQVWMDAGTQIFFSFAICQGCLTALGSYNKYHNNCYKDCIALCFLNS
ATSFVAGFVVFSILGFMSQEQGVPISEVAESGPGLAFIAFPKAVTMMPLSQLWSCLFFIMLIFLGL
DSQFVCVECLVTASIDMFPRQLRKSGRRELLILTIAVMCYLIGLFLVTEGGMYIFQLFDYYASSGIC
LLFLSLFEVVCISWVYGADRFYDNIEDMIGYRPWPLVKISWLFLTPGLCLATFLFSLSKYTPLKYNN
VYVYPPWGYSIGWFLALSSMVCVPLFVVITLLKTRGPFRKRLRHVITPDSSLPQPKQHPCLDGSA
GRNFGPSPTREGLIAGEKETHL

Figure 40B gtaccggttc ggaattcccg ggtcgaccca cgcgtccgga aggctacaga gagagccagg ttttggtgcc atgcacacag ggaaacttag
agttcagaga gggggtgtga tttgcctgac ctcacacagc aagttagaga cccagctcca cgactcattg tcttgctgcc cagagctgct
ggctcccctg tttactctga gctgatcgat caccttagca cacagctggc taggagagaa ccatgcagtc acttcggcca cacctgcccg
ttgacccttg ctacctcggc aggctttgat cccttctgac ctggaggcca gaggctaggc tgaggtcact cagcagacat caaggacctg
ggcagatggg ccggctggga tggtggcgag ctgtacagat aaaaagggac atgaaaatga aaagcccgag cctgagtttt catcacggtt
ccactcctga gtggtcttgg gtgaatcact tcatctgcca aggcctggat ttcctcatct gcaaactcag aaaactaagg ctttggccct
cgtcatcctg cccacccagc ggggcttccc aacccaccac acagccatgg acgggaaggt ggcagtgcaa gagcgtgggc ctcctgcggt
ctcctgggtc cccgaggagg gagagaagtt ggaccaggaa gacgaggacc aggtgaagga tcggggccaa tggaccaaca
agatggagtt tgtgctgtca gtggccgggg agatcattgg gctgggcaat gtctggaggt ttccctatct ctgctacaaa aacggaggtg
gagccttctt catcccctac ttcatcttct tctttgtctg cggcatcccg gtgttcttcc tggaggtggc gttgggccaa tacaccagcc aagggagtgt
cacagcctgg aggaagatct gccccctctt ccagggcatt ggtctggcat ctgtggtcat cgagtcatat ttgaatgtct actacatcat
catccttgcc tgggctctct tctacctgtt cagctccttc acttctgagc tgccctggac gacctgcaac aacttttgga acacagagca
ttgcacggac tttctgaacc actcaggagc cggcacagtg accccatttg agaattttac ctcacctgtc atggaattct gggagagacg
agttctgggc atcacctcgg gcatccatga cctgggctcc ctgcgctggg agctggccct gtgcctcctg ctcgcctggg tcatctgcta
tttctgcatc tggaaggggg tcaagtccac aggcaaggtg gtttatttca cagccacgtt tccgtacctg atgcttgtca ttttgctgat cagaggtgtc
acccttcccg gagcctacca gggcatcatc tactacttga agccagattt gttccgcctc aaggaccctc aggtgtggat ggatgcgggc
acccagatct tcttctcctt tgccatctgc caggggtgcc tgacagccct gggcagctac aacaagtatc acaacaactg ctacaaggac
tgcatcgccc tctgcttcct gaacagtgcc accagctttg tggctgggtt tgttgtcttc tccatcctgg gcttcatgtc ccaagagcaa
ggggtgccca tttctgaagt ggccgagtca ggtcctgggc tggccttcat cgccttcccc aaggctgtga ctatgatgcc cttatcccag
ctgtggtcct gcctgttctt tatcatgctc atattcctag ggctggacag ccagtttgtc tgtgtggagt gcctggtgac agcctccata gacatgttcc
ccaggcagct ccggaagagc gggcggcgcg agctcctcat cctcaccatc gccgtcatgt gctacctgat agggcttttc ctggtcaccg
agggcgggat gtacatcttc cagctgtttg actactatgc ttccagtggc atatgcctgc tgttcctgtc attgtttgaa gtggtctgca taagctgggt
gtatggggcg gaccgtttct atgacaacat tgaggacatg attggctacc ggccatggcc cctggtgaag atctcctggc tcttcctgac
ccctggactt tgcctggcca ctttcctctt ctccttgagc aagtacaccc ccctcaagta caacaacgtc tatgtgtacc cgccctgggg
atactccatt ggctggttcc tggctctgtc ctccatggtc tgtgtcccac tcttcgtcgt catcaccctc ctgaagactc ggggtccttt caggaagcgt
ctgcgtcacg tcatcacccc tgactccagt ctgccacagc ccaagcaaca tccctgcttg gatggcagtg ctggccggaa ctttgggccc
tccccaacaa gggaaggact gatagccggg gagaaggaga cccatttgta gggtgtggcc agagcgaggc ggctcctaag ccgggaacct
aggtcagggc caccctccat tctcagcgga cagcctctgc ctctgtctcc tgccacaatc ctgctgggaa ctctggagag ccacaggcac
ccccagctgg aggccagact cctctcttgt gctagctgga gcagctcctt cccctttgct gataacacca ccactgggac gtgccatgtt
gggacgccac tccctgtgga aggcaccatc gtttttataa aggggggtct tttggaggc cgccatctga ttgcaacacc tcgagttatg
aggattccac tgtggggatg cctcttgtta gagcgtactg catttgtaca cggggagagg agctataatt ggaacgcaca ctgccgtcca
atgtggagag cctgatggga caataccctg ttggaagtga caactgaaca cactgtgttg gatcggaggt tccgttaggg gatccttcct
taggcttaac gacagaggca agcctttgca tgccgtcagt ctggagtttc ctccgagtct ctcatggcat ctccagctcc tgccctagtt
ccgcactgtt cttgcagtgt ttcatcaact cctggagcat tggaatggaa ggggcttggg agatgattcc tagacttcac aaacactcgg
catgcctccc tgcactgtcc gttcctctgc ccaaggccga tattgctaac tgatcacaga ttctttccca cctcacaatc ctccgaatgt
gctccaggcg acaccatttg ccatcctgct tctaacgcaa acccctgact tcatggatga ggaacctgga gaccaaagag acaaagggac
tttttcaagt tcacatgggg accccccttct tgggggccag agatatgact aaaaccttat ctccttgtgc tcaggccagt gtcttcccat
taaccccctg ccttagttaa caagtgtgta tggattgcca

Figure 41A

MGTQKVTPALIFAITVATIGSFQFGYNTGVINAPEKIIKEFINKTLTDKGNAPPSEVLLTSLWSLSVAI
FSVGGMIGSFSVGLFVNRFGRRNSMLIVNLLAVTGGCFMGLCKVAKSVEMLILGRLVIGLFCGLC
TGFVPMYIGEISPTALRGAFGTLNQLGIVVGILVAQIFGLEFILGSEELWPLLLGFTILPAILQSAALP
FCPESPRFLLINRKEEENAKQILQRLWGTQDVSQDIQEMKDESARMSQEKQVTVLELFRVSSYR
QPIIISIVLQLSQQLSGINAVFYYSTGIFKDAGVQEPIYATIGAGVVNTIFTVVSLFLVERAGRRTLHM
IGLGGMAFCSTLMTVSLLLKDNYNGMSFVCIGAILVFVAFFEIGPGPIPWFIVAELFSQGPRPAAM
AVAGCSNWTSNFLVGLLFPSAAHYLGAYVFIIFTGFLITFLAFTFFKVPETRGRTFEDITRAFEGQA
HGADRSGKDGVMEMNSIEPAKETTTNV

Figure 41B gtggggtggg gtggggctgg gggcttgtcg ccctttcagg ctccaccctt tgcggagattataaatagtc atgatcccag cgagacccag
agatgcctgt aatggtgaga ctttggatcc ttcctgagga cgtggagaaa actttctgct gagaaggaca ttttgaaggt tttgttggct
gaaaaagctg tttctggaat cacccctaga tctttcttga agacttgaat tagattacag cgatggggac acagaaggtc accccagctc
tgatatttgc catcacagtt gctacaatcg gctctttcca atttggctac aacactgggg tcatcaatgc tcctgagaag atcataaagg
aatttatcaa taaaactttg acggacaagg gaaatgcccc accctctgag gtgctgctca cgtctctctg gtccttgtct gtggccatat
tttccgtcgg gggtatgatc ggctcctttt ccgtcggact cttcgtcaac cgctttggca ggcgcaattc aatgctgatt gtcaacctgt tggctgtcac
tggtggctgc tttatgggac tgtgtaaagt agctaagtcg gttgaaatgc tgatcctggg tcgcttggtt attggcctct tctgcggact ctgcacaggt
tttgtgccca tgtacattgg agagatctcg cctactgccc tgcggggtgc ctttggcact ctcaaccagc tgggcatcgt tgttggaatt
ctggtggccc agatctttgg tctggaattc atccttgggt ctgaagagct atggccgctg ctactgggtt ttaccatcct tcctgctatc ctacaaagtg
cagcccttcc attttgccct gaaagtccca gatttttgct cattaacaga aaagaagagg agaatgctaa gcagatcctc cagcggttgt
ggggcaccca ggatgtatcc caagacatcc aggagatgaa agatgagagt gcaaggatgt cacaagaaaa gcaagtcacc gtgctagagc
tctttagagt gtccagctac cgacagccca tcatcatttc cattgtgctc cagctctctc agcagctctc tgggatcaat gctgtgttct attactcaac
aggaatcttc aaggatgcag gtgttcaaga gcccatctat gccaccatcg gcgcgggtgt ggttaatact atcttcactg tagtttctct atttctggtg
gaaagggcag gaagaaggac tctgcatatg ataggccttg gagggatggc tttttgttcc acgctcatga ctgtttcttt gttattaaag
gataactata atgggatgag ctttgtctgt attggggcta tcttggtctt tgtagccttc tttgaaattg gaccaggccc cattccctgg tttattgtgg
ccgaactctt cagccagggc cccccgcccag ctgcgatggc agtggccggc tgctccaact ggacctccaa cttcctagtc ggattgctct
tcccctccgc tgctcactat ttaggagcct acgtttttat tatcttcacc ggcttcctca ttaccttctt ggcttttacc ttcttcaaag tccctgagac
ccgtggcagg actttgagg atatcacacg ggcctttgaa gggcaggcac acggtgcaga tagatctgga aaggacggcg tcatggagat
gaacagcatc gagcctgcta aggagaccac caccaatgtc taagtcgtgc ctccttccac ctccctcccg gcatgggaaa gccacctctc
cctcaacaag ggagagacct catcaggatg aacccaggac gcttctgaat gctgctactt aattcctttc tcatcccacg cactccatga
gcaccccaag gctgcggttt gttggatctt caatggcttt ttaaatttta tttcctggac atcctcttct gcttaggaga gaccgagtga acctaccttc
atttcaggag ggattggccg cttggcacat gacaactttg ccagcttttc ctcccttggg ttctgatatt gccgcactag gggatatagg
agaggaaaag taaggtgcag ttcccccaac ctcagactta ccaggaagca gatacatatg agtgtggaag ccggagggtg tttatgtaag
agcaccttcc tcacttccat acagctctac gtggcaaatt aacttgagtt ttatttattt tatcctctgg tttaattaca taattttttt ttttttactt
taagtttcag gatacatgtg ccgaatgtgc aggtttgtta cataggtata tatatgccat gatggaaata tttatttttt taagcgtaat tttgccaaat
aataaaaaca gaaggaaatt gagattagag ggaggtgttt aaagagaggt tatagagtag aagatttgat gctggagagg ttaaggtgca
ataagaattt agggagaaat gttgttcatt attggagggt aaatgatgtg gtgcctgagg tctgtacgtt acctcttaac aatttctgtc cttcagatgg
aaactcttta acttctcgta aaagtcatat acctatataa taaagctact gatttccttg gagctttttt ctttaagata atagtttaca tgtagtagta
cttgaaatct aggattatta actaatatgg gcattgtagt taatgatggt tgatgggttc taattttgga tggagtccag ggaagagaaa gtgatttcta
gaaagcctgt tcccctcact ggatgaaata actccttctt gtagtagtct cattactttt gaagtaatcc cgccacctat ctcgtgggag
agccatccaa ataagaaacc taaaataatt ggttcttggt agagattcat tatttttcca ctttgttctt taggagattt taggtgttga ttttctgttg
tattttaact catacctttta aaggaattcc ccaaagaatg tttatagcaa acttggaatt tgtaacctca gctctgggag aggatttttt tctgagcgat
tattatctaa agtgtgttgt tgctttaggc tcacggcacg cttgcgtatg tctgttacca tgtcactgtg gtcctatgcc gaatgccctc aggggacttg
aatctttcca ataaaccagg tttagacagt atgagtcaat gtgcagtgta gcccacactt gagaggatga atgtatgtgc actgtcactt
tgctctgggt ggaagtacgt tattgttgac ttattttctc tgtgtttgtt cctacagccc ctttttcata tgttgctcag tctccctttc ccttcttggt
gcttacacat ctcagaccct ttagccaaac ccttgtcagt gacagtattt tggttcttag ttctcactgt tccctctgct cctggagcct ttgaataaaa
atgcacgtag ctgaggccgg atgcggtggc tcacgcctgt aatcccagca ctttgggagg cctaggcggg cggtcagggg ttcgagacca
gtctggccaa catcgtgaaa ccctgtctct actaaaaatg caaaaattag ccgggcgtgg tggcgggcgc ctgtaatccc agctacttgg

Figure 41B (Continued)

gaagctgagg cgggagaatc atgtgaaccc gggacgcagg ggttgcagtg agcggagatc gcatcattgc actctagcct gggccacagg
gcgagactcc gtctcaaaaa aaaaaaaatg cacatagcta tcgagtgtgc tttagcttga aaaggtgacc ttgcaacttc atgtcaactt
tctggctcct caaacagtag gttggcagta aggcagggtc ccatttctca ctgagaagat tgtgaatatt tccatatgga ttttctattg ttactctggt
tctttgtttt aaaataaaaa ttctgaatgt acacg

Figure 42 gccgagagcg ggatccgcgc tccctcggtc cttcctccct cccctcttgc ggcctcccgc tgtcatctgg agccgctcct gccgccccct
ggcggcgacc gcgggaaggg ccggccccca tccgcacccc tgaccccgga ggtcaacaac gggatggtcc ctgggtccca
ggggaagaga catcacccag taggagggag tacggtctag acagaggcca cgagggcggg agggggcgag agtggagagt
ggcccagctg gccagggtcg tctaagtgag aggaaaaggg agagggcggt tgagaccagg ccctgaattc cgcgttcatc ttatcctgag
gtctgtgggg acctgttgaa ggactggggc aggggacgga cgcgggcatc cttccatttg gaacagccat tccggcagca tcaggatggg
gcggaggcaa agcggggagt gggcgaggca agtggtgctg taaacctgtg cgagaagggg gcggtgactc taagggcagg
aaggagccct ggtcacacac acactcccac gcaaggtatt cagtgccgag tgtggccttg gtgctaggat tcaaagagga aaggaagaaa
actttccatt ctaaaagaaa ctccacgtga ggcgaagaag atgaaatata gtcagaaaac cataccagta ggtggtaggt aaatgcagaa
gtatttaaga gctcatacag gagtacctgc ctcaggacag ggaatctgag atgctctgca gagctggatc ttaaagaacg gattaagttg
ataaatgatg catacgacat cctatagaag actgtcacca ccccacctca ctgatcagcc ctctgcctac agccacaccc acagaacatt
cagccatttc tcctgtggtt cccagcctgc agcacagcgt ctgcacgtgg tgagggctcc caaatctctg aggaatgaat ggctcactgc
tgagagcaac cttctgggag ttcagggcat gtggaactgg aataagagca acgtgtgaac agattacagg aaggcaatgc aggacagctg
gacccttlgg ggggaaactt atggggaaca cagttttctt acttataagc actgagattg cctgagaggg gagagatgat gcagagtgtc
ccaaatgtat ttgacgtgga atccttttac cagcgaaaca tctcttgggc ctagagttct gaaaattgca ctttgaaaaa cactgctctc
agctcttaca aacctcgtgt tttcatccta actgtgcttc agagaattgt gtcccagcag gaaaggaaac ccccgtataa ttccctacgt
tgctagcatt tggaagtggg atgaaaatgg acctacattc aaacccctaa tttcaagctc tgaaggaggt accaggatcc atcacgatgc
ttgtaaaatt gttcctttca ttttcctggt tgtaaactta tgcagactgt aaagtcaagg caagcctgtg cccagcaaat aataagaaaa
taagggaggc atggtaaaca aaacaaaaca ctttgagagt tggtcaactt gctgttattt tgagctgttt ctaaaaatct cagggtagat
tccctcccct gcttgcctcc ttaacccagt ccttttcttt cctcctccag gaactctgga atgctgacct acagtctgag ttcctgtgcc cttgcctggg
gctgactctc tacttgacct gtaacccaca actgggcaag agaaaattct gcagccacag ctctgaggac atgagcaaaa tggtttccag
acggaatgtc aaggattccc atgaagtgtc agggagtctt caggccacac ttcaggttat ctccttctct ttccctttc tgcttcacac ttgctctcat
cctctttctc accccacatc tggtcagagg agataggaag gttcttgtta cctggtacaa gacaactttt ggaatcccag atattcagat
tatttcccct tttcctcttt gcaaatgata atactcacag ccaagaggca tcacccggat ccgaggctgc ttctccttag gacatgcaga
cagaaggaga aggcggggct ggcagcctcc agtccacagc ctccctttct tcttccggcg atgattaact aggcctagac aatggagatc
tacggcatac gcccagggcc tcctcttctc aagcatggct gatcagtcac tttcccgtct atccttcatt tattgaagcc aactatgaac
gactaaagga aggatgagaa aagtcaccca aagtcaaagg ggacagcgtg ggagactgtt ctagacagaa ggaaacacct
ttgcaaagac cctgaggaag gcaggggact ctccaggagc agaagggctg tgtggcttca gagtccacaa aagagagcag atacaggaca
ctggctagag caggccctgg agcccgctgc tgtcctggag gccttgggga ggcccagtgt tcccagggtg gaagaagtag gggacagctt
gacgtagtgg ctgttgatca gctgatatgg aagtatgtca ttttattaac aattgagaaa ggagtgctgt gcaattccat tcaatgccag
tgatgcttat ggccgttttt atgagttctg tcattttcaa atgagcaaga ggaagcctct aagggggttt aagcagggac tgacgtaatc
agatctgtgt ttttccaaag ggagagggag aaaaagaaca tttcttattt ttcaaaaaag gtaatgcaaa agcatcattc cacaattctc
ttgtaatgaa aaaaataaat gcaaacttaa gcaaatccat cattctgaaa gaaaaaaaaa aaaaaaaaaa aaaaaaaaaa
aaaaaaaaaa aa

Figure 43A

MPLLWLRGFLLASCWIIVRSSPTPGSEGHSAAPDCPSCALAALPKDVPNSQPEMVEAVKKHILN
MLHLKKRPDVTQPVPKAALLNAIRKLHVGKVGENGYVEIEDDIGRRAEMNELMEQTSEIITFAESG
TARKTLHFEISKEGSDLSVVERAEVWLFLKVPKANRTRTKVTIRLFQQQKHPQGSLDTGEEAEEV
GLKGERSELLLSEKVVDARKSTWHVFPVSSSIQRLLDQGKSSLDVRIACEQCQESGASLVLLGKK
KKKEEEGEGKKKGGGEGGAGADEEKEQSHRPFLMLQARQSEDHPHRRRRRGLECDGKVNICC
KKQFFVSFKDIGWNDWIIAPSGYHANYCEGECPSHIAGTSGSSLSFHSTVINHYRMRGHSPFANL
KSCCVPTKLRPMSMLYYDDGQNIIKKDIQNMIVEECGCS

Figure 43B tccacacaca caaaaaacct gcgcgtgagg ggggaggaaa agcagggcct ttaaaaaggc aatcacaaca acttttgctg ccaggatgcc
cttgctttgg ctgagaggat ttctgttggc aagttgctgg attatagtga ggagttcccc caccccagga tccgaggggc acagcgcggc
ccccgactgt ccgtcctgtg cgctggccgc cctcccaaag gatgtaccca actctcagcc agagatggtg gaggccgtca agaagcacat
tttaaacatg ctgcacttga agaagagacc cgatgtcacc cagccggtac ccaaggcggc gcttctgaac gcgatcagaa agcttcatgt
gggcaaagtc ggggagaacg ggtatgtgga gatagaggat gacattggaa ggagggcaga aatgaatgaa cttatggagc agacctcgga
gatcatcacg tttgccgagt caggaacagc caggaagacg ctgcacttcg agatttccaa ggaaggcagt gacctgtcag tggtggagcg
tgcagaagtc tggctcttcc taaaagtccc caaggccaac aggaccagga ccaaagtcac catccgcctc ttccagcagc agaagcaccc
gcagggcagc ttggacacag ggaagaggc cgaggaagtg ggcttaaagg gggagaggag tgaactgttg ctctctgaaa aagtagtaga
cgctcggaag agcacctggc atgtcttccc tgtctccagc agcatccagc ggttgctgga ccagggcaag agctccctgg acgttcggat
tgcctgtgag cagtgccagg agagtggcgc cagcttggtt ctcctgggca agaagaagaa gaaagaagag gagggggaag
ggaaaaagaa gggcggaggt gaaggtgggg caggagcaga tgaggaaaag gagcagtcgc acagaccttt cctcatgctg
caggcccggc agtctgaaga ccaccctcat cgccggcgtc ggcggggctt ggagtgtgat ggcaaggtca acatctgctg taagaaacag
ttctttgtca gtttcaagga catcggctgg aatgactgga tcattgctcc ctctggctat catgccaact actgcgaggg tgagtgcccg
agccatatag caggcacgtc cgggtcctca ctgtccttcc actcaacagt catcaaccac taccgcatgc ggggccatag cccctttgcc
aacctcaaat cgtgctgtgt gcccaccaag ctgagaccca tgtccatgtt gtactatgat gatggtcaaa acatcatcaa aaaggacatt
cagaacatga tcgtggagga gtgtgggtgc tcatagagtt gcccagccca gggggaaagg gagcaagagt tgtccagaga agacagtggc
aaaatgaaga aatttttaag gtttctgagt taaccagaaa aatagaaatt aaaaacaaaa caaaacaaaa aaaaaaacaa aaaaaaacaa
aagtaaatta aaaacaaacc tgatgaaaca gatgaaacag atgaaggaag atgtggaaat cttagcctgc cttagccagg gctcagagat
gaagcagtga agagacagat tgggagggaa agggagaatg gtgtaccctt tatttcttct gaaatcacac tgatgacatc agttgtttaa
acggggtatt gtcctttccc cccttgaggt tcccttgtga gcttgaatca accaatctga tctgcagtag tgtggactag aacaacccaa
atagcatcta gaaagccatg agtttgaaag ggcccatcac aggcactttc ctagcctaat

Figure 44

MGLAEYFGFD DHDTDLRTEL VAGLTTFLAM SYIVLVNPVV MTQRTTAGEV VKPGIALANY
SHDQTVQMLA VVTLLASGVA MLVMAFYANR PFALAPGLGL NAFFAFTVVG TLGVPWQTAL
AAVFTEGLLF IVLTAVGARE YVITLFPEPV KLAVGTGIGL YLAIIGLEAM GIVVGDAGTI
LALGNLAQNP VAVVSILGLF FTIALHARGV TGSIVLGIIA TAATGGVLTF AGVVDPGVLI
GDFVRTGGIA TQRLPHAQYD ITPLVGAFLA GFQDIDAFSF ALIVFTFFFV DFFDTAGTLV
GVGQAGGFLN TDGNLPDADE PLMADAIGTT FGAIIGTSTV TTYIESATGV EEGGRTGMVA
LVVAVLFFLS LLVVPLAAAI PQYASHIALV VVALLMLANV TAIDWDDITH SIPAGLTIIV
MPFTYSIAYG IAAGIVSYPV VKVATGDADE VAIGQWLLAA AFIVYFYVRT SGVLAAAV

```
                         SEQUENCE LISTING


<160> NUMBER OF SEQ ID NOS: 69

<210> SEQ ID NO 1
<211> LENGTH: 263
<212> TYPE: PRT
<213> ORGANISM: Homo sapiens

<400> SEQUENCE: 1

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
```

-continued

```
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
                245                 250                 255

Glu Glu Glu Glu Asn Phe Val
            260


<210> SEQ ID NO 2
<211> LENGTH: 2500
<212> TYPE: DNA
<213> ORGANISM: Homo sapiens

<400> SEQUENCE: 2

gttcgccatg cgtcccgggg cgccagggcc actctggcct ctgccctggg gggccctggc      60

ttgggccgtg ggcttcgtga gctccatggg ctcggggaac ccgcgcccg gtggtgtttg     120

ctggctccag cagggccagg aggccacctg cagcctggtg ctccagactg atgtcacccg     180

ggccgagtgc tgtgcctccg gcaacattga caccgcctgg tccaacctca cccacccggg     240

gaacaagatc aacctcctcg gcttcttggg ccttgtccac tgccttccct gcaaagattc     300

gtgcgacggc gtggagtgcg gcccgggcaa ggcgtgccgc atgctggggg gccgcccgcg     360

ctgcgagtgc gcgcccgact gctcggggct cccggcgcgg ctgcaggtct gcggctcaga     420

cggcgccacc taccgcgacg agtgcgagct gcgcgccgcg cgctgccgcg gccacccgga     480

cctgagcgtc atgtaccggg gccgctgccg caagtcctgt gagcacgtgg tgtgcccgcg     540

gccacagtcg tgcgtcgtgg accagacggg cagcgcccac tgcgtggtgt gtcgagcggc     600

gccctgccct gtgccctcca gccccggcca ggagctttgc ggcaacaaca acgtcaccta     660

catctcctcg tgccacatgc gccaggccac ctgcttcctg ggccgctcca tcggcgtgcg     720

ccacgcgggc agctgcgcag gcacccctga ggagccgcca ggtggtgagt ctgcagaaga     780

ggaagagaac ttcgtgtgag cctgcaggac aggcctgggc ctggtgcccg aggcccccca     840

tcatcccctg ttatttattg ccacagcaga gtctaattta tatgccacgg acactcctta     900

gagcccggat tcggaccact tggggatccc agaacctccc tgacgatatc ctggaaggac     960
```

-continued

```
tgaggaaggg aggcctgggg gccggctggt gggtgggata gacctgcgtt ccggacactg   1020

agcgcctgat ttagggccct tctctaggat gccccagccc ctaccctaag acctattgcc   1080

ggggaggatt ccacacttcc gctcctttgg ggataaacct attaattatt gctactatca   1140

agagggctgg gcattctctg ctggtaattc ctgaagaggc atgactgctt ttctcagccc   1200

caagcctcta gtctgggtgt gtacggaggg tctagcctgg gtgtgtacgg agggtctagc   1260

ctgggtgagt acggagggtc tagcctgggt gagtacggag ggtctagcct gggtgagtac   1320

ggagagtcta gcctgggtgt gtatggagga tctagcctgg gtgagtatgg agggtctagc   1380

ctgggtgagt atggagggtc tagcctgggt gtgtatggag ggtctagcct gggtgagtat   1440

ggagggtcta gcctgggtgt gtatggaggg tctagcctgg gtgagtatgg agggtctagc   1500

ctgggtgtgt acggagggtc tagtctgagt gcgtgtgggg acctcagaac actgtgacct   1560

tagcccagca agccaggccc ttcatgaagg ccaagaaggc tgccaccatt ccctgccagc   1620

ccaagaactc cagcttcccc actgcctctg tgtgcccctt tgcgtcctgt gaaggccatt   1680

gagaaatgcc cagtgtgccc cctgggaaag ggcacggcct gtgctcctga cacgggctgt   1740

gcttggccac agaaccaccc agcgtctccc ctgctgctgt ccacgtcagt tcatgaggca   1800

acgtcgcgtg gtctcagacg tggagcagcc agcggcagct cagagcaggg cactgtgtcc   1860

ggcggagcca agtccactct gggggagctc tggcggggac cacgggccac tgctcaccca   1920

ctggccccga ggggggtgta gacgccaaga ctcacgcatg tgtgacatcc ggagtcctgg   1980

agccgggtgt cccagtggca ccactaggtg cctgctgcct ccacagtggg gttcacaccc   2040

agggctcctt ggtcccccac aacctgcccc ggccaggcct gcagacccag actccagcca   2100

gacctgcctc acccaccaat gcagccgggg ctggcgacac cagccaggtg ctggtcttgg   2160

gccagttctc ccacgacggc tcaccctccc ctccatctgc gttgatgctc agaatcgcct   2220

acctgtgcct gcgtgtaaac cacagcctca gaccagctat ggggagagga caacacggag   2280

gatatccagc ttccccggtc tggggtgagg agtgtgggga gcttgggcat cctcctccag   2340

cctcctccag cccccaggca gtgccttacc tgtggtgccc agaaaagtgc ccctaggttg   2400

gtgggtctac aggagcctca gccaggcagc ccaccccacc ctggggccct gcctcaccaa   2460

ggaaataaag actcaaagaa gccttttttt tttttttttt                         2500
```

```
<210> SEQ ID NO 3
<211> LENGTH: 99
<212> TYPE: PRT
<213> ORGANISM: Homo sapiens

<400> SEQUENCE: 3

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

-continued

<210> SEQ ID NO 4
<211> LENGTH: 5191
<212> TYPE: DNA
<213> ORGANISM: Homo sapiens

<400> SEQUENCE: 4
gaattcagta acccaggcat tattttatcc tcaagtctta ggttggttgg agaaagataa 60
caaaaagaaa catgattgtg cagaaacaga caaacctttt tggaaagcat ttgaaaatgg 120 cattcccccct ccacagtgtg ttcacagtgt gggcaaattc actgctctgt cgtactttct 180
gaaaatgaag aactgttaca ccaaggtgaa ttatttataa attatgtact tgcccagaag 240
cgaacagact tttactatca taagaaccct tccttggtgt gctctttatc tacagaatcc 300
aagacctttc aagaaaggtc ttggattctt ttcttcagga cactaggaca taaagccacc 360
tttttatgat ttgttgaaat ttctcactcc atccctttttg ctgatgatca tgggtcctca 420
gaggtcagac ttggtgtcct tggataaaga gcatgaagca acagtggctg aaccagagtt 480
ggaacccaga tgctctttcc actaagcata caactttcca ttagataaca cctccctccc 540
accccaacca agcagctcca gtgcaccact ttctggagca taaacatacc ttaactttac 600
aacttgagtg gccttgaata ctgttcctat ctggaatgtg ctgttctctt tcatcttcct 660
ctattgaagc cctcctattc ctcaatgcct tgctccaact gcctttggaa gattctgctc 720
ttatgcctcc actggaatta atgtcttagt accacttgtc tattctgcta tatagtcagt 780
ccttacattg ctttcttctt ctgatagacc aaactcttta aggacaagta cctagtctta 840
tctatttcta gatcccccac attactcaga aagttactcc ataaatgttt gtggaactga 900
tttctatgtg aagacatgtg ccccttcact ctgttaacta gcattagaaa aacaaatctt 960
ttgaaaagtt gtagtatgcc cctaagagca gtaacagttc ctagaaactc tctaaaatgc 1020
ttagaaaaag atttatttta aattacctcc ccaataaaat gattggctgg cttatcttca 1080
ccatcatgat agcatctgta attaactgaa aaaaaataat tatgccatta aaagaaaatc 1140
atccatgatc ttgttctaac acctgccact ctagtactat atctgtcaca tggtctatga 1200
taaagttatc tagaaataaa aaagcataca attgataatt caccaaattg tggagcttca 1260
gtattttaaa tgtatattaa aattaaatta ttttaaagat caaagaaaac tttcgtcata 1320
ctccgtattt gataaggaac aaataggaag tgtgatgact caggtttgcc ctgaggggat 1380
gggccatcag ttgcaaatcg tggaatttcc tctgacataa tgaaaagatg agggtgcata 1440
agttctctag tagggtgatg atataaaaag ccaccggagc actccataag gcacaaactt 1500
tcagagacag cagagcacac aagcttctag gacaagagcc aggaagaaac caccggaagg 1560
aaccattctc actgtgtgta aacatgactt ccaagctggc cgtggctctc ttggcagcct 1620
tcctgatttc tgcagctctg tgtgaaggta agcacatctt tctgacctac agcgttttcc 1680
tatgtctaaa tgtgatcctt agatagcaaa gctattcttg atgctttggt aacaaacatc 1740
ctttttattc agaaacagaa tataatctta gcagtcaatt aatgttaaat tgaagattta 1800 gaaaaaaacta tatataacac ttaggaaata taaaggtttg atcaatatag atattctgct 1860
tttataattt ataccaggta gcatgcatat atttaacgta aataagtaat ttatagtatg 1920
tcctattgag aaccacggtt acctatatta tgtattaata ttgagttgag caaggtaact 1980
cagacaattc cactccttgt agtatttcat tgacaagcct cagatttgtc attaattcct 2040
gtctggttta aagataccct gattatagac caggcatgta taacttattt atatatttct 2100
gttaattctt tctgaaggca atttctatgc tggagagtct tagcttgcct actataaata 2160

-continued acactgtggt atcacagagg attatgcaat attgaccaga taaaaatacc atgaagatgt 2220
tgatattgta caaaaagaac tctaactctt atataggaag ttgttcaatg ttgtcagtta 2280
tgactgtttt ttaaaacaaa gaactaactg aggtcaaggg ctaggagata ttcaggaatg 2340
agttcactag aaacatgatg ccttccatag tctccaaata atcatattgg aattagaagg 2400
aagtagctgg cagagctgtg cctgttgata aaatcaatcc ttaatcactt tttcccccaa 2460
caggtgcagt tttgccaagg agtgctaaag aacttagatg tcagtgcata aagacatact 2520
ccaaaccttt ccaccccaaa tttatcaaag aactgagagt gattgagagt ggaccacact 2580
gcgccaacac agaaattatg taagtacttt aaaaaagatt agatattttg ttttagcaaa 2640
cttaaaatta aggaaggtgg aaatatttag gaaagttcca ggtgttagga ttacagtagt 2700
aaatgaaaca aaacaaaata aaaatatttg tctacatgac atttaaatat ggtagcttcc 2760
acaactacta taaatgttat tttggactta gactttatgc ctgacttaag gaatcatgat 2820
ttgaatgcaa aaactaaata ttaatctgaa ccatttcttt cttatttcag tgtaaagctt 2880
tctgatggaa gagagctctg tctggacccc aaggaaaact gggtgcagag ggttgtggag 2940
aagtttttga agaggtaagt tatatatttt ttaatttaaa tttttcattt atcctgagac 3000
atataatcca aagtcagcct ataaatttct ttctgttgct aaaaatcgtc attaggtatc 3060
tgcctttttg gttaaaaaaa aaggaatagc atcaatagtg agtttgttgt acttatgacc 3120
agaaagacca tacatagttt gcccaggaaa ttctgggttt aagcttgtgt cctatactct 3180
tagtaaagtt ctttgtcact cccagtagtg tcctatttta gatgataatt tctttgatct 3240
ccctatttat agttgagaat atagagcatt tctaacacat gaatgtcaaa gactatattg 3300
acttttcaag aaccctactt tccttcttat taaacatagc tcatctttat atttttaatt 3360
ttattttagg gctgagaatt cataaaaaaa ttcattctct gtggtatcca agaatcagtg 3420
aagatgccag tgaaacttca agcaaatcta cttcaacact tcatgtattg tgtgggtctg 3480
ttgtagggtt gccagatgca atacaagatt cctggttaaa tttgaatttc agtaaacaat 3540
gaatagtttt tcattgtacc atgaaatatc cagaacatac ttatatgtaa agtattattt 3600
atttgaatct acaaaaaaca acaaataatt tttaaatata aggattttcc tagatattgc 3660
acgggagaat atacaaatag caaaattggg ccaagggcca agagaatatc cgaactttaa 3720
tttcaggaat tgaatgggtt tgctagaatg tgatatttga agcatcacat aaaaatgatg 3780
ggacaataaa ttttgccata aagtcaaatt tagctggaaa tcctggattt ttttctgtta 3840
aatctggcaa ccctagtctg ctagccagga tccacaagtc cttgttccac tgtgccttgg 3900
tttctccttt atttctaagt ggaaaaagta ttagccacca tcttacctca cagtgatgtt 3960
gtgaggacat gtggaagcac tttaagtttt ttcatcataa cataaattat tttcaagtgt 4020
aacttattaa cctatttatt atttatgtat ttatttaagc atcaaatatt tgtgcaagaa 4080
tttggaaaaa tagaagatga atcattgatt gaatagttat aaagatgtta tagtaaattt 4140
attttatttt agatattaaa tgatgtttta ttagataaat ttcaatcagg gtttttagat 4200
taaacaaaca aacaattggg tacccagtta aattttcatt tcagatatac aacaaataat 4260
tttttagtat aagtacatta ttgtttatct gaaattttaa ttgaactaac aatcctagtt 4320
tgatactccc agtcttgtca ttgccagctg tgttggtagt gctgtgttga attacggaat 4380
aatgagttag aactattaaa acagccaaaa ctccacagtc aatattagta atttcttgct 4440
ggttgaaact tgtttattat gtacaaatag attcttataa tattatttaa atgactgcat 4500
ttttaaatac aaggctttat atttttaact ttagtgtttt tatgtgctct ccaaattttt 4560

```
tttactgttt ctgattgtat ggaaatataa aagtaaatat gaaacattta aaatataatt   4620

tgttgtcaaa gtaatcaagt gtttgtcttt tttttagttt tagcttattg ggattctctt   4680

tgtttatatt taaaattata ctttgattta gaaaacataa atgcttcccc ttagcatttt   4740

gttatggaaa attacaaact tttattttta gaaaacagaa ctcctttcca gaaataggtt   4800

acaaacagta gtgtcctcca cagaatgttg gaaatgtttt caactcccca ctgtatacta   4860

tcttgctaat aagtctgtct tcagatttcg attaaccggt ttgtatgtct gtgcacttta   4920

gcatagctgg acattaaaga ggaaagagag tacatattat aagttgctta tcagtaactg   4980

aggagtaaaa ctgataaatg tgaggcaaag aagtttaaaa tatggttaaa gcctaagcat   5040

atttgcaaac aaatcaaaca atactctgag aagtaaaaac ataattattt aattaacaaa   5100

tttcagtgga taaattttat aacaaattag acacagttga aaataaaatt agaaaactag   5160

aaaatagaac aaaagaaact tctggaattc a                                  5191
```

<210> SEQ ID NO 5
<211> LENGTH: 366
<212> TYPE: PRT
<213> ORGANISM: Homo sapiens

<400> SEQUENCE: 5

```
Met Val Leu His Leu Leu Leu Phe Leu Leu Leu Thr Pro Gln Gly Gly
1               5                   10                  15

His Ser Cys Gln Gly Leu Glu Leu Ala Arg Glu Leu Val Leu Ala Lys
            20                  25                  30

Val Arg Ala Leu Phe Leu Asp Ala Leu Gly Pro Pro Ala Val Thr Arg
        35                  40                  45

Glu Gly Gly Asp Pro Gly Val Arg Arg Leu Pro Arg Arg His Ala Leu
    50                  55                  60

Gly Gly Phe Thr His Arg Gly Ser Glu Pro Glu Glu Glu Asp Val
65                  70                  75                  80

Ser Gln Ala Ile Leu Phe Pro Ala Thr Asp Ala Ser Cys Glu Asp Lys
                85                  90                  95

Ser Ala Ala Arg Gly Leu Ala Gln Glu Ala Glu Glu Gly Leu Phe Arg
            100                 105                 110

Tyr Met Phe Arg Pro Ser Gln His Thr Arg Ser Arg Gln Val Thr Ser
        115                 120                 125

Ala Gln Leu Trp Phe His Thr Gly Leu Asp Arg Gln Gly Thr Ala Ala
    130                 135                 140

Ser Asn Ser Ser Glu Pro Leu Leu Gly Leu Leu Ala Leu Ser Pro Gly
145                 150                 155                 160

Gly Pro Val Ala Val Pro Met Ser Leu Gly His Ala Pro Pro His Trp
                165                 170                 175

Ala Val Leu His Leu Ala Thr Ser Ala Leu Ser Leu Leu Thr His Pro
            180                 185                 190

Val Leu Val Leu Leu Leu Arg Cys Pro Leu Cys Thr Cys Ser Ala Arg
        195                 200                 205

Pro Glu Ala Thr Pro Phe Leu Val Ala His Thr Arg Thr Arg Pro Pro
    210                 215                 220

Ser Gly Gly Glu Arg Ala Arg Arg Ser Thr Pro Leu Met Ser Trp Pro
225                 230                 235                 240

Trp Ser Pro Ser Ala Leu Arg Leu Leu Gln Arg Pro Pro Glu Glu Pro
                245                 250                 255

Ala Ala His Ala Asn Cys His Arg Val Ala Leu Asn Ile Ser Phe Gln
```

-continued

```
            260                 265                 270

Glu Leu Gly Trp Glu Arg Trp Ile Val Tyr Pro Pro Ser Phe Ile Phe
        275                 280                 285

His Tyr Cys His Gly Gly Cys Gly Leu His Ile Pro Pro Asn Leu Ser
    290                 295                 300

Leu Pro Val Pro Gly Ala Pro Pro Thr Pro Ala Gln Pro Tyr Ser Leu
305                 310                 315                 320

Leu Pro Gly Ala Gln Pro Cys Cys Ala Ala Leu Pro Gly Thr Met Arg
                325                 330                 335

Pro Leu His Val Arg Thr Thr Ser Asp Gly Gly Tyr Ser Phe Lys Tyr
            340                 345                 350

Glu Thr Val Pro Asn Leu Leu Thr Gln His Cys Ala Cys Ile
        355                 360                 365


<210> SEQ ID NO 6
<211> LENGTH: 1338
<212> TYPE: DNA
<213> ORGANISM: Homo sapiens

<400> SEQUENCE: 6

gaaggactgg ggaagactgg atgagaaggg tagaagaggg tgggtgtggg atggggaggg      60

gagagtggaa aggccctggg cagaccctgg cagaaggggc acggggcagg gtgtgagttc     120

cccactagca gggccaggtg agctatggtg ctgcacctac tgctcttctt gctgctgacc     180

ccacagggtg ggcacagctg ccaggggctg gagctggccc gggaacttgt tctggccaag     240

gtgagggccc tgttcttgga tgccttgggg ccccccgcgg tgaccaggga aggtggggac     300

cctggagtca ggcggctgcc ccgaagacat gccctggggg gcttcacaca caggggctct     360

gagcccgagg aagaggagga tgtctcccaa gccatccttt tcccagccac agatgccagc     420

tgtgaggaca agtcagctgc cagagggctg gcccaggagg ctgaggaggg cctcttcaga     480

tacatgttcc ggccatccca gcatacacgc agccgccagg tgacttcagc ccagctgtgg     540

ttccacaccg ggctggacag gcagggcaca gcagcctcca atagctctga gcccctgcta     600

ggcctgctgg cactgtcacc gggaggaccc gtggctgtgc ccatgtcttt gggccatgct     660

ccccctcact gggccgtgct gcacctggcc acctctgctc tctctctgct gacccacccc     720

gtcctggtgc tgctgctgcg ctgtcccctc tgtacctgct cagcccggcc tgaggccacg     780

cccttcctgg tggcccacac tcggaccaga ccacccagtg gaggggagag agcccgacgc     840

tcaactcccc tgatgtcctg gccttggtct ccctctgctc tgcgcctgct gcagaggcct     900

ccggaggaac cggctgccca tgccaactgc cacagagtag cactgaacat ctccttccag     960

gagctgggct gggaacggtg gatcgtgtac cctcccagtt tcatcttcca ctactgtcat    1020

ggtggttgtg ggctgcacat cccaccaaac ctgtcccttc cagtccctgg ggctccccct    1080

accccagccc agccctactc cttgctgcca ggggcccagc cctgctgtgc tgctctccca    1140

gggaccatga ggcccctaca tgtccgcacc acctcggatg gaggttactc tttcaagtat    1200

gagacagtgc ccaaccttct cacgcagcac tgtgcttgta tctaagggtg gggggtcttc    1260

cttcttaatc ccatggctgg tggccacgcc cccaccatca tcagctggga ggaaaggcag    1320

agttgggaaa tagatggc                                                  1338


<210> SEQ ID NO 7
<211> LENGTH: 419
<212> TYPE: PRT
<213> ORGANISM: Homo sapiens
```

<400> SEQUENCE: 7

```
Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415
```

Gln Met Ser

<210> SEQ ID NO 8
<211> LENGTH: 2015
<212> TYPE: DNA
<213> ORGANISM: Homo sapiens

<400> SEQUENCE: 8
cgcggggtgt tctggtgtcc cccgccccgc ctctccaaaa agctacaccg acgcggaccg 60
cggcggcgtc ctccctcgcc ctcgcttcac ctcgcgggct ccgaatgcgg ggagctcgga 120
tgtccggttt cctgtgaggc ttttacctga cacccgccgc ctttccccgg cactggctgg 180
gagggcgccc tgcaaagttg ggaacgcgga gccccggacc cgctcccgcc gcctccggct 240
cgcccagggg gggtcgccgg gaggagcccg ggggagaggg accaggaggg gcccgcggcc 300
tcgcaggggc gcccgcgccc ccacccctgc ccccgccagc ggaccggtcc cccacccccg 360
gtccttccac catgcacttg ctgggcttct tctctgtggc gtgttctctg ctcgccgctg 420
cgctgctccc gggtcctcgc gaggcgcccg ccgccgccgc cgccttcgag tccggactcg 480
acctctcgga cgcggagccc gacgcgggcg aggccacggc ttatgcaagc aaagatctgg 540
aggagcagtt acggtctgtg tccagtgtag atgaactcat gactgtactc tacccagaat 600
attggaaaat gtacaagtgt cagctaagga aaggaggctg gcaacataac agagaacagg 660
ccaacctcaa ctcaaggaca gaagagacta taaaatttgc tgcagcacat tataatacag 720
agatcttgaa aagtattgat aatgagtgga gaaagactca atgcatgcca cgggaggtgt 780
gtatagatgt ggggaaggag tttggagtcg cgacaaacac cttctttaaa cctccatgtg 840
tgtccgtcta cagatgtggg ggttgctgca atagtgaggg gctgcagtgc atgaacacca 900
gcacgagcta cctcagcaag acgttatttg aaattacagt gcctctctct caaggcccca 960
aaccagtaac aatcagtttt gccaatcaca cttcctgccg atgcatgtct aaactggatg 1020
tttacagaca agttcattcc attattagac gttccctgcc agcaacacta ccacagtgtc 1080
aggcagcgaa caagacctgc cccaccaatt acatgtggaa taatcacatc tgcagatgcc 1140
tggctcagga agattttatg ttttcctcgg atgctggaga tgactcaaca gatggattcc 1200
atgacatctg tggaccaaac aaggagctgg atgaagagac ctgtcagtgt gtctgcagag 1260
cggggcttcg gcctgccagc tgtggacccc acaaagaact agacagaaac tcatgccagt 1320
gtgtctgtaa aaacaaactc ttccccagcc aatgtggggc caaccgagaa tttgatgaaa 1380
acacatgcca gtgtgtatgt aaaagaacct gccccagaaa tcaaccccta aatcctggaa 1440
aatgtgcctg tgaatgtaca gaaagtccac agaaatgctt gttaaaagga aagaagttcc 1500
accaccaaac atgcagctgt tacagacggc catgtacgaa ccgccagaag gcttgtgagc 1560
caggattttc atatagtgaa gaagtgtgtc gttgtgtccc ttcatattgg aaaagaccac 1620
aaatgagcta agattgtact gttttccagt tcatcgattt tctattatgg aaaactgtgt 1680
tgccacagta gaactgtctg tgaacagaga gacccttgtg ggtccatgct aacaaagaca 1740
aaagtctgtc tttcctgaac catgtggata actttacaga aatggactgg agctcatctg 1800
caaaaggcct cttgtaaaga ctggttttct gccaatgacc aaacagccaa gattttcctc 1860
ttgtgatttc tttaaaagaa tgactatata atttatttcc actaaaaata ttgtttctgc 1920
attcattttt atagcaacaa caattggtaa aactcactgt gatcaatatt tttatatcat 1980
gcaaaatatg tttaaaataa aatgaaaatt gtatt 2015

<210> SEQ ID NO 9

<211> LENGTH: 147
<212> TYPE: PRT
<213> ORGANISM: Homo sapiens

<400> SEQUENCE: 9

```
Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Arg Gly Leu Thr Ser Pro Cys Lys
    50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145
```

<210> SEQ ID NO 10
<211> LENGTH: 4668
<212> TYPE: DNA
<213> ORGANISM: Homo sapiens

<400> SEQUENCE: 10

```
tgtttgcatt aagttcatag attataattt gtaatggaat caacaccaaa tgcaaattag     60

aaagagagcc cactttgctc acccagtcac gtcttcccat gtaaccatag aacgttgggg    120

tcctgtgtct ttctagatcc acagtcttgc tctcagaaca ggctagccac accacaggcc    180

tagtgccagg acccatggcc tttttttaag ctcagactcc cttctgtgaa cagcaatatc    240

cccacaactt gtacaacatt ggtgcttcct gcaagggcta cagaactatt tgatacgaaa    300

atgttcattg acttacacac aagagaagca caaaataaaa aattaataat taatttaatg    360

tctttgaaaa tgtaccattt atttttacat ttggggtcat aagaattgta ttacacttaa    420

gaatgcaata caatttgaag atcagatttt tctccctttg tgagaatttc tcagtatgtg    480

tgatgactac caagaaatca tagccagtca taaattcagt gagttactca taaacgaaca    540

agaaccacct acttcttggg gaggtaggtc tgcttccctt caactcagga tacaactgct    600

ttcaactgct ttcttcacat tagctgacta attagctaga agcctgtcgt aaacaatttt    660

atggttgact ccttccctgg gctcagggtt ccctagaaca gagaggtccc caaatcccgg    720

tctgtggcct gtccgcctaa gctctgcctc ctgccagatc agcaggcagc attagattct    780

cataggagct ggacgcctat tgtgaactgc gcatgtgcgg gatccagatt gtgcactctt    840

tatgagaatc taactaatgc ttgatgatct atctgaacca gaacaatttc atcctgaaac    900

catcccccac caatccatag aaatactgtc ttccacaaaa atgatccctg gtgccaaaaa    960

tgttagagac cactccccta aaactctctt cttagctctc acctcctgta ttactatctc   1020

atctcagtac attgaagccc ccatcttttc cccatggatg cctcatttcc tattagggag   1080
```

-continued

```
gcattttttt atttttgtt tttattttt tccgagacgg agtctcgctc tgtcgccaag   1140
gctggagtgc agtggcgcga tctcggctca ctgcaagctc cgcctcccgg gttcacgcca   1200
ttctcctgcc tcagcctccc aagtagctgg gactacaggc gcccgcacta cgcccggcta   1260
atttttgta tttttagtag agacggggtt tcaccgtggt agccaggatg gtctcgatct   1320
cctgacctcg tgatccgccc gccttggcct cccaaagtgc tgggattaca ggcgtgagac   1380
cgcgcccggc cgtcatttgg tatgtcttaa tgtgcctcag gacctagcac agtccctggt   1440
acccagtaga gacctatgta atgttcgtta ttcaataata aatacatgaa ttaaagagtg   1500
agagtggatt ttgtaatgtt acgactgata gagaaatact cagtgattct aagggatggg   1560
gaagaacggt tggagctaga ggttgtgctc aggaaactat taaatagacg ttccgcagga   1620
agggattgac gaagtgtgag gttaatgagg aagggaaaat agaatataaa atttggtggt   1680
ggaaaagatc tgattcatga tgccgtgtca gagagcaaag ctcctgtcct tttggcctaa   1740
tttggtgatg ctgttcttgg gtctaccaca cctccttttg ccctccgcag gagcctgtgt   1800
tggaagagat ggtgatgggc ctgggcgttt tgttgttggt cttcgtgctg ggtctgggtc   1860
tgaccccacc gaccctggct caggataact ccaggtacac acacttcctg acccagcact   1920
atgatgccaa accacagggc cgggatgaca gatactgtga aagcatcatg aggagacggg   1980
gcctgacctc accctgcaaa gacatcaaca catttattca tggcaacaag cgcagcatca   2040
aggccatctg tgaaaacaag aatggaaacc ctcacagaga aaacctaaga ataagcaagt   2100
cttctttcca ggtcaccact tgcaagctac atggaggttc cccctggcct ccatgccagt   2160
accgagccac agcggggttc agaaacgttg ttgttgcttg tgaaaatggc ttacctgtcc   2220
acttggatca gtcaatttc cgtcgtccgt aaccagcggg cccctggtca agtgctggct   2280
ctgctgtcct tgccttccat ttcccctctg cacccagaac agtggtggca acattcattg   2340
ccaagggccc aaagaaagag ctacctggac cttttgtttt ctgtttgaca acatgtttaa   2400
taaataaaaa tgtcttgata tcagtaagaa tcagagtctt ctcactgatt ctgggcatat   2460
tgatctttcc cccatttct ctacttggct gctccctgag aggactgcat aggatagaaa   2520
tgcctttttc ttttcttttc gttttttttt tttttttt ttgagatgga gtctcactct   2580
gtcgcccagg cttaagtgca atggcacaat ctcggctcac tgcaacctct ctctcctggg   2640
ttcaagtgat tctcctgcct cagcctccca aatagctgag attacaggca tgcaccacca   2700
cacctggcta atttttgtgt ttttagtaga gacagggttt caccgttttg gccaggttgg   2760
tcttgaactc ctgacctcgg gagatccgcc caccttggcc tctctttgtg ctgggattac   2820
aggcatgagc cactgagccg ggccactttt tccttatcag tcagttttta caagtcatta   2880
gggaggtaga ctttacctct ctgtgaagga aagtatggta tgttgatcta cagagagaga   2940
tggaaaaatt ccagggctcg tagctactaa gcagaatttc caagataggc aaattgtttt   3000
ttctgtcaaa taataagcta atattacttc tacaaatatg agaccttgga gagaagtttc   3060
caaggaccaa gtaccaacat accaacagat tattatagtt tctctcactc ttacacacac   3120
acacacacat atacacatat gtaatccagc atgaatacca aaattcattc agggtagcca   3180
ccttttgtct taatcgagag ataattttga tgtttgaatg gaatgctccc aggatattct   3240
cttgtcatgg ttattttata taaaattcaa aaaccaatta cattatttcc tctgtaatct   3300
tttactttat caactaatgt ctggcaagtg tgatgttttg gggaagttat agaagattcc   3360
ggccaggcgc ttatctcacg cttgtaatcc agcactttgg gaagctgagg cggacagatc   3420
acgaggtcaa gagatcaaga ccatcctgga caacatggtg aaaccttgtc tctactaaaa   3480
```

-continued

```
atgtgaaaat tagctgggcg tggtggcaca cacctatagt cccagctact cgggaggctg   3540

aggcaggaga atcgcttgaa cctaggaggc ggaggttgca ctgagccgag atcacgccac   3600

tgcactccag cctgggcgac agagcgagac tccatctcaa aaaaaaaaaa aaaagaaaga   3660

tcccagttta tcccagttta tcccttattc ttcctcaatt ctcaagattt gtttttaagt   3720

taacataact taggttaaca cactctttgt aaaatacact gttcaatcta cagactcagt   3780

ggttagcttc ctgttaacta atttctgttg acaggtactt ggatatttta tttagaaagt   3840

ggttgccaat aaattagtta taagtcgcca gtttcactgc cttgtgaaca cataattatt   3900

gtggtctcag tattccctat ggtggcttct cctgctcctg gtattgccct gaaatgggcc   3960

aaaagccgtg gctccccaat gctcaggtta tagaacattg tccaggtacc acctaggaga   4020

gcccagcctc actgaaagta ttcaaattta ggaatgggtt tgagaagtag gtagctggta   4080

tgtgcttagc acaagaatct ctcttccttg ggttagtctg tttcaaaact gaaaacactg   4140

tcattcctta agaaaatagg aaaaagtatt ccaaacctct gtcactagaa aatttgccat   4200

attaccaaat ctcaaaaacc tctcaggaaa tgagaaagtc ccagtttctg gtaaactatt   4260

tgggcccttt tctcaagttc tccttccagt gctatttcct tgaggtgagg caaagttact   4320

caagatcatc gctgccactc aaggccttga tagggcaagt gaaaggcatg gaccattatt   4380

atattgatca cagcataagc tgtgaaaacc cacatcttct ccaaacatct gcttggagca   4440

ttatcatcgc atagtttgct ctggtgttca gggaaatcgc tgtttcatag gaaatcacat   4500

ggcagtggga tgggagtgtt tcctgacctg ccgatggtac tggcacctga gcaagcattc   4560

ctagtccttt ttggtctggg cctcttgttc tatcacaacc acaagctgtt taaaataaaa   4620

acgtcaagtc acaggcaggt cattttatcc tgcgtgaatc aattgaag                4668
```

<210> SEQ ID NO 11
<211> LENGTH: 734
<212> TYPE: PRT
<213> ORGANISM: Homo sapiens

<400> SEQUENCE: 11

```
Met Trp Val Leu Phe Leu Leu Ser Gly Leu Gly Gly Leu Arg Met Asp
1               5                   10                  15

Ser Asn Phe Asp Ser Leu Pro Val Gln Ile Thr Val Pro Glu Lys Ile
            20                  25                  30

Arg Ser Ile Ile Lys Glu Gly Ile Glu Ser Gln Ala Ser Tyr Lys Ile
        35                  40                  45

Val Ile Glu Gly Lys Pro Tyr Thr Val Asn Leu Met Gln Lys Asn Phe
    50                  55                  60

Leu Pro His Asn Phe Arg Val Tyr Ser Tyr Ser Gly Thr Gly Ile Met
65                  70                  75                  80

Lys Pro Leu Asp Gln Asp Phe Gln Asn Phe Cys His Tyr Gln Gly Tyr
                85                  90                  95

Ile Glu Gly Tyr Pro Lys Ser Val Val Met Val Ser Thr Cys Thr Gly
            100                 105                 110

Leu Arg Gly Val Leu Gln Phe Glu Asn Val Ser Tyr Gly Ile Glu Pro
        115                 120                 125

Leu Glu Ser Ser Val Gly Phe Glu His Val Ile Tyr Gln Val Lys His
    130                 135                 140

Lys Lys Ala Asp Val Ser Leu Tyr Asn Glu Lys Asp Ile Glu Ser Arg
145                 150                 155                 160

Asp Leu Ser Phe Lys Leu Gln Ser Ala Glu Pro Gln Gln Asp Phe Ala
                165                 170                 175
```

```
Lys Tyr Ile Glu Met His Val Ile Val Glu Lys Gln Leu Tyr Asn His
            180                 185                 190

Met Gly Ser Asp Thr Thr Val Val Ala Gln Lys Val Phe Gln Leu Ile
        195                 200                 205

Gly Leu Thr Asn Ala Ile Phe Val Ser Phe Asn Ile Thr Ile Ile Leu
    210                 215                 220

Ser Ser Leu Glu Leu Trp Ile Asp Glu Asn Lys Ile Ala Thr Thr Gly
225                 230                 235                 240

Glu Ala Asn Glu Leu Leu His Thr Phe Leu Arg Trp Lys Thr Ser Tyr
                245                 250                 255

Leu Val Leu Arg Pro His Asp Val Ala Phe Leu Leu Val Tyr Arg Glu
            260                 265                 270

Lys Ser Asn Tyr Val Gly Ala Thr Phe Gln Gly Lys Met Cys Asp Ala
        275                 280                 285

Asn Tyr Ala Gly Gly Val Val Leu His Pro Arg Thr Ile Ser Leu Glu
    290                 295                 300

Ser Leu Ala Val Ile Leu Ala Gln Leu Leu Ser Leu Ser Met Gly Ile
305                 310                 315                 320

Thr Tyr Asp Asp Ile Asn Lys Cys Gln Cys Ser Gly Ala Val Cys Ile
                325                 330                 335

Met Asn Pro Glu Ala Ile His Phe Ser Gly Val Lys Ile Phe Ser Asn
            340                 345                 350

Cys Ser Phe Glu Asp Phe Ala His Phe Ile Ser Lys Gln Lys Ser Gln
        355                 360                 365

Cys Leu His Asn Gln Pro Arg Leu Asp Pro Phe Phe Lys Gln Gln Ala
    370                 375                 380

Val Cys Gly Asn Ala Lys Leu Glu Ala Gly Glu Glu Cys Asp Cys Gly
385                 390                 395                 400

Thr Glu Gln Asp Cys Ala Leu Ile Gly Glu Thr Cys Cys Asp Ile Ala
                405                 410                 415

Thr Cys Arg Phe Lys Ala Gly Ser Asn Cys Ala Glu Gly Pro Cys Cys
            420                 425                 430

Glu Asn Cys Leu Phe Met Ser Lys Glu Arg Met Cys Arg Pro Ser Phe
        435                 440                 445

Glu Glu Cys Asp Leu Pro Glu Tyr Cys Asn Gly Ser Ser Ala Ser Cys
    450                 455                 460

Pro Glu Asn His Tyr Val Gln Thr Gly His Pro Cys Gly Leu Asn Gln
465                 470                 475                 480

Trp Ile Cys Ile Asp Gly Val Cys Met Ser Gly Asp Lys Gln Cys Thr
                485                 490                 495

Asp Thr Phe Gly Lys Glu Val Glu Phe Gly Pro Ser Glu Cys Tyr Ser
            500                 505                 510

His Leu Asn Ser Lys Thr Asp Val Ser Gly Asn Cys Gly Ile Ser Asp
        515                 520                 525

Ser Gly Tyr Thr Gln Cys Glu Ala Asp Asn Leu Gln Cys Gly Lys Leu
    530                 535                 540

Ile Cys Lys Tyr Val Gly Lys Phe Leu Leu Gln Ile Pro Arg Ala Thr
545                 550                 555                 560

Ile Ile Tyr Ala Asn Ile Ser Gly His Leu Cys Ile Ala Val Glu Phe
                565                 570                 575

Ala Ser Asp His Ala Asp Ser Gln Lys Met Trp Ile Lys Asp Gly Thr
            580                 585                 590

Ser Cys Gly Ser Asn Lys Val Cys Arg Asn Gln Arg Cys Val Ser Ser
```

-continued

```
        595                 600                 605

Ser Tyr Leu Gly Tyr Asp Cys Thr Thr Asp Lys Cys Asn Asp Arg Gly
    610                 615                 620

Val Cys Asn Asn Lys Lys His Cys His Cys Ser Ala Ser Tyr Leu Pro
625                 630                 635                 640

Pro Asp Cys Ser Val Gln Ser Asp Leu Trp Pro Gly Gly Ser Ile Asp
                645                 650                 655

Ser Gly Asn Phe Pro Pro Val Ala Ile Pro Ala Arg Leu Pro Glu Arg
            660                 665                 670

Arg Tyr Ile Glu Asn Ile Tyr His Ser Lys Pro Met Arg Trp Pro Phe
        675                 680                 685

Phe Leu Phe Ile Pro Phe Phe Ile Ile Phe Cys Val Leu Ile Ala Ile
    690                 695                 700

Met Val Lys Val Asn Phe Gln Arg Lys Lys Trp Arg Thr Glu Asp Tyr
705                 710                 715                 720

Ser Ser Asp Glu Gln Pro Glu Ser Glu Ser Glu Pro Lys Gly
                725                 730


<210> SEQ ID NO 12
<211> LENGTH: 2650
<212> TYPE: DNA
<213> ORGANISM: Homo sapiens

<400> SEQUENCE: 12

catctcgcac ttccaactgc cctgtaacca ccaactgccc ttattccggc tgggacccag     60

gacttcaagc catgtgggtc ttgtttctgc tcagcgggct cggcgggctg cggatggaca    120

gtaattttga tagtttacct gtgcaaatta cagttccgga gaaaatacgg tcaataataa    180

aggaaggaat tgaatcgcag gcatcctaca aaattgtaat tgaagggaaa ccatatactg    240

tgaatttaat gcaaaaaaac tttttacccc ataattttag agtttacagt tatagtggca    300

caggaattat gaaaccactt gaccaagatt ttcagaattt ctgccactac caagggtata    360

ttgaaggtta tccaaaatct gtggtgatgg ttagcacatg tactggactc aggggcgtac    420

tacagtttga aaatgttagt tatggaatag aacccctgga gtcttcagtt ggctttgaac    480

atgtaattta ccaagtaaaa cataagaaag cagatgtttc cttatataat gagaaggata    540

ttgaatcaag agatctgtcc tttaaattac aaagcgcaga gccacagcaa gattttgcaa    600

agtatataga aatgcatgtt atagttgaaa aacaattgta taatcatatg ggtctgata     660

caactgttgt cgctcaaaaa gttttccagt tgattggatt gacgaatgct atttttgttt    720

catttaatat tacaattatt ctgtcttcat tggagctttg gatagatgaa aataaaattg    780

caaccactgg agaagctaat gagttattac acacattttt aagatggaaa acatcttatc    840

ttgttttacg tcctcatgat gtggcatttt tacttgttta cagagaaaag tcaaattatg    900

ttggtgcaac ctttcaaggg aagatgtgtg atgcaaacta tgcaggaggt gttgttctgc    960

accccagaac cataagtctg gaatcacttg cagttatttt agctcaatta ttgagcctta   1020

gtatggggat cacttatgat gacattaaca aatgccagtg ctcaggagct gtctgcatta   1080

tgaatccaga agcaattcat ttcagtggtg tgaagatctt tagtaactgc agcttcgaag   1140

actttgcaca ttttatttca aagcagaagt cccagtgtct tcacaatcag cctcgcttag   1200

atcctttttt caaacagcaa gcagtgtgtg gtaatgcaaa gctggaagca ggagaggagt   1260

gtgactgtgg gactgaacag gattgtgccc ttattggaga aacatgctgt gatattgcca   1320

catgtagatt taaagccggt tcaaactgtg ctgaaggacc atgctgcgaa aactgtctat   1380
```

-continued

```
ttatgtcaaa agaaagaatg tgtaggcctt cctttgaaga atgcgacctc cctgaatatt   1440

gcaatggatc atctgcatca tgcccagaaa accactatgt tcagactggg catccgtgtg   1500

gactgaatca atggatctgt atagatggag tttgtatgag tggggataaa caatgtacag   1560

acacatttgg caaagaagta gagtttggcc cttcagaatg ttattctcac cttaattcaa   1620

agactgatgt atctggaaac tgtggtataa gtgattcagg atacacacag tgtgaagctg   1680

acaatctgca gtgcggaaaa ttaatatgta aatatgtagg taaattttta ttacaaattc   1740

caagagccac tattatttat gccaacataa gtggacatct ctgcattgct gtggaatttg   1800

ccagtgatca tgcagacagc caaaagatgt ggataaaaga tggaacttct tgtggttcaa   1860

ataaggtttg caggaatcaa agatgtgtga gttcttcata cttgggttat gattgtacta   1920

ctgacaaatg caatgataga ggtgtatgca ataacaaaaa gcactgtcac tgtagtgctt   1980

catatttacc tccagattgc tcagttcaat cagatctatg gcctggtggg agtattgaca   2040

gtggcaattt tccacctgta gctataccag ccagactccc tgaaaggcgc tacattgaga   2100

acatttacca ttccaaacca atgagatggc catttttctt attcattcct ttctttatta   2160

ttttctgtgt actgattgct ataatggtga aagttaattt ccaaaggaaa aaatggagaa   2220

ctgaggacta ttcaagcgat gagcaacctg aaagtgagag tgaacctaaa gggtagtctg   2280

gacaacagag atgccatgat atcacttctt ctagagtaat tatctgtgat ggatggacac   2340

aaaaaaatgg aaagaaaaga atgtacatta cctggtttcc tgggattcaa acctgcatat   2400

tgtgatttta atttgaccag aaaatatgat atatatgtat aatttcacag ataatttact   2460

tatttaaaaa tgcatgataa tgagttttac attacaaatt tctgtttttt taaagttatc   2520

ttacgctatt tctgttggtt agtagacact aattctgtca gtaggggcat ggtataagga   2580

aatatcataa tgtaatgagg tggtactatg attaaaagcc actgttacat ttcaaaaaaa   2640

aaaaaaaaaa                                                          2650
```

<210> SEQ ID NO 13
<211> LENGTH: 718
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (557)..(557)

<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t

<400> SEQUENCE: 13
agagngtcgc cccttttttt tttttttttt tttttttttt tttttttttt ttgacattta 60
taaatgaacc tttattaaag acacttcaat gccatttgtt anacacttca atattttaca 120
tggttttcaa tgtacactgt accaaaattt ctataaataa ataactttgt acataaaagt 180
aatactccct ctttcacatt gcctcncaga agcagcaaat tcatatattt tgtggaagta 240
agattagtca gttaactgtc aagaacaaaa ttctaaatgt gcttaccttt tgaacagtga 300
tgacacctga cagtaattgt taactatttt ctcagtaact cccttcagct tttggccaaa 360
ggaacatttg aaggaccttg tttcnattta agttttacta aatgacacat tggcactcan 420
aanatggtta gctaccagtc tcaaaagtgc aaattatacc canaacccag gtcaagggct 480
gtcctttcca agtcccagct cagtttcatc tggtgcgaag gaatggcatg gacaggcctg 540
ctccgggtcc ttaatanaaa taaggtancc ctgaaaagtc anaacttcct cctttctgtc 600
ccccaagggc aatgtaatac tcattanatt gggcaaaacn aaaacatcng tatagtaaaa 660
atccacaggt nccaacacca gcagccttta ccttanttn aaaggccnca aaatagca 718

<210> SEQ ID NO 14
<211> LENGTH: 135
<212> TYPE: PRT
<213> ORGANISM: Homo sapiens

<400> SEQUENCE: 14

Met Ser Pro His Leu Thr Ala Leu Leu Gly Leu Val Leu Cys Leu Ala
1 5 10 15

Gln Thr Ile His Thr Gln Glu Gly Ala Leu Pro Arg Pro Ser Ile Ser
20 25 30

Ala Glu Pro Gly Thr Val Ile Ser Pro Gly Ser His Val Thr Phe Met
35 40 45

```
Cys Arg Gly Pro Val Gly Val Gln Thr Phe Arg Leu Glu Arg Glu Asp
    50                  55                  60

Arg Ala Lys Tyr Lys Asp Ser Tyr Asn Val Phe Arg Leu Gly Pro Ser
65                  70                  75                  80

Glu Ser Glu Ala Arg Phe His Ile Asp Ser Val Ser Glu Gly Asn Ala
                85                  90                  95

Gly Leu Tyr Arg Cys Leu Tyr Tyr Lys Pro Pro Gly Trp Ser Glu His
            100                 105                 110

Ser Asp Phe Leu Glu Leu Leu Val Lys Gly Thr Val Pro Gly Thr Glu
        115                 120                 125

Ala Ser Gly Phe Asp Ala Pro
    130                 135


<210> SEQ ID NO 15
<211> LENGTH: 568
<212> TYPE: DNA
<213> ORGANISM: Homo sapiens

<400> SEQUENCE: 15

ccacgcgtcc ggggaccggg gccatgtctc cacacctcac tgctctcctg ggcctagtgc      60

tctgcctggc ccagaccatc cacacgcagg agggggccct tcccagaccc tccatctcgg     120

ctgagccagg cactgtgatc tccccgggga gccatgtgac tttcatgtgc cggggcccgg     180

ttggggttca aacattccgc ctggagaggg aggatagagc caagtacaaa gatagttata     240

atgtgtttcg acttggtcca tctgagtcag aggccagatt ccacattgac tcagtaagtg     300

aaggaaatgc cgggctttat cgctgcctct attataagcc ccctggatgg tctgagcaca     360

gtgacttcct ggagctgctg gtgaaaggga ctgtgccagg cactgaagcc tccggatttg     420

atgcaccatg aatgaggaga aatggcctcc cgtcttgtga acttcaatgg ggagaaataa     480

ttagaatgag caatagaaat gcacagatgc ctatacatac atatacaaat aaaaagatac     540

gattcgcaaa aaaaaaaaaa aaaagggc                                        568


<210> SEQ ID NO 16
<211> LENGTH: 426
<212> TYPE: PRT
<213> ORGANISM: Homo sapiens

<400> SEQUENCE: 16

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
```

```
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425
```

<210> SEQ ID NO 17
<211> LENGTH: 1840
<212> TYPE: DNA
<213> ORGANISM: Homo sapiens

<400> SEQUENCE: 17

```
tccacacaca caaaaaacct gcgcgtgagg ggggaggaaa agcagggcct ttaaaaaggc      60

aatcacaaca acttttgctg ccaggatgcc cttgctttgg ctgagaggat ttctgttggc     120

aagttgctgg attatagtga ggagttcccc caccccagga tccgaggggc acagcgcggc     180

ccccgactgt ccgtcctgtg cgctggccgc cctcccaaag gatgtaccca actctcagcc     240

agagatggtg gaggccgtca agaagcacat tttaaacatg ctgcacttga agaagagacc     300

cgatgtcacc cagccggtac ccaaggcggc gcttctgaac gcgatcagaa agcttcatgt     360

gggcaaagtc ggggagaacg ggtatgtgga gatagaggat gacattggaa ggagggcaga     420

aatgaatgaa cttatggagc agacctcgga gatcatcacg tttgccgagt caggaacagc     480
```

-continued

```
caggaagacg ctgcacttcg agatttccaa ggaaggcagt gacctgtcag tggtggagcg    540

tgcagaagtc tggctcttcc taaaagtccc caaggccaac aggaccagga ccaaagtcac    600

catccgcctc ttccagcagc agaagcaccc gcagggcagc ttggacacag ggaagaggc     660

cgaggaagtg ggcttaaagg gggagaggag tgaactgttg ctctctgaaa aagtagtaga    720

cgctcggaag agcacctggc atgtcttccc tgtctccagc agcatccagc ggttgctgga    780

ccagggcaag agctccctgg acgttcggat tgcctgtgag cagtgccagg agagtggcgc    840

cagcttggtt ctcctgggca agaagaagaa gaaagaagag gagggggaag ggaaaaagaa    900

gggcggaggt gaaggtgggg caggagcaga tgaggaaaag gagcagtcgc acagaccttt    960

cctcatgctg caggcccggc agtctgaaga ccaccctcat cgccggcgtc ggcggggctt   1020

ggagtgtgat ggcaaggtca acatctgctg taagaaacag ttctttgtca gtttcaagga   1080

catcggctgg aatgactgga tcattgctcc ctctggctat catgccaact actgcgaggg   1140

tgagtgcccg agccatatag caggcacgtc cgggtcctca ctgtccttcc actcaacagt   1200

catcaaccac taccgcatgc ggggccatag cccctttgcc aacctcaaat cgtgctgtgt   1260

gcccaccaag ctgagaccca tgtccatgtt gtactatgat gatggtcaaa acatcatcaa   1320

aaaggacatt cagaacatga tcgtggagga gtgtgggtgc tcatagagtt gcccagccca   1380

gggggaaagg gagcaagagt tgtccagaga agacagtggc aaaatgaaga aatttttaag   1440

gtttctgagt taaccagaaa aatagaaatt aaaaacaaaa caaaacaaaa aaaaaaacaa   1500

aaaaaaacaa aagtaaatta aaaacaaacc tgatgaaaca gatgaaacag atgaaggaag   1560

atgtggaaat cttagcctgc cttagccagg gctcagagat gaagcagtga agagacagat   1620

tgggagggaa agggagaatg gtgtaccctt tatttcttct gaaatcacac tgatgacatc   1680

agttgtttaa acggggtatt gtcctttccc cccttgaggt tcccttgtga gcttgaatca   1740

accaatctga tctgcagtag tgtggactag aacaacccaa atagcatcta gaaagccatg   1800

agtttgaaag ggcccatcac aggcactttc ctagcctaat                         1840


<210> SEQ ID NO 18
<211> LENGTH: 199
<212> TYPE: PRT
<213> ORGANISM: Homo sapiens

<400> SEQUENCE: 18

Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140
```

-continued

Ser Arg Leu Ala Leu Pro Gln Pro Pro Pro Asp Pro Pro Ala Pro Pro
145 150 155 160

Leu Ala Pro Pro Ser Ser Ala Trp Gly Gly Ile Arg Ala Ala His Ala
165 170 175

Ile Leu Gly Gly Leu His Leu Thr Leu Asp Trp Ala Val Arg Gly Leu
180 185 190

Leu Leu Leu Lys Thr Arg Leu
195

<210> SEQ ID NO 19
<211> LENGTH: 2281
<212> TYPE: DNA
<213> ORGANISM: Homo sapiens

<400> SEQUENCE: 19
gaagggttaa aggccccccgg ctccctgccc cctgccctgg ggaacccctg gccctgtggg 60
gacatgaact gtgtttgccg cctggtcctg gtcgtgctga gcctgtggcc agatacagct 120
gtcgcccctg ggccaccacc tggccccccct cgagtttccc cagaccctcg ggccgagctg 180
gacagcaccg tgctcctgac ccgctctctc ctggcggaca cgcggcagct ggctgcacag 240
ctgagggaca aattcccagc tgacggggac cacaacctgg attccctgcc caccctggcc 300
atgagtgcgg gggcactggg agctctacag ctcccaggtg tgctgacaag gctgcgagcg 360
gacctactgt cctacctgcg gcacgtgcag tggctgcgcc gggcaggtgg ctcttccctg 420
aagaccctgg agcccgagct gggcaccctg caggcccgac tggaccggct gctgcgccgg 480
ctgcagctcc tgatgtcccg cctggccctg ccccagccac ccccggaccc gccggcgccc 540
ccgctggcgc ccccctcctc agcctggggg ggcatcaggg ccgcccacgc catcctgggg 600
gggctgcacc tgacacttga ctgggccgtg aggggactgc tgctgctgaa gactcggctg 660
tgacccgggg cccaaagcca ccaccgtcct tccaaagcca gatcttattt atttatttat 720
ttcagtactg ggggcgaaac agccaggtga tccccccgcc attatctccc cctagttaga 780
gacagtcctt ccgtgaggcc tgggggacat ctgtgcctta tttatactta tttatttcag 840
gagcaggggt gggaggcagg tggactcctg ggtccccgag gaggaggga ctggggtccc 900 ggattcttgg gtctccaaga agtctgtcca cagacttctg ccctggctct tccccatcta 960
ggcctgggca ggaacatata ttatttattt aagcaattac ttttcatgtt ggggtgggga 1020
cggaggggaa agggaagcct gggtttttgt acaaaaatgt gagaaacctt tgtgagacag 1080
agaacaggga attaaatgtg tcatacatat ccacttgagg gcgatttgtc tgagagctgg 1140
ggctggatgc ttgggtaact ggggcagggc aggtggaggg gagacctcca ttcaggtgga 1200
ggtcccgagt gggcggggca gcgactggga gatgggtcgg tcacccagac agctctgtgg 1260
aggcagggtc tgagccttgc ctggggcccc gcactgcata gggccgtttg tttgtttttt 1320
gagatggagt ctcgctctgt tgcctaggct ggagtgcagt gaggcaatct aaggtcactg 1380
caagctccac ctcccgggtt caagcaattc tcctgcctca gcctcccgat tagctgggat 1440
cacaggtgtg caccaccatg cccagctaat tatttatttc ttttgtattt ttagtagaga 1500
cagggtttca ccatgttggc caggctggtt tcgaactcct gacctcaggt gatcctcctg 1560
cctcggcctc ccaaagtgct gggattacag gtgtgagcca ccacacctga cccataggtc 1620
ttcaataaat atttaatgga aggttccaca agtcaccctg tgatcaacag tacccgtatg 1680
ggacaaagct gcaaggtcaa gatggttcat tatggctgtg ttcaccatag caaactggaa 1740
agaatctaga tatccaacag tgagggttaa gcaacatggt gcatctgtgg atagaacacc 1800

```
acccagccgc ccggagcagg gactgtcatt cagggaggct aaggagagag gcttgcttgg   1860

gatatagaaa gatatcctga cattggccag gcatggtggc tcacgcctgt aatcctggca   1920

ctttgggagg acgaagcgag tggatcactg aagtccaaga gtttgagacc ggcctgcgag   1980

acatggcaaa accctgtctc aaaaaagaaa gaatgatgtc ctgacatgaa acagcaggct   2040

acaaaaccac tgcatgctgt gatcccaatt ttgtgttttt ctttctatat atggattaaa   2100

acaaaaatcc taaagggaaa tacgccaaaa tgttgacaat gactgtctcc aggtcaaagg   2160

agagaggtgg gattgtgggt gacttttaat gtgtatgatt gtctgtattt tacagaattt   2220

ctgccatgac tgtgtatttt gcatgacaca ttttaaaaat aataaacact atttttagaa   2280

t                                                                   2281
```

<210> SEQ ID NO 20
<211> LENGTH: 322
<212> TYPE: PRT
<213> ORGANISM: Homo sapiens

<400> SEQUENCE: 20

```
Met Ser Pro Asn Phe Lys Leu Gln Cys His Phe Ile Leu Ile Phe Leu
1               5                   10                  15

Thr Ala Leu Arg Gly Glu Ser Arg Tyr Leu Glu Leu Arg Glu Ala Ala
            20                  25                  30

Asp Tyr Asp Pro Phe Leu Leu Phe Ser Ala Asn Leu Lys Arg Asp Val
        35                  40                  45

Ala Gly Glu Gln Pro Tyr Arg Arg Ala Leu Arg Cys Leu Asp Met Leu
    50                  55                  60

Ser Leu Gln Gly Gln Phe Thr Phe Thr Ala Asp Arg Pro Gln Leu His
65                  70                  75                  80

Cys Ala Ala Phe Phe Ile Ser Glu Pro Glu Glu Phe Ile Thr Ile His
                85                  90                  95

Tyr Asp Gln Val Ser Ile Asp Cys Gln Gly Gly Asp Phe Leu Lys Val
            100                 105                 110

Phe Asp Gly Trp Ile Leu Lys Gly Glu Lys Phe Pro Ser Ser Gln Asp
        115                 120                 125

His Pro Leu Pro Ser Ala Glu Arg Tyr Ile Asp Phe Cys Glu Ser Gly
    130                 135                 140

Leu Ser Arg Arg Ser Ile Arg Ser Ser Gln Asn Val Ala Met Ile Phe
145                 150                 155                 160

Phe Arg Val His Glu Pro Gly Asn Gly Phe Thr Leu Thr Ile Lys Thr
                165                 170                 175

Asp Pro Asn Leu Phe Pro Cys Asn Val Ile Ser Gln Thr Pro Asn Gly
            180                 185                 190

Lys Phe Thr Leu Val Val Pro His Gln His Arg Asn Cys Ser Phe Ser
        195                 200                 205

Ile Ile Tyr Pro Val Val Ile Lys Ile Ser Asp Leu Thr Leu Gly His
    210                 215                 220

Val Asn Gly Leu Gln Leu Lys Lys Ser Ser Ala Gly Cys Glu Gly Ile
225                 230                 235                 240

Gly Asp Phe Val Glu Leu Leu Glu Gly Thr Gly Leu Asp Pro Ser Lys
                245                 250                 255

Met Thr Pro Leu Ala Asp Leu Cys Tyr Pro Phe His Gly Pro Ala Gln
            260                 265                 270

Met Lys Val Gly Cys Asp Asn Thr Val Val Arg Met Val Ser Ser Gly
        275                 280                 285
```

Lys His Val Asn Arg Val Thr Phe Glu Tyr Arg Gln Leu Glu Pro Tyr
    290                 295                 300

Glu Leu Glu Asn Pro Asn Gly Asn Ser Ile Gly Glu Phe Cys Leu Ser
305                 310                 315                 320

Gly Leu

<210> SEQ ID NO 21
<211> LENGTH: 1248
<212> TYPE: DNA
<213> ORGANISM: Homo sapiens

<400> SEQUENCE: 21
ggacctccgg agcagacagc acagcagctg cagaggcaag gccagcatgt cgcccaactt 60
caaacttcag tgtcacttca ttctcatctt cctgacggct ctaagagggg aaagccggta 120
cctagagctg agggaagcgg cggactacga tcctttcctg ctcttcagcg ccaacctgaa 180
gcgggacgtg gctggggagc agccgtaccg ccgcgctctg cggtgcctgg acatgctgag 240
cctccagggc cagttcacct tcaccgccga ccggccgcag ctgcactgcg cagccttctt 300
catcagcgag cccgaggagt tcattaccat ccactacgac caggtctcca tcgactgtca 360
gggcggcgac ttcctgaagg tatttgatgg ttggattctc aagggggaga agttccccag 420
ttcccaggat catcctctcc cctcagctga gcggtacata gatttctgtg agagtggtct 480
tagcaggagg agcatcagat cttcccagaa tgtggccatg atcttcttcc gagtccatga 540
accaggaaat ggattcacat taaccataaa gacagacccc aacctctttc cttgcaatgt 600
catttctcag actccaaatg gaaagtttac cctggtagtt ccacaccagc atcgaaactg 660
cagcttctcc ataatttatc ctgtggtgat caaaatatct gatcttaccc tgggacacgt 720
aaatggtctt cagttaaaga aatcctcagc aggttgcgag ggaataggag actttgtgga 780
gctgctggag ggaactggat tggacccttc caagatgacg cctttagctg atctctgcta 840 ccccttcat ggcccggccc agatgaaagt tggctgtgac aacactgtgg tgcgcatggt 900
ctccagtgga aaacacgtaa atcgtgtgac ttttgagtat cgtcagctgg agccgtacga 960
gctggaaaac ccaaatggaa acagtatcgg ggaattctgt ttgtctggtc tttgaataac 1020
caacccagtg atttacatgc tgatagctaa gtgagttttt aatggccatt gtgtatgatt 1080
ttgatgcaca actagttaaa agcctttcat accagtcagt atttcccagc cttgagcgca 1140
cgcacacacc acacacatac acacacgcat tatttttgtt actttgcttc tttttatgtt 1200
tgtaatctgt aaatgaacac atggcagaaa ataaccctga ttggtagg 1248

<210> SEQ ID NO 22
<211> LENGTH: 442
<212> TYPE: PRT
<213> ORGANISM: Homo sapiens

<400> SEQUENCE: 22

Thr Thr Pro Asp Arg Arg Leu Trp Asn Pro Pro Ala Thr Ser Ser Ser
1               5                   10                  15

Leu Arg Gln Met Glu Arg Met Leu Pro Leu Leu Thr Leu Gly Leu Leu
            20                  25                  30

Ala Ala Gly Phe Cys Pro Ala Val Leu Cys His Pro Asn Ser Pro Leu
        35                  40                  45

Asp Glu Glu Asn Leu Thr Gln Glu Asn Gln Asp Arg Gly Thr His Val
    50                  55                  60

Asp Leu Gly Leu Ala Ser Ala Asn Val Asp Phe Ala Phe Ser Leu Tyr

```
65                  70                  75                  80

Lys Gln Leu Val Leu Lys Ala Pro Asp Lys Asn Val Ile Phe Ser Pro
                85                  90                  95

Leu Ser Ile Ser Thr Ala Leu Ala Phe Leu Ser Leu Gly Ala His Asn
            100                 105                 110

Thr Thr Leu Thr Glu Ile Leu Lys Gly Leu Lys Phe Asn Leu Thr Glu
        115                 120                 125

Thr Ser Glu Ala Glu Ile His Gln Ser Phe Gln His Leu Leu Arg Thr
    130                 135                 140

Leu Asn Gln Ser Ser Asp Glu Leu Gln Leu Ser Met Gly Asn Ala Met
145                 150                 155                 160

Phe Val Lys Glu Gln Leu Ser Leu Leu Asp Arg Phe Thr Glu Asp Ala
                165                 170                 175

Lys Arg Leu Tyr Gly Ser Glu Ala Phe Ala Thr Asp Phe Gln Asp Ser
            180                 185                 190

Ala Ala Ala Lys Lys Leu Ile Asn Asp Tyr Val Lys Asn Gly Thr Arg
        195                 200                 205

Gly Lys Ile Thr Asp Leu Ile Lys Asp Leu Asp Ser Gln Thr Met Met
    210                 215                 220

Val Leu Val Asn Tyr Ile Phe Phe Lys Ala Lys Trp Glu Met Pro Phe
225                 230                 235                 240

Asp Pro Gln Asp Thr His Gln Ser Arg Phe Tyr Leu Ser Lys Lys Lys
                245                 250                 255

Trp Val Met Val Pro Met Met Ser Leu His His Leu Thr Ile Pro Tyr
            260                 265                 270

Phe Arg Asp Glu Glu Leu Ser Cys Thr Val Val Glu Leu Lys Tyr Thr
        275                 280                 285

Gly Asn Ala Ser Ala Leu Phe Ile Leu Pro Asp Gln Asp Lys Met Glu
    290                 295                 300

Glu Val Glu Ala Met Leu Leu Pro Glu Thr Leu Lys Arg Trp Arg Asp
305                 310                 315                 320

Ser Leu Glu Phe Arg Glu Ile Gly Glu Leu Tyr Leu Pro Lys Phe Ser
                325                 330                 335

Ile Ser Arg Asp Tyr Asn Leu Asn Asp Ile Leu Leu Gln Leu Gly Ile
            340                 345                 350

Glu Glu Ala Phe Thr Ser Lys Ala Asp Leu Ser Gly Ile Thr Gly Ala
        355                 360                 365

Arg Asn Leu Ala Val Ser Gln Val Val His Lys Ala Val Leu Asp Val
    370                 375                 380

Phe Glu Glu Gly Thr Glu Ala Ser Ala Ala Thr Ala Val Lys Ile Thr
385                 390                 395                 400

Leu Leu Ser Ala Leu Val Glu Thr Arg Thr Ile Val Arg Phe Asn Arg
                405                 410                 415

Pro Phe Leu Met Ile Ile Val Pro Thr Asp Thr Gln Asn Ile Phe Phe
            420                 425                 430

Met Ser Lys Val Thr Asn Pro Lys Gln Ala
        435                 440
```

<210> SEQ ID NO 23
<211> LENGTH: 561
<212> TYPE: DNA
<213> ORGANISM: Homo sapiens

<400> SEQUENCE: 23
ctgtctcaaa ataaaaataa aaaataaaaa gaaataaaaa agaaatatac caaaatgtta     60

-continued

```
gctggggtct tctctgggta gtaaagtgct gggggatatt ttccaaagtc cttctttaca    120

ttctctgagt ttttccatgt tcttcaatga gtatttaata agcagataaa aactaataca    180

acaaaggatt ttttctgtgt gcttttttga cctttggagg aagagattag agctagtccc    240

ataaccaggt tatttgagta ggtctaataa gcccgtatta ccagaaatta tcatctggtc    300

atttccagtc cgagaacaga acacttggtt gtcctggcat ttcccaagca gtgggaggag    360

ttctctgcag gaataaataa gcctcagcat tcatgaaaat ccactactcc agacagacgg    420

ctttggaatc caccagctac atccagctcc ctgaggcagg taatccatga tgttttacat    480

cctgggagcg gaggaatctg tttttccagg agagttttag gcagcagcct ggagtgtgtg    540

gagtgtgagg ggtaagcaga g                                              561
```

<210> SEQ ID NO 24
<211> LENGTH: 272
<212> TYPE: PRT
<213> ORGANISM: Homo sapiens

<400> SEQUENCE: 24

```
Met Val Leu Leu Thr Ala Val Leu Leu Leu Leu Ala Ala Tyr Ala Gly
1               5                   10                  15

Pro Ala Gln Ser Leu Gly Ser Phe Val His Cys Glu Pro Cys Asp Glu
            20                  25                  30

Lys Ala Leu Ser Met Cys Pro Pro Ser Pro Leu Gly Cys Glu Leu Val
        35                  40                  45

Lys Glu Pro Gly Cys Gly Cys Cys Met Thr Cys Ala Leu Ala Glu Gly
    50                  55                  60

Gln Ser Cys Gly Val Tyr Thr Glu Arg Cys Ala Gln Gly Leu Arg Cys
65                  70                  75                  80

Leu Pro Arg Gln Asp Glu Glu Lys Pro Leu His Ala Leu Leu His Gly
                85                  90                  95

Arg Gly Val Cys Leu Asn Glu Lys Ser Tyr Arg Glu Gln Val Lys Ile
            100                 105                 110

Glu Arg Asp Ser Arg Glu His Glu Glu Pro Thr Thr Ser Glu Met Ala
        115                 120                 125

Glu Glu Thr Tyr Ser Pro Lys Ile Phe Arg Pro Lys His Thr Arg Ile
    130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                165                 170                 175

Ile Ile Ser Ala Pro Glu Met Arg Gln Glu Ser Glu Gln Gly Pro Cys
            180                 185                 190

Arg Arg His Met Glu Ala Ser Leu Gln Glu Leu Lys Ala Ser Pro Arg
        195                 200                 205

Met Val Pro Arg Ala Val Tyr Leu Pro Asn Cys Asp Arg Lys Gly Phe
    210                 215                 220

Tyr Lys Arg Lys Gln Cys Lys Pro Ser Arg Gly Arg Lys Arg Gly Ile
225                 230                 235                 240

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
            260                 265                 270
```

<210> SEQ ID NO 25

<211> LENGTH: 1303
<212> TYPE: DNA
<213> ORGANISM: Homo sapiens

<400> SEQUENCE: 25
tgaaaaaaaa aaaaggaaag aaagggattg aaggagcttg ccaagggtag gctgcctaaa 60
ttcacatttt ccctgggtct ttccgtgaaa tggggacacc agaaacccaa gggtcgggtc 120
tagtgccctc aactctctgg ggatgagagt cttgccttgg ggtagacaag aggcagggca 180
gggaggagca gagccctggg gtgcggccgt cctcaccgcc tgttgctcta ctcaccccag 240
tgcaaacctt cccgtggccg caagcgtggc atctgctggt gcgtggacaa gtacgggatg 300
aagctgccag gcatggagta cgttgacggg gactttcagt gccacacctt cgacagcagc 360
aacgttgagt gatgcgtccc cccccaacct ttccctcacc ccctcccacc cccagccccg 420
actccagcca gcgcctccct ccaccccagg acgccactca tttcatctca tttaagggaa 480
aaatatatat ctatctattt gaggaaactg aggacctcgg aatctctagc aagggctcaa 540
cttcgaaaat ggcaacaaca gagatgcaaa aagctaaaaa gacacccccc ccctttaaat 600
ggttttcttt ttgaggcaag ttggatgaac agagaaggga agagaggaag aacgagagga 660
agagaaggga aggaagtgtt tgtgtagaag agagagaaag acgaatagag ttaggaaaag 720
gaagacaagc aggtgggcag gaaggacatg caccgagacc aggcaggggc ccaactttca 780
cgtccagccc tggcctgggg tcgggagagg tgggcgctag aagatgcagc ccaggatgtg 840
gcaatcaatg acactattgg ggtttcccag gatggattgg tcaggggag aaaggaaaag 900 gcaaaacact ccaggacctc tcccggatct gtctcctcct ctagccagca gtatggacag 960
ctggacccct gaacttcctc tcctcttacc tgggcagagt gttgtctctc cccaaattta 1020
taaaaactaa aatgcattcc attcctctga aagcaaaaca aattcataat tgagtgatat 1080
taaatagaga ggttttcgga agcagatctg tgaatatgaa atacatgtgc atatttcatt 1140
ccccaggcag acatttttta gaaatcaata catgccccaa tattggaaag acttgttctt 1200
ccacggtgac tacagtacat gctgaagcgt gccgtttcag ccctcattta attcaatttg 1260
taagtagcgc acgagcctct gtgggggagg ataggctgaa aaa 1303

<210> SEQ ID NO 26
<211> LENGTH: 448
<212> TYPE: PRT
<213> ORGANISM: Homo sapiens

<400> SEQUENCE: 26

Met Val Leu Ile Gln Ile Pro Met Tyr Asn Glu Lys Glu Val Cys Gln
1 5 10 15

Leu Ser Ile Gly Ala Ala Cys Arg Leu Ser Trp Pro Leu Asp Arg Met
20 25 30

Ile Val Gln Val Leu Asp Asp Ser Thr Asp Pro Ala Ser Lys Glu Leu
35 40 45

Val Asn Ala Glu Cys Asp Lys Trp Ala Arg Lys Gly Ile Asn Ile Met
50 55 60

Ser Glu Ile Arg Asp Asn Arg Ile Gly Tyr Lys Ala Gly Ala Leu Lys
65 70 75 80

Ala Gly Met Met His Asn Tyr Val Lys Gln Cys Glu Phe Val Ala Ile
85 90 95

Phe Asp Ala Asp Phe Gln Pro Asp Pro Asp Phe Leu Glu Arg Thr Ile
100 105 110

Pro Phe Leu Ile His Asn His Glu Ile Ser Leu Val Gln Cys Arg Trp

```
        115                 120                 125

Lys Phe Val Asn Ala Asn Glu Cys Leu Met Thr Arg Met Gln Glu Met
    130                 135                 140

Ser Leu Asn Tyr His Phe Val Ala Glu Gln Glu Ser Gly Ser Ser Ile
145                 150                 155                 160

His Ala Phe Phe Gly Phe Asn Gly Thr Ala Gly Val Trp Arg Ile Ala
                165                 170                 175

Ala Leu Asn Glu Ala Gly Gly Trp Lys Asp Arg Thr Thr Val Glu Asp
            180                 185                 190

Met Asp Leu Ala Val Arg Ala Cys Leu His Gly Trp Lys Phe Val Tyr
        195                 200                 205

Val His Asp Val Glu Val Lys Asn Glu Leu Pro Ser Thr Phe Lys Ala
    210                 215                 220

Tyr Arg Phe Gln Gln His Arg Trp Ser Cys Gly Pro Ala Asn Leu Trp
225                 230                 235                 240

Arg Lys Met Thr Met Glu Ile Leu Gln Asn Lys Lys Val Ser Ala Trp
                245                 250                 255

Lys Lys Leu Tyr Leu Ile Tyr Asn Phe Phe Phe Ile Arg Lys Ile Val
            260                 265                 270

Val His Ile Phe Thr Phe Val Phe Tyr Cys Leu Ile Leu Pro Thr Thr
        275                 280                 285

Val Leu Phe Pro Glu Leu Gln Val Pro Lys Trp Ala Thr Val Tyr Phe
    290                 295                 300

Pro Thr Thr Ile Thr Ile Leu Asn Ala Ile Ala Thr Pro Arg Met Ile
305                 310                 315                 320

Lys Ser Leu Thr Tyr Ile Val Tyr Cys Arg Ser Leu His Leu Leu Val
                325                 330                 335

Phe Trp Ile Leu Phe Glu Asn Val Met Ser Met His Arg Thr Lys Ala
            340                 345                 350

Thr Phe Ile Gly Leu Leu Glu Ala Gly Arg Val Asn Glu Trp Val Val
        355                 360                 365

Thr Glu Lys Leu Gly Asp Thr Leu Lys Ser Lys Leu Ile Gly Lys Ala
    370                 375                 380

Thr Thr Lys Leu Tyr Thr Arg Phe Gly Gln Arg Leu Asn Trp Arg Glu
385                 390                 395                 400

Leu Val Val Gly Leu Tyr Ile Phe Phe Cys Gly Cys Tyr Asp Phe Ala
                405                 410                 415

Tyr Gly Gly Ser Tyr Phe Tyr Val Tyr Leu Phe Leu Gln Ser Cys Ala
            420                 425                 430

Phe Phe Val Ala Gly Val Gly Tyr Ile Gly Thr Phe Val Pro Thr Val
        435                 440                 445
```

<210> SEQ ID NO 27
<211> LENGTH: 422
<212> TYPE: PRT
<213> ORGANISM: Homo sapiens

<400> SEQUENCE: 27

```
Met Pro Ala Gly Arg Arg Gly Pro Ala Ala Gln Ser Ala Arg Arg Pro
1               5                   10                  15

Pro Pro Leu Leu Pro Leu Leu Leu Leu Leu Cys Val Leu Gly Ala Pro
            20                  25                  30

Arg Ala Gly Ser Gly Ala His Thr Ala Val Ile Ser Pro Gln Asp Pro
        35                  40                  45

Thr Leu Leu Ile Gly Ser Ser Leu Leu Ala Thr Cys Ser Val His Gly
```

```
    50                  55                  60

Asp Pro Pro Gly Ala Thr Ala Glu Gly Leu Tyr Trp Thr Leu Asn Gly
65                  70                  75                  80

Arg Arg Leu Pro Pro Glu Leu Ser Arg Val Leu Asn Ala Ser Thr Leu
                85                  90                  95

Ala Leu Ala Leu Ala Asn Leu Asn Gly Ser Arg Gln Arg Ser Gly Asp
            100                 105                 110

Asn Leu Val Cys His Ala Arg Asp Gly Ser Ile Leu Ala Gly Ser Cys
        115                 120                 125

Leu Tyr Val Gly Leu Pro Pro Glu Lys Pro Val Asn Ile Ser Cys Trp
    130                 135                 140

Ser Lys Asn Met Lys Asp Leu Thr Cys Arg Trp Thr Pro Gly Ala His
145                 150                 155                 160

Gly Glu Thr Phe Leu His Thr Asn Tyr Ser Leu Lys Tyr Lys Leu Arg
                165                 170                 175

Trp Tyr Gly Gln Asp Asn Thr Cys Glu Glu Tyr His Thr Val Gly Pro
            180                 185                 190

His Ser Cys His Ile Pro Lys Asp Leu Ala Leu Phe Thr Pro Tyr Glu
        195                 200                 205

Ile Trp Val Glu Ala Thr Asn Arg Leu Gly Ser Ala Arg Ser Asp Val
    210                 215                 220

Leu Thr Leu Asp Ile Leu Asp Val Val Thr Thr Asp Pro Pro Pro Asp
225                 230                 235                 240

Val His Val Ser Arg Val Gly Gly Leu Glu Asp Gln Leu Ser Val Arg
                245                 250                 255

Trp Val Ser Pro Pro Ala Leu Lys Asp Phe Leu Phe Gln Ala Lys Tyr
            260                 265                 270

Gln Ile Arg Tyr Arg Val Glu Asp Ser Val Asp Trp Lys Val Val Asp
        275                 280                 285

Asp Val Ser Asn Gln Thr Ser Cys Arg Leu Ala Gly Leu Lys Pro Gly
    290                 295                 300

Thr Val Tyr Phe Val Gln Val Arg Cys Asn Pro Phe Gly Ile Tyr Gly
305                 310                 315                 320

Ser Lys Lys Ala Gly Ile Trp Ser Glu Trp Ser His Pro Thr Ala Ala
                325                 330                 335

Ser Thr Pro Arg Ser Glu Arg Pro Gly Pro Gly Gly Gly Ala Cys Glu
            340                 345                 350

Pro Arg Gly Gly Glu Pro Ser Ser Gly Pro Val Arg Arg Glu Leu Lys
        355                 360                 365

Gln Phe Leu Gly Trp Leu Lys Lys His Ala Tyr Cys Ser Asn Leu Ser
    370                 375                 380

Phe Arg Leu Tyr Asp Gln Trp Arg Ala Trp Met Gln Lys Ser His Lys
385                 390                 395                 400

Thr Arg Asn Gln Asp Glu Gly Ile Leu Pro Ser Gly Arg Arg Gly Thr
                405                 410                 415

Ala Arg Gly Pro Ala Arg
            420
```

<210> SEQ ID NO 28
<211> LENGTH: 1716
<212> TYPE: DNA
<213> ORGANISM: Homo sapiens

<400> SEQUENCE: 28
cgcccagcga cgtgcgggcg gcctggcccg cgccctcccg cgcccggcct gcgtcccgcg 60

```
ccctgcgcca ccgccgccga gccgcagccc gccgcgcgcc cccggcagcg ccggccccat    120
gcccgccggc cgccggggcc ccgccgccca atccgcgcgg cggccgccgc cgttgctgcc    180
cctgctgctg ctgctctgcg tcctcggggc gccgcgagcc ggatcaggag cccacacagc    240
tgtgatcagt ccccaggatc ccacgcttct catcggctcc tccctgctgg ccacctgctc    300
agtgcacgga gacccaccag gagccaccgc cgagggcctc tactggaccc tcaacgggcg    360
ccgcctgccc cctgagctct cccgtgtact caacgcctcc accttggctc tggccctggc    420
caacctcaat gggtccaggc agcggtcggg ggacaacctc gtgtgccacg cccgtgacgg    480
cagcatcctg gctggctcct gcctctatgt tggcctgccc ccagagaaac ccgtcaacat    540
cagctgctgg tccaagaaca tgaaggactt gacctgccgc tggacgccag ggcccacggg    600
ggagaccttc ctccacacca actactccct caagtacaag cttaggtggt atggccagga    660
caacacatgt gaggagtacc acacagtggg gccccactcc tgccacatcc ccaaggacct    720
ggctctcttt acgccctatg agatctgggt ggaggccacc aaccgcctgg gctctgcccg    780
ctccgatgta ctcacgctgg atatcctgga tgtggtgacc acggaccccc cgcccgacgt    840
gcacgtgagc cgcgtcgggg gcctggagga ccagctgagc gtgcgctggg tgtcgccacc    900
cgccctcaag gatttcctct ttcaagccaa ataccagatc cgctaccgag tggaggacag    960
tgtggactgg aaggtggtgg acgatgtgag caaccagacc tcctgccgcc tggccggcct   1020
gaaacccggc accgtgtact tcgtgcaagt gcgctgcaac ccctttggca tctatggctc   1080
caagaaagcc gggatctgga gtgagtggag ccaccccaca gccgcctcca ctccccgcag   1140
tgagcgcccg ggcccgggcg gcggggcgtg cgaaccgcgg ggcggagagc cgagctcggg   1200
gccggtgcgg cgcgagctca agcagttcct gggctggctc aagaagcacg cgtactgctc   1260
caacctcagc ttccgcctct acgaccagtg gcgagcctgg atgcagaagt cgcacaagac   1320
ccgcaaccag gacgagggga tcctgccctc gggcagacgg ggcacggcga gaggtcctgc   1380
cagataagct gtaggggctc aggccaccct ccctgccacg tggagacgca gaggccgaac   1440
ccaaactggg gccacctctg taccctcact tcagggcacc tgagccaccc tcagcaggag   1500
ctggggtggc ccctgagctc caacggccat aacagctctg actcccacgt gaggccacct   1560
ttgggtgcac cccagtgggt gtgtgtgtgt gtgtgagggt tggttgagtt gcctagaacc   1620
cctgccaggg ctgggggtga gaaggggagt cattactccc cattacctag ggcccctcca   1680
aaagagtcct tttaaataaa tgagctattt aggtgc                              1716
```

<210> SEQ ID NO 29
<211> LENGTH: 228
<212> TYPE: PRT
<213> ORGANISM: Homo sapiens

<400> SEQUENCE: 29

```
Met Leu His Val Glu Met Leu Thr Leu Val Phe Leu Val Leu Trp Met
1               5                   10                  15

Cys Val Phe Ser Gln Asp Pro Gly Ser Lys Ala Val Ala Asp Arg Tyr
            20                  25                  30

Ala Val Tyr Trp Asn Ser Ser Asn Pro Arg Phe Gln Arg Gly Asp Tyr
        35                  40                  45

His Ile Asp Val Cys Ile Asn Asp Tyr Leu Asp Val Phe Cys Pro His
    50                  55                  60

Tyr Glu Asp Ser Val Pro Glu Asp Lys Thr Glu Arg Tyr Val Leu Tyr
65                  70                  75                  80
```

-continued

```
Met Val Asn Phe Asp Gly Tyr Ser Ala Cys Asp His Thr Ser Lys Gly
                85                  90                  95

Phe Lys Arg Trp Glu Cys Asn Arg Pro His Ser Pro Asn Gly Pro Leu
            100                 105                 110

Lys Phe Ser Glu Lys Phe Gln Leu Phe Thr Pro Phe Ser Leu Gly Phe
        115                 120                 125

Glu Phe Arg Pro Gly Arg Glu Tyr Phe Tyr Ile Ser Ser Ala Ile Pro
    130                 135                 140

Asp Asn Gly Arg Arg Ser Cys Leu Lys Leu Lys Val Phe Val Arg Pro
145                 150                 155                 160

Thr Asn Ser Cys Met Lys Thr Ile Gly Val His Asp Arg Val Phe Asp
                165                 170                 175

Val Asn Asp Lys Val Glu Asn Ser Leu Glu Pro Ala Asp Asp Thr Val
            180                 185                 190

His Glu Ser Ala Glu Pro Ser Arg Gly Glu Asn Ala Ala Gln Thr Pro
        195                 200                 205

Arg Ile Pro Ser Arg Leu Leu Ala Ile Leu Leu Phe Leu Leu Ala Met
    210                 215                 220

Leu Leu Thr Leu
225


<210> SEQ ID NO 30
<211> LENGTH: 737
<212> TYPE: PRT
<213> ORGANISM: Homo sapiens

<400> SEQUENCE: 30

Met Gly Gly Cys Thr Val Lys Pro Gln Leu Leu Leu Leu Ala Leu Val
1               5                   10                  15

Leu His Pro Trp Asn Pro Cys Leu Gly Ala Asp Ser Glu Lys Pro Ser
            20                  25                  30

Ser Ile Pro Thr Asp Lys Leu Leu Val Ile Thr Val Ala Thr Lys Glu
        35                  40                  45

Ser Asp Gly Phe His Arg Phe Met Gln Ser Ala Lys Tyr Phe Asn Tyr
    50                  55                  60

Thr Val Lys Val Leu Gly Gln Gly Glu Glu Trp Arg Gly Gly Asp Gly
65                  70                  75                  80

Ile Asn Ser Ile Gly Gly Gly Gln Lys Val Arg Leu Met Lys Glu Val
                85                  90                  95

Met Glu His Tyr Ala Asp Gln Asp Asp Leu Val Val Met Phe Thr Glu
            100                 105                 110

Cys Phe Asp Val Ile Phe Ala Gly Gly Pro Glu Glu Val Leu Lys Lys
        115                 120                 125

Phe Gln Lys Ala Asn His Lys Val Val Phe Ala Ala Asp Gly Ile Leu
    130                 135                 140

Trp Pro Asp Lys Arg Leu Ala Asp Lys Tyr Pro Val Val His Ile Gly
145                 150                 155                 160

Lys Arg Tyr Leu Asn Ser Gly Gly Phe Ile Gly Tyr Ala Pro Tyr Val
                165                 170                 175

Asn Arg Ile Val Gln Gln Trp Asn Leu Gln Asp Asn Asp Asp Asp Gln
            180                 185                 190

Leu Phe Tyr Thr Lys Val Tyr Ile Asp Pro Leu Lys Arg Glu Ala Ile
        195                 200                 205

Asn Ile Thr Leu Asp His Lys Cys Lys Ile Phe Gln Thr Leu Asn Gly
    210                 215                 220
```

-continued

```
Ala Val Asp Glu Val Val Leu Lys Phe Glu Asn Gly Lys Ala Arg Ala
225                 230                 235                 240

Lys Asn Thr Phe Tyr Glu Thr Leu Pro Val Ala Ile Asn Gly Asn Gly
                245                 250                 255

Pro Thr Lys Ile Leu Leu Asn Tyr Phe Gly Asn Tyr Val Pro Asn Ser
            260                 265                 270

Trp Thr Gln Asp Asn Gly Cys Thr Leu Cys Glu Phe Asp Thr Val Asp
        275                 280                 285

Leu Ser Ala Val Asp Val His Pro Asn Val Ser Ile Gly Val Phe Ile
    290                 295                 300

Glu Gln Pro Thr Pro Phe Leu Pro Arg Phe Leu Asp Ile Leu Leu Thr
305                 310                 315                 320

Leu Asp Tyr Pro Lys Glu Ala Leu Lys Leu Phe Ile His Asn Lys Glu
                325                 330                 335

Val Tyr His Glu Lys Asp Ile Lys Val Phe Phe Asp Lys Ala Lys His
            340                 345                 350

Glu Ile Lys Thr Ile Lys Ile Val Gly Pro Glu Glu Asn Leu Ser Gln
        355                 360                 365

Ala Glu Ala Arg Asn Met Gly Met Asp Phe Cys Arg Gln Asp Glu Lys
    370                 375                 380

Cys Asp Tyr Tyr Phe Ser Val Asp Ala Asp Val Val Leu Thr Asn Pro
385                 390                 395                 400

Arg Thr Leu Lys Ile Leu Ile Glu Gln Asn Arg Lys Ile Ile Ala Pro
                405                 410                 415

Leu Val Thr Arg His Gly Lys Leu Trp Ser Asn Phe Trp Gly Ala Leu
            420                 425                 430

Ser Pro Asp Gly Tyr Tyr Ala Arg Ser Glu Asp Tyr Val Asp Ile Val
        435                 440                 445

Gln Gly Asn Arg Val Gly Val Trp Asn Val Pro Tyr Met Ala Asn Val
    450                 455                 460

Tyr Leu Ile Lys Gly Lys Thr Leu Arg Ser Glu Met Asn Glu Arg Asn
465                 470                 475                 480

Tyr Phe Val Arg Asp Lys Leu Asp Pro Asp Met Ala Leu Cys Arg Asn
                485                 490                 495

Ala Arg Glu Met Gly Val Phe Met Tyr Ile Ser Asn Arg His Glu Phe
            500                 505                 510

Gly Arg Leu Leu Ser Thr Ala Asn Tyr Asn Thr Ser His Tyr Asn Asn
        515                 520                 525

Asp Leu Trp Gln Ile Phe Glu Asn Pro Val Asp Trp Lys Glu Lys Tyr
    530                 535                 540

Ile Asn Arg Asp Tyr Ser Lys Ile Phe Thr Glu Asn Ile Val Glu Gln
545                 550                 555                 560

Pro Cys Pro Asp Val Phe Trp Phe Pro Ile Phe Ser Glu Lys Ala Cys
                565                 570                 575

Asp Glu Leu Val Glu Glu Met Glu His Tyr Gly Lys Trp Ser Gly Gly
            580                 585                 590

Lys His His Asp Ser Arg Ile Ser Gly Gly Tyr Glu Asn Val Pro Thr
        595                 600                 605

Asp Asp Ile His Met Lys Gln Val Asp Leu Glu Asn Val Trp Leu Asp
    610                 615                 620

Phe Ile Arg Glu Phe Ile Ala Pro Val Thr Leu Lys Val Phe Ala Gly
625                 630                 635                 640

Tyr Tyr Thr Lys Gly Phe Ala Leu Leu Asn Phe Val Val Lys Tyr Ser
                645                 650                 655
```

-continued

```
Pro Glu Arg Gln Arg Ser Leu Arg Pro His His Asp Ala Ser Thr Phe
            660                 665                 670

Thr Ile Asn Ile Ala Leu Asn Asn Val Gly Glu Asp Phe Gln Gly Gly
        675                 680                 685

Gly Cys Lys Phe Leu Arg Tyr Asn Cys Ser Ile Glu Ser Pro Arg Lys
    690                 695                 700

Gly Trp Ser Phe Met His Pro Gly Arg Leu Thr His Leu His Glu Gly
705                 710                 715                 720

Leu Pro Val Lys Asn Gly Thr Arg Tyr Ile Ala Val Ser Phe Ile Asp
                725                 730                 735

Pro


<210> SEQ ID NO 31
<211> LENGTH: 3503
<212> TYPE: DNA
<213> ORGANISM: Homo sapiens

<400> SEQUENCE: 31

atggggggat gcacggtgaa gcctcagctg ctgctcctgg cgctcgtcct ccacccctgg      60

aatccctgtc tgggtgcgga ctcggagaag ccctcgagca tccccacaga taaattatta     120

gtcataactg tagcaacaaa agaaagtgat ggattccatc gatttatgca gtcagccaaa     180

tatttcaatt atactgtgaa ggtccttggt caaggagaag aatggagagg tggtgatgga     240

attaatagta ttggaggggg ccagaaagtg agattaatga aagaagtcat ggaacactat     300

gctgatcaag atgatctggt tgtcatgttt actgaatgct ttgatgtcat atttgctggt     360

ggtccagaag aagttctaaa aaaattccaa aaggcaaacc acaaagtggt ctttgcagca     420

gatggaattt tgtggccaga taaaagacta gcagacaagt atcctgttgt gcacattggg     480

aaacgctatc tgaattcagg aggatttatt ggctatgctc catatgtcaa ccgtatagtt     540

caacaatgga atctccagga taatgatgat gatcagctct tttacactaa agtttacatt     600

gatccactga aaagggaagc tattaacatc acattggatc acaaatgcaa aattttccag     660

accttaaatg gagctgtaga tgaagttgtt ttaaaatttg aaaatggcaa agccagagct     720

aagaatacat tttatgaaac attaccagtg gcaattaatg gaaatggacc caccaagatt     780

ctcctgaatt attttggaaa ctatgtaccc aattcatgga cacaggataa tggctgcact     840

ctttgtgaat tcgatacagt cgacttgtct gcagtagatg tccatccaaa cgtatcaata     900

ggtgttttta ttgagcaacc aaccccttttt ctacctcggt ttctggacat attgttgaca     960

ctggattacc caaaagaagc acttaaactt tttattcata acaaagaagt ttatcatgaa    1020

aaggacatca aggtattttt tgataaagct aagcatgaaa tcaaaactat aaaaatagta    1080

ggaccagaag aaaatctaag tcaagcggaa gccagaaaca tgggaatgga cttttgccgt    1140

caggatgaaa agtgtgatta ttactttagt gtggatgcag atgttgtttt gacaaatcca    1200

aggactttaa aaattttgat tgaacaaaac agaaagatca ttgctcctct tgtaactcgt    1260

catggaaagc tgtggtccaa tttctgggga gcattgagtc ctgatggata ctatgcacga    1320

tctgaagatt atgtggatat tgttcaaggg aatagagtag gagtatggaa tgtcccatat    1380

atggctaatg tgtacttaat taaaggaaag acactccgat cagagatgaa tgaaaggaac    1440

tattttgttc gtgataaact ggatcctgat atggctcttt gccgaaatgc tagagaaatg    1500

ggtgtattta tgtacatttc taatagacat gaatttggaa ggctattatc cactgctaat    1560

tacaatactt cccattataa caatgacctc tggcagattt ttgaaaatcc tgtggactgg    1620
```

aaggaaaagt atataaaccg tgattattca aagattttca ctgaaaatat agttgaacag 1680
ccctgtccag atgtcttttg gttccccata ttttctgaaa aagcctgtga tgaattggta 1740
gaagaaatgg aacattacgg caaatggtct gggggaaaac atcatgatag ccgtatatct 1800
ggtggttatg aaaatgtccc aactgatgat atccacatga agcaagttga tctggagaat 1860
gtatggcttg attttatccg ggagttcatt gcaccagtta cactgaaggt ctttgcaggc 1920
tattatacga agggatttgc actactgaat tttgtagtaa aatactcccc tgaacgacag 1980
cgttctcttc gtcctcatca tgatgcttct acatttacca taaacattgc acttaataac 2040
gtgggagaag actttcaggg aggtggttgc aaatttctaa ggtacaattg ctctattgag 2100
tcaccacgaa aaggctggag cttcatgcat cctgggagac tcacacattt gcatgaagga 2160
cttcctgtta aaaatggaac aagatacatt gcagtgtcat ttatagatcc ctaagttatt 2220
tacttttcat tgaattgaaa tttattttgg gtgaatgact ggcatgaaca cgtctttgaa 2280
gttgtggctg agaagatgag aggaatattt aaataacatc aacagaacaa cttcactttg 2340
ggccaaacat ttgaaaaact ttttataaaa aattgtttga tatttcttaa tgtctgctct 2400
gagccttaaa acacagattg aagaagaaaa gaaagaaaaa acttaaatat ttatttctat 2460
gctttgttgc ctctgagaat aatgacaatt tatgaatttg tgtttcaaat tgataaaata 2520
tttaggtaca aataacaaga ctaataatat tttcttattt aaaaaaagca tgggaagatt 2580
tttatttatc aaaatataga ggaaatgtag acaaaatgga tataaatgaa aattaccatg 2640
ttgtaaaacc ttgaaaatca gattctaact gattgtatgc aactaagtat ttctgaacac 2700
ctatgcaggt cttatttaca gtgttactaa gggaacacac aaagaattac acaacgtttt 2760
cctcaagaaa atggtacaaa acacaaccga ggagcgtata cagttgaaaa catttttgtt 2820
ttgattggaa ggcagattat tttatattag tattaaaaat caaaccctat gtttctttca 2880
gatgaatctt ccaaagtgga ttatattaag caggtattag atttagaaaa cctttccatt 2940
tcttaaagta ttatcaagtg tcaagatcag caagtgtcct taagtcaaat aggttttttt 3000
ttgttggtgg ttgtgcttgc tttccttttt tagaaagttc tagaaaatag gaaaacgaaa 3060
aatttcattg agatgagtag tgcatttaat tattttttaa aaaacttttt aagtacttga 3120
attttatatc aggaaaacaa agttgttgag ccttgcttct tccgttttgc cctttgtctc 3180
gctccttatt ctttttgggg gggagggtta tttgcttttt tatcttcctg gcataatttc 3240
cattttattc ttctgagtgt ctatgttaac ttccctctat cccgcttata aaaaaattct 3300
ccaacaaaaa tacttgttga cttgatgttt tatcacttct ctaagtaagg ttgaaatatc 3360
cttattgtag ctactgtttt taatgtaaag gttaaacttg aaaagaaatt cttaatcacg 3420
gtgccaaaat tcattttcta acaccatgtg ttagaaaatt ataaaaaata aaataatttt 3480
aaaaaaaaaa aaaaaaaaaa aaa 3503

<210> SEQ ID NO 32
<211> LENGTH: 247
<212> TYPE: PRT
<213> ORGANISM: Homo sapiens

<400> SEQUENCE: 32

Met Leu Gln Asn Ser Ala Val Leu Leu Val Leu Val Ile Ser Ala Ser
1 5 10 15

Ala Thr His Glu Ala Glu Gln Asn Asp Ser Val Ser Pro Arg Lys Ser
20 25 30

Arg Val Ala Ala Gln Asn Ser Ala Glu Val Val Arg Cys Leu Asn Ser
35 40 45

-continued

```
Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
    130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Arg Thr Asn Glu Pro Gln Lys Leu Lys Val
    210                 215                 220

Leu Leu Arg Asn Leu Arg Gly Glu Glu Asp Ser Pro Ser His Ile Lys
225                 230                 235                 240

Arg Thr Ser His Glu Ser Ala
                245
```

```
<210> SEQ ID NO 33
<211> LENGTH: 3901
<212> TYPE: DNA
<213> ORGANISM: Homo sapiens

<400> SEQUENCE: 33

cagtttgcaa aagccagagg tgcaagaagc agcgactgca gcagcagcag cagcagcggc      60

ggtggcagca gcagcagcag cggcggcagc agcagcagca gcggaggcac cggtggcagc     120

agcagcatca ccagcaacaa caacaaaaaa aaatcctcat caaatcctca cctaagcttt     180

cagtgtatcc agatccacat cttcactcaa gccaggagag ggaaagagga aagggggggca    240

ggaaaaaaaa aaaacccaac aacttagcgg aaacttctca gagaatgctc caaaactcag     300

cagtgcttct ggtgctggtg atcagtgctt ctgcaaccca tgaggcggag cagaatgact     360

ctgtgagccc caggaaatcc cgagtggcgg ctcaaaactc agctgaagtg gttcgttgcc     420

tcaacagtgc tctacaggtc ggctgcgggg cttttgcatg cctggaaaac tccacctgtg     480

acacagatgg gatgtatgac atctgtaaat ccttcttgta cagcgctgct aaatttgaca     540

ctcagggaaa agcattcgtc aaagagagct taaaatgcat cgccaacggg gtcacctcca     600

aggtcttcct cgccattcgg aggtgctcca ctttccaaag gatgattgct gaggtgcagg     660

aagagtgcta cagcaagctg aatgtgtgca gcatcgccaa gcggaaccct gaagccatca     720

ctgaggtcgt ccagctgccc aatcacttct ccaacagata ctataacaga cttgtccgaa     780

gcctgctgga atgtgatgaa gacacagtca gcacaatcag agacagcctg atggagaaaa     840

ttgggcctaa catggccagc ctcttccaca tcctgcagac agaccactgt gcccaaacac     900

acccacgagc tgacttcaac aggagacgca ccaatgagcc gcagaagctg aaagtcctcc     960
```

-continued

```
tcaggaacct ccgaggtgag gaggactctc cctcccacat caaacgcaca tcccatgaga   1020
gtgcataacc agggagaggt tattcacaac ctcaccaaac tagtatcatt ttaggggtgt   1080
tgacacacca attttgagtg tactgtgcct ggtttgattt ttttaaagta gttcctattt   1140
tctatccccc ttaaagaaaa ttgcatgaaa ctaggcttct gtaatcaata tcccaacatt   1200
ctgcaatggc agcattccca ccaacaaaat ccatgtgatc attctgcctc tcctcaggag   1260
aaagtaccct cttttaccaa cttcctctgc catgtctttt cccctgctcc cctgagacca   1320
cccccaaaca caaaacattc atgtaactct ccagccattg taatttgaag atgtggatcc   1380
ctttagaacg gttgccccag tagagttagc tgataaggaa actttattta aatgcatgtc   1440
ttaaatgctc ataaagatgt taaatggaat tcgtgttatg aatctgtgct ggccatggac   1500
gaatatgaat gtcacatttg aattcttgat ctctaatgag ctagtgtctt atggtcttga   1560
tcctccaatg tctaattttc tttccgacac atttaccaaa ttgcttgagc ctggctgtcc   1620
aaccagactt tgagcctgca tcttcttgca tctaatgaaa aacaaaaagc taacatcttt   1680
acgtactgta actgctcaga gctttaaaag tatctttaac aattgtctta aaaccagaga   1740
atcttaaggt ctaactgtgg aatataaata gctgaaaact aatgtactgt acataaattc   1800
cagaggactc tgcttaaaca aagcagtata taataacttt attgcatata gatttagttt   1860
tgtaacttag ctttattttt cttttcctgg gaatggaata actatctcac ttccagatat   1920
ccacataaat gctccttgtg gccttttttta taactaaggg ggtagaagta gttttaattc   1980
aacatcaaaa cttaagatgg gcctgtatga gacaggaaaa accaacaggt ttatctgaag   2040
gaccccaggt aagatgttaa tctcccagcc cacctcaacc cagaggctac tcttgactta   2100
gacctatact gaaagatctc tgtcacatcc aactggaaat tccaggaacc aaaaagagca   2160
tccctatggg cttggaccac ttacagtgtg ataaggccta ctatacatta ggaagtggta   2220
gttctttact cgtccccttt catcggtgcc tggtactctg gcaaatgatg atggggtggg   2280
agactttcca ttaaatcaat caggaatgag tcaatcagcc tttaggtctt tagtccgggg   2340
gacttggggc tgagagagta taaataaccc tgggctgtcc agccttaata gacttctctt   2400
acattttcgt cctgtagcac gctgcctgcc aaagtagtcc tggcagctgg accatctctg   2460
taggatcgta aaaaaataga aaaaaagaaa aaaaaaagaa agaaagaggg aaaaagagct   2520
ggtggtttga tcatttctgc catgatgttt acaagatggc gaccaccaaa gtcaaacgac   2580
taacctatct atgaacaaca gtagtttctc agggtcactg tccttgaacc caacagtccc   2640
ttatgagcgt cactgcccac caaaggtcaa tgtcaagaga ggaagagagg gaggaggggt   2700
aggactgcag gggccactcc aaactcgctt aggtagaaac tattggtgct cgactctcac   2760
taggctaaac tcaagatttg accaaatcga gtgataggga tcctggtggg aggagagagg   2820
gcacatctcc agaaaaatga aaagcaatac aactttacca taaagccttt aaaaccagta   2880
acgtgctgct caaggaccaa gagcaattgc agcagaccca gcagcagcag cagcagcaca   2940
aacattgctg cctttgtccc cacacagcct ctaagcgtgc tgacatcaga ttgttaaggg   3000
catttttata ctcagaactg tcccatcccc aggtccccaa acttatggac actgccttag   3060
cctcttggaa atcaggtaga ccatattcta agttagactc ttcccctccc tcccacactt   3120
cccaccccca ggcaaggctg acttctctga atcagaaaag ctattaaagt ttgtgtgttg   3180
tgtccatttt gcaaacccaa ctaagccagg accccaatgc gacaagtagt tcatgagtat   3240
tcctagcaaa tttctctctt tcttcagttc agtagatttc cttttttctt ttcttttttt   3300
tttttttttt tttttggctg tgacctcttc aaaccgtggt acccccccctt ttctccccac   3360
```

-continued

```
gatgatatct atatatgtat ctacaataca tatatctaca catacagaaa gaagcagttc   3420

tcacatgttg ctagtttttt gcttctcttt cccccaccct actccctcca attccccccct  3480

taaacttcca aagcttcgtc ttgtgtttgc tgcagagtga ttcgggggct gacctagacc   3540

agtttgcatg attcttctct tgtgatttgg ttgcacttta gacatttttg tgccattata   3600

tttgcattat gtatttataa tttaaatgat atttaggttt ttggctgagt actggaataa   3660

acagtgagca tatctggtat atgtcattat ttattgttaa attacatttt ttaagctcca   3720

tgtgcatata aaggttatga aacatatcat ggtaatgaca gatgcaagtt attttatttg   3780

cttatttttt ataattaaag atgccatagc ataatatgaa gcctttggtg aattccttct   3840

aagataaaaa taataataaa gtgttacgtt ttattggttt caaaaaaaaa aaaaaaaaaa   3900

a                                                                   3901


<210> SEQ ID NO 34
<211> LENGTH: 313
<212> TYPE: PRT
<213> ORGANISM: Homo sapiens

<400> SEQUENCE: 34

Met Gly Ile Gly Arg Ser Glu Gly Gly Arg Arg Gly Ala Leu Gly Val
1               5                   10                  15

Leu Leu Ala Leu Gly Ala Ala Leu Leu Ala Val Gly Ser Ala Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gln Gln Ala Ser Ser Trp
                85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Lys Lys Ile
    210                 215                 220

Val Pro Lys Lys Lys Lys Pro Leu Lys Leu Gly Pro Ile Lys Lys Lys
225                 230                 235                 240

Asp Leu Lys Lys Leu Val Leu Tyr Leu Lys Asn Gly Ala Asp Cys Pro
                245                 250                 255

Cys His Gln Leu Asp Asn Leu Ser His His Phe Leu Ile Met Gly Arg
            260                 265                 270

Lys Val Lys Ser Gln Tyr Leu Leu Thr Ala Ile His Lys Trp Asp Lys
```

-continued

```
        275                 280                 285

Lys Asn Lys Glu Phe Lys Asn Phe Met Lys Lys Met Lys Asn His Glu
    290                 295                 300

Cys Pro Thr Phe Gln Ser Val Phe Lys
305                 310


<210> SEQ ID NO 35
<211> LENGTH: 4469
<212> TYPE: DNA
<213> ORGANISM: Homo sapiens

<400> SEQUENCE: 35

cctgcagcct ccggagtcag tgccgcgcgc ccgccgcccc gcgccttcct gctcgccgca      60

cctccgggag ccggggcgca cccagcccgc agcgccgcct ccccgcccgc gccgcctccg     120

accgcaggcc gagggccgcc actggccggg gggaccgggc agcagcttgc ggccgcggag     180

ccgggcaacg ctggggactg cgccttttgt ccccggaggt ccctggaagt ttgcggcagg     240

acgcgcgcgg ggaggcggcg gaggcagccc cgacgtcgcg gagaacaggg cgcagagccg     300

gcatgggcat cgggcgcagc gaggggggcc gccgcggggc cctgggcgtg ctgctggcgc     360

tgggcgcggc gcttctggcc gtgggctcgg ccagcgagta cgactacgtg agcttccagt     420

cggacatcgg cccgtaccag agcgggcgct tctacaccaa gccacctcag tgcgtggaca     480

tccccgcgga cctgcggctg tgccacaacg tgggctacaa gaagatggtg ctgcccaacc     540

tgctggagca cgagaccatg gcggaggtga agcagcaggc cagcagctgg gtgcccctgc     600

tcaacaagaa ctgccacgcc gggacccagg tcttcctctg ctcgctcttc gcgcccgtct     660

gcctggaccg gcccatctac ccgtgtcgct ggctctgcga ggccgtgcgc gactcgtgcg     720

agccggtcat gcagttcttc ggcttctact ggcccgagat gcttaagtgt gacaagttcc     780

cggaggggga cgtctgcatc gccatgacgc cgcccaatgc caccgaagcc tccaagcccc     840

aaggcacaac ggtgtgtcct ccctgtgaca acgagttgaa atctgaggcc atcattgaac     900

atctctgtgc cagcgagttt gcactgagga tgaaaataaa agaagtgaaa aaagaaaatg     960

gcgacaagaa gattgtcccc aagaagaaga agcccctgaa gttggggccc atcaagaaga    1020

aggacctgaa gaagcttgtg ctgtacctga agaatggggc tgactgtccc tgccaccagc    1080

tggacaacct cagccaccac ttcctcatca tgggccgcaa ggtgaagagc cagtacttgc    1140

tgacggccat ccacaagtgg gacaagaaaa acaaggagtt caaaaacttc atgaagaaaa    1200

tgaaaaacca tgagtgcccc acctttcagt ccgtgtttaa gtgattctcc cgggggcagg    1260

gtggggaggg agcctcgggt ggggtgggag cggggggggac agtgcccggg aacccgtggt    1320

cacacacacg cactgccctg tcagtagtgg acattgtaat ccagtcggct tgttcttgca    1380

gcattcccgc tccctttccc tccatagcca cgctccaaac cccagggtag ccatggccgg    1440

gtaaagcaag ggccatttag attaggaagg tttttaagat ccgcaatgtg gagcagcagc    1500

cactgcacag gaggaggtga caaaccattt ccaacagcaa cacagccact aaaacacaaa    1560

aagggggatt gggcggaaag tgagagccag cagcaaaaac tacattttgc aacttgttgg    1620

tgtggatcta ttggctgatc tatgcctttc aactagaaaa ttctaatgat tggcaagtca    1680

cgttgttttc aggtccagag tagtttcttt ctgtctgctt taaatggaaa cagactcata    1740

ccacacttac aattaaggtc aagcccagaa agtgataagt gcagggagga aaagtgcaag    1800

tccattatct aatagtgaca gcaaagggac caggggagag gcattgcctt ctctgcccac    1860

agtctttccg tgtgattgtc tttgaatctg aatcagccag tctcagatgc cccaaagttt    1920
```

-continued

```
cggttcctat gagcccgggg catgatctga tccccaagac atgtggaggg gcagcctgtg   1980
cctgcctttg tgtcagaaaa aggaaaccac agtgagcctg agagagacgg cgattttcgg   2040
gctgagaagg cagtagtttt caaaacacat agttaaaaaa gaaacaaatg aaaaaaattt   2100
tagaacagtc cagcaaattg ctagtcaggg tgaattgtga aattgggtga agagcttagg   2160
attctaatct catgtttttt ccttttcaca tttttaaaag aacaatgaca aacacccact   2220
tatttttcaa ggttttaaaa cagtctacat tgagcatttg aaaggtgtgc tagaacaagg   2280
tctcctgatc cgtccgaggc tgcttcccag aggagcagct ctccccaggc atttgccaag   2340
ggaggcggat ttccctggta gtgtagctgt gtggctttcc ttcctgaaga gtccgtggtt   2400
gccctagaac ctaacacccc ctagcaaaac tcacagagct ttccgttttt ttctttcctg   2460
taaagaaaca tttcctttga acttgattgc ctatggatca aagaaattca gaacagcctg   2520
cctgttcccc cgcacttttt acatatattt gtttcatttc tgcagatgga aagttgacat   2580
gggtggggtg tccccatcca gcgagagagt ttcaaaagca aaacatctct gcagtttttc   2640
ccaagtaccc tgagatactt cccaaagccc ttatgtttaa tcagcgatgt atataagcca   2700
gttcacttag acaactttac ccttcttgtc caatgtacag gaagtagttc taaaaaaaat   2760
gcatattaat ttcttccccc aaagccggat tcttaattct ctgcaacact ttgaggacat   2820
ttatgattgt ccctctgggc caatgcttat acccagtgag gatgctgcag tgaggctgta   2880
aagtggcccc ctgcggccct agcctgaccc ggagaaagga tggtagattc tgttaactct   2940
tgaagactcc agtatgaaaa tcagcatgcc cgcctagtta cctaccggag agttatcctg   3000
ataaattaac ctctcacagt tagtgatcct gtccttttaa cacctttttt gtggggttct   3060
ctctgacctt tcatcgtaaa gtgctgggga ccttaagtga tttgcctgta attttggatg   3120
attaaaaaat gtgtatatat attagctaat tagaaatatt ctacttctct gttgtcaaac   3180
tgaaattcag agcaagttcc tgagtgcgtg gatctgggtc ttagttctgg ttgattcact   3240
caagagttca gtgctcatac gtatctgctc attttgacaa agtgcctcat gcaaccgggc   3300
cctctctctg cggcagagtc cttagtggag gggtttacct ggaacataag tagttaccac   3360
agaatacgga agagcaggtg actgtgctgt gcagctctct aaatgggaat tctcaggtag   3420
gaagcaacag cttcagaaag agctcaaaat aaattggaaa tgtgaatcgc agctgtgggt   3480
tttaccaccg tctgtctcag agtcccagga ccttgagtgt cattagttac tttattgaag   3540
gttttagacc catagcagct ttgtctctgt cacatcagca atttcagaac caaaagggag   3600
gctctctgta ggcacagagc tgcactatca cgagcctttg tttttctcca caaagtatct   3660
aacaaaacca atgtgcagac tgattggcct ggtcattggt ctccgagaga ggaggtttgc   3720
ctgtgatttg cctgtgattt cctaattatc gctagggcca aggtgggatt tgtaaagctt   3780
tacaataatc attctggata gagtcctggg aggtccttgg cagaactcag ttaaatcttt   3840
gaagaatatt tgtagttatc ttagaagata gcatgggagg tgaggattcc aaaaacattt   3900
tatttttaaa atatcctgtg taacacttgg ctcttggtac ctgtgggtta gcatcaagtt   3960
ctccccaggg tagaattcaa tcagagctcc agtttgcatt tggatgtgta aattacagta   4020
atcccatttc ccaaacctaa aatctgtttt tctcatcaga ctctgagtaa ctggttgctg   4080
tgtcataact tcatagatgc aggaggctca ggtgatctgt ttgaggagag caccctaggc   4140
agcctgcagg gaataacata ctggccgttc tgacctgttg ccagcagata cacaggacat   4200
ggatgaaatt cccgtttcct ctagtttctt cctgtagtac tcctctttta gatcctaagt   4260
ctcttacaaa agctttgaat actgtgaaaa tgttttacat tccatttcat ttgtgttgtt   4320
```

```
tttttaactg cattttacca gatgttttga tgttatcgct tatgttaata gtaattcccg   4380

tacgtgttca ttttattttc atgctttttc agccatgtat caatattcac ttgactaaaa   4440

tcactcaatt aatcaatgaa aaaaaaaaa                                     4469


<210> SEQ ID NO 36
<211> LENGTH: 250
<212> TYPE: PRT
<213> ORGANISM: Homo sapiens

<400> SEQUENCE: 36

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr His
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Pro Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250


<210> SEQ ID NO 37
<211> LENGTH: 914
<212> TYPE: DNA
<213> ORGANISM: Homo sapiens

<400> SEQUENCE: 37

ccagccaacg agcggaaaat ggcagacaat ttttcgctcc atgatgcgtt atctgggtct     60

ggaaacccaa accctcaagg atggcctggc gcatgggga accagcctgc tggggcaggg    120

ggctacccag ggcttccta tcctggggcc taccccgggc aggcaccccc aggggcttat    180

cctggacagg cacctccagg cgcctaccat ggagcacctg gagcttatcc cggagcacct    240

gcacctggag tctacccagg gccacccagc ggccctgggg cctacccatc ttctggacag    300
```

```
ccaagtgccc ccggagccta ccctgccact ggcccctatg gcgcccctgc tgggccactg    360

attgtgcctt ataacctgcc tttgcctggg ggagtggtgc ctcgcatgct gataacaatt    420

ctgggcacgg tgaagcccaa tgcaaacaga attgctttag atttccaaag agggaatgat    480

gttgccttcc actttaaccc acgcttcaat gagaacaaca ggagagtcat tgtttgcaat    540

acaaagctgg ataataactg ggggaaggaa gaaagacagt cggttttccc atttgaaagt    600

gggaaaccat tcaaaataca agtactggtt gaacctgacc acttcaaggt tgcagtgaat    660

gatgctcact tgttgcagta caatcatcgg gttaaaaaac tcaatgaaat cagcaaactg    720

ggaatttctg gtgacataga cctcaccagt gcttcatata ccatgatata atctgaaagg    780

ggcagattaa aaaaaaaaaa aaagaatcta aaccttacat gtgtaaaggt ttcatgttca    840

ctgtgagtga aaatttttac attcatcaat atccctcttg taagtcatct acttaataaa    900

tattacagtg aaag                                                      914
```

<210> SEQ ID NO 38
<211> LENGTH: 94
<212> TYPE: PRT
<213> ORGANISM: Homo sapiens

<400> SEQUENCE: 38

```
Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Asp Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90
```

<210> SEQ ID NO 39
<211> LENGTH: 3710
<212> TYPE: DNA
<213> ORGANISM: Homo sapiens

<400> SEQUENCE: 39

```
gaattccctg taagccctgt tacaggggct gcaccccaga tacaacctga cctgtgtcca     60

aggcgggcaa ctcaaccctt agatattgaa tgggtcccat ggcaccaatg cttaaacacc    120

agcagccctc acaaccacag atcgtgtttt aaggatgagg aggtagttct ctggatgcac    180

aggcttcaat ccaaatgggc tcatgacgcc gcagcacaca cccagtctgc agcctgaaga    240

gttggagcat tgcattcaca gaaagcatcc agacatgatc atgggctcag ggatacacct    300

gttctccgat gtgtaccagt gaaggatgga aactcctatg cctcccagaa agcaccactc    360

aagcttttgc tgaatgcttc tctgaaggcc cacaaggctg agaggctgtg caacaccagc    420

agtaaagtga atgcccagac tcccacctcc tttcttgggt ggccatctgg aaaggccact    480

cccaccctga tggctaatgc ctcagaccag ttcttggccc agatgatcct agacaattgt    540

ttaagcttaa actgttcatt ggccaagcaa acaggtgata gtacctctgg ggaaccacat    600

gccgcgtgta catccagatc tcaggagaac ccaaaaaatgt ctgttccaca tagcaacaga    660

agcccaggta gcactcagtc tcacctgggt gttctccaac atcccagctc agccaaatgg    720
```

-continued

```
ctttcattag tttttatggt tagaccccag gtcctcggga cactgcttta gaaacacatt    780
ccaaatcctc ctctgtgtgc aggtggcatt cctatcccaa tctctttgca gggcgtatac    840
tgtgatacgc agccaggctg tcccagaggc cttaaatatt cccttggtgc aggtagttca    900
gcttagccac agccaatgca tcacagggtc aactgtgtta ggagccattg agaatccata    960
gttggttgct gcctgggcct ggccagggct gaccaaggta gatgagaggt tcctctgtgg   1020
agttctactt taacctcacc ttcccaccaa atttctcaac tgtccttgcc accacaatta   1080
tttaatggac ccaacagaaa gtaaccccgg aaattaggac acctcatccc aaaagacctt   1140
taaatagggg aagtccactt gtgcacggct gctccttgct atagaagacc tgggacagag   1200
gactgctgtc tgccctctct ggtcaccctg cctagctaga ggatctgtaa gtactacaaa   1260
acttaaactt tacactgagt tttcatcatt gaagctatgc ctccaatctg acctctgact   1320
gtggggccgc cccagaggga cccagcgggt gaatccctgc taggaacgtc tgtccggacc   1380
tctggtgact gctggggacg atggcttcca gctaacttaa tagagaaact caagcagttt   1440
ccttctaaat acacatgtca catgtcctgg ttgacatgtc cagtaagaag actatcacag   1500
gtctttggaa cattcttttg agagaaacct atttaggtcc ttggtctgtt tttcaatcag   1560
gttgtttgat ttttgctatt gagttgttgg aattccttat gtattcagat atttgcccct   1620
tctgccatgt aggttttgca aatattttct ctcattttct gggttatctt ttcactcggt   1680
tgattgtttc ctttgctgtg cagatgcttt agcgttaaat gaagccacac ttgtctattt   1740
tcccttttat tgcctgtgcc tttggtgtca tagccaagaa atcattacct acatcaatgt   1800
caaaagcttt atccttctat acacttctag tagtttatgg tttcagttgt tacatttagg   1860
ttttcaattc attctgagtt gatgttccta catggtgtga gataaagatt taaatacata   1920
catatataaa atcatgaggt agtgtacact ataaatatac aattgttaat tgttactcaa   1980
gtctaagtag aggtggaaat aataaacttt cttttttta cttaaaccac tctgtgtcac   2040
tgagctgatt tcacctttag cctgataaaa tcattgtcct ctccaccctg attcctacag   2100
gagactactc accccataac ctcaaaaacc tcttcatgag gatggtaagt cacctgaatc   2160
ctgaagtgaa ttactcgcta ttccattgga actcatatag gacaccagaa tctagacctc   2220
cagagaacag caggacccat cttcagaaaa taagaagcat ttgttccctg agcctgttga   2280
atcaaagtgc aatttctatt ctttttggaa tgttaaaaag tgaatcataa tatttaagca   2340
ggtgaaccca cgagtaacat agcagggtct ttcttgtcat tattagctcc aacctagcac   2400
agacattaaa ggtacagatg tatactagca tgaaactggg agaacaggag cattcgagca   2460
accttgagac caatgggcct ctcttataaa atgcacacct cctctcactg agattgagga   2520
aggtttcttg tctccgagcc ttctcccagt agagctataa atccaggctg gctcctccct   2580
ccccacacag ctgctcctgc tctccctcct ccaggtgacc ccagccatga ggaccctcgc   2640
catccttgct gccattctcc tggtggccct gcaggcccag gctgagccac tccaggcaag   2700
agctgatgag gttgctgcag ccccggagca gattgcagcg gacatcccag aagtggttgt   2760
ttcccttgca tgggacgaaa gcttggctcc aaagcatcca ggtgagagag gcaggcatgc   2820
agagctgcta agtctagagg gaaggacggg agagaggttc cagagttggg tctcagcagt   2880
ctatgtcact gaggtggctt cacttagaat ctctgggcat tgattttctc atctagaaat   2940
tgaacagaga gccaaataaa cctgagaaac tttatttctc caaagacttg attccaagaa   3000
acatctgtga aattcactaa gtttaagata tgaagagaca gactagttat ttctggatct   3060
aaacaagtag acttagttgt aaagagaaca ttttactcta tctacagaag agcttttaaa   3120
```

-continued aactgcagcc aagcctgagg gtaagttcag gtgtgtgtgt gatggggcag gaatgcaaaa 3180
atgagagcaa aggagaatga gtctcaaatt ctgtgtgaca agcactgctc tgcgtgttta 3240
ttcctatcga ctgaggttgt tcgtgctacc ggctgcaatg cagccagcat cacctgtcag 3300
ctagcatgtg acttccccga gattcttttt cttacccact gctaactcca tactcaattt 3360
ctcatgctct ccctgtccca ggctcaagga aaaacatgga ctgctattgc agaataccag 3420
cgtgcattgc aggagaacgt cgctatggaa cctgcatcta ccagggaaga ctctgggcat 3480
tctgctgctg agcttgcaga aaaagaaaaa tgagctcaaa atttgctttg agagctacag 3540
ggaattgcta ttactcctgt accttctgct caatttcctt tcctcatctc aaataaatgc 3600
cttgttacaa gatttctgtg tttccacctc tttaatgtgt gatatgtgtc tgtgtcaaga 3660
cacttgggat acacgtacca aaacgcaaaa tcaaattttt gaacaatata 3710

<210> SEQ ID NO 40
<211> LENGTH: 1201
<212> TYPE: PRT
<213> ORGANISM: Homo sapiens

<400> SEQUENCE: 40

Ser Leu Trp Leu Ile Ala Ala Ala Leu Val Glu Val Arg Thr Ser Ala
1 5 10 15

Asp Gly Gln Ala Gly Asn Glu Glu Met Val Gln Ile Asp Leu Pro Ile
20 25 30

Lys Arg Tyr Arg Glu Tyr Glu Leu Val Thr Pro Val Ser Thr Asn Leu
35 40 45

Glu Gly Arg Tyr Leu Ser His Thr Leu Ser Ala Ser His Lys Lys Arg
50 55 60

Ser Ala Arg Asp Val Ser Ser Asn Pro Glu Gln Leu Phe Phe Asn Ile
65 70 75 80

Thr Ala Phe Gly Lys Asp Phe His Leu Arg Leu Lys Pro Asn Thr Gln
85 90 95

Leu Val Ala Pro Gly Ala Val Val Glu Trp His Glu Thr Ser Leu Val
100 105 110

Pro Gly Asn Ile Thr Asp Pro Ile Asn Asn His Gln Pro Gly Ser Ala
115 120 125

Thr Tyr Arg Ile Arg Lys Thr Glu Pro Leu Gln Thr Asn Cys Ala Tyr
130 135 140

Val Gly Asp Ile Val Asp Ile Pro Gly Thr Ser Val Ala Ile Ser Asn
145 150 155 160

Cys Asp Gly Leu Ala Gly Met Ile Lys Ser Asp Asn Glu Glu Tyr Phe
165 170 175

Ile Glu Pro Leu Glu Arg Gly Lys Gln Met Glu Glu Glu Lys Gly Arg
180 185 190

Ile His Val Val Tyr Lys Arg Ser Ala Val Glu Gln Ala Pro Ile Asp
195 200 205

Met Ser Lys Asp Phe His Tyr Arg Glu Ser Asp Leu Glu Gly Leu Asp
210 215 220

Asp Leu Gly Thr Val Tyr Gly Asn Ile His Gln Gln Leu Asn Glu Thr
225 230 235 240

Met Arg Arg Arg Arg His Ala Gly Glu Asn Asp Tyr Asn Ile Glu Val
245 250 255

Leu Leu Gly Val Asp Asp Ser Val Val Arg Phe His Gly Lys Glu His
260 265 270

Val Gln Asn Tyr Leu Leu Thr Leu Met Asn Ile Val Asn Glu Ile Tyr

-continued

```
        275                 280                 285

His Asp Glu Ser Leu Gly Val His Ile Asn Val Val Leu Val Arg Met
    290                 295                 300

Ile Met Leu Gly Tyr Ala Lys Ser Ile Ser Leu Ile Glu Arg Gly Asn
305                 310                 315                 320

Pro Ser Arg Ser Leu Glu Asn Val Cys Arg Trp Ala Ser Gln Gln Gln
                325                 330                 335

Arg Ser Asp Leu Asn His Ser Glu His His Asp His Ala Ile Phe Leu
            340                 345                 350

Thr Arg Gln Asp Phe Gly Pro Ala Gly Met Gln Gly Tyr Ala Pro Val
        355                 360                 365

Thr Gly Met Cys His Pro Val Arg Ser Cys Thr Leu Asn His Glu Asp
    370                 375                 380

Gly Phe Ser Ser Ala Phe Val Val Ala His Glu Thr Gly His Val Leu
385                 390                 395                 400

Gly Met Glu His Asp Gly Gln Gly Asn Arg Cys Gly Asp Glu Thr Ala
                405                 410                 415

Met Gly Ser Val Met Ala Pro Leu Val Gln Ala Ala Phe His Arg Tyr
            420                 425                 430

His Trp Ser Arg Cys Ser Gly Gln Glu Leu Lys Arg Tyr Ile His Ser
        435                 440                 445

Tyr Asp Cys Leu Leu Asp Asp Pro Phe Asp His Asp Trp Pro Lys Leu
    450                 455                 460

Pro Glu Leu Pro Gly Ile Asn Tyr Ser Met Asp Glu Gln Cys Arg Phe
465                 470                 475                 480

Asp Phe Gly Val Gly Tyr Lys Met Cys Thr Ala Phe Arg Thr Phe Asp
                485                 490                 495

Pro Cys Lys Gln Leu Trp Cys Ser His Pro Asp Asn Pro Tyr Phe Cys
            500                 505                 510

Lys Thr Lys Lys Gly Pro Pro Leu Asp Gly Thr Glu Cys Ala Ala Gly
        515                 520                 525

Lys Trp Cys Tyr Lys Gly His Cys Met Trp Lys Asn Ala Asn Gln Gln
    530                 535                 540

Lys Gln Asp Gly Asn Trp Gly Ser Trp Thr Lys Phe Gly Ser Cys Ser
545                 550                 555                 560

Arg Thr Cys Gly Thr Gly Val Arg Phe Arg Thr Arg Gln Cys Asn Asn
                565                 570                 575

Pro Met Pro Ile Asn Gly Gly Gln Asp Cys Pro Gly Val Asn Phe Glu
            580                 585                 590

Tyr Gln Leu Cys Asn Thr Glu Glu Cys Gln Lys His Phe Glu Asp Phe
        595                 600                 605

Arg Ala Gln Gln Cys Gln Gln Arg Asn Ser His Phe Glu Tyr Gln Asn
    610                 615                 620

Thr Lys His His Trp Leu Pro Tyr Glu His Pro Asp Pro Lys Lys Arg
625                 630                 635                 640

Cys His Leu Tyr Cys Gln Ser Lys Glu Thr Gly Asp Val Ala Tyr Met
                645                 650                 655

Lys Gln Leu Val His Asp Gly Thr His Cys Ser Tyr Lys Asp Pro Tyr
            660                 665                 670

Ser Ile Cys Val Arg Gly Glu Cys Val Lys Val Gly Cys Asp Lys Glu
        675                 680                 685

Ile Gly Ser Asn Lys Val Glu Asp Lys Cys Gly Val Cys Gly Gly Asp
    690                 695                 700
```

-continued

```
Asn Ser His Cys Arg Thr Val Lys Gly Thr Phe Thr Arg Thr Pro Arg
705                 710                 715                 720

Lys Leu Gly Tyr Leu Lys Met Phe Asp Ile Pro Pro Gly Ala Arg His
                725                 730                 735

Val Leu Ile Gln Glu Asp Glu Ala Ser Pro His Ile Leu Ala Ile Lys
            740                 745                 750

Asn Gln Ala Thr Gly His Tyr Ile Leu Asn Gly Lys Gly Glu Glu Ala
        755                 760                 765

Lys Ser Arg Thr Phe Ile Asp Leu Gly Val Glu Trp Asp Tyr Asn Ile
    770                 775                 780

Glu Asp Asp Ile Glu Ser Leu His Thr Asp Gly Pro Leu His Asp Pro
785                 790                 795                 800

Val Ile Val Leu Ile Ile Pro Gln Glu Asn Asp Thr Arg Ser Ser Leu
                805                 810                 815

Thr Tyr Lys Tyr Ile Ile His Glu Asp Ser Val Pro Thr Ile Asn Ser
            820                 825                 830

Asn Asn Val Ile Gln Glu Glu Leu Asp Thr Phe Glu Trp Ala Leu Lys
        835                 840                 845

Ser Trp Ser Gln Val Ser Lys Pro Cys Gly Gly Gly Phe Gln Tyr Thr
    850                 855                 860

Lys Tyr Gly Cys Arg Arg Lys Ser Asp Asn Lys Met Val His Arg Ser
865                 870                 875                 880

Phe Cys Glu Ala Asn Lys Lys Pro Lys Pro Ile Arg Arg Met Cys Asn
                885                 890                 895

Ile Gln Glu Cys Thr His Pro Leu Trp Val Ala Glu Glu Trp Glu His
            900                 905                 910

Cys Thr Lys Thr Cys Gly Ser Ser Gly Tyr Gln Leu Arg Thr Val Arg
        915                 920                 925

Cys Leu Gln Pro Leu Leu Asp Gly Thr Asn Arg Ser Val His Ser Lys
    930                 935                 940

Tyr Cys Met Gly Asp Arg Pro Glu Ser Arg Arg Pro Cys Asn Arg Val
945                 950                 955                 960

Pro Cys Pro Ala Gln Trp Lys Thr Gly Pro Trp Ser Glu Cys Ser Val
                965                 970                 975

Thr Cys Gly Glu Gly Thr Glu Val Arg Gln Val Leu Cys Arg Ala Gly
            980                 985                 990

Asp His Cys Asp Gly Glu Lys Pro  Glu Ser Val Arg Ala  Cys Gln Leu
        995                 1000                1005

Pro Pro  Cys Asn Asp Glu Pro  Cys Leu Gly Asp Lys  Ser Ile Phe
    1010                1015                1020

Cys Gln  Met Glu Val Leu Ala  Arg Tyr Cys Ser Ile  Pro Gly Tyr
    1025                1030                1035

Asn Lys  Leu Cys Cys Glu Ser  Cys Ser Lys Arg Ser  Ser Thr Leu
    1040                1045                1050

Pro Pro  Pro Tyr Leu Leu Glu  Ala Ala Glu Thr His  Asp Asp Val
    1055                1060                1065

Ile Ser  Asn Pro Ser Asp Leu  Pro Arg Ser Leu Val  Met Pro Thr
    1070                1075                1080

Ser Leu  Val Pro Tyr His Ser  Glu Thr Pro Ala Lys  Lys Met Ser
    1085                1090                1095

Leu Ser  Ser Ile Ser Ser Val  Gly Gly Pro Asn Ala  Tyr Ala Ala
    1100                1105                1110

Phe Arg  Pro Asn Ser Lys Pro  Asp Gly Ala Asn Leu  Arg Gln Arg
    1115                1120                1125
```

```
Ser Ala  Gln Gln Ala Gly Ser  Lys Thr Val Arg Leu  Val Thr Val
    1130                 1135                 1140

Pro Ser  Ser Pro Pro Thr Lys  Arg Val His Leu Ser  Ser Ala Ser
    1145                 1150                 1155

Gln Met  Ala Ala Ala Ser Phe  Phe Ala Ala Ser Asp  Ser Ile Gly
    1160                 1165                 1170

Ala Ser  Ser Gln Ala Arg Thr  Ser Lys Lys Asp Gly  Lys Ile Ile
    1175                 1180                 1185

Asp Asn  Arg Arg Pro Thr Arg  Ser Ser Thr Leu Glu  Arg
    1190                 1195                 1200


<210> SEQ ID NO 41
<211> LENGTH: 5774
<212> TYPE: DNA
<213> ORGANISM: Homo sapiens

<400> SEQUENCE: 41

gtcactttgg ttgatagcag ccgctctggt agaggttagg acttcagctg atggacaagc     60

tggtaatgaa gaaatggtgc aaatagattt accaataaag agatatagag agtatgagct    120

ggtgactcca gtcagcacaa atctagaagg acgctatctc tcccatactc tttctgcgag    180

tcacaaaaag aggtcagcga gggacgtgtc ttccaaccct gagcagttgt tctttaacat    240

cacggcattt ggaaaagatt ttcatctgcg actaaagccc aacactcaac tagtagctcc    300

tggggctgtt gtggagtggc atgagacatc tctggtgcct gggaatataa ccgatcccat    360

taacaaccat caaccaggaa gtgctacgta tagaatccgg aaaacagagc ctttgcagac    420

taactgtgct tatgttggtg acatcgtgga cattccagga acctctgttg ccatcagcaa    480

ctgtgatggt ctggctggaa tgataaaaag tgataatgaa gagtatttca ttgaaccctt    540

ggaaagaggt aaacagatgg aggaagaaaa aggaaggatt catgttgtct acaagagatc    600

agctgtagaa caggctccca tagacatgtc caaagacttc cactacagag agtcggacct    660

ggaaggcctt gatgatctag gtactgttta tggcaacatc caccagcagc tgaatgaaac    720

aatgagacgc cgcagacacg cgggagaaaa cgattacaat atcgaggtac tgctgggagt    780

ggatgactct gtggtccgtt tccatggcaa agagcacgtc caaaactacc tcctgaccct    840

aatgaacatt gtgaatgaaa tttaccatga tgagtccctc ggagtgcata taaatgtggt    900

cctggtgcgc atgataatgc tgggatatgc aaagtccatc agcctcatag aaaggggaaa    960

cccatccaga agcttggaga atgtgtgtcg ctgggcgtcc caacagcaaa gatctgatct   1020

caaccactct gaacaccatg accatgcaat ttttttaacc aggcaagact ttggacctgc   1080

tggaatgcaa ggatatgctc cagtcaccgg catgtgtcat ccagtgagaa gttgtaccct   1140

gaatcatgag gatggttttt catctgcttt tgtagtagcc catgaaacgg gccatgtgtt   1200

gggaatggag catgatggac aaggcaacag gtgtggtgat gagactgcta tgggaagtgt   1260

catggctccc ttggtacaag cagcattcca tcgttaccac tggtcccgat gcagtggtca   1320

agaactgaaa agatatatcc attcctatga ctgtctcctt gatgaccctt ttgatcatga   1380

ttggcctaaa ctcccagaac ttcctggaat caattattct atggatgagc aatgtcgttt   1440

tgattttggt gttggctata aaatgtgcac cgcgttccga acctttgacc catgtaaaca   1500

gctgtggtgt agccatcctg ataatcccta cttttgtaag actaaaaagg gacctccact   1560

tgatgggact gaatgtgctg ctggaaaatg gtgctataag ggtcattgca tgtggaagaa   1620

tgctaatcag caaaaacaag atggcaattg gggtcatgg actaaatttg gctcctgttc   1680
```

-continued

```
tcggacatgt ggaactggtg ttcgtttcag aacacgccag tgcaataatc ccatgcccat   1740
caatggtggt caggattgtc ctggtgttaa ttttgagtac cagctttgta acacagaaga   1800
atgccaaaaa cactttgagg acttcagagc acagcagtgt cagcagcgaa actcccactt   1860
tgaataccag aataccaaac accactggtt gccatatgaa catcctgacc ccaagaaaag   1920
atgccacctt tactgtcagt ccaaggagac tggagatgtt gcttacatga aacaactggt   1980
gcatgatgga acgcactgtt cttacaaaga tccatatagc atatgtgtgc gaggagagtg   2040
tgtgaaagtg ggctgtgata aagaaattgg ttctaataag gttgaggata agtgtggtgt   2100
ctgtggagga gataattccc actgccgaac cgtgaagggg acatttacca gaactcccag   2160
gaagcttggg taccttaaga tgtttgatat acccccctggg gctagacatg tgttaatcca   2220
agaagacgag gcttctcctc atattcttgc tattaagaac caggctacag gccattatat   2280
tttaaatggc aaaggggagg aagccaagtc gcggaccttc atagatcttg gtgtggagtg   2340
ggattataac attgaagatg acattgaaag tcttcacacc gatggacctt tacatgatcc   2400
tgttattgtt ttgattatac ctcaagaaaa tgatacccgc tctagcctga catataagta   2460
catcatccat gaagactctg tacctacaat caacagcaac aatgtcatcc aggaagaatt   2520
agatactttt gagtgggctt tgaagagctg gtctcaggtt tccaaaccct gtggtggagg   2580
tttccagtac actaaatatg gatgccgtag gaaaagtgat aataaaatgg tccatcgcag   2640
cttctgtgag gccaacaaaa agccgaaacc tattagacga atgtgcaata ttcaagagtg   2700
tacacatcca ctctgggtag cagaagaatg ggaacactgc accaaaacct gtggaagttc   2760
tggctatcag cttcgcactg tacgctgcct tcagccactc cttgatggca ccaaccgctc   2820
tgtgcacagc aaatactgca tgggtgaccg tcccgagagc cgccggccct gtaacagagt   2880
gccctgccct gcacagtgga aaacaggacc ctggagtgag tgttcagtga cctgcggtga   2940
aggaacggag gtgaggcagg tcctctgcag ggctggggac cactgtgatg gtgaaaagcc   3000
tgagtcggtc agagcctgtc aactgcctcc ttgtaatgat gaaccatgtt tgggagacaa   3060
gtccatattc tgtcaaatgg aagtgttggc acgatactgc tccataccag gttataacaa   3120
gttatgttgt gagtcctgca gcaagcgcag tagcaccctg ccaccaccat accttctaga   3180
agctgctgaa actcatgatg atgtcatctc taaccctagt gacctcccta gatctctagt   3240
gatgcctaca tctttggttc cttatcattc agagacccct gcaaagaaga tgtctttgag   3300
tagcatctct tcagtgggag gtccaaatgc atatgctgct ttcaggccaa acagtaaacc   3360
tgatggtgct aatttacgcc agaggagtgc tcagcaagca ggaagtaaga ctgtgagact   3420
ggtcaccgta ccatcctccc cacccaccaa gagggtccac ctcagttcag cttcacaaat   3480
ggctgctgct tccttctttg cagccagtga ttcaataggt gcttcttctc aggcaagaac   3540
ctcaaagaaa gatggaaaga tcattgacaa cagacgtccg acaagatcat ccaccttaga   3600
aagatgagaa agtgaaccaa aaaggctaga aaccagagga aaacctggac aacctctctc   3660
ttcccatggt gcatatgctt gtttaaagtg gaaatctcta tagatcgtca gctcatttta   3720
tctgtaattg gaagaacaga aagtgctggc tcactttcta gttgctttca tcctcctttt   3780
gttctgcatt gactcattta ccagaattca ttggaagaaa tcaccaaaga ttattacaaa   3840
agaaaaatat gttgctaaga ttgtgttggt cgctctctga agcagaaaag ggactggaac   3900
caattgtgca tatcagctga ctttttgttt gttttagaaa agttacagta aaaattaaaa   3960
agagatacca atggtttaca ctttaacaag aaattttgga tatggaacaa agaattctta   4020
gacttgtatt cctatttatc tatattagaa atattgtatg agcaaatttg cagctgttgt   4080
```

-continued

```
gtaaatactg tatattgcaa aaatcagtat tattttaaga gatgtgttct caaatgattg   4140

tttactatat tacatttctg gatgttctag gtgcctgtcg ttgagtattg ccttgtttga   4200

cattctatag gttaattttc aaagcagagt attacaaaag agaagttaga attacagcta   4260

ctgacaatat aaagggtttt gttgaatcaa caatgtgata cgtaaattat agaaaaagaa   4320

aagaaacaca aaagctatag atatacagat atcagcttac ctattgcctt ctatacttat   4380

aatttaaagg attggtgtct tagtacactt gtggtcacag ggatcaacga atagtaaata   4440

atgaactcgt gcaagacaaa actgaaaccc tctttccagg acctcagtag gcaccgttga   4500

ggtgtccttt gtttttgtgt gtgtgtgttc ttttttaatt ttcgcattgt tgacagatac   4560

aaacagttat actcaatgta ctgtaataat cgcaaaggaa aaagttttgg gataacttat   4620

ttgtatgttg gtagctgaga aaaatatcat cagtctagaa ttgatatttg agtatagtag   4680

agctttgggg ctttgaaggc aggttcaaga aagcatatgt cgatggttga gatatttatt   4740

ttccatatgg ttcatgttca aatgttcaca accacaatgc atctgactgc aataatgtgc   4800

taataattta tgtcagtagt caccttgctc acagcaaagc cagaaatgct ctctccaggg   4860

agtagatgta aagtacttgt acatagaatt cagaactgaa gatatttatt aaaagttgat   4920

ttttttttct tgatagtatt tttatgtact aaatatttac actaatatca attacatatt   4980

ttggtaaact agagagacat aattagagat gcatgctttg ttctgtgcat agagaccttt   5040

aagcaaacta ctacagccaa ctcaaaagct aaaactgaac aaatttgatg ttatgcaaac   5100

atcttgcatt tttagtagtt gatattaagt tgatgacttg tttcccttca aggaaacatt   5160

aaattgtatg gactcagcta gctgttcaat gaaattgtga attagaaaca tttttaaaag   5220

tttttgaaag agataagtgc atcatgaatt acatgtacat gagaggagat agtgatatca   5280

gcataatgat tttgaggtca gtacctgagc tgtctaaaaa tatattatac aaactaaaat   5340

gtagatgaat taacctctca aagcacagaa tgtgcaagaa cttttgcatt ttaatcgttg   5400

taaactaaca gcttaaacta ttgactctat acctctaaag aattgctgct actttgtgca   5460

agaactttga aggtcaaatt aggcaaattc cagatagtaa aacaatccct aagccttaag   5520

tctttttttt ttcctaaaaa ttcccataga ataaaattct ctctagttta cttgtgtgtg   5580

catacatctc atccacaggg gaagataaag atggtcacac aaacagtttc cataaagatg   5640

tacatattca ttatacttct gacctttggg ctttcttttc tactaagcta aaaattcctt   5700

tttatcaaag tgtacactac tgatgctgtt tgttgtactg agagcacgta ccaataaaaa   5760

tgttaacaaa atat                                                     5774
```

<210> SEQ ID NO 42
<211> LENGTH: 629
<212> TYPE: DNA
<213> ORGANISM: Homo sapiens
<220> FEATURE:
<221> NAME/KEY: misc_feature
<222> LOCATION: (596)..(596)
<223> OTHER INFORMATION: n is a, c, g, or t

<400> SEQUENCE: 42

```
ttttttttc agattgaaat cactttaata gcataacaac attttcagac caggagtcac     60

agatgaagaa aacattttgt cttccatttg cacaattctg gtgaggtgtg tggttgcact    120

ggacaatctt acagacacat ttttcacatt gagaacttaa taaatagata catacaatgt    180

caaactccac agacaatgag ttatgagtgt gattgttttc ttattctgcc tcctctgggt    240

tgggaggttg cttcccgttg ggctgatggc ggctgggtcc tctaggaggg gtactcatac    300
```

-continued

```
tcctcggcac tgcgacggcc aaaatccatc cagcccatgt agtcccggtc acttatcctg    360

tggctggggt ccaggttctg caggttctta acgatggaca ttcgtccaga aggagctttc    420

cgggcctgct ggatgtatct tgccagcagg gcgcccaggt gcgctcggga ctcgccatcc    480

gttctctgcg ataccctcag ctgcctacgg ggcgcctcct ctgcccgctg cagcccggag    540

cccgcgggat ctgcgggagg caccggctgc gtcagggcgc cagccgccag taccgncatc    600

agcacgcaca ggcacacgcc gctgttcat                                     629
```

```
<210> SEQ ID NO 43
<211> LENGTH: 94
<212> TYPE: PRT
<213> ORGANISM: Homo sapiens

<400> SEQUENCE: 43

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```

```
<210> SEQ ID NO 44
<211> LENGTH: 1371
<212> TYPE: DNA
<213> ORGANISM: Homo sapiens

<400> SEQUENCE: 44

ctccttccaa gaagagcagc aaagctgaag tagcagcaac agcaccagca gcaacagcaa     60

aaaacaaaca tgagtgtgaa gggcatggct atagccttgg ctgtgatatt gtgtgctaca    120

gttgttcaag gcttccccat gttcaaaaga ggacgctgtc tttgcatagg ccctggggta    180

aaagcagtga aagtggcaga tattgagaaa gcctccataa tgtacccaag taacaactgt    240

gacaaaatag aagtgattat taccctgaaa gaaaataaag gacaacgatg cctaaatccc    300

aaatcgaagc aagcaaggct tataatcaaa aaagttgaaa gaaagaattt ttaaaaatat    360

caaaacatat gaagtcctgg aaaagggcat ctgaaaaacc tagaacaagt ttaactgtga    420

ctactgaaat gacaagaatt ctacagtagg aaactgagac ttttctatgg ttttgtgact    480

ttcaactttt gtacagttat gtgaaggatg aaaggtgggt gaaaggacca aaaacagaaa    540

tacagtcttc ctgaatgaat gacaatcaga attccactgc ccaaaggagt ccagcaatta    600

aatggatttc taggaaaagc taccttaaga aaggctggtt accatcggag tttacaaagt    660

gctttcacgt tcttacttgt tgtattatac attcatgcat ttctaggcta gagaaccttc    720

tagatttgat gcttacaact attctgttgt gactatgaga acatttctgt ctctagaagt    780

tatctgtctg tattgatctt tatgctatat tactatctgt ggttacagtg gagacattga    840

cattattact ggagtcaagc ccttataagt caaaagcatc tatgtgtcgt aaagcattcc    900

tcaaacattt tttcatgcaa atacacaytt ctttccccaa atatcatgta gcacatcaat    960

atgtagggaa acattcttat gcatcatttg gtttgtttta taaccaattc attaaatgta   1020
```

-continued

```
attcataaaa tgtactatga aaaaaattat acgctatggg atactggcaa cagtgcacat   1080

atttcataac caaattagca gcaccggtct taatttgatg tttttcaact tttattcatt   1140

gagatgtttt gaagcaatta ggatatgtgt gtttactgta ctttttgttt tgatccgttt   1200

gtataaatga tagcaatatc ttggacacat ttgaaataca aaatgttttt gtctaccaaa   1260

gaaaaatgtt gaaaaataag caaatgtata cctagcaatc acttttactt tttgtaattc   1320

tgtctcttag aaaaatacat aatctaatca aaaaaaaaaa aaaaaaaaaa a            1371


<210> SEQ ID NO 45
<211> LENGTH: 251
<212> TYPE: PRT
<213> ORGANISM: Homo sapiens

<400> SEQUENCE: 45

Met Thr Arg Leu Thr Val Leu Ala Leu Leu Ala Gly Leu Leu Ala Ser
1               5                   10                  15

Ser Arg Ala Gly Ser Ser Pro Leu Leu Asp Ile Val Gly Gly Arg Lys
            20                  25                  30

Ala Arg Pro Arg Gln Phe Pro Phe Leu Ala Ser Ile Gln Asn Gln Gly
        35                  40                  45

Arg His Phe Cys Gly Gly Ala Leu Ile His Ala Arg Phe Val Met Thr
    50                  55                  60

Ala Ala Ser Cys Phe Gln Ser Gln Asn Pro Gly Val Ser Thr Val Val
65                  70                  75                  80

Leu Gly Ala Tyr Asp Leu Arg Arg Arg Glu Arg Gln Ser Arg Gln Thr
                85                  90                  95

Phe Ser Ile Ser Ser Met Ser Glu Asn Gly Tyr Asp Pro Gln Gln Asn
            100                 105                 110

Leu Asn Asp Leu Met Leu Leu Gln Leu Asp Arg Glu Ala Asn Leu Thr
        115                 120                 125

Ser Ser Val Thr Ile Leu Pro Leu Pro Leu Gln Asn Ala Thr Val Glu
    130                 135                 140

Ala Gly Thr Arg Cys Gln Val Ala Gly Trp Gly Ser Gln Arg Ser Gly
145                 150                 155                 160

Gly Arg Leu Ser Arg Phe Pro Arg Phe Val Asn Val Thr Val Thr Pro
                165                 170                 175

Glu Asp Gln Cys Arg Pro Asn Asn Val Cys Thr Gly Val Leu Thr Arg
            180                 185                 190

Arg Gly Gly Ile Cys Asn Gly Asp Gly Gly Thr Pro Leu Val Cys Glu
        195                 200                 205

Gly Leu Ala His Gly Val Ala Ser Phe Ser Leu Gly Pro Cys Gly Arg
    210                 215                 220

Gly Pro Asp Phe Phe Thr Arg Val Ala Leu Phe Arg Asp Trp Ile Asp
225                 230                 235                 240

Gly Val Leu Asn Asn Pro Gly Pro Gly Pro Ala
                245                 250


<210> SEQ ID NO 46
<211> LENGTH: 5002
<212> TYPE: DNA
<213> ORGANISM: Homo sapiens

<400> SEQUENCE: 46

ggatccactg gttcctgaca ccctcacctg cccctggggg tgtggccatc ttctagagag     60

ggaaactgag gatcagtgca gaatgtaggg ggagcccagg ctggcccagg gagcagttgg    120
```

-continued

```
cggtggaggc cttgggcaat ttcccgtgtt cccactgagt ggggctgtcc ctgggcctgg    180
gcggggacgc caccaactgc caaggcctgt gtataagggc agccgccgcc ttagccacag    240
acctgccccg ccatgacccg gctgacagtc ctggccctgc tggctggtct gctggcatcc    300
tcgagggccg gtgagtgcct ctctgtgccg gtggtccccc atctgtgcta gggcccggct    360
gccagggcag aactcagact taaagcacag agaaggcaag cggcttggcc tgggtcacac    420
agccagcccg gcctggacga tcccgcgaaa ggcgtgaggg cggacggtgt gcgggactca    480
ggggccccct gtcctcttag ggagtgggac gatgggggag ggtgggtccc cccgcagccc    540
cactgggtgg atagagctga ggctgcagct tcacacgccc tcccggccac tgtgtggatt    600
cttggggatc tcagagctgt ctccccccga cccaggctcc agcccccttt tggacatcgt    660
tggcggccgg aaggcgaggc ccgcgccagtt cccgttcctg gcctccattc agaatcaagg    720
caggcacttc tgcgggggtg ccctgatcca tgcccgcttc gtgatgaccg cggccagctg    780
cttccaaagc cagtgagggg tcctggggag ggggcctagg gggcattggg gctcagagaa    840
ggggcttggg gggcttaggc attcagtggg ggtgcttggt aggtgaggag gggaggggat    900
tgcaaaagga ggggctcagg gaaaggaggg ggcttggaga gggaaatggg gactgagttg    960
aggagggacc caaggatatt ggggggctca gatggaggag gcccagagaa gggaaggggg   1020
tcagatggag gaggcccaga gaaaggaaga ggctcagatg gaggaggtgc agtgaaggaa   1080
agggggtcag atgggggagg cccagagaag ggaaggggct cagatggagg agggggccca   1140
gagaaaggaa ggggctcaga tggaggaggt gcagagaagg gaagggggtc agatgggggg   1200
aggcccagag aagggaaggg gctcagatgg aggaggtgca gagaagggaa ggggctcaga   1260
tggaggaggt gcagagaaga gaagggcctc agatggagga ggtgcagaga agagaagggc   1320
ctcagatgga ggaggtgcag agaagggaag ggcctcagat ggaggaggtg cggagaaggg   1380
aagggggtca gatggaggag gtgcagagaa gggaaggggg tcagatgggg gaggcccagg   1440
gaagggaagg ggctcagatg gaggaggggc agagaaggga agggggtcag atgggggagg   1500
cccagggaag ggaaggggct cagatggggg aggcgcagag aagggaaggg ggtcagatgg   1560
aggaggtgca gagaagggaa gggggtcaga tgggggaggc ccagataagg gaatggggtc   1620
agatggggga ggtgcagaga agggaagggg gtcagatggg ggaggcccag ataagggaag   1680
gggctcagat ggaggaggtg cagagaaggg gagggggtca gatggaggag gctcagagaa   1740
gggaagggac tcagatggag gagggggcgc agagaagaga aggggctcag atggaggagg   1800
aggcgcagag aagggaaggg gctcaagatg ggaagggggc cctggaaagt ctcggctctg   1860
cttctgtaaa agcgggggag ttttcagggt gaaggattgc agtctgcagg ctgggatccc   1920
ccctaatttg caagccggct tgctctgtgc ccaggcccca gcctggtgtc ctccctctgc   1980
cctttcctcc gctactctca ggaaccccgg ggttagcacc gtggtgctgg gtgcctatga   2040
cctgaggcgg cgggagaggc agtcccgcca gacgttttcc atcagcagca tgagcgagaa   2100
tggctacgac ccccagcaga acctgaacga cctgatgctg cttcaggtga gaggatggtg   2160
ccacctgtga tcccagcacc tcgggaggcc gacgttagcc agggaaacaa gtccaaactt   2220
ggtctctaca aaaaaataca aaaattagcc gggagtggtg gcgcgcacct gtggcccctg   2280
tgcttcagga ggccgaggcg gaaggacggc ttgaggtcag gagttcgaga ccagcctggg   2340
caacatggcc aaactcagtc tctacaaaaa tatatatgtg tgtgtgtgtg tgtgtgtgtg   2400
tgtgtgtgtg tgtgtatctt gccgggtgag gtggctcatg cctgtaatcc cagcattttg   2460
ggaggccgag gtgggcggat cacgaggtca ggagattgag accagcctgg ccaacatggt   2520
```

-continued

```
gaaaccccat ctctactaaa aatacaaaaa ttagccaggc atggcagcgg gcgcctctag   2580
tcccagctac tcaggaggct gaggcaggag aatcgcttga acccgggagg cggagcttgc   2640
agtgagccga gatcgcgccc ctgcactcca gcctgggtaa cagagccaga ccctatctca   2700
aaaaaaactt ccaaaaacaa tacagcaaca catacagatg taccacggtt cgcgtatgga   2760
gcctcctgtt ggtggagact gacgtcgttt tcaaatgctt ttgctatgac agaatcatgt   2820
gaatgttttt catgtttggt ttttttcttt gagaaaatga taaaattatc tcaaaaatat   2880
cattaaaaaa tttaaaaaag tagagacggg ggtttcacct tgttggccag tttggtctcg   2940
aactcctggc ctcaagtgat ccacccacct tggcctcgca acgtgctggg aatacaggcg   3000
tgagccaccg cacccggccc ctgccgggaa ttaaacgcaa accacttaca gactacagtt   3060
aatgtcgctg acacttctgc tcccaggggt ccccatgagg ctccagtccc cagggccacc   3120
ctcccctgac tccatttcct tccccagctg gaccgtgagg ccaacctcac cagcagcgtg   3180
acgatactgc cactgcctct gcagaacgcc acggtggaag ccggcaccag atgccaggtg   3240
gccggctggg ggagccagcg cagtgggggg cgtctctccc gttttcccag gtttgtcaac   3300
gtgactgtga cccccgagga ccagtgtcgc cccaacaacg tgtgcaccgg tgtgctcacc   3360
cgccgcggtg gcatctgcaa tgtgagtgct ccctgtggcg ggaggagggg tcctgagagg   3420
tactgagctc tccgtggcag gagaaagcaa gtgcaggctg agggcggcac agcagggggg   3480
ccccaggatt gagcattttc acggtaggag aaacagtatc tttttttttt tttttgagac   3540
agagtctcgc tctgtcgccc aggctggagt gtagtggcgt gatctcggcg gctcactgca   3600
acctccgcct cctgggttca agcgattctc ctgcctcagc ctcctaagta gctgggatta   3660
caggcatgcg ccaccacgcc cggctaattt tgtattttta gtagagacag ggtttctcca   3720
tgtgggtcag gctggtctcg aactcctgac ctcatgatcg acccaccttg gcctcccaaa   3780
gtgttaggat aacaggcatg agccaccgtg cctggctgag aaacagtagc tatcaaacgc   3840
cggctgtgag ccacgtctgt gctggggggtt ggggacccag caggcatggt agagccggtc   3900
actgagggac tcaggcgtgt gattgccagg ggaggggcac ctggcccagc ctggaggtgc   3960
caggaagctc cagaaagcaa ctgatcccaa agtccactag cagttaacca gggcagagaa   4020
agagaagagc catgcaaagg ccctggggct ggatcaggac ttgtaggttc caggggcagc   4080
aagaggcctc tgcagttctg ggtggcgtg ggagccaggc cctgggacgc cctgacacag   4140
ctgctgcctg cccaggggga cgggggcacc cccctcgtct gcgagggcct ggcccacggc   4200
gtggcctcct tttccctggg gccctgtggc cgaggccctg acttcttcac ccgagtggcg   4260
ctcttccgag actggatcga tggtgttctc aacaacccgg gaccggggcc agcctagggg   4320
ggcctgtgac ctcccatgga gcccagcccc cgccctccac acctccggcg ctccgcaccc   4380
acctcccacg gccccgcccc tgccccccgct ccggccagag gggccctggc tgtaataaag   4440
aagccgatct ctcctctgct cctggtttct gttcattggt gggggagggg gctgtgggga   4500
cgcgtgagtg gcaccttcac cggccttagg ggcacccacc gcaggtgcac tgcctgtgca   4560
gatgtcagat gttcagagat tccctcaaag cccggggaag caggggctgg tgttatctgc   4620
acccgacagc ggggtgttgg ggggaggccc aggttcagag aggttgggtg gctgcccaga   4680
ggtcacacag tgaatgccgc ccagcacttt gggaggccga ggtgggcgga tcacctgagg   4740
tcaggagttc aagaccagcc cggccaacct ggtgaaaccc catctctata aaaatacaaa   4800
aattagccgg gcatgatggc gggcgcctgt aatcccagtt acttgggagg ctgaggcagg   4860
agaatcacct gaacccggga ggcggaggtt gcagcgaacc gagatggcgc cactgcactc   4920
```

-continued

```
cagcctgggc gacagcgaga ctccagctca aaaaaaaaca aaaaccacgg gagaaaacgg   4980

ggaacattct cctcttggat cc                                             5002


<210> SEQ ID NO 47
<211> LENGTH: 687
<212> TYPE: PRT
<213> ORGANISM: Homo sapiens

<400> SEQUENCE: 47

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365
```

```
Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685
```

<210> SEQ ID NO 48
<211> LENGTH: 2651
<212> TYPE: DNA
<213> ORGANISM: Homo sapiens

<400> SEQUENCE: 48

```
gcggacactc ctctcggctc ctccccggca gcggcggcgg ctcggagcgg gctccggggc      60

tcgggtgcag cggccagcgg gcctggcggc gaggattacc cggggaagtg gttgtctcct     120

ggctggagcc gcgagacggg cgctcagggc gcggggccgg cggcggcgaa cgagaggacg     180

gactctggcg gccgggtcgt tggccggggg agcgcgggca ccgggcgagc aggccgcgtc     240

gcgctcacca tggtcagcta ctgggacacc ggggtcctgc tgtgcgcgct gctcagctgt     300

ctgcttctca caggatctag ttcaggttca aaattaaaag atcctgaact gagtttaaaa     360
```

-continued

```
ggcacccagc acatcatgca agcaggccag acactgcatc tccaatgcag gggggaagca    420
gcccataaat ggtctttgcc tgaaatggtg agtaaggaaa gcgaaaggct gagcataact    480
aaatctgcct gtggaagaaa tggcaaacaa ttctgcagta ctttaacctt gaacacagct    540
caagcaaacc acactggctt ctacagctgc aaatatctag ctgtacctac ttcaaagaag    600
aaggaaacag aatctgcaat ctatatattt attagtgata caggtagacc tttcgtagag    660
atgtacagtg aaatccccga aattatacac atgactgaag gaagggagct cgtcattccc    720
tgccgggtta cgtcacctaa catcactgtt actttaaaaa agtttccact tgacactttg    780
atccctgatg gaaaacgcat aatctgggac agtagaaagg gcttcatcat atcaaatgca    840
acgtacaaag aaatagggct tctgacctgt gaagcaacag tcaatgggca tttgtataag    900
acaaactatc tcacacatcg acaaaccaat acaatcatag atgtccaaat aagcacacca    960
cgcccagtca aattacttag aggccatact cttgtcctca attgtactgc taccactccc   1020
ttgaacacga gagttcaaat gacctggagt taccctgatg aaaaaaataa gagagcttcc   1080
gtaaggcgac gaattgacca aagcaattcc catgccaaca tattctacag tgttcttact   1140
attgacaaaa tgcagaacaa agacaaagga ctttatactt gtcgtgtaag gagtggacca   1200
tcattcaaat ctgttaacac ctcagtgcat atatatgata aagcattcat cactgtgaaa   1260
catcgaaaac agcaggtgct tgaaaccgta gctggcaagc ggtcttaccg gctctctatg   1320
aaagtgaagg catttccctc gccggaagtt gtatggttaa aagatgggtt acctgcgact   1380
gagaaatctg ctcgctattt gactcgtggc tactcgttaa ttatcaagga cgtaactgaa   1440
gaggatgcag ggaattatac aatcttgctg agcataaaac agtcaaatgt gtttaaaaac   1500
ctcactgcca ctctaattgt caatgtgaaa ccccagattt acgaaaaggc cgtgtcatcg   1560
tttccagacc cggctctcta cccactgggc agcagacaaa tcctgacttg taccgcatat   1620
ggtatccctc aacctacaat caagtggttc tggcacccct gtaaccataa tcattccgaa   1680
gcaaggtgtg acttttgttc caataatgaa gagtccttta tcctggatgc tgacagcaac   1740
atgggaaaca gaattgagag catcactcag cgcatggcaa taatagaagg aaagaataag   1800
atggctagca ccttggttgt ggctgactct agaatttctg gaatctacat ttgcatagct   1860
tccaataaag ttgggactgt gggaagaaac ataagctttt atatcacaga tgtgccaaat   1920
gggtttcatg ttaacttgga aaaaatgccg acggaaggag aggacctgaa actgtcttgc   1980
acagttaaca agttcttata cagagacgtt acttggattt tactgcggac agttaataac   2040
agaacaatgc actacagtat tagcaagcaa aaaatggcca tcactaagga gcactccatc   2100
actcttaatc ttaccatcat gaatgtttcc ctgcaagatt caggcaccta tgcctgcaga   2160
gccaggaatg tatacacagg ggaagaaatc ctccagaaga aagaaattac aatcagaggt   2220
gagcactgca acaaaaaggc tgttttctct cggatctcca aatttaaaag cacaaggaat   2280
gattgtacca cacaaagtaa tgtaaaacat taaaggactc attaaaaagt aacagttgtc   2340
tcatatcatc ttgatttatt gtcactgttg ctaactttca ggctcggagg agatgctcct   2400
cccaaaatga gttcggagat gatagcagta ataatgagac cccgggctc cagctctggg   2460
ccccccattc aggccgaggg ggctgctccg gggggccgac ttggtgcacg tttggatttg   2520
gaggatccct gcactgcctt ctctgtgttt gttgctcttg ctgttttctc ctgcctgata   2580
aacaacaact tgggatgatc ctttccattt tgatgccaac ctctttttat ttttaagcgg   2640
cgccctatag t                                                        2651
```

<210> SEQ ID NO 49
<211> LENGTH: 1321
<212> TYPE: PRT
<213> ORGANISM: Homo sapiens

<400> SEQUENCE: 49

```
Met Ser Asp Ser Val Ile Leu Arg Ser Ile Lys Lys Phe Gly Glu Glu
1               5                   10                  15

Asn Asp Gly Phe Glu Ser Asp Lys Ser Tyr Asn Asn Asp Lys Lys Ser
            20                  25                  30

Arg Leu Gln Asp Glu Lys Lys Gly Asp Gly Val Arg Val Gly Phe Phe
        35                  40                  45

Gln Leu Phe Arg Phe Ser Ser Ser Thr Asp Ile Trp Leu Met Phe Val
    50                  55                  60

Gly Ser Leu Cys Ala Phe Leu His Gly Ile Ala Gln Pro Gly Val Leu
65                  70                  75                  80

Leu Ile Phe Gly Thr Met Thr Asp Val Phe Ile Asp Tyr Asp Val Glu
                85                  90                  95

Leu Gln Glu Leu Gln Ile Pro Gly Lys Ala Cys Val Asn Asn Thr Ile
            100                 105                 110

Val Trp Thr Asn Ser Ser Leu Asn Gln Asn Met Thr Asn Gly Thr Arg
        115                 120                 125

Cys Gly Leu Leu Asn Ile Glu Ser Glu Met Ile Lys Phe Ala Ser Tyr
    130                 135                 140

Tyr Ala Gly Ile Ala Val Ala Val Leu Ile Thr Gly Tyr Ile Gln Ile
145                 150                 155                 160

Cys Phe Trp Val Ile Ala Ala Ala Arg Gln Ile Gln Lys Met Arg Lys
                165                 170                 175

Phe Tyr Phe Arg Arg Ile Met Arg Met Glu Ile Gly Trp Phe Asp Cys
            180                 185                 190

Asn Ser Val Gly Glu Leu Asn Thr Arg Phe Ser Asp Asp Ile Asn Lys
        195                 200                 205

Ile Asn Asp Ala Ile Ala Asp Gln Met Ala Leu Phe Ile Gln Arg Met
    210                 215                 220

Thr Ser Thr Ile Cys Gly Phe Leu Leu Gly Phe Phe Arg Gly Trp Lys
225                 230                 235                 240

Leu Thr Leu Val Ile Ile Ser Val Ser Pro Leu Ile Gly Ile Gly Ala
                245                 250                 255

Ala Thr Ile Gly Leu Ser Val Ser Lys Phe Thr Asp Tyr Glu Leu Lys
            260                 265                 270

Ala Tyr Ala Lys Ala Gly Val Val Ala Asp Glu Val Ile Ser Ser Met
        275                 280                 285

Arg Thr Val Ala Ala Phe Gly Gly Glu Lys Arg Glu Val Glu Arg Tyr
    290                 295                 300

Glu Lys Asn Leu Val Phe Ala Gln Arg Trp Gly Ile Arg Lys Gly Ile
305                 310                 315                 320

Val Met Gly Phe Phe Thr Gly Phe Val Trp Cys Leu Ile Phe Leu Cys
                325                 330                 335

Tyr Ala Val Ala Phe Trp Tyr Gly Ser Thr Leu Val Leu Asp Glu Gly
            340                 345                 350

Glu Tyr Thr Pro Gly Thr Leu Val Gln Ile Phe Leu Ser Val Ile Val
        355                 360                 365

Gly Ala Leu Asn Leu Gly Asn Ala Ser Pro Cys Leu Glu Ala Phe Ala
    370                 375                 380

Thr Gly Arg Ala Ala Ala Thr Ser Ile Phe Glu Thr Ile Asp Arg Lys
```

-continued

```
385                 390                 395                 400

Pro Ile Ile Asp Cys Met Ser Glu Asp Gly Tyr Lys Leu Asp Arg Ile
                405                 410                 415

Lys Gly Glu Ile Glu Phe His Asn Val Thr Phe His Tyr Pro Ser Arg
            420                 425                 430

Pro Glu Val Lys Ile Leu Asn Asp Leu Asn Met Val Ile Lys Pro Gly
        435                 440                 445

Glu Met Thr Ala Leu Val Gly Pro Ser Gly Ala Gly Lys Ser Thr Ala
    450                 455                 460

Leu Gln Leu Ile Gln Arg Phe Tyr Asp Pro Cys Glu Gly Met Val Thr
465                 470                 475                 480

Val Asp Gly His Asp Ile Arg Ser Leu Asn Ile Gln Trp Leu Arg Asp
                485                 490                 495

Gln Ile Gly Ile Val Glu Gln Glu Pro Val Leu Phe Ser Thr Thr Ile
            500                 505                 510

Ala Glu Asn Ile Arg Tyr Gly Arg Glu Asp Ala Thr Met Glu Asp Ile
        515                 520                 525

Val Gln Ala Ala Lys Glu Ala Asn Ala Tyr Asn Phe Ile Met Asp Leu
    530                 535                 540

Pro Gln Gln Phe Asp Thr Leu Val Gly Glu Gly Gly Gly Gln Met Ser
545                 550                 555                 560

Gly Gly Gln Lys Gln Arg Val Ala Ile Ala Arg Ala Leu Ile Arg Asn
                565                 570                 575

Pro Lys Ile Leu Leu Leu Asp Met Ala Thr Ser Ala Leu Asp Asn Glu
            580                 585                 590

Ser Glu Ala Met Val Gln Glu Val Leu Ser Lys Ile Gln His Gly His
        595                 600                 605

Thr Ile Ile Ser Val Ala His Arg Leu Ser Thr Val Arg Ala Ala Asp
    610                 615                 620

Thr Ile Ile Gly Phe Glu His Gly Thr Ala Val Glu Arg Gly Thr His
625                 630                 635                 640

Glu Glu Leu Leu Glu Arg Lys Gly Val Tyr Phe Thr Leu Val Thr Leu
                645                 650                 655

Gln Ser Gln Gly Asn Gln Ala Leu Asn Glu Glu Asp Ile Lys Asp Ala
            660                 665                 670

Thr Glu Asp Asp Met Leu Ala Arg Thr Phe Ser Arg Gly Ser Tyr Gln
        675                 680                 685

Asp Ser Leu Arg Ala Ser Ile Arg Gln Arg Ser Lys Ser Gln Leu Ser
    690                 695                 700

Tyr Leu Val His Glu Pro Pro Leu Ala Val Val Asp His Lys Ser Thr
705                 710                 715                 720

Tyr Glu Glu Asp Arg Lys Asp Lys Asp Ile Pro Val Gln Glu Glu Val
                725                 730                 735

Glu Pro Ala Pro Val Arg Arg Ile Leu Lys Phe Ser Ala Pro Glu Trp
            740                 745                 750

Pro Tyr Met Leu Val Gly Ser Val Gly Ala Ala Val Asn Gly Thr Val
        755                 760                 765

Thr Pro Leu Tyr Ala Phe Leu Phe Ser Gln Ile Leu Gly Thr Phe Ser
    770                 775                 780

Ile Pro Asp Lys Glu Glu Gln Arg Ser Gln Ile Asn Gly Val Cys Leu
785                 790                 795                 800

Leu Phe Val Ala Met Gly Cys Val Ser Leu Phe Thr Gln Phe Leu Gln
                805                 810                 815
```

```
Gly Tyr Ala Phe Ala Lys Ser Gly Glu Leu Leu Thr Lys Arg Leu Arg
            820                 825                 830

Lys Phe Gly Phe Arg Ala Met Leu Gly Gln Asp Ile Ala Trp Phe Asp
        835                 840                 845

Asp Leu Arg Asn Ser Pro Gly Ala Leu Thr Thr Arg Leu Ala Thr Asp
    850                 855                 860

Ala Ser Gln Val Gln Gly Ala Ala Gly Ser Gln Ile Gly Met Ile Val
865                 870                 875                 880

Asn Ser Phe Thr Asn Val Thr Val Ala Met Ile Ile Ala Phe Ser Phe
                885                 890                 895

Ser Trp Lys Leu Ser Leu Val Ile Leu Cys Phe Phe Pro Phe Leu Ala
            900                 905                 910

Leu Ser Gly Ala Thr Gln Thr Arg Met Leu Thr Gly Phe Ala Ser Arg
        915                 920                 925

Asp Lys Gln Ala Leu Glu Met Val Gly Gln Ile Thr Asn Glu Ala Leu
    930                 935                 940

Ser Asn Ile Arg Thr Val Ala Gly Ile Gly Lys Glu Arg Arg Phe Ile
945                 950                 955                 960

Glu Ala Leu Glu Thr Glu Leu Glu Lys Pro Phe Lys Thr Ala Ile Gln
                965                 970                 975

Lys Ala Asn Ile Tyr Gly Phe Cys Phe Ala Phe Ala Gln Cys Ile Met
            980                 985                 990

Phe Ile Ala Asn Ser Ala Ser Tyr  Arg Tyr Gly Gly Tyr  Leu Ile Ser
        995                 1000                1005

Asn Glu  Gly Leu His Phe Ser  Tyr Val Phe Arg Val  Ile Ser Ala
    1010                1015                1020

Val Val  Leu Ser Ala Thr Ala  Leu Gly Arg Ala Phe  Ser Tyr Thr
    1025                1030                1035

Pro Ser  Tyr Ala Lys Ala Lys  Ile Ser Ala Ala Arg  Phe Phe Gln
    1040                1045                1050

Leu Leu  Asp Arg Gln Pro Pro  Ile Ser Val Tyr Asn  Thr Ala Gly
    1055                1060                1065

Glu Lys  Trp Asp Asn Phe Gln  Gly Lys Ile Asp Phe  Val Asp Cys
    1070                1075                1080

Lys Phe  Thr Tyr Pro Ser Arg  Pro Asp Ser Gln Val  Leu Asn Gly
    1085                1090                1095

Leu Ser  Val Ser Ile Ser Pro  Gly Gln Thr Leu Ala  Phe Val Gly
    1100                1105                1110

Ser Ser  Gly Cys Gly Lys Ser  Thr Ser Ile Gln Leu  Leu Glu Arg
    1115                1120                1125

Phe Tyr  Asp Pro Asp Gln Gly  Lys Val Met Ile Asp  Gly His Asp
    1130                1135                1140

Ser Lys  Lys Val Asn Val Gln  Phe Leu Arg Ser Asn  Ile Gly Ile
    1145                1150                1155

Val Ser  Gln Glu Pro Val Leu  Phe Ala Cys Ser Ile  Met Asp Asn
    1160                1165                1170

Ile Lys  Tyr Gly Asp Asn Thr  Lys Glu Ile Pro Met  Glu Arg Val
    1175                1180                1185

Ile Ala  Ala Ala Lys Gln Ala  Gln Leu His Asp Phe  Val Met Ser
    1190                1195                1200

Leu Pro  Glu Lys Tyr Glu Thr  Asn Val Gly Ser Gln  Gly Ser Gln
    1205                1210                1215

Leu Ser  Arg Gly Glu Lys Gln  Arg Ile Ala Ile Ala  Arg Ala Ile
    1220                1225                1230
```

```
Val Arg  Asp Pro Lys Ile Leu  Leu Leu Asp Glu Ala  Thr Ser Ala
    1235                 1240                 1245

Leu Asp  Thr Glu Ser Glu Lys  Thr Val Gln Val Ala  Leu Asp Lys
    1250                 1255                 1260

Ala Arg  Glu Gly Arg Thr Cys  Ile Val Ile Ala His  Arg Leu Ser
    1265                 1270                 1275

Thr Ile  Gln Asn Ala Asp Ile  Ile Ala Val Met Ala  Gln Gly Val
    1280                 1285                 1290

Val Ile  Glu Lys Gly Thr His  Glu Glu Leu Met Ala  Gln Lys Gly
    1295                 1300                 1305

Ala Tyr  Tyr Lys Leu Val Thr  Thr Gly Ser Pro Ile  Ser
    1310                 1315                 1320


<210> SEQ ID NO 50
<211> LENGTH: 4776
<212> TYPE: DNA
<213> ORGANISM: Homo sapiens
<220> FEATURE:
<221> NAME/KEY: misc_feature
<222> LOCATION: (4208)..(4208)
<223> OTHER INFORMATION: n is a, c, g, or t
<220> FEATURE:
<221> NAME/KEY: misc_feature
<222> LOCATION: (4210)..(4212)
<223> OTHER INFORMATION: n is a, c, g, or t
<220> FEATURE:
<221> NAME/KEY: misc_feature
<222> LOCATION: (4227)..(4229)
<223> OTHER INFORMATION: n is a, c, g, or t
<220> FEATURE:
<221> NAME/KEY: misc_feature
<222> LOCATION: (4231)..(4231)
<223> OTHER INFORMATION: n is a, c, g, or t
<220> FEATURE:
<221> NAME/KEY: misc_feature
<222> LOCATION: (4253)..(4253)
<223> OTHER INFORMATION: n is a, c, g, or t
<220> FEATURE:
<221> NAME/KEY: misc_feature
<222> LOCATION: (4677)..(4677)
<223> OTHER INFORMATION: n is a, c, g, or t
<220> FEATURE:
<221> NAME/KEY: misc_feature
<222> LOCATION: (4691)..(4691)
<223> OTHER INFORMATION: n is a, c, g, or t
<220> FEATURE:
<221> NAME/KEY: misc_feature
<222> LOCATION: (4707)..(4707)
<223> OTHER INFORMATION: n is a, c, g, or t
<220> FEATURE:
<221> NAME/KEY: misc_feature
<222> LOCATION: (4721)..(4721)
<223> OTHER INFORMATION: n is a, c, g, or t
<220> FEATURE:
<221> NAME/KEY: misc_feature
<222> LOCATION: (4752)..(4752)
<223> OTHER INFORMATION: n is a, c, g, or t
<220> FEATURE:
<221> NAME/KEY: misc_feature
<222> LOCATION: (4754)..(4754)
<223> OTHER INFORMATION: n is a, c, g, or t
<220> FEATURE:
<221> NAME/KEY: misc_feature
<222> LOCATION: (4772)..(4773)
<223> OTHER INFORMATION: n is a, c, g, or t

<400> SEQUENCE: 50

gaatgatgaa aaccgaggtt ggaaaaggtt gtgaaacctt ttaactctcc acagtggagt     60

ccattatttc ctctggcttc ctcaaattca tattcacagg gtcgttggct gtgggttgca    120

attaccatgt ctgactcagt aattcttcga agtataaaga aatttggaga ggagaatgat    180
```

```
ggttttgagt cagataaatc atataataat gataagaaat caaggttaca agatgagaag    240
aaaggtgatg gcgttagagt tggcttcttt caattgtttc ggttttcttc atcaactgac    300
atttggctga tgtttgtggg aagtttgtgt gcatttctcc atggaatagc ccagccaggc    360
gtgctactca tttttggcac aatgacagat gtttttattg actacgacgt tgagttacaa    420
gaactccaga ttccaggaaa agcatgtgtg aataacacca ttgtatggac taacagttcc    480
ctcaaccaga acatgacaaa tggaacacgt tgtgggttgc tgaacatcga gagcgaaatg    540
atcaaatttg ccagttacta tgctggaatt gctgtcgcag tacttatcac aggatatatt    600
caaatatgct tttgggtcat tgccgcagct cgtcagatac agaaaatgag aaaattttac    660
tttaggagaa taatgagaat ggaaataggg tggtttgact gcaattcagt gggggagctg    720
aatacaagat tctctgatga tattaataaa atcaatgatg ccatagctga ccaaatggcc    780
cttttcattc agcgcatgac ctcgaccatc tgtggtttcc tgttgggatt tttcaggggt    840
tggaaactga ccttggttat tatttctgtc agccctctca ttgggattgg agcagccacc    900
attggtctga gtgtgtccaa gtttacggac tatgagctga aggcctatgc caaagcaggg    960
gtggtggctg atgaagtcat ttcatcaatg agaacagtgg ctgcttttgg tggtgagaaa   1020
agagaggttg aaaggtatga gaaaaatctt gtgttcgccc agcgttgggg aattagaaaa   1080
ggaatagtga tgggattctt tactggattc gtgtggtgtc tcatcttttt gtgttatgca   1140
gtggccttct ggtacggctc cacacttgtc ctggatgaag gagaatatac accaggaacc   1200
cttgtccaga ttttcctcag tgtcatagta ggagctttaa atcttggcaa tgcctctcct   1260
tgtttggaag cctttgcaac tggacgtgca gcagccacca gcatttttga gacaatagac   1320
aggaaaccca tcattgactg catgtcagaa gatggttaca agttggatcg aatcaagggt   1380
gaaattgaat tccataatgt gaccttccat tatccttcca gaccagaggt gaagattcta   1440
aatgacctca acatggtcat taaaccaggg gaaatgacag ctctggtagg acccagtgga   1500
gctggaaaaa gtacagcact gcaactcatt cagcgattct atgacccctg tgaaggaatg   1560
gtgaccgtgg atggccatga cattcgctct cttaacattc agtggcttag agatcagatt   1620
gggatagtgg agcaagagcc agttctgttc tctaccacca ttgcagaaaa tattcgctat   1680
ggcagagaag atgcaacaat ggaagacata gtccaagctg ccaaggaggc caatgcctac   1740
aacttcatca tggacctgcc acagcaattt gacacccttg ttggagaagg aggaggccag   1800
atgagtggtg gccagaaaca aagggtagct atcgccagag ccctcatccg aaatcccaag   1860
attctgcttt tggacatggc cacctcagct ctggacaatg agagtgaagc catggtgcaa   1920
gaagtgctga gtaagattca gcatgggcac acaatcattt cagttgctca tcgcttgtct   1980
acggtcagag ctgcagatac catcattggt tttgaacatg gcactgcagt ggaaagaggg   2040
acccatgaag aattactgga aaggaaaggt gtttacttca ctctagtgac tttgcaaagc   2100
cagggaaatc aagctcttaa tgaagaggac ataaaggatg caactgaaga tgacatgctt   2160
gcgaggacct ttagcagagg gagctaccag gatagtttaa gggcttccat ccggcaacgc   2220
tccaagtctc agctttctta cctggtgcac gaacctccat tagctgttgt agatcataag   2280
tctacctatg aagaagatag aaaggacaag gacattcctg tgcaggaaga agttgaacct   2340
gccccagtta ggaggattct gaaattcagt gctccagaat ggccctacat gctggtaggg   2400
tctgtgggtg cagctgtgaa cgggacagtc acacccttgt atgccttttt attcagccag   2460
attcttggga ctttttcaat tcctgataaa gaggaacaaa ggtcacagat caatggtgtg   2520
tgcctacttt ttgtagcaat gggctgtgta tctcttttca cccaatttct acagggatat   2580
```

```
gcctttgcta aatctgggga gctcctaaca aaaaggctac gtaaatttgg tttcagggca   2640
atgctggggc aagatattgc ctggtttgat gacctcagaa atagccctgg agcattgaca   2700
acaagacttg ctacagatgc ttcccaagtt caaggggctg ccggctctca gatcgggatg   2760
atagtcaatt ccttcactaa cgtcactgtg gccatgatca ttgccttctc ctttagctgg   2820
aagctgagcc tggtcatctt gtgcttcttc cccttcttgg ctttatcagg agccacacag   2880
accaggatgt tgacaggatt tgcctctcga gataagcagg ccctggagat ggtgggacag   2940
attacaaatg aagccctcag taacatccgc actgttgctg gaattggaaa ggagaggcgg   3000
ttcattgaag cacttgagac tgagctggag aagcccttca agacagccat tcagaaagcc   3060
aatatttacg gattctgctt tgcctttgcc cagtgcatca tgtttattgc gaattctgct   3120
tcctacagat atggaggtta cttaatctcc aatgaggggc tccatttcag ctatgtgttc   3180
agggtgatct ctgcagttgt actgagtgca acagctcttg gaagagcctt ctcttacacc   3240
ccaagttatg caaaagctaa aatatcagct gcacgctttt ttcaactgct ggaccgacaa   3300
cccccaatca gtgtatacaa tactgcaggt gaaaaatggg acaacttcca ggggaagatt   3360
gattttgttg attgtaaatt tacatatcct tctcgacctg actcgcaagt tctgaatggt   3420
ctctcagtgt cgattagtcc agggcagaca ctggcgtttg ttgggagcag tggatgtggc   3480
aaaagcacta gcattcagct gttggaacgt ttctatgatc ctgatcaagg gaaggtgatg   3540
atagatggtc atgacagcaa aaaagtaaat gtccagttcc tccgctcaaa cattggaatt   3600
gtttcccagg aaccagtgtt gtttgcctgt agcataatgg acaatatcaa gtatggagac   3660
aacaccaaag aaattcccat ggaaagagtc atagcagctg caaaacaggc tcagctgcat   3720
gattttgtca tgtcactccc agagaaatat gaaactaacg ttgggtccca ggggtctcaa   3780
ctctctagag gggagaaaca acgcattgct attgctcggg ccattgtacg agatcctaaa   3840
atcttgctac tagatgaagc cacttctgcc ttagacacag aaagtgaaaa gacggtgcag   3900
gttgctctag acaaagccag agagggtcgg acctgcattg tcattgccca tcgcttgtcc   3960
accatccaga acgcggatat cattgctgtc atggcacagg gggtggtgat tgaaaagggg   4020
acccatgaag aactgatggc ccaaaaagga gcctactaca aactagtcac cactggatcc   4080
cccatcagtt gacccaatgc aagaatctca gacacacatg acgcaccagt tacaggggtt   4140
gtttttaaag aaaaaaacaa tcccagcacg agggattgct gggattgttt tttctttaaa   4200
gaagaatntn nntattttac ttttacnnnc nttttcctac atcggaatcc aanctaattt   4260
ctaatggcct tccataataa ttctgcttta gatgtgtata cagaaaatga aagaaactag   4320
ggtccatgtg agggaaaacc caatgtcaag tggcagctca gccaccactc agtgcttctc   4380
tgtgcaggag ccagtcctga ttaatatgtg ggaattagtg agacatcagg gagtaagtga   4440
cactttgaac tcctcaagga cagagaactg tctttcattt ttgaaccctc ggtgtacaca   4500
gaggcgggtc tgtaacaggc aatcaacaaa cgtttcttga gctagaccaa ggtcagattt   4560
gaaaagaaca gaaggactga agaccagctg tgtttcttaa ctaaatttgt ctttcaagtg   4620
aaaccagctt ccttcatctc taaggctaag gatagggaaa gggtgggatg ctctcangct   4680
gagggaggca naaagggaaa gtattancat gagctttcca nttagggctg ttgatttatg   4740
ctttaacttc anantgagtg tagggtggtg anncta                             4776
```

<210> SEQ ID NO 51
<211> LENGTH: 138
<212> TYPE: PRT
<213> ORGANISM: Homo sapiens

<400> SEQUENCE: 51

Met Asp Thr Gln Thr His Ser Leu Pro Ile Thr His Thr Gln Leu His
1 5 10 15

Ser Asn Ser Gln Pro Gln Ser Arg Thr Cys Thr Arg His Cys Gln Thr
20 25 30

Phe Ser Gln Ser Cys Arg Gln Ser His Arg Gly Ser Arg Ser Gln Ser
35 40 45

Ser Ser Gln Ser Pro Ala Ser His Arg Asn Pro Thr Gly Ala His Ser
50 55 60

Ser Ser Gly His Gln Ser Gln Ser Pro Asn Thr Ser Pro Pro Pro Lys
65 70 75 80

Arg His Lys Lys Thr Met Asn Ser His His Ser Pro Met Arg Pro Thr
85 90 95

Ile Leu His Cys Arg Cys Pro Lys Asn Arg Lys Asn Leu Glu Gly Lys
100 105 110

Leu Lys Lys Lys Lys Met Ala Lys Arg Ile Gln Gln Val Tyr Lys Thr
115 120 125

Lys Thr Arg Ser Ser Gly Trp Lys Ser Asn
130 135

<210> SEQ ID NO 52
<211> LENGTH: 1776
<212> TYPE: DNA
<213> ORGANISM: Homo sapiens

<400> SEQUENCE: 52
agactcagct taatctgacc caagggctcc taccctgaac cagtagctgg gactatcccc 60
agggtacccc tgagagctgc cccagcctgg ggtgagggta aggggtaggg ggctttgtct 120
tggctgagcc acatctctca cacccctgtg gcctgggcat cataatcagc cccaactata 180
taaccaggtg ggcctgccag ggcctctgta aagctaggcc tgctgggaga ggatgaggag 240
gaggccctgc cctcaaacgt ggcctcctat ggacacccag actcacagcc ttcctatcac 300
ccacactcag ctccatagca actctcagcc ccaaagccgc acctgcaccc gccattgcca 360
aaccttcagc cagagttgca gacagagcca tcgtggcagc cggagccaga gctccagcca 420
gagcccggcc agccaccgca acccaactgg agcccacagc tcatccggcc accagagcca 480
gagtcccaac actagtccac caccaaagcg ccacaaaaag actatgaact cccaccactc 540
tcccatgcgg cccaccatcc tgcactgccg ctgccccaag aacagaaaga acttggaagg 600
caagctgaaa aagaaaaaaa tggccaagag gatccagcag gtgtacaaaa ccaagacgcg 660
gagctcaggt accctttaag gaggtgggga agggccaccg agccacagat gatggagagc 720
agaccttggg ggcagtgaga ggaaggctgc agccaggtca caaaggaacc acaggcaaga 780
aggaagaggg agaagagaaa caatggcagt tggctagctg aatgtatgat acgttgacgg 840
aaagtcttct ttgaaattgg atgggttgat taggaggatg gaaagatgga cagatagcag 900
ataagctaga tgaaagcatg aatggagttg agaggttggg ttgatgactg ggtgggtaaa 960
caataaatag gttatagaaa ggatagttgg aagaatgcat tggctgaatg ataggaagtt 1020
tggatacgat tagctggatg gatggataaa tggatgaatg cactggctgg ctagttattt 1080
ggttggttag gtagatgatc agtttgaaga ttgtggttgg tggatgaatt ggttagaaat 1140
agagttaaat agttgtagaa gttttgatgg gttggtttga ttggttaaat attatcttaa 1200
tagagtaata tagagtaatt gaataaacag agagaagaat agatatctag actaatggga 1260

```
tagaatggga aagaaatgtt gaataaatga atggaatgag tgaactaatg aatgggtgga   1320

tgacaaatgg aagggataaa tggatggata cctggattca cataggtcaa aaggacactg   1380

acggtagtct aaactctatc tatgtcccat atcaatcaca aatgagtagt tgtaagacct   1440

tacaggaggt caaggaggtc actgacttca tgaagtgctc agctattaaa ggttcctttc   1500

ccactcttat cccttaggat ggaaatccaa ctaatgagac cgcactcctt ggcttgttcc   1560

tgcgtgtttc acccaaagga gaaaatgcta ggatgaagtc aatcttcttg caggaacatg   1620

ttactatggt gatttctacg caacactaat taaagcttgt acctggaaga ctatccctga   1680

gtagtcattt tgatttcact aataaaggtg ttatgtgttt tgggggcctg cacaggggca   1740

gaaatgaatg ggggtaggat gccaagaagc ctgcag                             1776
```

<210> SEQ ID NO 53
<211> LENGTH: 750
<212> TYPE: PRT
<213> ORGANISM: Homo sapiens

<400> SEQUENCE: 53

```
Met Gly Lys Ser Glu Ser Gln Met Asp Ile Thr Asp Ile Asn Thr Pro
1               5                   10                  15

Lys Pro Lys Lys Lys Gln Arg Trp Thr Arg Leu Glu Ile Ser Leu Ser
            20                  25                  30

Val Leu Val Leu Leu Leu Thr Ile Ile Ala Val Arg Met Ile Ala Leu
        35                  40                  45

Tyr Ala Thr Tyr Asp Asp Gly Ile Cys Lys Ser Ser Asp Cys Ile Lys
    50                  55                  60

Ser Ala Ala Arg Leu Ile Gln Asn Met Asp Ala Thr Thr Glu Pro Cys
65                  70                  75                  80

Arg Asp Phe Phe Lys Tyr Ala Cys Gly Gly Trp Leu Lys Arg Asn Val
                85                  90                  95

Ile Pro Glu Thr Ser Ser Arg Tyr Gly Asn Phe Asp Ile Leu Arg Asp
            100                 105                 110

Glu Leu Glu Val Val Leu Lys Asp Val Leu Gln Glu Pro Lys Thr Glu
        115                 120                 125

Asp Ile Val Ala Val Gln Lys Ala Lys Ala Leu Tyr Arg Ser Cys Ile
    130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190

Ser Lys Tyr Gly Lys Lys Val Leu Ile Asn Leu Phe Val Gly Thr Asp
        195                 200                 205

Asp Lys Asn Ser Val Asn His Val Ile His Ile Asp Gln Pro Arg Leu
    210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
            260                 265                 270

Met Asn Lys Val Met Glu Leu Glu Lys Glu Ile Ala Asn Ala Thr Ala
        275                 280                 285
```

-continued

```
Lys Pro Glu Asp Arg Asn Asp Pro Met Leu Leu Tyr Asn Lys Met Arg
    290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
            340                 345                 350

Thr Lys Leu Lys Pro Ile Leu Thr Lys Tyr Ser Ala Arg Asp Leu Gln
        355                 360                 365

Asn Leu Met Ser Trp Arg Phe Ile Met Asp Leu Val Ser Ser Leu Ser
    370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
                405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
        435                 440                 445

Glu Val Phe Ile Gln Thr Leu Asp Asp Leu Thr Trp Met Asp Ala Glu
    450                 455                 460

Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
                485                 490                 495

Tyr Leu Glu Leu Asn Tyr Lys Glu Asp Glu Tyr Phe Glu Asn Ile Ile
            500                 505                 510

Gln Asn Leu Lys Phe Ser Gln Ser Lys Gln Leu Lys Lys Leu Arg Glu
        515                 520                 525

Lys Val Asp Lys Asp Glu Trp Ile Ser Gly Ala Ala Val Val Asn Ala
    530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
                565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
        595                 600                 605

Gln Gln Ser Ala Ser Asn Phe Lys Glu Gln Ser Gln Cys Met Val Tyr
    610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
                645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
        675                 680                 685

Asn Phe Ala Gln Val Trp Cys Gly Thr Tyr Arg Pro Glu Tyr Ala Val
    690                 695                 700

Asn Ser Ile Lys Thr Asp Val His Ser Pro Gly Asn Phe Arg Ile Ile
705                 710                 715                 720
```

```
Gly Thr Leu Gln Asn Ser Ala Glu Phe Ser Glu Ala Phe His Cys Arg
                725                 730                 735

Lys Asn Ser Tyr Met Asn Pro Glu Lys Lys Cys Arg Val Trp
            740                 745                 750


<210> SEQ ID NO 54
<211> LENGTH: 5508
<212> TYPE: DNA
<213> ORGANISM: Homo sapiens

<400> SEQUENCE: 54

gattttaggt gatgggcaag tcagaaagtc agatggatat aactgatatc aacactccaa     60

agccaaagaa gaaacagcga tggactcgac tggagatcag cctctcggtc cttgtcctgc    120

tcctcaccat catagctgtg agaatgatcg cactctatgc aacctacgat gatggtattt    180

gcaagtcatc agactgcata aaatcagctg ctcgactgat ccaaaacatg gatgccacca    240

ctgagccttg tagagacttt ttcaaatatg cttgcggagg ctggttgaaa cgtaatgtca    300

ttcccgagac cagctcccgt tacggcaact ttgacatttt aagagatgaa ctagaagtcg    360

ttttgaaaga tgtccttcaa gaacccaaaa ctgaagatat agtagcagtg cagaaagcaa    420

aagcattgta caggtcttgt ataaatgaat ctgctattga tagcagaggt ggagaacctc    480

tactcaaact gttaccagac atatatgggt ggccagtagc aacagaaaac tgggagcaaa    540

aatatggtgc ttcttggaca gctgaaaaag ctattgcaca actgaattct aaatatggga    600

aaaaagtcct tattaatttg tttgttggca ctgatgataa gaattctgtg aatcatgtaa    660

ttcatattga ccaacctcga cttggcctcc cttctagaga ttactatgaa tgcactggaa    720

tctataaaga ggcttgtaca gcatatgtgg attttatgat ttctgtggcc agattgattc    780

gtcaggaaga aagattgccc atcgatgaaa accagcttgc tttggaaatg aataaagtta    840

tggaattgga aaaagaaatt gccaatgcta cggctaaacc tgaagatcga aatgatccaa    900

tgcttctgta taacaagatg agattggccc agatccaaaa taacttttca ctagagatca    960

atgggaagcc attcagctgg ttgaatttca caaatgaaat catgtcaact gtgaatatta   1020

gtattacaaa tgaggaagat gtggttgttt atgctccaga atatttaacc aaacttaagc   1080

ccattcttac caaatattct gccagagatc ttcaaaattt aatgtcctgg agattcataa   1140

tggatcttgt aagcagcctc agccgaacct acaaggagtc cagaaatgct ttccgcaagg   1200

ccctttatgg tacaacctca gaaacagcaa cttggagacg ttgtgcaaac tatgtcaatg   1260

ggaatatgga aaatgctgtg gggaggcttt atgtggaagc agcatttgct ggagagagta   1320

aacatgtggt cgaggatttg attgcacaga tccgagaagt ttttattcag actttagatg   1380

acctcacttg gatggatgcc gagacaaaaa agagagctga agaaaaggcc ttagcaatta   1440

aagaaaggat cggctatcct gatgacattg tttcaaatga taacaaactg aataatgagt   1500

acctcgagtt gaactacaaa gaagatgaat acttcgagaa cataattcaa aatttgaaat   1560

tcagccaaag taaacaactg aagaagctcc gagaaaaggt ggacaaagat gagtggataa   1620

gtggagcagc tgtagtcaat gcattttact cttcaggaag aaatcagata gtcttcccag   1680

ccggcattct gcagcccccc ttctttagtg cccagcagtc caactcattg aactatgggg   1740

gcatcggcat ggtcatagga cacgaaatca cccatggctt cgatgacaat ggcagaaact   1800

ttaacaaaga tggagacctc gttgactggt ggactcaaca gtctgcaagt aactttaagg   1860

agcaatccca gtgcatggtg tatcagtatg gaaacttttc ctgggacctg gcaggtggac   1920

agcaccttaa tggaattaat acactgggag aaaacattgc tgataatgga ggtcttggtc   1980
```

aagcatacag agcctatcag aattatatta aaaagaatgg cgaagaaaaa ttacttcctg 2040
gacttgacct aaatcacaaa caactatttt tcttgaactt tgcacaggtg tggtgtggaa 2100
cctataggcc agagtatgcg gttaactcca ttaaaacaga tgtgcacagt ccaggcaatt 2160
tcaggattat tgggactttg cagaactctg cagagttttc agaagccttt cactgccgca 2220
agaattcata catgaatcca gaaaagaagt gccgggtttg gtgatcttca aaagaagcat 2280
tgcagccctt ggctagactt gccaacacca cagaaatggg gaattctcta atcgaaagaa 2340
aatgggccct aggggtcact gtactgactt gagggtgatt aacagagagg gcaccatcac 2400
aatacagata acattaggtt gtcctagaaa gggtgtggag ggaggaaggg ggtctaaggt 2460
ctatcaagtc aatcatttct cactgtgtac ataatgctta atttctaaag ataatattac 2520
tgtttatttc tgtttctcat atggtctacc agtttgctga tgtccctaga aaacaatgca 2580
aaacctttga ggtagaccag gatttctaat caaaagggaa aagaagatgt tgaagaatag 2640
agttaggcac cagaagaaga gtaggtgaca ctatagttta aaacacattg cctaactact 2700
agtttttact tttatttgca acatttacag tccttcaaaa tccttccaaa gaattcttat 2760
acacattggg gccttggagc ttacatagtt ttaaactcat ttttgccata catcagttat 2820
tcattctgtg atcatttatt ttaagcactc ttaaagcaaa aaatgaatgt ctaaaattgt 2880
tttttgttgt acctgctttg actgatgctg agattcttca ggcttcctgc aattttctaa 2940
gcaatttctt gctctatctc tcaaaacttg gtatttttca gagatttata taaatgtaaa 3000
aataataatt tttatattta attattaact acatttatga gtaactatta ttataggtaa 3060
tcaatgaata ttgaagtttc agcttaaaat aaacagttgt gaaccaagat ctataaagcg 3120
atatacagat gaaaatttga gactatttaa acttataaat catattgatg aaaagattta 3180
agcacaaact ttagggtaaa aattgcgatt ggacagttgt ctagagatat atatacttgt 3240
ggttttcaaa ttggactttc aaaattaaat ctgtccctga gagtgtctct gataaaaggg 3300
caaatctgca cctatgtagc tctgcatctc ctgtcttttc aggtttgtca tcagatggaa 3360
atattttgat aataaattga aattgtgaac tcattgctcc ctaagactgt gacaactgtc 3420
taactttaga agtgcatttc tgaatagaaa tgggaggcct ctgatggacc ttctagaatt 3480
ataagtcaca aagagttctg gaaaagaact gtttactgct tgataggaat tcatcttttg 3540
aggcttctgt tcctctcttt tcctgttgta ttgactattt tcgttcatta cttgattaag 3600
attttacaaa agaggagcac ttccaaaatt cttatttttc ctaacaaaag atgaaagcag 3660
ggaatttcta tctaaatgat gagtattagt tccctgtctc ttgaaaaatg cccatttgcc 3720
tttaaaaaaa aaagttacag aaatactata acatatgtac ataaattgca taaagcataa 3780
gtatacagtt caataaactt aactttaact gaacaatggc cctgtagcca gcacctgtaa 3840
gaaacagagc agtaccagcg ctctaaaagc acctccttgt cactttatta ctcccagaac 3900
aacaactatc ctgacttcta atatcattca ctagctttgc ctggttttgt cttttatgca 3960
gatagaatca atcagtatgt attcttttgt gcctggcttc tttctctcag ccttacattt 4020
gtgagattcc tctgtattgt gctgattgtg gatcttttca ttctcattgc agaataatgt 4080
tctattgtgg gacttattac aatttgttca tcctattgtt gatgggcact tgagaacttt 4140
ccattttggc gctattacaa atagtgcaac tatgaatgta ctgcatgtta ccatcttact 4200
tgagccttta atggacttat ttcttcaaat ccttccaaaa attattataa gcattgaaat 4260
tatagtttca agccaactgt ggataccctt accctttcct cctttatcac aaccaccgtt 4320
acaagtatac ttatatttcc ctaaaataca tttaaaactt acctaagtga catttgtagt 4380

```
tggagtaata ggagcttcca gctctaataa aacagctgtc tctaacttat tttatttcca   4440

tcatgtcaga gcaggtgaag agccagaagt gaagagtgac tagtacaaat tataaaaagc   4500

cactagactc ttcactgtta gctttttaaa acattaggct cccatcccta tggaggaaca   4560

actctccagt gcctggatcc cctctgtcta caaatataag attttctggg cctaaaggat   4620

agatcaaagt caaaaatagc aatgcctccc tatccctcac acatccagac atcatgaatt   4680

ttacatggta ctcttgttga gttctataga gccttctgat gtctctaaag cactaccgat   4740

tctttggagt tgtcacatca gataagacat atctctaatt ccatccataa atccagttct   4800

actatggctg agttctggtc aaagaaagaa agtttagaag ctgagacaca aagggttggg   4860

agctgatgaa actcacaaat gatggtagga agaagctctc gacaataccc gttggcaagg   4920

agtctgcctc catgctgcag tgttcgagtg gattgtaggt gcaagatgga aaggattgta   4980

ggtgcaagct gtccagagaa aagagtcctt gttccagccc tattctgcca ctcctgacag   5040

ggtgaccttg ggtatttgca atattccttt gggcctctgc ttctctcacc taaaaaaaga   5100

gaattagatt atattggtgg ttctcagcaa gagaaggagt atgtgtccaa tgctgccttc   5160

ccatgaatct gtctcccagt tatgaatcag tgggcaggat aaactgaaaa ctcccattta   5220

agtgtctgaa tcgagtgaga caaaatttta gtccaaataa caagtaccaa agttttatca   5280

agtttgggtc tgtgctgctg ttactgttaa ccatttaagt ggggcaaaac cttgctaatt   5340

ttctcaaaag catttatcat tcttgttgcc acagctggag ctctcaaact aaaagacatt   5400

tgttattttg gaaagaagaa agactctatt ctcaaagttt cctaatcaga aatttttatc   5460

agtttccagt ctcaaaaata caaaataaaa acaaacgttt ttaatact                5508
```

```
<210> SEQ ID NO 55
<211> LENGTH: 79
<212> TYPE: PRT
<213> ORGANISM: Homo sapiens

<400> SEQUENCE: 55

Met Ala His Lys Gln Ile Tyr Tyr Ser Asp Lys Tyr Phe Asp Glu His
1               5                   10                  15

Tyr Glu Tyr Arg His Val Met Leu Pro Arg Glu Leu Ser Lys Gln Val
            20                  25                  30

Pro Lys Thr His Leu Met Ser Glu Glu Glu Trp Arg Arg Leu Gly Val
        35                  40                  45

Gln Gln Ser Leu Gly Trp Val His Tyr Met Ile His Glu Pro Glu Pro
    50                  55                  60

His Ile Leu Leu Phe Arg Arg Pro Leu Pro Lys Asp Gln Gln Lys
65                  70                  75


<210> SEQ ID NO 56
<211> LENGTH: 627
<212> TYPE: DNA
<213> ORGANISM: Homo sapiens

<400> SEQUENCE: 56

agtctccggc gagttgttgc ctgggctgga cgtggttttg tctgctgcgc ccgctcttcg     60

cgctctcgtt tcattttctg cagcgcgcca cgaggatggc ccacaagcag atctactact    120

cggacaagta cttcgacgaa cactacgagt accggcatgt tatgttaccc agagaacttt    180

ccaaacaagt acctaaaact catctgatgt ctgaagagga gtggaggaga cttggtgtcc    240

aacagagtct aggctgggtt cattacatga ttcatgagcc agaaccacat attcttctct    300
```

ttagacgacc tcttccaaaa gatcaacaaa aatgaagttt atctggggat cgtcaaatct 360
ttttcaaatt taatgtatat gtgtatataa ggtagtattc agtgaatact tgagaaatgt 420
acaaatcttt catccatacc tgtgcatgag ctgtattctt cacagcaaca gagctcagtt 480
aaatgcaact gcaagtaggt tactgtaaga tgtttaagat aaaagttctt ccagtcagtt 540
tttctcttaa gtgcctgttt gagtttactg aaacagttta cttttgttca ataaagtttg 600
tatgttgcat ttaaaaaaaa aaaaaaa 627

<210> SEQ ID NO 57
<211> LENGTH: 5769
<212> TYPE: DNA
<213> ORGANISM: Homo sapiens
<220> FEATURE:
<221> NAME/KEY: misc_feature
<222> LOCATION: (5512)..(5517)
<223> OTHER INFORMATION: n is a, c, g, or t

<400> SEQUENCE: 57
gagctctcca tgcacacctg ttactgtttc tgtttttacc tgtaaatatc tgtctctgac 60
ttccatgtct catgcacctc tatagggcaa agactgtgtc ttaaacatca cggtagcctc 120
agcatgttgt gcaatcaagg tttttttgtt tttgttcttt gttttttttt tggtattagc 180
tttatttgta tcattttgaa atttttatca aaaaagcagc gtgcctgctg tggttcccat 240
cctctgggat ttaggaatct ttacccgatt ctccatccaa gtctgtcttt cgtattctag 300
gctcttccta aagttgtcat tcacatatac cctccagaat tttatagggt gtataatctg 360
taacaactcg gaggaagcca attgcccttt agaaatatgg ctgcaattgc ctcacttcct 420
gtgtcatgtg actctcctag tcatcacatg acccatccac attgggaagc cagaattact 480
tgcaggagta acctagtgcc tatagctatg gcaggtacct gcatccttgt ttttgtttag 540
tggatcctct atccttcaga gactctggaa cccctgtgct cttctcctca tctagtgacc 600
ctgaggtgat ggagttttca agtccttcca gagaggtaag agagagagct cccaatcagc 660
attgtcacag tgcttctgga atcctggcac tggaatttaa tgaatgacag actctctttg 720
aatccagggc catcatggct ctttgagcaa ggcacagatg gaggggaggg tcgaagttga 780
aatgggtggg aagagtggtg gggagcatcc tgatttgggg tgggcagaga gttgtcatca 840
gaagggttgc agggagagct gcacccaggt gtctgtgggc cttgtcctaa tgaatgtggg 900
agaccaggcc atgggcaccc aaaggcagct aagccctgcc cgggagagta gttgaggggt 960
ggagagggac ttgcttttca gtcattcctc attctgtcct caggaatgtc ccaagccttc 1020
gggtagggta agcatcatgg ctggcagcct cacaggattg cttctacttc aggcagtgtc 1080
gtgggcatca gatgagtgag tcaaggcagt ggggaggtag cacagagcct cccttctgcc 1140
tcatagtcct ttggtagcct tccagtaagc tggtggtaga cttttagtag gtgctcaata 1200
aatccttttg agtgactgag accaactttg gggtgaggat ttttgaaacc gtcttcagtc 1260
tctccaaaca gctgtgtccg ttctccacat ccttgtcaga cctcacctct gcttgtgctc 1320
cctccctccc aggtggtgcc cctgcatccc taaaagcttc agtacagctc ggtggtctgt 1380
gtctgcaatg ccacatactg tgactcttga cccccccgacc tttcctgccc taggtgcctt 1440
cagccgctac aagagcagaa gcagtgggca ttggatggag ctgagtacag gaccatacag 1500
gctaattgca ccggcacagg taaccattac acccttcacc ccccgggcca ggctgggtcc 1560
tcctagaggt aaacggtgtc agtgatcacc atggagtttc tccctgggca ctgataaccc 1620
tgtggatgtc ctcaggcctg ctactgatcc tgcagccaga agttccagaa agtgaaggga 1680

-continued

```
tttggagggg ccgtgacaga tgcaggtgcc ctcaacatcc ttgccctgtc accccctgcc   1740
cagaatttgc tacttaaatg gtacttctct gaagaagatg aggaggaagg ggacaggatg   1800
acatagagcc actgacactt ttctttgcca attctttgga ccctgacttc tgcccatccc   1860
tgacatttgg ttcctgtctt aatgccagtg aaataagatt tcgccgccta tcatctgcta   1920
actgctacgg actcaggctc agaaaggcct gcgcttcacc caggtgccag cctccacagg   1980
ttccaaccca ggagcccaag ttccttttgg ccctgactca gacactatta ggactggcaa   2040
gtgataagca gagtcccata ctctcctatt gactcggact accatatctt gatcatcctt   2100
ttctgtagga atcggatata acatcatctg ggtacccatg gccagctgtg acttctccat   2160
ccgcacctac acctatgcag acacccctga tgatttccag ttgcacaact tcagcctccc   2220
agaggaagat accaagctca aggtaggcat tctagctttt tcaggccctg agggccctga   2280
tgtctggggg ttgagaaact gtagggtagg tctgcttgta cagacatttt gtcccctgct   2340
gttttgtcct gggggtggga gggtgggggc taatggctga accggatgca ctggttgggc   2400
tagtatgtgt tccaactctg ggtgcttctc tcttcactac ctttgtctct agataccct    2460
gattcaccga gccctgcagt tggcccagcg tcccgtttca ctccttgcca gcccctggac   2520
atcacccact tggctcaaga ccaggggagc ggggaatggg aaggggccac tcaagggaca   2580
gcccagagac atctaccacc agacctgggc cagatacatt gtgaagtaag ggatcaacaa   2640
ggatgtggga tcaggactgg cctccccttt ggccatgctg atctgtgtcc caaccctcaa   2700
cctggttcca cttccagatc tgcctgtcct cagctcacct ttctaccttc tgggcctttc   2760
aaccttgggc ctgtcagtct tgcccactcc atcaggcttc ctgttctctc ggtctggccc   2820
actttcttgg ctggatcatt catgaccttt ctcttgccag gttcctggat gcctatgctg   2880
agcacaagtt acagttctgg gcagtgacag gtgaaaatga gccttctgct gggctgttga   2940
gtggataccc cttccagtgc ctgggcttca cccctgaaca tcagcgagac ttcattgccc   3000
gtgacctagg tcctaccctt gccaacggta ctcaccacaa tgtccgccta ctcatgctgg   3060
atgaccaacg cttgctgctg ccccactggg caaaggtggt aaggcctgga cctccatggt   3120
gctccagtga ccttcaaatc cagcatccaa atgattggct cccaaactta gagggatttt   3180
tctacccaac tatggatccc tagagcacca ttccccggga cctccagggt gccatggatc   3240
ccacagttgg gacttgaaac ctctctaggg ctgggggtgg tagctcatgg ctataattcc   3300
agcactttgg gaaccaaggt gggtggatca cttgaaccta aggagttcaa gatgagcctg   3360
ggaaacatgg tgaaacccta actctacaaa aaaaaaaata gaaaagttag ccgggtgtgg   3420
tggtggcacg ctatagtccc agtattctgg aggctaaggc gggaggttta gttgagccta   3480
ggaatttcag gctgcagtga gctatgattg tgccactgta ctccagcctg tgtgacagag   3540
ggagaccctg tctcaaaaac aaaaacaaaa aatccctccc aaaacctctg tagttgcatt   3600
cttcccacca cctaattcag gattcctaca agaggaacta gaagttccag aagcctgtgg   3660
gcagggtcca gggtgacttg ttcttccttt gcaggtactg acagacccag aagcagctaa   3720
gtatgttcat ggtattgctg tacattggta cctggacttt ctggctccag ccaaagccac   3780
cctaagggag acacaccacc tgttccccaa caccatgctc tttgcctcag aggcctgtgt   3840
gggttccaag ttctgggagc agagtgtgcg gctaggctcc tgggatcgag ggatgcagta   3900
cagccacagc atcatcacag taagccaccc cagtctccct tcctgcaaag gagacctcag   3960
acccattagt agtctcacca aagactgata gaagcccttc ctgtccagct ttccccaggt   4020
agcctgccct tttgcgcaac tctggggaac catgattccc tgtcttgcct ttccttcaca   4080
```

-continued

```
ggtctgcaca cctcattgcc ccttttgcaa ctactgaggc acttgcagct gcctcagact   4140

tctcagctcc ccttgagatg cctggatctt cacaccccca actccttagc tactaaggaa   4200

tgtgccctca cagggctgac ctacccacag ctgcctctcc cacatgtgac ccttacctac   4260

actctctggg gacccccagt gttgagcctt tgtctctttg cctttgtcct taccctagaa   4320

cctcctgtac catgtggtcg gctggaccga ctggaaccca tcattgtaga catcaccaag   4380

cacacgtttt acaaacagcc catgttctac caccttggcc acttcaggtg agtggagggc   4440

gggcaccccc attccatacc aggcctatca tctcctacat cggatggctt acatcactct   4500

acaccacgag ggagcaggaa ggtgttcagg gtggaacctc ggaagaggca cacccatccc   4560

cttttgcacc atggaggcag gaagtgacta ggtagcaaca gaaaacccca atgcctgagg   4620

ctggactgcg atgcagaaaa gcagggtcag tgcccagcag catggctcca ggcctagaga   4680

gccagggcag agcctttgca ggagttatgg ggtgggtccg tgggtgggcg acttcttaga   4740

tgagggtttc atgggaggta ccccgaggga ctctgaccat ctgttcccac attcagcaag   4800

ttcattcctg agggctccca gagagtgggg ctggttgcca gtcagaagaa cgacccggac   4860

gcagtggcac tgatgcatcc cgatggctct cctgttgtgg tcgtcctaaa ccggtgaggg   4920

caatggtgag gtctgggaag tgggctgaag acagcgttgg gggccttggc aggatcacac   4980

tctcagcttc tcctccctgc tccctagctc ctctaaggat gtgcctctta ccatcaagga   5040

tcctgctgtg ggcttcctgg agacaatctc acctggctac tccattcaca cctacctgtg   5100

gcgtcgccag tgatggagca gatactcaag gaggcactgg gctcagcctg ggcattaaag   5160

ggacagagtc agctcacacg ctgtctgtga ctaaagaggg cacaacaggg ccagtgtgag   5220

cttacagcga cgtaagccca ggggcaatgg tttgggtgac tcactttccc ctctaggtgg   5280

tgcccagggc tggaggcccc tagaaaaaga tcagtaagcc ccagtgtccc cccagccccc   5340

atgcttatgt gaacatgcgc tgtgtgctgc ttgctttgga aactggcctg ggtccaggcc   5400

tagggtgagc tcactgtccg tacaaacaca agatcagggc tgagggtaag gaaaagaaga   5460

gactaggaaa gctgggccca aaactggaga ctgtttgtct ttcctggaga tnnnnnnctg   5520

ggcccgtgga gcagcagtgt cagcatcagg gcggaagcct taaagcagca gcgggtgtgc   5580

ccaggcaccc agatgattcc tatggcacca gccaggaaaa atggcagctc ttaaaggaga   5640

aaatgtttga gcccagtcag tgtgagtggc tttattctgg gtggcagcac ccgtgtccgg   5700

ctgtaccaac aacgaggagc acgggggcct ctggaagtca tgagagtaga aaaaccagtc   5760

ttggggagt                                                           5769
```

```
<210> SEQ ID NO 58
<211> LENGTH: 732
<212> TYPE: PRT
<213> ORGANISM: Homo sapiens

<400> SEQUENCE: 58

Met Thr Glu Gly Thr Cys Leu Arg Arg Arg Gly Gly Pro Tyr Lys Thr
1               5                   10                  15

Glu Pro Ala Thr Asp Leu Gly Arg Trp Arg Leu Asn Cys Glu Arg Gly
            20                  25                  30

Arg Gln Thr Trp Thr Tyr Leu Gln Asp Glu Arg Ala Gly Arg Glu Gln
        35                  40                  45

Thr Gly Leu Glu Ala Tyr Ala Leu Gly Leu Asp Thr Lys Asn Tyr Phe
    50                  55                  60

Lys Asp Leu Pro Lys Ala His Thr Ala Phe Glu Gly Ala Leu Asn Gly
65                  70                  75                  80
```

```
Met Thr Phe Tyr Val Gly Leu Gln Ala Glu Asp Gly His Trp Thr Gly
                85                  90                  95

Asp Tyr Gly Gly Pro Leu Phe Leu Leu Pro Gly Leu Leu Ile Thr Cys
            100                 105                 110

His Val Ala Arg Ile Pro Leu Pro Ala Gly Tyr Arg Glu Glu Ile Val
        115                 120                 125

Arg Tyr Leu Arg Ser Val Gln Leu Pro Asp Gly Gly Trp Gly Leu His
    130                 135                 140

Ile Glu Asp Lys Ser Thr Val Phe Gly Thr Ala Leu Asn Tyr Val Ser
145                 150                 155                 160

Leu Arg Ile Leu Gly Val Gly Pro Asp Asp Pro Asp Leu Val Arg Ala
                165                 170                 175

Arg Asn Ile Leu His Lys Lys Gly Gly Ala Val Ala Ile Pro Ser Trp
            180                 185                 190

Gly Lys Phe Trp Leu Ala Val Leu Asn Val Tyr Ser Trp Glu Gly Leu
        195                 200                 205

Asn Thr Leu Phe Pro Glu Met Trp Leu Phe Pro Asp Trp Ala Pro Ala
    210                 215                 220

His Pro Ser Thr Leu Trp Cys His Cys Arg Gln Val Tyr Leu Pro Met
225                 230                 235                 240

Ser Tyr Cys Tyr Ala Val Arg Leu Ser Ala Ala Glu Asp Pro Leu Val
                245                 250                 255

Gln Ser Leu Arg Gln Glu Leu Tyr Val Glu Asp Phe Ala Ser Ile Asp
            260                 265                 270

Trp Leu Ala Gln Arg Asn Asn Val Ala Pro Asp Glu Leu Tyr Thr Pro
        275                 280                 285

His Ser Trp Leu Leu Arg Val Val Tyr Ala Leu Leu Asn Leu Tyr Glu
    290                 295                 300

His His His Ser Ala His Leu Arg Gln Arg Ala Val Gln Lys Leu Tyr
305                 310                 315                 320

Glu His Ile Val Ala Asp Asp Arg Phe Thr Lys Ser Ile Ser Ile Gly
                325                 330                 335

Pro Ile Ser Lys Thr Ile Asn Met Leu Val Arg Trp Tyr Val Asp Gly
            340                 345                 350

Pro Ala Ser Thr Ala Phe Gln Glu His Val Ser Arg Ile Pro Asp Tyr
        355                 360                 365

Leu Trp Met Gly Leu Asp Gly Met Lys Met Gln Gly Thr Asn Gly Ser
    370                 375                 380

Gln Ile Trp Asp Thr Ala Phe Ala Ile Gln Ala Leu Leu Glu Ala Gly
385                 390                 395                 400

Gly His His Arg Pro Glu Phe Ser Ser Cys Leu Gln Lys Ala His Glu
                405                 410                 415

Phe Leu Arg Leu Ser Gln Val Pro Asp Asn Pro Pro Asp Tyr Gln Lys
            420                 425                 430

Tyr Tyr Arg Gln Met Arg Lys Gly Gly Phe Ser Phe Ser Thr Leu Asp
        435                 440                 445

Cys Gly Trp Ile Val Ser Asp Cys Thr Ala Glu Ala Leu Lys Ala Val
    450                 455                 460

Leu Leu Leu Gln Glu Lys Cys Pro His Val Thr Glu His Ile Pro Arg
465                 470                 475                 480

Glu Arg Leu Cys Asp Ala Val Ala Val Leu Leu Asn Met Arg Asn Pro
                485                 490                 495

Asp Gly Gly Phe Ala Thr Tyr Glu Thr Lys Arg Gly Gly His Leu Leu
```

-continued 500 505 510

Glu Leu Leu Asn Pro Ser Glu Val Phe Gly Asp Ile Met Ile Asp Tyr
515 520 525

Thr Tyr Val Glu Cys Thr Ser Ala Val Met Gln Ala Leu Lys Tyr Phe
530 535 540

His Lys Arg Phe Pro Glu His Arg Ala Ala Glu Ile Arg Glu Thr Leu
545 550 555 560

Thr Gln Gly Leu Glu Phe Cys Arg Arg Gln Gln Arg Ala Asp Gly Ser
565 570 575

Trp Glu Gly Ser Trp Gly Val Cys Phe Thr Tyr Gly Thr Trp Phe Gly
580 585 590

Leu Glu Ala Phe Ala Cys Met Gly Gln Thr Tyr Arg Asp Gly Thr Ala
595 600 605

Cys Ala Glu Val Ser Arg Ala Cys Asp Phe Leu Leu Ser Arg Gln Met
610 615 620

Ala Asp Gly Gly Trp Gly Glu Asp Phe Glu Ser Cys Glu Glu Arg Arg
625 630 635 640

Tyr Leu Gln Ser Ala Gln Ser Gln Ile His Asn Thr Cys Trp Ala Met
645 650 655

Met Gly Leu Met Ala Val Arg His Pro Asp Ile Glu Ala Gln Glu Arg
660 665 670

Gly Val Arg Cys Leu Leu Glu Lys Gln Leu Pro Asn Gly Asp Trp Pro
675 680 685

Gln Glu Asn Ile Ala Gly Val Phe Asn Lys Ser Cys Ala Ile Ser Tyr
690 695 700

Thr Ser Tyr Arg Asn Ile Phe Pro Ile Trp Ala Leu Gly Arg Phe Ser
705 710 715 720

Gln Leu Tyr Pro Glu Arg Ala Leu Ala Gly His Pro
725 730

<210> SEQ ID NO 59
<211> LENGTH: 3206
<212> TYPE: DNA
<213> ORGANISM: Homo sapiens

<400> SEQUENCE: 59
cccttgccta ctgctcatgg gtgtggagac tgatattctg gaagactgat aggcagattt 60
actattaaca aacacatagt ctgtggccca gcaaagccac cccaatccct gcacaagggt 120
aaaaggccag cattagagca ctgcagcagc aatgacggag ggcacgtgtc tgcggcgccg 180
agggggcccc tacaagaccg agcccgccac cgacctcggc cgctggcgac tcaactgcga 240
gaggggccgg cagacgtgga cctacctgca ggacgagcgc gccggccgcg agcagaccgg 300
cctggaagcc tacgccctgg ggctggacac caagaattac tttaaggact tgcccaaagc 360
ccacaccgcc tttgaggggg ctctgaacgg gatgacattt tacgtggggc tgcaggctga 420
ggatgggcac tggacgggtg attatggtgg cccacttttc ctcctgccag gcctcctgat 480
cacttgccac gtggcacgca tccctctgcc agccggatac agagaagaga ttgtgcggta 540
cctgcggtca gtgcagctcc ctgacggtgg ctggggcctg cacattgagg ataagtccac 600
cgtgtttggg actgcgctca actatgtgtc tctcagaatt ctgggtgttg ggcctgacga 660
tcctgacctg gtacgagccc ggaacattct tcacaagaaa ggtggtgctg tggccatccc 720
ctcctggggg aagttctggc tggctgtcct gaatgtttac agctgggaag gcctcaatac 780
cctgttccca gagatgtggc tgtttcctga ctgggcaccg gcacacccct ccacactctg 840

-continued

```
gtgccactgc cggcaggtgt acctgcccat gagctactgc tacgccgttc ggctgagtgc    900

cgcggaagac ccgctggtcc agagcctccg ccaggagctc tatgtggagg acttcgccag    960

cattgactgg ctggcgcaga ggaacaacgt ggccccccgac gagctgtaca cgcccccacag   1020

ctggctgctc cgcgtggtat atgcgctcct caacctgtat gagcaccacc acagtgccca   1080

cctgcggcag cgggccgtgc agaagctgta tgaacacatt gtggccgacg accgattcac   1140

caagagcatc agcatcggcc cgatctcgaa aaccatcaac atgcttgtgc gctggtatgt   1200

ggacgggccc gcctccactg ccttccagga gcatgtctcc agaatcccgg actatctctg   1260

gatgggcctt gacggcatga aaatgcaggg caccaacggc tcacagatct gggacaccgc   1320

attcgccatc caggctctgc ttgaggcggg cgggcaccac aggcccgagt tttcgtcctg   1380

cctgcagaag gctcatgagt tcctgaggct ctcacaggtc ccagataacc ctcccgacta   1440

ccagaagtac taccgccaga tgcgcaaggg tggcttctcc ttcagtacgc tggactgcgg   1500

ctggatcgtt tctgactgca cggctgaggc cttgaaggct gtgctgctcc tgcaggagaa   1560

gtgtccccat gtcaccgagc acatccccag agaacggctc tgcgatgctg tggctgtgct   1620

gctgaacatg agaaatccag atggagggtt cgccacctat gagaccaagc gtggggggca   1680

cttgctggag ctgctgaacc cctcggaggt cttcggggac atcatgattg actacaccta   1740

tgtggagtgc acctcagccg tgatgcaggc gcttaagtat ttccacaagc gtttcccgga   1800

gcacagggca gcggagatcc gggagaccct cacgcagggc ttagagttct gtcggcggca   1860

gcagagggcc gatggctcct gggaaggctc ctggggagtt tgcttcacct acggcacctg   1920

gtttggcctg gaggccttcg cctgtatggg gcagacctac cgagatggga ctgcctgtgc   1980

agaggtctcc cgggcctgtg acttcctgct gtcccggcag atggcagacg gaggctgggg   2040

ggaggacttt gagtcctgcg aggagcggcg ttatttgcag agtgcccagt cccagatcca   2100

taacacatgc tgggccatga tggggctgat ggccgttcgg catcctgaca tcgaggccca   2160

ggagagagga gtccggtgtc tacttgagaa acagctcccc aatggcgact ggccgcagga   2220

aaacattgct ggggtcttca acaagtcctg tgccatctcc tacacgagct acaggaacat   2280

cttccccatc tgggccctcg gccgcttctc ccagctgtac cctgagagag cccttgctgg   2340

ccacccctga gaacatgcct acctgctggg tgccgtctgt gcgttccagt gaggccaagg   2400

ggtcctggcc gggttgggga gccctcccat aaccctgtct tgggctccaa cccctcaacc   2460

tctatctcat agatgtgaat ctgggggcca ggctggaggc agggatgggg acagggtggg   2520

tggcttagac tcttgatttt tactgtaggt tcatttctga aagtagcttg tcgggcttgg   2580

gtgaggaagg gggcacagga gccgtgaccc ctgaggaggc acagcgcctt ctgccacctc   2640

tgggcacggc ctcaaggtag tgaggctagg aggtttttttc tgaccaatag ctgagttctt   2700

gggagaggag cagctgtgcc tgtgtgattc cttagtgtcg agtgggctct gggctggggt   2760

cggccctggg caggcttctc ctgcaccttt tgtctgctgg gctgagggac acgagggcaa   2820

ccctgtgaca atggcaggta gtgtgcatcc gtgaatagcc cagtgcgggg gttgctcatg   2880

gagcatcctg aggccgtgca gcagggagcc ccatgcccct gggtcgtgag cttgcctgcg   2940

tatggggtgg tgtcatggag cctcatgccc ctgggtcgtg agctcgcctg agtatggggt   3000

ggtgtcatgg agccgcatac ccctgggttg tgagctcgcc tgcatatgca gggtctgtca   3060

tggaacatcc caagtctgtg cagcagggag ccccatgccc ctgggacatg aacccacctg   3120

cgtggaatgc tgtttgtgag gtgtctacag ggtttatagt agtcttgtgg acacagaaat   3180

gcacagggga cacttacgga cacaga                                        3206
```

<210> SEQ ID NO 60
<211> LENGTH: 506
<212> TYPE: DNA
<213> ORGANISM: Homo sapiens

<400> SEQUENCE: 60
gacgacgact tgctgttcga ggatgtgtac gagctgtgcg aggtgatcgg aaagggtccc 60
ttcagtgttg tacgacgatg tatcaacaga gaaactgggc aacaatttgc tgtaaaaatt 120
gttgatgtag ccaagttcac atcaagtcca gggttaagta cagaagatct aaagcgggaa 180
gccagtatct gtcatatgct gaaacatcca cacattgtag agttattgga gacatatagc 240
tcagatggaa tgctttacat ggttttcgaa ttgtgagtgt gtattttaat tcttaaaggg 300
taaaacttga agcaatgttg gtgttggata atgctaacac ttttctcttg aaatttagca 360
gtagttgtga acttatctgt tcagaaagac ctaaagtcac aagaaaaaag gattatgtca 420
tcataaggtt tacagtggca aaggaagcaa aagctgggca tattcagtta ctcttcatgc 480
tttcagcatg cttcagagaa gagact 506

<210> SEQ ID NO 61
<211> LENGTH: 229
<212> TYPE: DNA
<213> ORGANISM: Homo sapiens

<400> SEQUENCE: 61
gagcctcaaa tatctccaaa atctgatacc aatccttttg attgtgaatt atattctgta 60
gctaccaaag aaggaagaag aaaactagga aggagtaagc acaaagatct cttcacattc 120
tccgggactg cggtaccaaa tatcagcaca gcacttcttg aaaaaggatg tagattttaa 180
tctgaacttt gaaccatcac tgaggtggcc cgccggtttc tgagccttc 229

<210> SEQ ID NO 62
<211> LENGTH: 614
<212> TYPE: PRT
<213> ORGANISM: Homo sapiens

<400> SEQUENCE: 62

Met Asp Gly Lys Val Ala Val Gln Glu Arg Gly Pro Pro Ala Val Ser
1 5 10 15

Trp Val Pro Glu Glu Gly Glu Lys Leu Asp Gln Glu Asp Glu Asp Gln
20 25 30

Val Lys Asp Arg Gly Gln Trp Thr Asn Lys Met Glu Phe Val Leu Ser
35 40 45

Val Ala Gly Glu Ile Ile Gly Leu Gly Asn Val Trp Arg Phe Pro Tyr
50 55 60

Leu Cys Tyr Lys Asn Gly Gly Gly Ala Phe Phe Ile Pro Tyr Phe Ile
65 70 75 80

Phe Phe Phe Val Cys Gly Ile Pro Val Phe Phe Leu Glu Val Ala Leu
85 90 95

Gly Gln Tyr Thr Ser Gln Gly Ser Val Thr Ala Trp Arg Lys Ile Cys
100 105 110

Pro Leu Phe Gln Gly Ile Gly Leu Ala Ser Val Val Ile Glu Ser Tyr
115 120 125

Leu Asn Val Tyr Tyr Ile Ile Ile Leu Ala Trp Ala Leu Phe Tyr Leu
130 135 140

Phe Ser Ser Phe Thr Ser Glu Leu Pro Trp Thr Thr Cys Asn Asn Phe
145 150 155 160

-continued

```
Trp Asn Thr Glu His Cys Thr Asp Phe Leu Asn His Ser Gly Ala Gly
                165                 170                 175

Thr Val Thr Pro Phe Glu Asn Phe Thr Ser Pro Val Met Glu Phe Trp
            180                 185                 190

Glu Arg Arg Val Leu Gly Ile Thr Ser Gly Ile His Asp Leu Gly Ser
        195                 200                 205

Leu Arg Trp Glu Leu Ala Leu Cys Leu Leu Leu Ala Trp Val Ile Cys
    210                 215                 220

Tyr Phe Cys Ile Trp Lys Gly Val Lys Ser Thr Gly Lys Val Val Tyr
225                 230                 235                 240

Phe Thr Ala Thr Phe Pro Tyr Leu Met Leu Val Ile Leu Leu Ile Arg
                245                 250                 255

Gly Val Thr Leu Pro Gly Ala Tyr Gln Gly Ile Ile Tyr Tyr Leu Lys
            260                 265                 270

Pro Asp Leu Phe Arg Leu Lys Asp Pro Gln Val Trp Met Asp Ala Gly
        275                 280                 285

Thr Gln Ile Phe Phe Ser Phe Ala Ile Cys Gln Gly Cys Leu Thr Ala
    290                 295                 300

Leu Gly Ser Tyr Asn Lys Tyr His Asn Asn Cys Tyr Lys Asp Cys Ile
305                 310                 315                 320

Ala Leu Cys Phe Leu Asn Ser Ala Thr Ser Phe Val Ala Gly Phe Val
                325                 330                 335

Val Phe Ser Ile Leu Gly Phe Met Ser Gln Glu Gln Gly Val Pro Ile
            340                 345                 350

Ser Glu Val Ala Glu Ser Gly Pro Gly Leu Ala Phe Ile Ala Phe Pro
        355                 360                 365

Lys Ala Val Thr Met Met Pro Leu Ser Gln Leu Trp Ser Cys Leu Phe
    370                 375                 380

Phe Ile Met Leu Ile Phe Leu Gly Leu Asp Ser Gln Phe Val Cys Val
385                 390                 395                 400

Glu Cys Leu Val Thr Ala Ser Ile Asp Met Phe Pro Arg Gln Leu Arg
                405                 410                 415

Lys Ser Gly Arg Arg Glu Leu Leu Ile Leu Thr Ile Ala Val Met Cys
            420                 425                 430

Tyr Leu Ile Gly Leu Phe Leu Val Thr Glu Gly Gly Met Tyr Ile Phe
        435                 440                 445

Gln Leu Phe Asp Tyr Tyr Ala Ser Ser Gly Ile Cys Leu Leu Phe Leu
    450                 455                 460

Ser Leu Phe Glu Val Val Cys Ile Ser Trp Val Tyr Gly Ala Asp Arg
465                 470                 475                 480

Phe Tyr Asp Asn Ile Glu Asp Met Ile Gly Tyr Arg Pro Trp Pro Leu
                485                 490                 495

Val Lys Ile Ser Trp Leu Phe Leu Thr Pro Gly Leu Cys Leu Ala Thr
            500                 505                 510

Phe Leu Phe Ser Leu Ser Lys Tyr Thr Pro Leu Lys Tyr Asn Asn Val
        515                 520                 525

Tyr Val Tyr Pro Pro Trp Gly Tyr Ser Ile Gly Trp Phe Leu Ala Leu
    530                 535                 540

Ser Ser Met Val Cys Val Pro Leu Phe Val Val Ile Thr Leu Leu Lys
545                 550                 555                 560

Thr Arg Gly Pro Phe Arg Lys Arg Leu Arg His Val Ile Thr Pro Asp
                565                 570                 575

Ser Ser Leu Pro Gln Pro Lys Gln His Pro Cys Leu Asp Gly Ser Ala
            580                 585                 590
```

-continued

```
Gly Arg Asn Phe Gly Pro Ser Pro Thr Arg Glu Gly Leu Ile Ala Gly
        595                 600                 605

Glu Lys Glu Thr His Leu
    610
```

<210> SEQ ID NO 63
<211> LENGTH: 3410
<212> TYPE: DNA
<213> ORGANISM: Homo sapiens

<400> SEQUENCE: 63

```
gtaccggttc ggaattcccg ggtcgaccca cgcgtccgga aggctacaga gagagccagg     60

ttttggtgcc atgcacacag ggaaacttag agttcagaga gggggtgtga tttgcctgac    120

ctcacacagc aagttagaga cccagctcca cgactcattg tcttgctgcc cagagctgct    180

ggctcccctg tttactctga gctgatcgat caccttagca cacagctggc taggagagaa    240

ccatgcagtc acttcggcca cacctgcccg ttgacccttg ctacctcggc aggctttgat    300

cccttctgac ctggaggcca gaggctaggc tgaggtcact cagcagacat caaggacctg    360

ggcagatggg ccggctggga tggtggcgag ctgtacagat aaaaagggac atgaaaatga    420

aaagcccgag cctgagtttt catcacggtt ccactcctga gtggtcttgg gtgaatcact    480

tcatctgcca aggcctggat ttcctcatct gcaaactcag aaaactaagg ctttggccct    540

cgtcatcctg cccacccagc ggggcttccc aacccaccac acagccatgg acgggaaggt    600

ggcagtgcaa gagcgtgggc ctcctgcggt ctcctgggtc cccgaggagg gagagaagtt    660

ggaccaggaa gacgaggacc aggtgaagga tcggggccaa tggaccaaca agatggagtt    720

tgtgctgtca gtggccgggg agatcattgg gctgggcaat gtctggaggt ttccctatct    780

ctgctacaaa aacggaggtg gagccttctt catcccctac ttcatcttct tctttgtctg    840

cggcatcccg gtgttcttcc tggaggtggc gttgggccaa tacaccagcc aagggagtgt    900

cacagcctgg aggaagatct gcccccctctt ccagggcatt ggtctggcat ctgtggtcat    960

cgagtcatat ttgaatgtct actacatcat catccttgcc tgggctctct tctacctgtt   1020

cagctccttc acttctgagc tgccctggac gacctgcaac aacttttgga acacagagca   1080

ttgcacggac tttctgaacc actcaggagc cggcacagtg accccatttg agaattttac   1140

ctcacctgtc atggaattct gggagagacg agttctgggc atcacctcgg gcatccatga   1200

cctgggctcc ctgcgctggg agctggccct gtgcctcctg ctcgcctggg tcatctgcta   1260

tttctgcatc tggaaggggg tcaagtccac aggcaaggtg gtttatttca cagccacgtt   1320

tccgtacctg atgcttgtca ttttgctgat cagaggtgtc acccttcccg gagcctacca   1380

gggcatcatc tactacttga agccagattt gttccgcctc aaggaccctc aggtgtggat   1440

ggatgcgggc acccagatct tcttctcctt tgccatctgc caggggtgcc tgacagccct   1500

gggcagctac aacaagtatc acaacaactg ctacaaggac tgcatcgccc tctgcttcct   1560

gaacagtgcc accagctttg tggctgggtt tgttgtcttc tccatcctgg gcttcatgtc   1620

ccaagagcaa ggggtgccca tttctgaagt ggccgagtca ggtcctgggc tggccttcat   1680

cgccttcccc aaggctgtga ctatgatgcc cttatcccag ctgtggtcct gcctgttctt   1740

tatcatgctc atattcctag ggctggacag ccagtttgtc tgtgtggagt gcctggtgac   1800

agcctccata gacatgttcc ccaggcagct ccggaagagc gggcggcgcg agctcctcat   1860

cctcaccatc gccgtcatgt gctacctgat agggcttttc ctggtcaccg agggcgggat   1920

gtacatcttc cagctgtttg actactatgc ttccagtggc atatgcctgc tgttcctgtc   1980
```

```
attgtttgaa gtggtctgca taagctgggt gtatggggcg gaccgtttct atgacaacat   2040

tgaggacatg attggctacc ggccatggcc cctggtgaag atctcctggc tcttcctgac   2100

ccctggactt tgcctggcca ctttcctctt ctccttgagc aagtacaccc ccctcaagta   2160

caacaacgtc tatgtgtacc cgccctgggg atactccatt ggctggttcc tggctctgtc   2220

ctccatggtc tgtgtcccac tcttcgtcgt catcaccctc ctgaagactc ggggtccttt   2280

caggaagcgt ctgcgtcacg tcatcacccc tgactccagt ctgccacagc ccaagcaaca   2340

tccctgcttg gatggcagtg ctggccggaa ctttgggccc tccccaacaa gggaaggact   2400

gatagccggg gagaaggaga cccatttgta gggtgtggcc agagcgaggc ggctcctaag   2460

ccgggaacct aggtcagggc caccctccat tctcagcgga cagcctctgc ctctgtctcc   2520

tgccacaatc ctgctgggaa ctctggagag ccacaggcac ccccagctgg aggccagact   2580

cctctcttgt gctagctgga gcagctcctt cccctttgct gataacacca ccactgggac   2640

gtgccatgtt gggacgccac tccctgtgga aggcaccatc gtttttataa agggggggtct   2700

ttttggaggc cgccatctga ttgcaacacc tcgagttatg aggattccac tgtggggatg   2760

cctcttgtta gagcgtactg catttgtaca cggggagagg agctataatt ggaacgcaca   2820

ctgccgtcca atgtggagag cctgatggga caataccctg ttggaagtga caactgaaca   2880

cactgtgttg gatcggaggt tccgttaggg gatccttcct taggcttaac gacagaggca   2940

agcctttgca tgccgtcagt ctggagtttc ctccgagtct ctcatggcat ctccagctcc   3000

tgccctagtt ccgcactgtt cttgcagtgt ttcatcaact cctggagcat tggaatggaa   3060

ggggcttggg agatgattcc tagacttcac aaacactcgg catgcctccc tgcactgtcc   3120

gttcctctgc ccaaggccga tattgctaac tgatcacaga ttctttccca cctcacaatc   3180

ctccgaatgt gctccaggcg acaccatttg ccatcctgct tctaacgcaa acccctgact   3240

tcatggatga ggaacctgga gaccaaagag acaaagggac tttttcaagt tcacatgggg   3300

accccccttct tgggggccag agatatgact aaaaccttat ctccttgtgc tcaggccagt   3360

gtcttcccat taaccccctg ccttagttaa caagtgtgta tggattgcca             3410


<210> SEQ ID NO 64
<211> LENGTH: 496
<212> TYPE: PRT
<213> ORGANISM: Homo sapiens

<400> SEQUENCE: 64

Met Gly Thr Gln Lys Val Thr Pro Ala Leu Ile Phe Ala Ile Thr Val
1               5                   10                  15

Ala Thr Ile Gly Ser Phe Gln Phe Gly Tyr Asn Thr Gly Val Ile Asn
            20                  25                  30

Ala Pro Glu Lys Ile Ile Lys Glu Phe Ile Asn Lys Thr Leu Thr Asp
        35                  40                  45

Lys Gly Asn Ala Pro Pro Ser Glu Val Leu Leu Thr Ser Leu Trp Ser
    50                  55                  60

Leu Ser Val Ala Ile Phe Ser Val Gly Gly Met Ile Gly Ser Phe Ser
65                  70                  75                  80

Val Gly Leu Phe Val Asn Arg Phe Gly Arg Arg Asn Ser Met Leu Ile
                85                  90                  95

Val Asn Leu Leu Ala Val Thr Gly Gly Cys Phe Met Gly Leu Cys Lys
            100                 105                 110

Val Ala Lys Ser Val Glu Met Leu Ile Leu Gly Arg Leu Val Ile Gly
        115                 120                 125
```

```
Leu Phe Cys Gly Leu Cys Thr Gly Phe Val Pro Met Tyr Ile Gly Glu
    130                 135                 140

Ile Ser Pro Thr Ala Leu Arg Gly Ala Phe Gly Thr Leu Asn Gln Leu
145                 150                 155                 160

Gly Ile Val Val Gly Ile Leu Val Ala Gln Ile Phe Gly Leu Glu Phe
                165                 170                 175

Ile Leu Gly Ser Glu Glu Leu Trp Pro Leu Leu Leu Gly Phe Thr Ile
            180                 185                 190

Leu Pro Ala Ile Leu Gln Ser Ala Ala Leu Pro Phe Cys Pro Glu Ser
        195                 200                 205

Pro Arg Phe Leu Leu Ile Asn Arg Lys Glu Glu Glu Asn Ala Lys Gln
    210                 215                 220

Ile Leu Gln Arg Leu Trp Gly Thr Gln Asp Val Ser Gln Asp Ile Gln
225                 230                 235                 240

Glu Met Lys Asp Glu Ser Ala Arg Met Ser Gln Glu Lys Gln Val Thr
                245                 250                 255

Val Leu Glu Leu Phe Arg Val Ser Ser Tyr Arg Gln Pro Ile Ile Ile
            260                 265                 270

Ser Ile Val Leu Gln Leu Ser Gln Gln Leu Ser Gly Ile Asn Ala Val
        275                 280                 285

Phe Tyr Tyr Ser Thr Gly Ile Phe Lys Asp Ala Gly Val Gln Glu Pro
    290                 295                 300

Ile Tyr Ala Thr Ile Gly Ala Gly Val Val Asn Thr Ile Phe Thr Val
305                 310                 315                 320

Val Ser Leu Phe Leu Val Glu Arg Ala Gly Arg Arg Thr Leu His Met
                325                 330                 335

Ile Gly Leu Gly Gly Met Ala Phe Cys Ser Thr Leu Met Thr Val Ser
            340                 345                 350

Leu Leu Leu Lys Asp Asn Tyr Asn Gly Met Ser Phe Val Cys Ile Gly
        355                 360                 365

Ala Ile Leu Val Phe Val Ala Phe Phe Glu Ile Gly Pro Gly Pro Ile
    370                 375                 380

Pro Trp Phe Ile Val Ala Glu Leu Phe Ser Gln Gly Pro Arg Pro Ala
385                 390                 395                 400

Ala Met Ala Val Ala Gly Cys Ser Asn Trp Thr Ser Asn Phe Leu Val
                405                 410                 415

Gly Leu Leu Phe Pro Ser Ala Ala His Tyr Leu Gly Ala Tyr Val Phe
            420                 425                 430

Ile Ile Phe Thr Gly Phe Leu Ile Thr Phe Leu Ala Phe Thr Phe Phe
        435                 440                 445

Lys Val Pro Glu Thr Arg Gly Arg Thr Phe Glu Asp Ile Thr Arg Ala
    450                 455                 460

Phe Glu Gly Gln Ala His Gly Ala Asp Arg Ser Gly Lys Asp Gly Val
465                 470                 475                 480

Met Glu Met Asn Ser Ile Glu Pro Ala Lys Glu Thr Thr Thr Asn Val
                485                 490                 495
```

<210> SEQ ID NO 65
<211> LENGTH: 3915
<212> TYPE: DNA
<213> ORGANISM: Homo sapiens

<400> SEQUENCE: 65

```
gtggggtggg gtggggctgg gggcttgtcg ccctttcagg ctccaccctt tgcggagatt      60
```

-continued

```
ataaatagtc atgatcccag cgagacccag agatgcctgt aatggtgaga ctttggatcc    120
ttcctgagga cgtggagaaa actttctgct gagaaggaca ttttgaaggt tttgttggct    180
gaaaaagctg tttctggaat caccccctaga tctttcttga agacttgaat tagattacag    240
cgatggggac acagaaggtc accccagctc tgatatttgc catcacagtt gctacaatcg    300
gctctttcca atttggctac aacactgggg tcatcaatgc tcctgagaag atcataaagg    360
aatttatcaa taaaactttg acggacaagg gaaatgcccc accctctgag gtgctgctca    420
cgtctctctg gtccttgtct gtggccatat tttccgtcgg gggtatgatc ggctcctttt    480
ccgtcggact cttcgtcaac cgctttggca ggcgcaattc aatgctgatt gtcaacctgt    540
tggctgtcac tggtggctgc tttatgggac tgtgtaaagt agctaagtcg gttgaaatgc    600
tgatcctggg tcgcttggtt attggcctct tctgcggact ctgcacaggt tttgtgccca    660
tgtacattgg agagatctcg cctactgccc tgcggggtgc ctttggcact ctcaaccagc    720
tgggcatcgt tgttggaatt ctggtggccc agatctttgg tctggaattc atccttgggt    780
ctgaagagct atggccgctg ctactgggtt ttaccatcct tcctgctatc ctacaaagtg    840
cagcccttcc attttgccct gaaagtccca gatttttgct cattaacaga aaagaagagg    900
agaatgctaa gcagatcctc cagcggttgt ggggcaccca ggatgtatcc caagacatcc    960
aggagatgaa agatgagagt gcaaggatgt cacaagaaaa gcaagtcacc gtgctagagc   1020
tctttagagt gtccagctac cgacagccca tcatcatttc cattgtgctc cagctctctc   1080
agcagctctc tgggatcaat gctgtgttct attactcaac aggaatcttc aaggatgcag   1140
gtgttcaaga gcccatctat gccaccatcg gcgcgggtgt ggttaatact atcttcactg   1200
tagtttctct atttctggtg gaaagggcag gaagaaggac tctgcatatg ataggccttg   1260
gagggatggc tttttgttcc acgctcatga ctgtttcttt gttattaaag gataactata   1320
atgggatgag ctttgtctgt attggggcta tcttggtctt tgtagccttc tttgaaattg   1380
gaccaggccc cattccctgg tttattgtgg ccgaactctt cagccagggc ccccgcccag   1440
ctgcgatggc agtggccggc tgctccaact ggacctccaa cttcctagtc ggattgctct   1500
tcccctccgc tgctcactat ttaggagcct acgtttttat tatcttcacc ggcttcctca   1560
ttaccttctt ggcttttacc ttcttcaaag tccctgagac ccgtggcagg acttttgagg   1620
atatcacacg ggcctttgaa gggcaggcac acggtgcaga tagatctgga aaggacggcg   1680
tcatggagat gaacagcatc gagcctgcta aggagaccac caccaatgtc taagtcgtgc   1740
ctccttccac ctccctcccg gcatgggaaa gccacctctc cctcaacaag ggagagacct   1800
catcaggatg aacccaggac gcttctgaat gctgctactt aattcctttc tcatcccacg   1860
cactccatga gcaccccaag gctgcggttt gttggatctt caatggcttt ttaaatttta   1920
tttcctggac atcctcttct gcttaggaga gaccgagtga acctaccttc atttcaggag   1980
ggattggccg cttggcacat gacaactttg ccagcttttc ctcccttggg ttctgatatt   2040
gccgcactag gggatatagg agaggaaaag taaggtgcag ttccccccaac ctcagactta   2100
ccaggaagca gatacatatg agtgtggaag ccggagggtg tttatgtaag agcaccttcc   2160
tcacttccat acagctctac gtggcaaatt aacttgagtt ttatttattt tatcctctgg   2220
tttaattaca taattttttt ttttttactt taagtttcag gatacatgtg ccgaatgtgc   2280
aggtttgtta catagtata tatatgccat gatggaaata tttatttttt taagcgtaat    2340
tttgccaaat aataaaaaca gaaggaaatt gagattagag ggaggtgttt aaagagaggt   2400
tatagagtag aagatttgat gctggagagg ttaaggtgca ataagaattt agggagaaat   2460
```

-continued

```
gttgttcatt attggagggt aaatgatgtg gtgcctgagg tctgtacgtt acctcttaac   2520
aatttctgtc cttcagatgg aaactcttta acttctcgta aaagtcatat acctatataa   2580
taaagctact gatttccttg gagcttttt ctttaagata atagtttaca tgtagtagta    2640
cttgaaatct aggattatta actaatatgg gcattgtagt taatgatggt tgatgggttc   2700
taattttgga tggagtccag ggaagagaaa gtgatttcta gaaagcctgt tcccctcact   2760
ggatgaaata actccttctt gtagtagtct cattactttt gaagtaatcc cgccacctat   2820
ctcgtgggag agccatccaa ataagaaacc taaaataatt ggttcttggt agagattcat   2880
tatttttcca ctttgttctt taggagattt taggtgttga ttttctgttg tattttaact   2940
catacctta aaggaattcc ccaaagaatg tttatagcaa acttggaatt tgtaacctca    3000
gctctgggag aggatttttt tctgagcgat tattatctaa agtgtgttgt tgctttaggc   3060
tcacggcacg cttgcgtatg tctgttacca tgtcactgtg gtcctatgcc gaatgccctc   3120
aggggacttg aatctttcca ataaaccagg tttagacagt atgagtcaat gtgcagtgta   3180
gcccacactt gagaggatga atgtatgtgc actgtcactt tgctctgggt ggaagtacgt   3240
tattgttgac ttattttctc tgtgtttgtt cctacagccc ctttttcata tgttgctcag   3300
tctccctttc ccttcttggt gcttacacat ctcagaccct ttagccaaac ccttgtcagt   3360
gacagtattt tggttcttag ttctcactgt tccctctgct cctggagcct ttgaataaaa   3420
atgcacgtag ctgaggccgg atgcggtggc tcacgcctgt aatcccagca ctttgggagg   3480
cctaggcggg cggtcagggg ttcgagacca gtctggccaa catcgtgaaa ccctgtctct   3540
actaaaaatg caaaaattag ccgggcgtgg tggcgggcgc ctgtaatccc agctacttgg   3600
gaagctgagg cgggagaatc atgtgaaccc gggacgcagg ggttgcagtg agcggagatc   3660
gcatcattgc actctagcct gggccacagg gcgagactcc gtctcaaaaa aaaaaaaatg   3720
cacatagcta tcgagtgtgc tttagcttga aaaggtgacc ttgcaacttc atgtcaactt   3780
tctggctcct caaacagtag gttggcagta aggcagggtc ccatttctca ctgagaagat   3840
tgtgaatatt tccatatgga ttttctattg ttactctggt tctttgtttt aaaataaaaa   3900
ttctgaatgt acacg                                                    3915
```

<210> SEQ ID NO 66
<211> LENGTH: 2862
<212> TYPE: DNA
<213> ORGANISM: Homo sapiens

<400> SEQUENCE: 66

```
gccgagagcg ggatccgcgc tccctcggtc cttcctccct cccctcttgc ggcctcccgc     60
tgtcatctgg agccgctcct gccgccccct ggcggcgacc gcgggaaggg ccggccccca    120
tccgcacccc tgaccccgga ggtcaacaac gggatggtcc ctgggtccca ggggaagaga    180
catcacccag taggagggag tacggtctag acagaggcca cgagggcggg agggggcgag    240
agtggagagt ggcccagctg gccagggtcg tctaagtgag aggaaaaggg agagggcggt    300
tgagaccagg ccctgaattc cgcgttcatc ttatcctgag gtctgtgggg acctgttgaa    360
ggactggggc aggggacgga cgcgggcatc cttccatttg gaacagccat tccggcagca    420
tcaggatggg gcggaggcaa agcggggagt gggcgaggca agtggtgctg taaacctgtg    480
cgagaagggg gcggtgactc taagggcagg aaggagccct ggtcacacac acactcccac    540
gcaaggtatt cagtgccgag tgtggccttg gtgctaggat tcaaagagga aaggaagaaa    600
actttccatt ctaaaagaaa ctccacgtga ggcgaagaag atgaaatata gtcagaaaac    660
```

```
cataccagta ggtggtaggt aaatgcagaa gtatttaaga gctcatacag gagtacctgc    720
ctcaggacag ggaatctgag atgctctgca gagctggatc ttaaagaacg gattaagttg    780
ataaatgatg catacgacat cctatagaag actgtcacca ccccacctca ctgatcagcc    840
ctctgcctac agccacaccc acagaacatt cagccatttc tcctgtggtt cccagcctgc    900
agcacagcgt ctgcacgtgg tgagggctcc caaatctctg aggaatgaat ggctcactgc    960
tgagagcaac cttctgggag ttcagggcat gtggaactgg aataagagca acgtgtgaac   1020
agattacagg aaggcaatgc aggacagctg gaccctttgg ggggaaactt atggggaaca   1080
cagttttctt acttataagc actgagattg cctgagaggg gagagatgat gcagagtgtc   1140
ccaaatgtat ttgacgtgga atccttttac cagcgaaaca tctcttgggc ctagagttct   1200
gaaaattgca ctttgaaaaa cactgctctc agctcttaca aacctcgtgt tttcatccta   1260
actgtgcttc agagaattgt gtcccagcag gaaaggaaac cccgtataa ttccctacgt    1320
tgctagcatt tggaagtggg atgaaaatgg acctacattc aaacccctaa tttcaagctc   1380
tgaaggaggt accaggatcc atcacgatgc ttgtaaaatt gttcctttca ttttcctggt   1440
tgtaaactta tgcagactgt aaagtcaagg caagcctgtg cccagcaaat aataagaaaa   1500
taagggaggc atggtaaaca aaacaaaaca ctttgagagt tggtcaactt gctgttattt   1560
tgagctgttt ctaaaaatct cagggtagat tccctcccct gcttgcctcc ttaacccagt   1620
cctttttctt cctcctccag gaactctgga atgctgacct acagtctgag ttcctgtgcc   1680
cttgcctggg gctgactctc tacttgacct gtaacccaca actgggcaag agaaaattct   1740
gcagccacag ctctgaggac atgagcaaaa tggtttccag acggaatgtc aaggattccc   1800
atgaagtgtc agggagtctt caggccacac ttcaggttat ctccttctct ttcccttttc   1860
tgcttcacac ttgctctcat cctctttctc accccacatc tggtcagagg agataggaag   1920
gttcttgtta cctggtacaa gacaactttt ggaatcccag atattcagat tatttcccct   1980
tttcctcttt gcaaatgata atactcacag ccaagaggca tcacccggat ccgaggctgc   2040
ttctccttag gacatgcaga cagaaggaga aggcggggct ggcagcctcc agtccacagc   2100
ctccctttct tcttccggcg atgattaact aggcctagac aatggagatc tacggcatac   2160
gcccagggcc tcctcttctc aagcatggct gatcagtcac tttcccgtct atccttcatt   2220
tattgaagcc aactatgaac gactaaagga aggatgagaa aagtcaccca aagtcaaagg   2280
ggacagcgtg ggagactgtt ctagacagaa ggaaacacct ttgcaaagac cctgaggaag   2340
gcaggggact ctccaggagc agaagggctg tgtggcttca gagtccacaa aagagagcag   2400
atacaggaca ctggctagag caggccctgg agcccgctgc tgtcctggag gccttgggga   2460
ggcccagtgt tcccagggtg gaagaagtag gggacagctt gacgtagtgg ctgttgatca   2520
gctgatatgg aagtatgtca ttttattaac aattgagaaa ggagtgctgt gcaattccat   2580
tcaatgccag tgatgcttat ggccgttttt atgagttctg tcattttcaa atgagcaaga   2640
ggaagcctct aaggggggttt aagcagggac tgacgtaatc agatctgtgt ttttccaaag   2700
ggagagggag aaaaagaaca tttcttattt ttcaaaaaag gtaatgcaaa agcatcattc   2760
cacaattctc ttgtaatgaa aaaaataaat gcaaacttaa gcaaatccat cattctgaaa   2820
gaaaaaaaaa aaaaaaaaaa aaaaaaaaaa aaaaaaaaaa aa                       2862
```

<210> SEQ ID NO 67
<211> LENGTH: 426
<212> TYPE: PRT
<213> ORGANISM: Homo sapiens

<400> SEQUENCE: 67

Met Pro Leu Leu Trp Leu Arg Gly Phe Leu Leu Ala Ser Cys Trp Ile
1 5 10 15

Ile Val Arg Ser Ser Pro Thr Pro Gly Ser Glu Gly His Ser Ala Ala
20 25 30

Pro Asp Cys Pro Ser Cys Ala Leu Ala Ala Leu Pro Lys Asp Val Pro
35 40 45

Asn Ser Gln Pro Glu Met Val Glu Ala Val Lys Lys His Ile Leu Asn
50 55 60

Met Leu His Leu Lys Lys Arg Pro Asp Val Thr Gln Pro Val Pro Lys
65 70 75 80

Ala Ala Leu Leu Asn Ala Ile Arg Lys Leu His Val Gly Lys Val Gly
85 90 95

Glu Asn Gly Tyr Val Glu Ile Glu Asp Asp Ile Gly Arg Arg Ala Glu
100 105 110

Met Asn Glu Leu Met Glu Gln Thr Ser Glu Ile Ile Thr Phe Ala Glu
115 120 125

Ser Gly Thr Ala Arg Lys Thr Leu His Phe Glu Ile Ser Lys Glu Gly
130 135 140

Ser Asp Leu Ser Val Val Glu Arg Ala Glu Val Trp Leu Phe Leu Lys
145 150 155 160

Val Pro Lys Ala Asn Arg Thr Arg Thr Lys Val Thr Ile Arg Leu Phe
165 170 175

Gln Gln Gln Lys His Pro Gln Gly Ser Leu Asp Thr Gly Glu Glu Ala
180 185 190

Glu Glu Val Gly Leu Lys Gly Glu Arg Ser Glu Leu Leu Leu Ser Glu
195 200 205

Lys Val Val Asp Ala Arg Lys Ser Thr Trp His Val Phe Pro Val Ser
210 215 220

Ser Ser Ile Gln Arg Leu Leu Asp Gln Gly Lys Ser Ser Leu Asp Val
225 230 235 240

Arg Ile Ala Cys Glu Gln Cys Gln Glu Ser Gly Ala Ser Leu Val Leu
245 250 255

Leu Gly Lys Lys Lys Lys Lys Glu Glu Glu Gly Glu Gly Lys Lys Lys
260 265 270

Gly Gly Gly Glu Gly Gly Ala Gly Ala Asp Glu Glu Lys Glu Gln Ser
275 280 285

His Arg Pro Phe Leu Met Leu Gln Ala Arg Gln Ser Glu Asp His Pro
290 295 300

His Arg Arg Arg Arg Arg Gly Leu Glu Cys Asp Gly Lys Val Asn Ile
305 310 315 320

Cys Cys Lys Lys Gln Phe Phe Val Ser Phe Lys Asp Ile Gly Trp Asn
325 330 335

Asp Trp Ile Ile Ala Pro Ser Gly Tyr His Ala Asn Tyr Cys Glu Gly
340 345 350

Glu Cys Pro Ser His Ile Ala Gly Thr Ser Gly Ser Ser Leu Ser Phe
355 360 365

His Ser Thr Val Ile Asn His Tyr Arg Met Arg Gly His Ser Pro Phe
370 375 380

Ala Asn Leu Lys Ser Cys Cys Val Pro Thr Lys Leu Arg Pro Met Ser
385 390 395 400

Met Leu Tyr Tyr Asp Asp Gly Gln Asn Ile Ile Lys Lys Asp Ile Gln
405 410 415

```
Asn Met Ile Val Glu Glu Cys Gly Cys Ser
            420                 425
```

<210> SEQ ID NO 68
<211> LENGTH: 1840
<212> TYPE: DNA
<213> ORGANISM: Homo sapiens

<400> SEQUENCE: 68

```
tccacacaca caaaaaacct gcgcgtgagg ggggaggaaa agcagggcct ttaaaaaggc     60
aatcacaaca actttgctg ccaggatgcc cttgctttgg ctgagaggat ttctgttggc    120
aagttgctgg attatagtga ggagttcccc caccccagga tccgaggggc acagcgcggc    180
ccccgactgt ccgtcctgtg cgctggccgc cctcccaaag gatgtaccca actctcagcc    240
agagatggtg gaggccgtca agaagcacat tttaaacatg ctgcacttga agaagagacc    300
cgatgtcacc cagccggtac ccaaggcggc gcttctgaac gcgatcagaa agcttcatgt    360
gggcaaagtc ggggagaacg ggtatgtgga gatagaggat gacattggaa ggagggcaga    420
aatgaatgaa cttatggagc agacctcgga gatcatcacg tttgccgagt caggaacagc    480
caggaagacg ctgcacttcg agatttccaa ggaaggcagt gacctgtcag tggtggagcg    540
tgcagaagtc tggctcttcc taaaagtccc caaggccaac aggaccagga ccaaagtcac    600
catccgcctc ttccagcagc agaagcaccc gcagggcagc ttggacacag gggaagaggc    660
cgaggaagtg ggcttaaagg gggagaggag tgaactgttg ctctctgaaa aagtagtaga    720
cgctcggaag agcacctggc atgtcttccc tgtctccagc agcatccagc ggttgctgga    780
ccagggcaag agctccctgg acgttcggat tgcctgtgag cagtgccagg agagtggcgc    840
cagcttggtt ctcctgggca agaagaagaa gaaagaagag gagggggaag ggaaaaagaa    900
gggcggaggt gaaggtgggg caggagcaga tgaggaaaag gagcagtcgc acagaccttt    960
cctcatgctg caggcccggc agtctgaaga ccaccctcat cgccggcgtc ggcggggctt   1020
ggagtgtgat ggcaaggtca acatctgctg taagaaacag ttctttgtca gtttcaagga   1080
catcggctgg aatgactgga tcattgctcc ctctggctat catgccaact actgcgaggg   1140
tgagtgcccg agccatatag caggcacgtc cgggtcctca ctgtccttcc actcaacagt   1200
catcaaccac taccgcatgc ggggccatag ccccttttgcc aacctcaaat cgtgctgtgt   1260
gcccaccaag ctgagaccca tgtccatgtt gtactatgat gatggtcaaa acatcatcaa   1320
aaaggacatt cagaacatga tcgtggagga gtgtgggtgc tcatagagtt gcccagccca   1380
gggggaaagg gagcaagagt tgtccagaga agacagtggc aaaatgaaga aatttttaag   1440
gtttctgagt taaccagaaa aatagaaatt aaaaacaaaa caaaacaaaa aaaaaaacaa   1500
aaaaaaacaa aagtaaatta aaaacaaacc tgatgaaaca gatgaaacag atgaaggaag   1560
atgtggaaat cttagcctgc cttagccagg gctcagagat gaagcagtga agagacagat   1620
tgggagggaa agggagaatg gtgtaccctt tatttcttct gaaatcacac tgatgacatc   1680
agttgtttaa acggggtatt gtcctttccc cccttgaggt tcccttgtga gcttgaatca   1740
accaatctga tctgcagtag tgtggactag aacaacccaa atagcatcta gaaagccatg   1800
agtttgaaag ggcccatcac aggcactttc ctagcctaat                         1840
```

<210> SEQ ID NO 69
<211> LENGTH: 478
<212> TYPE: PRT
<213> ORGANISM: Homo sapiens

<400> SEQUENCE: 69

```
Met Gly Leu Ala Glu Tyr Phe Gly Phe Asp Asp His Asp Thr Asp Leu
1               5                   10                  15

Arg Thr Glu Leu Val Ala Gly Leu Thr Thr Phe Leu Ala Met Ser Tyr
            20                  25                  30

Ile Val Leu Val Asn Pro Val Val Met Thr Gln Arg Thr Thr Ala Gly
        35                  40                  45

Glu Val Val Lys Pro Gly Ile Ala Leu Ala Asn Tyr Ser His Asp Gln
    50                  55                  60

Thr Val Gln Met Leu Ala Val Val Thr Leu Leu Ala Ser Gly Val Ala
65                  70                  75                  80

Met Leu Val Met Ala Phe Tyr Ala Asn Arg Pro Phe Ala Leu Ala Pro
                85                  90                  95

Gly Leu Gly Leu Asn Ala Phe Phe Ala Phe Thr Val Val Gly Thr Leu
            100                 105                 110

Gly Val Pro Trp Gln Thr Ala Leu Ala Ala Val Phe Thr Glu Gly Leu
        115                 120                 125

Leu Phe Ile Val Leu Thr Ala Val Gly Ala Arg Glu Tyr Val Ile Thr
    130                 135                 140

Leu Phe Pro Glu Pro Val Lys Leu Ala Val Gly Thr Gly Ile Gly Leu
145                 150                 155                 160

Tyr Leu Ala Ile Ile Gly Leu Glu Ala Met Gly Ile Val Val Gly Asp
                165                 170                 175

Ala Gly Thr Ile Leu Ala Leu Gly Asn Leu Ala Gln Asn Pro Val Ala
            180                 185                 190

Val Val Ser Ile Leu Gly Leu Phe Phe Thr Ile Ala Leu His Ala Arg
        195                 200                 205

Gly Val Thr Gly Ser Ile Val Leu Gly Ile Ile Ala Thr Ala Ala Thr
    210                 215                 220

Gly Gly Val Leu Thr Phe Ala Gly Val Val Asp Pro Gly Val Leu Ile
225                 230                 235                 240

Gly Asp Phe Val Arg Thr Gly Gly Ile Ala Thr Gln Arg Leu Pro His
                245                 250                 255

Ala Gln Tyr Asp Ile Thr Pro Leu Val Gly Ala Phe Leu Ala Gly Phe
            260                 265                 270

Gln Asp Ile Asp Ala Phe Ser Phe Ala Leu Ile Val Phe Thr Phe Phe
        275                 280                 285

Phe Val Asp Phe Phe Asp Thr Ala Gly Thr Leu Val Gly Val Gly Gln
    290                 295                 300

Ala Gly Gly Phe Leu Asn Thr Asp Gly Asn Leu Pro Asp Ala Asp Glu
305                 310                 315                 320

Pro Leu Met Ala Asp Ala Ile Gly Thr Thr Phe Gly Ala Ile Ile Gly
                325                 330                 335

Thr Ser Thr Val Thr Thr Tyr Ile Glu Ser Ala Thr Gly Val Glu Glu
            340                 345                 350

Gly Gly Arg Thr Gly Met Val Ala Leu Val Val Ala Val Leu Phe Phe
        355                 360                 365

Leu Ser Leu Leu Val Val Pro Leu Ala Ala Ala Ile Pro Gln Tyr Ala
    370                 375                 380

Ser His Ile Ala Leu Val Val Val Ala Leu Leu Met Leu Ala Asn Val
385                 390                 395                 400

Thr Ala Ile Asp Trp Asp Asp Ile Thr His Ser Ile Pro Ala Gly Leu
                405                 410                 415

Thr Ile Ile Val Met Pro Phe Thr Tyr Ser Ile Ala Tyr Gly Ile Ala
```

-continued

```
        420                 425                 430

Ala Gly Ile Val Ser Tyr Pro Val Val Lys Val Ala Thr Gly Asp Ala
        435                 440                 445

Asp Glu Val Ala Ile Gly Gln Trp Leu Leu Ala Ala Ala Phe Ile Val
    450                 455                 460

Tyr Phe Tyr Val Arg Thr Ser Gly Val Leu Ala Ala Ala Val
465                 470                 475
```

NUCLEIC ACIDS AND POLYPEPTIDES USEFUL FOR DIAGNOSING COMPLICATIONS OF PREGNANCY

CROSS-REFERENCE TO RELATED APPLICATIONS

This application claims the benefit of the filing date of U.S. provisional application No. 60/636,275, filed Dec. 15, 2004, herein incorporated by reference.

STATEMENT AS TO FEDERALLY SPONSORED RESEARCH

This research was funded, in part, by NIH Grant R03 DK064255-02. The U.S. government has certain rights to the invention.

FIELD OF THE INVENTION

In general, this invention relates to the detection and treatment of subjects having a pregnancy related hypertensive disorder.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the $20^{th}$ week of pregnancy and are usually detected by routine measuring of the woman's blood pressure and urine. However, these monitoring methods are ineffective for diagnosis of the syndrome at an early stage, which could reduce the risk to the subject or developing fetus, if an effective treatment were available.

Currently there are no known cures for pre-eclampsia. Pre-eclampsia can vary in severity from mild to life-threatening. A mild form of pre-eclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby the pregnancy is terminated and the baby is delivered pre-term.

The proper development of the fetus and the placenta is mediated by several growth factors or angiogenic factors. Careful regulation of angiogenic and mitogenic signaling pathways is critical for maintaining appropriate proliferation, migration, and angiogenesis by trophoblast cells in the developing placenta. While several of these factors, such as VEGF and PlGF, have been identified, there are still many proteins for which a role in the pathogenesis of pre-eclampsia or eclampsia has not yet been identified.

There is a need for methods of accurately diagnosing subjects at risk for or having pregnancy related hypertensive disorders, such as pre-eclampsia or eclampsia, particularly before the onset of the most severe symptoms. A treatment that would save maternal and fetal lives and prevent premature deliveries is also needed.

SUMMARY OF THE INVENTION

We have discovered a means for diagnosing and effectively treating pregnancy related hypertensive disorders, including pre-eclampsia and eclampsia. In some cases both the diagnosis and treatment may occur prior to the development of symptoms. Such early diagnosis and treatment could save maternal and fetal lives and prevent premature deliveries.

We have discovered-that the levels of expression of genes encoding the following secreted gene products (with GenBank numbers shown in parentheses) were significantly upregulated in the placental samples taken from women with pre-eclampsia as compared to placental specimens obtained from normal pregnant patients: follistatin related protein (U76702), interleukin 8 (M28130), inhibin A (M13981), VEGF-C (U43142), angiogenin (M11567), beta fertilin (U38805), hypothetical protein (AL039458), leukocyte associated Ig-like receptor secreted protein (AF013250), erythroid differentiation protein (J03634), adipogenesis inhibitory factor (X58377), corticotropin releasing factor binding protein (X58022), alpha-i anti-chymotrypsin (X68733), insulin-like growth factor binding protein-5 (L27559), CD33L (D86368), cytokine receptor like factor 1 (AF059293), platelet derived endothelial growth factor (NP_001953), lysyl hydroxylase isoform 2 (U84573), stanniocalcin precursor (U25997), secreted frizzled related protein (AF056087), and galectin-3 (NM_002306). We have also discovered that expression levels of the gene for the following secreted gene products were significantly decreased in placental samples taken from women with pre-eclampsia: alpha defensin (L12691), ADAM-TS3 (AB002364), cholecystokinin precursor (AW043690), interferon stimulated T-cell alpha chemoattractant precursor (AF030514), and azurocidin (M96326). These genes and the polypeptides encoded by the genes can be used to diagnose, treat, manage, and prevent pregnancy related hypertensive disorders.

We have also discovered intracellular targets that are differentially expressed in pre-eclamptic placentas and are suitable candidates for screening of novel therapeutic compounds. The intracellular gene products that are increased in pre-eclamptic placentas are: sperminine oxidase (U01134), UDP glycosyltransferase 2 family polypeptide B28 (AF 091582), neurotrophic tyrosine kinase receptor 2 (X 63759), neutral endopeptidase (J03779), CDC28 protein kinase regulatory subunit 2 (X54942) and beta glucosidase (J03060). The intracellular gene products that are decreased in pre-eclamptic placentas are: lanosterol synthase (U22526), calcium/calmodulin-dependent serine protein kinase (AI688589), estrogen receptor-alternatively spliced transcript H (X86816), chemokine (CX3C motif) receptor 1 (U27699), tyrosinase-related protein 1 (M20681), hydoxy-delta-5-steroid dehydrogenase (AL080151), dihydropyramidinase-like-4 (J03634), and cytochrome P450-family 11 (D84361).

For the purposes of the descriptions below, all of the polypeptides described above are collectively referred to as "the polypeptides of the invention." The polypeptides are further grouped as "secreted polypeptides" and "intracellular polypeptides" as described above. While the detailed description presented herein refers specifically to polypeptides associated with specific GenBank accession numbers, it will be clear to one skilled in the art that the detailed description can also apply to family members, isoforms, homologs, and/or variants that are substantially identical to the specified polypeptides.

Based on this data, we have discovered that compounds that decrease the levels or biological activity of a polypeptide of the invention for which the gene was upregulated in pre-eclampsia can be used to treat or prevent pregnancy related hypertensive disorders, such as pre-eclampsia or eclampsia, in a subject. Similarly, we have discovered that compounds that increase the levels or biological activity of a polypeptide of the invention for which the gene was downregulated in samples from women with pre-eclampsia can be used to treat or prevent pregnancy related hypertensive disorders, such as pre-eclampsia or eclampsia, in a subject. Such agents include, but are not limited to, antibodies specific to the protein, nucleobase oligomers for antisense or RNAi targeting the protein, purified proteins, purified natural or synthetic compounds, chemical compounds, and small molecules.

Accordingly, the invention features methods for measuring the levels of any one or more of the polypeptides (secreted or intracellular) of the invention or a nucleic acid encoding a polypeptide of the invention as a detection tool for early diagnosis and management of pregnancy related hypertensive disorders, such as pre-eclampsia or eclampsia.

In one aspect, the invention features a method of diagnosing a subject as having or having a predisposition to a pregnancy related hypertensive disorder, such as pre-eclampsia or eclampsia, that includes measuring the level of any one or more of the following secreted or intracellular polypeptides, or fragments thereof, in a sample from the subject: follistatin related protein, interleukin 8, inhibin A, VEGF-C, angiogenin, beta fertilin, hypothetical protein (GenBank Accession Number AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta-glucosidase. In this method, an increase (e.g., 10%, 20%, 30%, 40%, 50%, 60%, 70%, 80%, 90%, 95%, 96%, 97%, 98%, 99% or more) in the level of any one or more of the above polypeptides, or fragments thereof, as compared to a normal reference sample, standard or level is a diagnostic indicator of a pregnancy related hypertensive disorder, or a predisposition to a pregnancy related hypertensive disorder, such as pre-eclampsia or eclampsia. The method can also include measuring two, three, four, or five or more of the secreted or intracellular polypeptides listed above, or fragments thereof. In preferred embodiments, the polypeptide is follistatin related protein, inhibin-A, beta fertilin, insulin-like growth factor binding protein-5, or secreted frizzled related protein.

Non-limiting examples of pregnancy related hypertensive disorders include pre-eclampsia, eclampsia, gestational hypertension, chronic hypertension, HELLP syndrome, and pregnancy with a small for gestational age infant (SGA).

In a related aspect, the invention features a method of diagnosing a subject as having or having a predisposition to a pregnancy related hypertensive disorder, such as pre-eclampsia or eclampsia, that includes measuring the level of any one ore more of the following secreted or intracellular polypeptides, or fragments thereof, in a sample from the subject: alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11. In this method, a decrease (e.g., 10%, 20%, 30%, 40%, 50%, 60%, 70%, 80%, 90%, 95%, 96%, 97%, 98%, 99% or more) in the level of any one or more of the above polypeptides, or fragments thereof, as compared to a normal reference sample, standard, or level is a diagnostic indicator of a pregnancy related hypertensive disorder, or a predisposition to a pregnancy related hypertensive disorder, such as pre-eclampsia or eclampsia.

For any of the diagnostic methods that include measuring the level of a polypeptide or fragment thereof, the measuring can be done using an immunological assay (e.g., an ELISA or a western blot). The method can also include measuring two, three, four, or five or more of the secreted or intracellular polypeptides or the nucleic acids encoding the polypeptides listed above, or fragments thereof. The measuring can also be performed for more than one polypeptide at a time, using for example, microarrays which can be formatted as an array of binding molecules (e.g., an array of antibodies, also known as antibody arrays) to detect the polypeptides of the invention, or as an array of polypeptides of the invention, also known as protein arrays, which can be used to detect levels of antibodies to the polypeptides in a biological sample.

In another aspect, the invention features a method of diagnosing a subject as having or having a predisposition to a pregnancy related hypertensive disorder, such as pre-eclampsia or eclampsia, that includes measuring the level of a nucleic acid molecule encoding any one of the following secreted or intracellular polypeptides, or fragments thereof, in a sample from the subject: follistatin related protein, interleukin 8, inhibin A, VEGF-C, angiogenin, beta fertilin, hypothetical protein (GenBank Accession Number AL039458), leukocyte associated Ig-like receptor secreted protein, erythroid differentiation protein, adipogenesis inhibitory factor, corticotropin releasing factor binding protein, alpha- I anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta-glucosidase. In this method, an increase (e.g., 10%, 20%, 30%, 40%, 50%, 60%, 70%, 80%, 90%, 95%, 96%, 97%, 98%, 99% or more) in the level of any one or more of the nucleic acid molecules encoding the above polypeptides, or fragments thereof, as compared to a normal reference sample, standard, or level is a diagnostic indicator of a pregnancy related hypertensive disorder, or a predisposition to a pregnancy related hypertensive disorder, such as pre-eclampsia or eclampsia. In preferred embodiments, the nucleic acid encodes follistatin related protein, inhibin-A, beta fertilin, insulin-like growth factor binding protein-5, or secreted frizzled related protein.

In a related aspect, the invention features a method of diagnosing a subject as having or having a predisposition to a pregnancy related hypertensive disorder, such as pre-eclampsia or eclampsia, that includes measuring the level of a nucleic acid molecule encoding any one of the following secreted or intracellular polypeptides, or fragments thereof, in a sample from the subject: alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11. In this method, a decrease (e.g., 10%, 20%, 30%, 40%, 50%, 60%, 70%, 80%, 90%, 95%, 96%, 97%, 98%, 99% or more) in the level of a nucleic acid molecule encoding any one or more of the above polypeptides, or fragments thereof, as compared to a normal reference sample, standard, or level is a diagnostic indicator of a pregnancy related hypertensive disorder, or a predisposition to a pregnancy related hypertensive disorder, such as pre-eclampsia or eclampsia.

The methods above can also include measuring two, three, four, or five or more of the nucleic acids encoding the secreted or intracellular polypeptides listed above, or fragments thereof.

The diagnosis of a pregnancy related hypertensive disorder or a predisposition to a pregnancy related hypertensive disorder can result from an alteration (e.g., an increase or decrease) in the relative level of a polypeptide of the invention as compared to a normal reference sample or from the detection of an absolute level of a polypeptide of the invention that is above or below a normal reference level. The diagnosis can also result from an alteration in the level of a polypeptide as compare to the level in a prior sample obtained from the same subject. In additional preferred embodiments, the reference standard or level is a level or number derived from such a sample. In additional preferred embodiments, the reference sample is obtained at least 1 week, 2 weeks, 3 weeks, 4 weeks, 5 weeks, 6 weeks, 9 weeks, 12 weeks, 15 weeks, 18 weeks or more prior to the measuring of the levels for diagnosis. The reference standard or level can also be a value derived from a normal subject that is matched to the sample subject by at least one of the following criteria: gestational age of the fetus, age of the mother, blood pressure prior to pregnancy, blood pressure during pregnancy, BMI of the mother, weight of the fetus, prior diagnosis of a pregnancy related hypertensive disorder, such as pre-eclampsia or eclampsia, and a family history of a pregnancy related hypertensive disorder, such as pre-eclampsia or eclampsia. In additional preferred embodiments, the reference sample is a sample taken from a non-pregnant subject; a pregnant subject that does not have a pregnancy related hypertensive disorder, such as pre-eclampsia or eclampsia or a predisposition to a pregnancy related hypertensive disorder, such as pre-eclampsia or eclampsia; or a purified protein at known normal concentrations or a level representative of any of the reference samples described above.

In additional preferred embodiments, the method further includes measuring the level of at least one of sFlt-1, VEGF, PlGF, or soluble endoglin polypeptide in a sample from a subject as described in U.S. Patent Application Publication Numbers 20040126828, 20050025762, and 20050170444; PCT Publication Numbers WO 2004/008946 and WO 2005/077007; and U.S. patent application Ser. No. 11/235,577. The method can also include measuring the level of at least two of sFlt-1, VEGF, PlGF, or soluble endoglin polypeptide in a sample from a subject and calculating the relationship between the levels of sFlt-1, VEGF, PlGF, or soluble endoglin using a metric, where an alteration in the relationship between the levels in the subject sample relative to a reference sample diagnoses a pregnancy related hypertensive disorder or a predisposition to a pregnancy related hypertensive disorder. In preferred embodiments, the method also includes determining the body mass index (BMI), the gestational age (GA) of the fetus, or both and including the BMI or GA or both in the metric. For example, the metric can be a pre-eclampsia anti-angiogenic index (PAAI): [sFlt-1/VEGF+PlGF], a soluble endoglin anti-angiogenic index: (sFlt-I+0.25(soluble endoglin polypeptide))/PlGF, sFlt1/PlGF, (sFlt1+soluble endoglin)/PlGF, (sFlt1+soluble endoglin+follistatin related protein)/PlGF, or any combination thereof.

In another aspect, the invention provides a method of diagnosing a subject as having, or having a predisposition to a pregnancy related hypertensive disorder, such as pre-eclampsia or eclampsia, that includes determining the nucleic acid sequence of a gene encoding a polypeptide selected from the group consisting of: follistatin related protein, interleukin 8, inhibin A, VEGF-C, angiogenin, beta fertilin, hypothetical protein, leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta glucosidase. An alteration in the subject's nucleic acid sequence that is an alteration that increases the expression level or biological activity of the gene product in the subject diagnoses the subject with a pregnancy related hypertensive disorder, or a predisposition to a pregnancy related hypertensive disorder, such as pre-eclampsia or eclampsia, or a propensity to develop such a condition.

In another related aspect, the invention features a method of diagnosing a subject as having, or having a predisposition to a pregnancy related hypertensive disorder, such as pre-eclampsia or eclampsia, that includes determining the nucleic acid sequence of a gene encoding a polypeptide selected from the group consisting of: alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11. An alteration in the subject's nucleic acid sequence that is an alteration that decreases the expression level or biological activity of the gene product in the subject diagnoses the subject with a pregnancy related hypertensive disorder, such as pre-eclampsia or eclampsia, or a predisposition to a pregnancy related hypertensive disorder, such as pre-eclampsia or eclampsia.

In preferred embodiments of any of the above aspects, the polypeptide or the nucleic acid encoding the polypeptide is follistatin related protein, inhibin-A, beta fertilin, insulin-like growth factor binding protein-5, or secreted frizzled related protein.

In additional embodiments of any of the above aspects, the levels are measured on two or more occasions and a change in the levels between measurements is a diagnostic indicator of pregnancy related hypertensive disorder, or a predisposition to a pregnancy related hypertensive disorder, such as pre-eclampsia or eclampsia. In preferred embodiments, an alteration (e.g., an increase or a decrease of 10%, 20%, 30%, 40%, 50%, 60%, 70%, 80%, 90%, 95%, 96%, 97%, 98%, 99% or more) in the level of any of the polypeptides of the invention or nucleic acids encoding a polypeptide of the invention from the first measurement to the next measurement is a diagnostic indicator of pregnancy related hypertensive disorder, such as pre-eclampsia or eclampsia. Desirably, the diagnostic methods are used to diagnose a pregnancy related hypertensive disorder prior to the onset of symptoms (e.g., at least 4, 5, 6, 7, 8, 9, or 10 weeks prior).

In various embodiments of any of the above diagnostic aspects, the pregnancy related hypertensive disorder is pre-eclampsia, eclampsia, gestational hypertension, chronic hypertension, HELLP syndrome, or pregnancy with an SGA infant.

In various embodiments of the above aspects, the sample is a bodily fluid (e.g., urine, blood, amniotic fluid, serum, saliva, plasma, or cerebrospinal fluid) of the subject in which the polypeptide or nucleic acid encoding a polypeptide of the invention is normally detectable. In additional embodiments, the sample is a tissue or a cell (e.g., placental tissue or placental cells, endothelial cells, leukocytes, and monocytes). In other embodiments of the above aspects, the subject is a pregnant human, a post-partum human, or a non-pregnant human. In other embodiments of the above aspects, the subject is a non-human (e.g., a cow, a horse, a sheep, a pig, a goat, a dog, or a cat). In one embodiment, the subject is a non-pregnant human and the method is used to diagnose a propensity to develop a pregnancy related hypertensive disorder, such as pre-eclampsia or eclampsia, prior to a pregnancy. In additional embodiments, the BMI or GA or both is also measured.

In another aspect, the invention provides a kit for the diagnosis of a pregnancy related hypertensive disorder, or a predisposition to a pregnancy related hypertensive disorder, such as pre-eclampsia or eclampsia, in a subject that includes at least one nucleic acid sequence, or a sequence complementary thereto, that is selected from nucleic acids that encode the following group of polypeptides: follistatin related protein, interleukin 8, inhibin A, VEGF-C, angiogenin, beta fertilin, hypothetical protein, leukocyte associated Ig-like receptor secreted protein, erythroid differentiation protein, adipogenesis inhibitory factor, corticotropin releasing factor binding-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, beta glucosidase, alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor-alternatively spliced transcript H, chemokine (CX3C motif) receptor 1, tyrosinase-related protein 1, hydoxy-delta-5-steroid dehydrogenase, dihydropyramidinase-like-4, and cytochrome P450-family 11. The kit also includes directions for the use of the nucleic acid sequence, or sequence complementary thereto, for the diagnosis of a pregnancy related hypertensive disorder, or a predisposition to a pregnancy related hypertensive disorder, such as pre-eclampsia or eclampsia. In preferred embodiments, the kit includes at least two, at least three, at least four, or at least five or more of the nucleic acid sequences.

In another aspect, the invention provides a kit for the diagnosis of a pregnancy related hypertensive disorder, or a predisposition to a pregnancy related hypertensive disorder, such as pre-eclampsia or eclampsia, in a subject comprising a component or reagent used to detect a polypeptide that is selected from the following group of polypeptides: follistatin related protein, interleukin 8, inhibin A, VEGF-C, angiogenin, beta fertilin, hypothetical protein, leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, beta glucosidase, alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11. The kit also includes directions for the use of the components to detect the polypeptide for the diagnosis of a pregnancy related hypertensive disorder, such as pre-eclampsia or eclampsia. In preferred embodiments, the kit includes components or reagents used to detect at least two, at least three, at least four, or at least five or more of the polypeptides of the invention. Preferred polypeptides or nucleic acids include follistatin related protein, inhibin-A, beta fertilin, insulin-like growth factor binding protein-5, or secreted frizzled related protein. In preferred embodiments, the components or reagents used to detect a polypeptide include a binding molecule, such as an antibody or antigen binding fragment that is specific for the polypeptide and the polypeptide is detected by any one of the following assays: an immunological assay, an enzymatic assay, or a colorimetric assay. The component or reagent can also be a polypeptide, or fragment thereof, that can bind to an antibody that specifically binds the polypeptide. Such a kit can be used to detect antibodies present in a bodily fluid sample from a subject that are indicative of levels of the protein in the subject.

In additional preferred embodiments of any of the above kit aspects of the invention, the kit also includes a reference sample, standard, or level. The reference sample, standard, or level can be a normal reference sample, standard or level taken from a subject not having a pregnancy related hypertensive disorder, such as pre-eclampsia or eclampsia, or a subject that is not pregnant. The reference sample can also be a purified polypeptide at a known normal concentration.

In preferred embodiments, the diagnostic kit is labeled or includes instructions for use in the diagnosis of a pregnancy related hypertensive disorder, such as pre-eclampsia or eclampsia, or a predisposition to a pregnancy related hypertensive disorder, in a subject. In yet another embodiment, the diagnostic kit is labeled or includes instructions for use in therapeutic monitoring or therapeutic dosage determination. Desirably, the diagnostic kit includes a label or instructions for the use of the kit to determine the levels of a polypeptide of the invention of the subject sample and to compare those subject sample levels to a reference sample value or a standard curve of reference sample values, where the standard curve shows values indicative of a pregnancy related hypertensive disorder, such as pre-eclampsia or eclampsia, and normal values. It will be understood that the reference sample values will depend on the intended use of the kit. For example, in a kit used for diagnostic purposes, the subject sample can be compared to a reference value or reference sample for a polypeptide of the invention taken from a subject that does not have a pregnancy related hypertensive disorder, such as pre-eclampsia or eclampsia, or is not pregnant. In another example, a kit used for therapeutic monitoring can have a reference value or reference sample that is a positive reference indicative of a pregnancy related hypertensive disorder, such as pre-eclampsia or eclampsia, wherein an alteration (increase or decrease) in the value of the subject sample relative to the reference sample can be used to indicate an improvement in the pregnancy related hypertensive disorder, such as pre-eclampsia or eclampsia, or effective dosages of therapeutic compounds.

In a related aspect, the invention features a device for diagnosing a subject as having or a predisposition to a pregnancy related hypertensive disorder, such as pre-eclampsia or eclampsia. The device includes a component useful for comparing the levels of a polypeptide of the invention or a nucleic acid encoding a polypeptide of the invention, wherein an alteration (increase or decrease) in the levels of a polypeptide of the invention is a diagnostic indicator of a pregnancy related hypertensive disorder, or a predisposition to a pregnancy related hypertensive disorder, such as pre-eclampsia or eclampsia, in the subject. In preferred embodiments, the device includes a membrane in a lateral flow or dipstick format used to measure and compare polypeptide levels in urine sample. The device can also include components for comparing the levels of one or more polypeptides of the invention or nucleic acid molecules encoding the polypeptides of the invention and at least one of soluble endoglin sFlt-1, VEGF, and PlGF nucleic acid molecules or polypeptides in a sample from a subject, relative to a reference sample, wherein an alteration (increase or decrease) diagnoses a pregnancy related hypertensive disorder or a predisposition to a pregnancy related hypertensive disorder, such as pre-eclampsia or eclampsia in the subject. In a preferred embodiment the device includes a component or components for use with a metric to compare the levels of one or more polypeptides of the invention and at least one, and preferably two, of soluble endoglin, sFlt-1, VEGF, and PlGF polypeptides.

In another aspect, the invention features a nucleic acid array comprising one or more substrate supports which are stably associated with a plurality of polynucleotide probes, wherein the polynucleotide probes are capable of hybridizing under highly stringent conditions to RNA transcripts, or the complements thereof, of nucleic acids encoding any of the polypeptides of the invention.

In another aspect, the invention features a polypeptide array comprising one or more substrate supports which are stably associated with a plurality of polypeptides of the invention; variants of the polypeptides; antibodies specific for the polypeptides or variants; or any combination of the polypeptides, variants, or antibodies.

Each of the arrays described above can also include instructions for the use of the array for the diagnosis of a pregnancy related hypertensive disorder or a predisposition thereto.

Any of the diagnostic methods, kits, or arrays described herein can also be used to monitor a pregnancy related hypertensive disorder, such as pre-eclampsia or eclampsia, in a subject. In preferred embodiments, the diagnostic methods are used to monitor the subject during therapy or to determine effective therapeutic dosages. The level of a polypeptide of the invention or a nucleic acid encoding a polypeptide of the invention is measured alone or in combination with the levels of soluble endoglin, sFlt-1, VEGF, or PlGF protein or nucleic acids, or any combination thereof. In preferred embodiments the levels of are measured on two or more occasions and an alteration (increase or decrease) in the levels is a diagnostic indicator of a pregnancy related hypertensive disorder, such as pre-eclampsia or eclampsia. In additional preferred embodiments, the levels are compared to a reference sample and an alteration (increase or decrease) in the levels of any of the polypeptides relative to the reference sample is a diagnostic indicator of a pregnancy related hypertensive disorder, such as pre-eclampsia or eclampsia. In one embodiment, the level of at least one of the following polypeptides or nucleic acids encoding the following secreted or intracellular polypeptides, or fragments thereof, is measured during or after administering therapy and compared to the value before therapy: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-I anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta-glucosidase. In this embodiment, a decrease in the level of any one or more of the above polypeptides, or fragments thereof, as compared to the value before therapy indicates an improvement in the pregnancy related hypertensive disorder, such as pre-eclampsia or eclampsia.

In another embodiment, the level of at least one of the following secreted or intracellular polypeptides or nucleic acid encoding the secreted polypeptides, or fragments thereof is measured during or after administering therapy and compared to the value before therapy: alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor—alternatively spliced transcript H, chemokine receptor 1, tyrosinase-related protein 1, hydoxy-delta-5-steroid dehydrogenase, dihydropyramidinase-like-4, and cytochrome P450—family 11. In this embodiment, an increase in the level of any one or more of the above polypeptides, or fragments thereof, as compared to the value before therapy indicates an improvement in the pregnancy related hypertensive disorder, such as pre-eclampsia or eclampsia.

In preferred embodiments of the diagnostic monitoring methods of the invention that include the measurement of sFlt- 1, VEGF, or PlGF, the method can include calculating the relationship between the levels of sFlt-1, VEGF, or PlGF using a metric, wherein an alteration in the relationship between said levels in the subject sample relative to a reference sample, is a diagnostic indicator of a pregnancy related hypertensive disorder, such as pre-eclampsia or eclampsia. One example of such a metric is the PAAI. In this example, a decrease in the PAAI value of a subject (e.g., less than 20, preferably less than 10) indicates an improvement in the pregnancy related hypertensive disorder, such as pre-eclampsia or eclampsia. A decrease in the PAAI (e.g., less than 20, preferably less than 10) can also indicate an effective dosage of a therapeutic compound. In preferred embodiments of the aspects relating to diagnosis or monitoring of therapeutic treatments, polypeptides are measured using an immunological assay, such as ELISA or western blot, or a protein array or antibody array for the measurement of expression levels of more than one polypeptide. For any of the monitoring methods, the measuring of levels can be done on two or more occasions and a change in the levels between measurements is a diagnostic indicator of a pregnancy related hypertensive disorder, such as pre-eclampsia or eclampsia.

In another aspect, the invention provides a method of treating or preventing a pregnancy related hypertensive disorder, or a predisposition to a pregnancy related hypertensive disorder, such as pre-eclampsia or eclampsia, in a subject by administering to the subject a compound capable of decreasing the biological activity or the expression level of a polypeptide or nucleic acid molecule encoding a polypeptide selected from the group of secreted polypeptides consisting of: follistatin related protein, interleukin 8, inhibin A, VEGF-C, angiogenin, beta fertilin, hypothetical protein, leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3, where the administering is for a time and in an amount sufficient to treat or prevent a pregnancy related hypertensive disorder, such as pre-eclampsia or eclampsia, in a subject. In preferred embodiments, the compound is a nucleobase oligomer that is at least 90%, 95%, 96%, 97%, 98%, 99% or 100% complementary to at least a portion of the nucleic acid sequence encoding any of the polypeptides listed above. The nucleobase oligomer can be an antisense nucleobase oligomer, preferably at least 90%, 95%, 96%, 97%, 98%, 99% or 100% complementary to at least 8 to 30 nucleotides of the desired nucleic acid sequence. The nucleobase oligomer can also be a double stranded RNA (dsRNA), preferably a small interfering RNA (siRNA) that is preferably at least 90%, 95%, 96%, 97%, 98%, 99%, or 100% complementary to at least 18, 19, 20, 21, 22, 23, 24, 25, 35, 45, or 50 nucleotides of the desired nucleic acid sequence.

In additional preferred embodiments of this aspect, the compound is an antibody or antigen-binding fragment, preferably a monoclonal antibody, that specifically binds any one of the following polypeptides, or fragments thereof: follistatin related protein, interleukin 8, inhibin A, VEGF-C, angiogenin, beta fertilin, hypothetical protein, leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3. In preferred embodiments, the antibody or antigen-binding fragment thereof is a human or humanized antibody.

In another aspect, the invention features a method of treating or preventing a pregnancy related hypertensive disorder, or a predisposition to a pregnancy related hypertensive disorder, such as pre-eclampsia or eclampsia, in a subject by administering to the subject a compound capable of increasing the biological activity or the expression level of a polypeptide or nucleic acid molecule encoding a secreted polypeptide selected from the group consisting of: alpha defensin, ADAM-TS3, cholecystokinin precursor, interferon stimulated T-cell alpha chemoattractant precursor, and azurocidin, where the administering is for a time and in an amount sufficient to treat or prevent a pregnancy related hypertensive disorder, such as pre-eclampsia or eclampsia, in a subject. In a preferred embodiment, the compound is a purified polypeptide selected from the group consisting of: alpha defensin, ADAM-TS3, cholecystokinin precursor, interferon stimulated T-cell alpha chemoattractant precursor, and azurocidin. In various embodiments of any of the above aspects, the method further involves the step of administering to a subject an anti-hypertensive compound (e.g., adenosine, nifedipine, minoxidil, and magnesium sulfate). In other embodiments of the above aspects, the subject is a pregnant human, a post-partum human, a non-pregnant human, or a non-human (e.g., a cow, a horse, a sheep, a pig, a goat, a dog, or a cat). The therapeutic methods of the invention can be used to treat or prevent a pregnancy related hypertensive disorder that includes pre-eclampsia, eclampsia, gestational hypertension, chronic hypertension, HELLP syndrome, and pregnancy with an SGA infant. Preferred disorders are pre-eclampsia and eclampsia. In various embodiments of the above aspects, the method can be combined with the diagnostic methods of the invention, described below, to monitor the subject during therapy or to determine effective therapeutic dosages.

Any of the therapeutic aspects of the invention can also include administering one ore more additional compounds, such as a purified sFlt-1 antibody, a sFlt-1 antigen-binding fragment, nicotine, theophylline, adenosine, nifedipine, minoxidil, magnesium sulfate, vascular endothelial growth factor (VEGF), including all isoforms such as VEGF189, VEGF121, or VEGF165, or fragments thereof; placental growth factor (PlGF), including all isoforms and fragments thereof; a purified soluble endoglin antibody or soluble endoglin antigen-binding fragment; where the administering is for a time and in an amount sufficient to treat or prevent the pregnancy related hypertensive disorder, such as pre-eclampsia or eclampsia, in a subject. Preferred examples of such compounds are described in U.S. Patent Application Publication Numbers 20040126828, 20050025762, and 20050170444; PCT Publication Numbers WO 2004/008946 and WO 2005/077007; and U.S. patent application Ser. No. 11/235,577. Desirably, the compound will be a compound capable of binding to sFlt-1 or decreasing sFlt-1 expression.

Any of the therapeutic aspects of the invention can be used alone or in combination with one or more additional methods (diagnostic or treatment) of the invention.

In another aspect, the invention provides a method of identifying a compound that ameliorates a pregnancy related hypertensive disorder, such as pre-eclampsia or eclampsia, that includes contacting a cell that expresses a polypeptide of the invention or a nucleic acid molecule encoding a polypeptide of the invention with a candidate compound, and comparing the level of expression or biological activity of the polypeptide of the invention or the nucleic acid molecule encoding the polypeptide of the invention in the cell contacted by the candidate compound with the level of expression or biological activity in a control cell not contacted by the candidate compound, where an alteration in expression or biological activity of the polypeptide of the invention or the nucleic acid molecule encoding the polypeptide of the invention identifies the candidate compound as a compound that ameliorates the pregnancy related hypertensive disorder.

In one embodiment, the method is used to identify a compound that decreases the expression of a polypeptide, or fragment thereof, or a nucleic acid molecule encoding the polypeptide, or fragment thereof, selected from the following group of polypeptides: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta-glucosidase. In another embodiment, the method is used to identify a compound that promotes an increase in the expression of a polypeptide, or fragment thereof, or a nucleic acid molecule encoding the polypeptide, or fragment thereof, selected from the following group of polypeptides: alpha defensin, ADAM-TS3, cholecystokinin precursor, interferon stimulated T-cell alpha chemoattractant precursor, and azurocidin, or the level of any one of the following intracellular polypeptides, or fragments thereof, in a sample from the subject: lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11. The alteration can be, for example, in transcription, translation, protein stability, production, or biological activity.

For the purpose of the present invention, the following abbreviations and terms are defined below.

By "alteration" is meant a change (increase or decrease) in the expression levels of a gene or polypeptide as detected by standard art known methods such as those described below. As used herein, an alteration includes a 10% change in expression levels, preferably a 25% change, more preferably a 40% change, and most preferably a 50%, 60%, 70%, 80%, 90%, 95%, 96%, 97%, 98%, 99% or greater change in expression levels. "Alteration" can also indicate a change (increase or decrease) in the biological activity of any of the polypeptides of the invention. Examples of biological activities include ligand binding, enzymatic activity, cell migration, cell proliferation, induction of endothelial dysfunction, or induction of an anti-angiogenic state. Biological activities can be measured, for example, by ligand binding assays; cell migration assays; assays for enzymatic activity (e.g., kinase activity); Scatchard plot analysis; immunoassays; cell proliferation assays such as BrdU labeling, cell counting experiments, or quantitative assays for DNA synthesis such as $^3$H thymidine incorporation; and angiogenesis assays that are standard in the art or are described herein. As used herein, an alteration includes a 10% change in biological activity, preferably a 25% change, more preferably a 40% change, and most preferably a 50%, 60%, 70%, 80%, 90%, 95%, 96%, 97%, 98%, 99% or greater change in biological activity.

By "antisense nucleobase oligomer" is meant a nucleobase oligomer, regardless of length, that is complementary to the coding strand or mRNA of a nucleic acid encoding a polypeptide of the invention. The antisense nucleobase oligomer can also be targeted to the translational start and stop sites. Preferably the antisense nucleobase oligomer comprises from about 8 to 30 nucleotides. The antisense nucleobase oligomer can also contain at least 40, 60, 85, 120, or more consecutive nucleotides that are complementary to mRNA or DNA encoding the polypeptide of the invention, and may be as long as the full-length mRNA or gene.

By "body mass index" is meant a number, derived by using height and weight measurements, that gives a general indication of whether or not weight falls within a healthy range. The formula generally used to determine the body mass index is a person's weight in kilograms divided by a person's height in meters squared or weight (kg)/(height (m))$^2$.

By "compound" is meant any small molecule chemical compound, antibody, nucleic acid molecule, polypeptide, or fragments thereof.

By "chimeric antibody" is meant a polypeptide comprising at least the antigen-binding portion of an antibody molecule linked to at least part of another protein (typically an immunoglobulin constant domain).

By "decrease" is meant the ability to cause an overall reduction, preferably of 10%, 20%, 30%, 40%, 50%, 60%, 70%, 80%, 90%, 95%, 96%, 97%, 98%, 99% or greater, in the level of polypeptide or nucleic acid; detected by the assays described herein (see "expression") or the biological activity of the polypeptide, detected by the assays described herein (see "biological activity"), as compared to a reference sample.

By "double-stranded RNA (dsRNA)" is meant a ribonucleic acid molecule comprised of both a sense and an anti-sense strand. dsRNAs can be used to mediate RNA interference.

By "expression" is meant the detection of a gene or polypeptide by standard art known methods. For example, polypeptide expression is often detected by immunoassays (e.g., ELISA or western blotting), DNA expression is often detected by Southern blotting or polymerase chain reaction (PCR), and RNA expression is often detected by northern blotting, PCR, or RNAse protection assays.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000 or more amino acids or nucleotides up to the entire length of the polypeptide or nucleic acid molecule.

By "gestational age" is meant a reference to the age of the fetus, counting from the first day of the mother's last menstrual period usually referred to in weeks.

By "gestational hypertension" is meant the development of high blood pressure without proteinuria after 20 weeks of pregnancy.

By a "history of pre-eclampsia or eclampsia" is meant a previous diagnosis of pre-eclampsia or eclampsia or pregnancy induced hypertension in the subject themselves or in a related family member.

By "homologous" is meant any gene or polypeptide sequence that bears at least 30% homology, more preferably 40%, 50%, 60%, 70%, 80%, and most preferably 90% or more homology to a known gene or polypeptide sequence over the length of the comparison sequence. A "homologous" polypeptide can also have at least one biological activity of the comparison polypeptide. For polypeptides, the length of comparison sequences will generally be at least 6 amino acids, preferably at least 10 or 20 amino acids, more preferably at least 25 amino acids, and most preferably 50, 100, 150, 200 amino acids or more, up to the entire length of the polypeptide. For nucleic acids, the length of comparison sequences will generally be at least 18 nucleotides, preferably at least 25 or 50 nucleotides, more preferably at least 75 nucleotides, and most preferably from at least 100, 150, 200, 250, 300 nucleotides or more up to the entire length of the nucleic acid. "Homology" can also refer to a substantial similarity between an epitope used to generate antibodies and the polypeptide or fragment thereof to which the antibodies are directed. In this case, homology refers to a similarity sufficient to elicit the production of antibodies that can specifically recognize the polypeptide at issue.

By "humanized antibody" is meant an immunoglobulin amino acid sequence variant or fragment thereof that is capable of binding to a predetermined antigen. Ordinarily, the antibody will contain both the light chain as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin (the "import" sequences).

Generally, a humanized antibody has one or more amino acid residues introduced into it from a source that is non-human. In general, the humanized antibody will comprise substantially all of at least one, and typically two, variable domains (Fab, Fab', $F(ab')_2$, Fabc, Fv) in which all or substantially all of the CDR regions correspond to those of a non-human immunoglobulin and all or substantially all of the FR regions are those of a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75%, preferably 90%, and most preferably at least 95%, 96%, 97%, 98%, 99% or 100% of the humanized antibody residues will correspond to those of the parental FR and CDR sequences.

By "hybridize" is meant pair to form a double-stranded molecule between complementary polynucleotide sequences, or portions thereof, under various conditions of stringency. (See, e.g., Wahl and Berger (1987) *Methods Enzymol.* 152:399; Kimmel, *Methods Enzymol.* 152:507, 1987.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1 % SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (*Proc. Natl. Acad. Sci.*, USA 72:3961, 1975); Ausubel et al. (*Current Protocols in Molecular Biology*, Wiley Interscience, New York, 2001); Berger and Kimmel (*Guide to Molecular Cloning Techniques,* 1987, Academic Press, New York); and Sambrook et al., *Molecular Cloning: A Laboratory Manual*, Cold Spring Harbor Laboratory Press, New York.

By "increase" is meant the ability to cause an overall increase preferably of 10%, 20%, 30%, 40%, 50%, 60%, 70%, 80%, 90%, 95%, 96%, 97%, 98%, 99% or greater, in the level of polypeptide or nucleic acid, detected by the aforementioned assays (see "expression") or the biological activity of the polypeptide, detected by the aforementioned assays (see "biological activity"), as compared to a reference sample.

By "intrauterine growth retardation (IUGR)" is meant a syndrome resulting in a birth weight which is less that 10 percent of the predicted fetal weight for the gestational age of the fetus. The current World Health Organization criterion for low birth weight is a weight less than 2,500 gm (5 lbs. 8 oz.) or below the $10^{th}$ percentile for gestational age according to U.S. tables of birth weight for gestational age by race, parity, and infant sex (Zhang and Bowes, *Obstet. Gynecol.* 86:200-208, 1995). These low birth weight babies are also referred to as "small for gestational age (SGA)." Pre-eclampsia is a condition known to be associated with IUGR or SGA.

By "metric" is meant a measure. A metric may be used, for example, to compare the levels of a polypeptide or nucleic acid molecule of the invention. Exemplary metrics include, but are not limited to, mathematical formulas or algorithms, such as ratios. Depending on the metric that is used, the diagnostic indicator of eclampsia or pre-eclampsia may be significantly above or below a value using the same metric with a reference sample or level (e.g., from a control subject not having a pregnancy related hypertensive disorder, such as pre-eclampsia or eclampsia). The metric to be used is that which best discriminates between levels of a polypeptide or nucleic acid molecule of the invention, and/or soluble endoglin, sFlt-1, VEGF, PlGF, or any combination thereof, in a subject having pregnancy related hypertensive disorder, such as pre-eclampsia or eclampsia, and a reference sample or level. For example, the metric can be a pre-eclampsia anti-angiogenic index (PAAI): [sFlt-1/VEGF +PlGF], a soluble endoglin anti-angiogenic index: (sFlt-1+0.25(soluble endoglin polypeptide))/PlGF, sFlt 1/PlGF, (sFlt1+soluble endoglin)/PlGF, (sFlt1+soluble endoglin+follistatin related protein)/PlGF, or any combination thereof. Some examples of metrics that are useful are described in U.S. Patent Application Publication Numbers 20040126828, 20050025762, and 20050170444; PCT Publication Numbers WO 2004/008946 and WO 2005/077007; and U.S. patent application Ser. No. 11/235,577.

By a "nucleobase oligomer" is meant a compound that includes a chain of at least eight nucleobases, preferably at least twelve, and most preferably at least sixteen bases, joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Examples of numerous nucleobases and linkage groups that may be used in the nucleobase oligomers of the invention, can be found in U.S. Patent Application Publication Nos. 20030114412, paragraphs [0030] to [0046] and 20030114407, paragraphs [0036] to [0055], and 20030190659, paragraphs [0083] to [0106], herein incorporated by reference.

By "operably linked" is meant that a gene and a regulatory sequence(s) are connected in such a way as to permit gene expression when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, ($20^{th}$ edition), ed. A. Gennaro, 2000, Lippincott, Williams & Wilkins, Philadelphia, Pa.

By "polymorphism" is meant a genetic variation, mutation, deletion or addition in a nucleic acid molecule encoding a polypeptide of the invention that is indicative of a predisposition to develop a pregnancy related hypertensive disorder, such as pre-eclampsia or eclampsia. A polymorphism may be present in the promoter sequence, an open reading frame, intronic sequence, or untranslated 3' region of a gene.

By "pregnancy related hypertensive disorder" is meant any condition or disease or pregnancy that is associated with or characterized by an increase in blood pressure. Included among these conditions are pre-eclampsia (including premature pre-eclampsia, severe pre-eclampsia), eclampsia, gestational hypertension, HELLP syndrome, (hemolysis, elevated liver enzymes, low platelets), abruption placenta, chronic hypertension, pregnancy with intra uterine growth restriction, and pregnancy with a small for gestational age (SGA) infant. It should be noted that although pregnancy with a SGA infant is not often associated with hypertension, it is included in this definition.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. Pre-eclampsia generally occurs after the $20^{th}$ week of gestation. Pre-eclampsia is generally defined as some combination of the following symptoms: (1) a systolic blood pressure (BP) >140 mmHg and a diastolic BP >90 mmHg after 20 weeks gestation (generally measured on two occasions, 4-168 hours apart), (2) new onset proteinuria (1+ by dipstik on urinanaysis, >300mg of protein in a 24-hour urine collection, or a single random urine sample having a protein/creatinine ratio >0.3), and (3) resolution of hypertension and proteinuria by 12 weeks postpartum. Severe pre-eclampsia is generally defined as (1) a diastolic BP >110 mmHg (generally measured on two occasions, 4-168 hours apart) or (2) proteinuria characterized by a measurement of 3.5 g or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "pre-eclampsia anti-angiogenesis index (PAAI)" is meant the ratio of sFlt-1/VEGF+PlGF used as an indicator of anti-angiogenic activity. A PAAI greater than 10, more preferably greater than 20, is considered to be indicative of pre-eclampsia or risk of pre-eclampsia.

By "premature pre-eclampsia" is meant pre-eclampsia with onset of symptoms <37 weeks or <34 weeks.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "polypeptide of the invention" is meant any of the following secreted polypeptides where the number in parenthesis indicates the GenBank accession number for the polypeptide: follistatin related protein (FLRG, U76702), interleukin 8 (IL-8, M28130), inhibin A (M13981), VEGF-C (U43142), angiogenin (M11567), beta fertilin (U38805), hypothetical protein (AL039458), leukocyte associated Ig-like receptor secreted protein (LAIR-2, AF013250), erythroid differentiation protein (J03634), adipogenesis inhibitory factor (X58377), corticotropin releasing factor binding protein (CRF-BP, X58022), alpha-I anti-chymotrypsin (X68733), insulin-like growth factor binding protein-5 (IGFBP-5, L27559), CD33L (D86358), cytokine receptor like factor 1 (CRLF1, AF059293), platelet derived endothelial growth factor (ECGF-1, NP_001953), lysyl hydroxylase isoform 2 (PLOD2, U84573), stanniocalcin precursor (U25997), secreted frizzled related protein (AF056087), galectin -3 (NM_002306), alpha defensin (L12691), ADAM-TS3 (AB002364), cholecystokinin precursor (AW043690), interferon stimulated T-cell alpha chemoattractant precursor (AF030514), and azurocidin (M96326); or any of the following intracellular polypeptides sperminine oxidase (U01134), UDP glycosyltransferase 2 family polypeptide B28 (AF091582), neurotrophic tyrosine kinase receptor 2 (X63759), neutral endopeptidase (J03779), CDC28 protein kinase regulatory subunit 2 (X54942) and beta glucosidase (J03060), lanosterol synthase (U22526), calcium/calmodulin-dependent serine protein kinase (AI688589), estrogen receptor-alternatively spliced transcript H (X86816), chemokine (CX3C motif) receptor 1 (U27699), tyrosinase-related protein 1 (M2068 1), hydoxy-delta-5-steroid dehydrogenase (AL08015 1), dihydropyramidinase-like-4 (J03634) and cytochrome P450-family 11 (D84361). Included in this definition are splice variants, isoforms, homologs, degradation products, and fragments of any of the above polypeptides.

By "reference sample" is meant any sample, standard, or level that is used for comparison purposes. A "normal reference sample" can be a prior sample taken from the same subject, a sample from a pregnant subject not having any pregnancy related hypertensive disorder, such as pre-eclampsia or eclampsia, a sample from a pregnant subject not having a pregnancy related hypertensive disorder, such as pre-eclampsia or eclampsia, a subject that is pregnant but the sample was taken early in pregnancy (e.g., in the first or second trimester or before the detection of a pregnancy related hypertensive disorder, such as pre-eclampsia or eclampsia), a subject that is pregnant and has no history of a pregnancy related hypertensive disorder, such as pre-eclampsia or eclampsia, a subject that is not pregnant, a sample of a purified reference polypeptide at a known normal concentration (i.e., not indicative of a pregnancy related hypertensive disorder, such as pre-eclampsia or eclampsia). By "reference standard or level" is meant a value or number derived from a reference sample. A normal reference standard or level can be a value or number derived from a normal subject that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of pre-eclampsia or eclampsia, and a family history of pregnancy related hypertensive disorders, such as pre-eclampsia or eclampsia. A "positive reference" sample, standard or value is a sample or value or number derived from a subject that is known to have a pregnancy related hypertensive disorder, such as pre-eclampsia or eclampsia, that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of a pregnancy related hypertensive disorder, and a family history of a pregnancy related hypertensive disorder By "reduce or inhibit" is meant the ability to cause an overall decrease preferably of 10%, 20%, 30%, 40%, 50%, 60%, 70%, 80%, 90%, 95%, 96%, 97%, 98%, 99% or more in the level of polypeptide or nucleic acid, detected by the aforementioned assays (see "expression") or the biological activity of the polypeptide, detected by the aforementioned assays (see "biological activity"), as compared to a reference sample or a sample not treated with antisense nucleobase oligomers, dsRNA, or siRNA used for RNA interference.

By "sample" is meant a tissue biopsy, cell, bodily fluid (e.g., blood, serum, plasma, urine, saliva, amniotic fluid, or cerebrospinal fluid) or other specimen obtained from a subject. Desirably, the biological sample includes polypeptides of the invention or nucleic acid molecules encoding polypeptides of the invention or both.

By "small interfering RNAs (siRNAs)" is meant a nucleobase oligomer that is preferably a dsRNA molecule, and is preferably greater than 10 nucleotides (nt) in length, more preferably greater than 15 nucleotides in length, and most preferably greater than 19 nucleotides in length that is used to identify the target gene or mRNA to be degraded. Desirably, the siRNA is at least 90%, 95%, 96%, 97%, 98%, 99%, 100% complementary to 18, 19, 20, 21, 22, 23, 24, 25, 35, 45, 50 nucleotides of the desired nucleic acid sequence. A range of 19-25 nucleotides is the most preferred size for siRNAs. siRNAs can also include short hairpin RNA (shRNA) in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23 nt RNA or internally (at one or more nucleotides of the RNA). In a preferred embodiment, the RNA molecules contain a 3' hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). As used herein, RNAi refers to the ATP-dependent targeted cleavage and degradation of a specific mRNA molecule through the introduction of small interfering RNAs or dsRNAs into a cell or an organism. As used herein "mediate RNAi" refers to the ability to distinguish or identify which RNAs are to be degraded.

By "specifically binds" is meant a compound or antibody which recognizes and binds a polypeptide of the invention but that does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline. Included in this definition are pregnant, post-partum, and non-pregnant mammals.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99% or 100% sequence identity with a second nucleic acid or amino acid sequence, e.g., an endoglin or soluble endoglin sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) *J. Mol. Biol.* 147:195-7); "Best Fit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) *J. Mol. Biol.* 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 6 amino acids, preferably 10, 20, 30, 40, 50, 60, 70, 80, 90, 100, 110, 120, 130, 140, 150, 200, 250, 300,350, 400, or 500 amino acids or more up to the entire length of the protein. For nucleic acids, the length of comparison sequences will generally be at least 18, 25, 50, 100, 125, 150, 200, 250, 300, 350, 400, 450, 500, 550, 600, 650, 700, 800, 900, 1000, 1100, 1200, or at least 1500 nucleotides or more up to the entire length of the nucleic acid molecule. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "substrate" or "solid support is meant any material that can be modified to contain discrete individual sites appropriate for the attachment or association of the nucleic acid probes, polypeptides, or polypeptide binding molecules of the invention and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, etc. In general, the substrates allow optical detection and have low background fluorescence.

By "symptoms of pre-eclampsia" is meant any of the following: (1) a systolic blood pressure (BP) >140 mmHg and a diastolic BP >90 mmHg after 20 weeks gestation, (2) new onset proteinuria (1+ by dipstik on urinanaysis, >300 mg of protein in a 24 hour urine collection, or random urine protein/creatinine ratio >0.3), and (3) resolution of hypertension and proteinuria by 12 weeks postpartum. The symptoms of pre-eclampsia can also include renal dysfunction and glomerular endotheliosis or hypertrophy. By "symptoms of eclampsia" is meant the development of any of the following symptoms due to pregnancy or the influence of a recent pregnancy: seizures, coma, thrombocytopenia, liver edema, pulmonary edema, and cerebral edema.

By "therapeutic amount" is meant an amount that when administered to a patient suffering from a pregnancy related hypertensive disorder, such as pre-eclampsia or eclampsia, is sufficient to cause a qualitative or quantitative reduction in the symptoms of the pregnancy related hypertensive disorder as described herein. A therapeutic amount can also mean an amount that when administered to a patient suffering from a pregnancy related hypertensive disorder, such as pre-eclampsia or eclampsia, is sufficient to cause a reduction in the expression levels of any one or more of the following: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 antichymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta glucosidase. A therapeutic amount can also mean an amount that when administered to a patient suffering from a pregnancy related hypertensive disorder, such as pre-eclampsia or eclampsia, is sufficient to cause an increase in the expression levels of any one or more of the following: alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor-alternatively spliced transcript H, chemokine (CX3C motif) receptor 1, tyrosinase-related protein 1, hydoxy-delta-5-steroid dehyrogenase, dihydropyramidinase-like-4, and cytochrome P450-family 11. Assays for the measurement of the expression levels of polypeptides or a nucleic acid encoding the above polypeptides are known in the art, some of which are described herein.

By "treating" is meant administering a compound or a pharmaceutical composition for prophylactic and/or therapeutic purposes. To "treat disease" or use for "therapeutic treatment" refers to administering treatment to a subject already suffering from a disease to improve the subject's condition. Preferably, the subject is diagnosed as suffering from a pregnancy related hypertensive disorder, such as pre-eclampsia or eclampsia, based on identification of any of the characteristic symptoms described below or the use of the diagnostic methods described herein. To "prevent disease" refers to prophylactic treatment of a subject who is not yet ill, but who is susceptible to, or otherwise at risk of, developing a particular disease. Preferably a subject is determined to be at risk of developing a pregnancy related hypertensive disorder, such as pre-eclampsia or eclampsia, using the diagnostic methods described herein. Thus, in the claims and embodiments, treating is the administration to a mammal either for therapeutic or prophylactic purposes.

By "trophoblast" is meant the mesectodermal cell layer covering the blastocyst that erodes the uterine mucosa and through which the embryo receives nourishment from the mother; the cells contribute to the formation of the placenta.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

Other features and advantages of the invention will be apparent from the following description of the preferred embodiments thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A shows the amino acid sequence of follistatin related protein (FLRG) (SEQ ID NO: 1). FIG. 6B shows the DNA sequence of follistatin related protein (FLRG) (SEQ ID NO: 2).

FIG. 7A shows the amino acid sequence of interleukin 8 (SEQ ID NO: 3). FIG. 7B shows the DNA sequence of interleukin 8 (SEQ ID NO: 4).

FIG. 8A shows the amino acid sequence of inhibin A (SEQ ID NO: 5). FIG. 8B shows the DNA sequence of inhibin A (SEQ ID NO: 6).

FIG. 9A shows the amino acid sequence of VEGF-C (SEQ ID NO: 7). FIG. 9B shows the DNA sequence of VEGF-C (SEQ ID NO: 8).

FIG. 10A shows the amino acid sequence of angiogenin (SEQ ID NO: 9). FIG. 10B shows the DNA sequence of angiogenin (SEQ ID NO: 10).

FIG. 11A shows the amino acid sequence of beta fertilin (SEQ ID NO: 11). FIG. 11B shows the DNA sequence of beta fertilin (SEQ ID NO: 12).

FIG. 12 shows the DNA sequence of hypothetical protein (SEQ ID NO: 13).

FIG. 13A shows the amino acid sequence of leukocyte associated Ig-like receptor secreted protein (SEQ ID NO: 14). FIG. 13B shows the DNA sequence of leukocyte associated Ig-like receptor secreted protein (SEQ ID NO: 15).

FIG. 14A shows the amino acid sequence of erythroid differentiation protein (SEQ ID NO: 16). FIG. 14B shows the DNA sequence of erythroid differentiation prtoein (SEQ ID NO: 17).

FIG. 15A shows the amino acid sequence of adipogenesis inhibitory factor (SEQ ID NO: 18). FIG. 18B shows the DNA sequence of adipogenesis inhibitory factor (SEQ ID NO: 19).

FIG. 16A shows the amino acid sequence of corticotropin releasing factor binding protein (SEQ ID NO: 20). FIG. 16B shows the DNA sequence of corticotropin releasing factor binding protein (SEQ ID NO: 21).

FIG. 17A shows the amino acid sequence of alpha-1 anti-chymotrypsin (SEQ ID NO: 22). FIG. 17B shows the DNA sequence of alpha-1 anti-chymotrypsin (SEQ ID NO: 23).

FIG. 18A shows the amino acid sequence of insulin-like growth factor binding protein-5 (SEQ ID NO: 24). FIG. 18B shows the DNA sequence of insulin-like growth factor binding protein-S (SEQ ID NO: 25).

FIG. 19 shows the amino acid sequence of CD33L (SEQ ID NO: 26).

FIG. 20A shows the amino acid sequence of cytokine receptor like factor 1 (SEQ ID NO: 27). FIG. 20B shows the DNA sequence of cytokine receptor like factor 1 (SEQ ID NO: 28).

FIG. 21 shows the amino acid sequence of platelet derived endothelial growth factor (SEQ ID NO: 29).

FIG. 22A shows the amino acid sequence of lysyl hydroxylase isoform 2 (SEQ ID NO: 30). FIG. 22B shows the DNA sequence of lysyl hydroxylase isoform 2 (SEQ ID NO: 31).

FIG. 23A shows the amino acid sequence of stanniocalcin precursor (SEQ ID NO: 32). FIG. 23B shows the DNA sequence of stanniocalcin precursor (SEQ ID NO: 33).

FIG. 24A shows the amino acid sequence of secreted frizzled related protein (SEQ ID NO: 34). FIG. 24B shows the DNA sequence of secreted frizzled related protein (SEQ ID NO: 35).

FIG. 25A shows the amino acid sequence of galectin-3 (SEQ ID NO: 36). FIG. 25B shows the DNA sequence of galectin-3 (SEQ ID NO: 37).

FIG. 26A shows the amino acid sequence of alpha defensin (SEQ ID NO: 38). FIG. 26B shows the DNA sequence of alpha defensin (SEQ ID NO: 39).

FIG. 27A shows the amino acid sequence of ADAM-TS3 (SEQ ID NO: 40). FIG. 27B shows the DNA sequence of ADAM-TS3 (SEQ ID NO: 41).

FIG. 28 shows the DNA sequence of cholecystokinin precursor (SEQ ID NO: 42).

FIG. 29A shows the amino acid sequence of interferon stimulated T-cell alpha chemoattractant precursor (SEQ ID NO: 43). FIG. 29B shows the DNA sequence of interferon stimulated T-cell alpha chemoattractant precursor (SEQ ID NO: 44).

FIG. 30A shows the amino acid sequence of azurocidin (SEQ ID NO: 45). FIG. 30B shows the DNA sequence of azurocidin (SEQ ID NO: 46).

FIG. 31 A shows the amino acid sequence of spermine oxidase (SEQ ID NO: 47). FIG. 3 1B shows the DNA sequence of spermine oxidase (SEQ ID NO: 48).

FIG. 32A shows the amino acid sequence of UDP glycosyltransferase 2 family polypeptide B28 (SEQ ID NO: 49). FIG. 32B shows the DNA sequence of UDP glycosyltransferase 2 family polypeptide B28 (SEQ ID NO: 50).

FIG. 33A shows the amino acid sequence of neurotrophic tyrosine kinase receptor 2 (SEQ ID NO: 51). FIG. 33B shows the DNA sequence of neurotrophic tyrosine kinase receptor 2 (SEQ ID NO: 52).

FIG. 34A shows the amino acid sequence of neutral endopeptidase (SEQ ID NO: 53). FIG. 34B shows the DNA sequence of neutral endopeptidase (SEQ ID NO: 54).

FIG. 35A shows the amino acid sequence of CDC28 protein kinase regulatory subunit 2 (SEQ ID NO: 55). FIG. 35B shows the DNA sequence of CDC28 protein kinase regulatory subunit 2 (SEQ ID NO: 56).

FIG. 36 shows the DNA sequence of beta glucosidase (SEQ ID NO: 57).

FIG. 37A shows the amino acid sequence of lanosterol synthase (SEQ ID NO: 58). FIG. 37B shows the DNA sequence of lanosterol synthase (SEQ ID NO: 59).

FIG. 38 shows the DNA sequence of calcium/calmodulin-dependent serine protein kinase (SEQ ID NO: 60).

FIG. 39 shows the DNA sequence of estrogen receptor-alternatively spliced transcript H (SEQ ID NO: 61).

FIG. 40A shows the amino acid sequence of chemokine (CX3C motif) receptor 1 (SEQ ID NO: 62). FIG. 40B shows the DNA sequence of chemokine (CX3C motif) receptor 1 (SEQ ID NO: 63).

FIG. 41A shows the amino acid sequence of tyrosinase-related protein 1 (SEQ ID NO: 64). FIG. 41B shows the DNA sequence of tyrosinase-related protein 1 (SEQ ID NO: 65).

FIG. 42 shows the DNA sequence of hydroxy-delta-5-steroid dehydrogenase (SEQ ID NO: 66).

FIG. 43A shows the amino acid sequence of dihydropyramidinase-like-4 (SEQ ID NO: 67). FIG. 43B shows the DNA sequence of dihydropyramidinase-like-4 (SEQ ID NO: 68).

FIG. 44 shows the amino acid sequence of cytochrome P450 family 11 (SEQ ID NO: 69).

DETAILED DESCRIPTION

Figure 1:
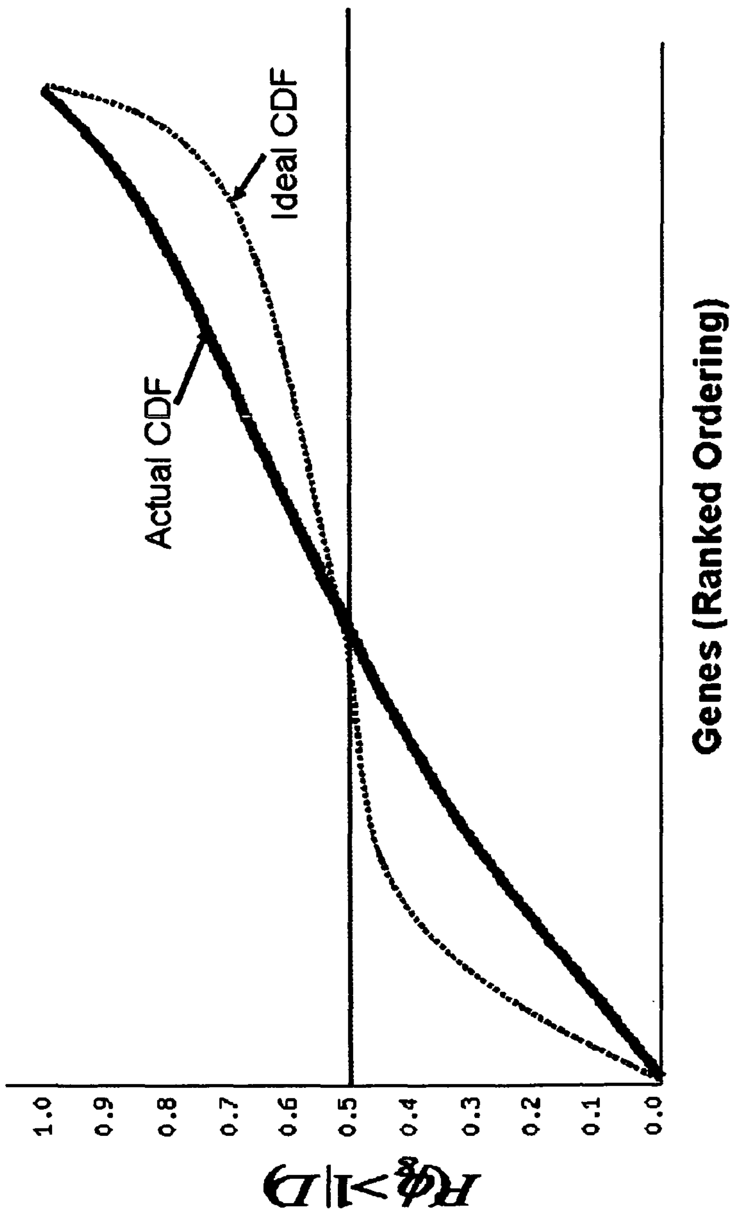
FIG. 1 is a graph showing the cumulative distribution function (CDF) for expression ratio greater than 1.0. Software BADGE (Bayesian Analysis of Gene Expression) v1.0 implements a Bayesian approach to identify differentially expressed genes across different experimental conditions. The genes are ranked in order of the conditional probability of increased fold expression given the expression data; the null probability value is 0.5. The ideal CDF has most genes near the null probability value, and few genes have high or low probabilities. For an expected false positive rate of 0.5%, we selected 78 genes, 42 upregulated and 36 downregulated.

In order to identify secreted factors involved in the pathogenesis of pregnancy related hypertensive disorders, such as pre-eclampsia, we performed gene expression profiling of placental tissue from 19 women with pre-eclampsia and 15 nomotensive pregnant women using Affymetrix U95A microarray chips. Data were analyzed using the computer program BADGE (Bayesian Analysis of Differential Gene Expression version 1.0) (http://genomethods.org/badge) (see Ramoni and Sebastiani, in Berthold and Hand eds. *Intelligent Data Analysis: An Introduction*, Springer, New York, N.Y. (1999)) and hierarchical clustering analysis (Eisen et al., *Proc. Natl. Acad. Sci.,* 95:14863-8 (1998)) to identify differentially expressed genes across experimental conditions. We discovered that the gene encoding the following secreted polypeptides showed increased expression in blood samples taken from women with pre-eclampsia: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3. We also discovered that expression levels of the genes encoding the following secreted polypeptides were decreased in blood samples taken from women with pre-eclampsia: alpha defensin, ADAM-TS3, cholecystokinin precursor, interferon stimulated T-cell alpha chemoattractant precursor, and azurocidin. In addition, we also discovered that genes encoding the following intracellular polypeptides or enzymes showed increased expression in placentas from women with pre-eclampsia: sperminine oxidase, UDP glycosyltransferase 2 family polypeptide B28, neurotrophic tyrosine kinase receptor 2, neutral endopeptidase, CDC28 protein kinase regulatory subunit 2, and beta glucosidase. Genes encoding the following intracellular gene polypeptides showed decreased expression in placentas from women with pre-eclampsia: lanosterol synthase, calcium/calmodulin-dependent serine protein kinase, estrogen receptor-alternatively spliced transcript H, chemokine (CX3C motif) receptor 1, tyrosinase-related protein 1, hydoxy-delta-5-steroid dehydrogenase, dihydropyramidinase-like-4, and cytochrome P450-family 11.

For the purposes of the descriptions below, all of the polypeptides described above are collectively referred to as “the polypeptides of the invention.” While the detailed description presented herein refers specifically to polypeptides associated with specific GenBank accession numbers, it will be clear to one skilled in the art that the detailed description can also apply to family members, isoforms, homologs, fragments, and/or variants or the specified polypeptides.

We have also discovered therapeutic agents that reduce the expression or biological activity of any one or more of the following polypeptides: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein -5, CD33L, cytokine receptor like factor 1, platelet derived endothelial growth factor, lysyl hydroxylase isoform 2, stanniocalcin precursor, secreted frizzled related protein, and galectin -3, or agents that increase the expression levels or biological activity of any one or more of the following polypeptides: alpha defensin, ADAM-TS3, cholecystokinin precursor, interferon stimulated T-cell alpha chemoattractant precursor, or azurocidin, can be used to treat or prevent pregnancy related hypertensive disorders, such as pre-eclampsia or eclampsia in a subject. Such agents include, but are not limited to, antibodies, nucleobase oligomers for antisense or RNAi, purified natural or synthetic compounds, chemical compounds, and small molecules.

The invention also features methods for measuring levels of any one or more of the polypeptides of the invention or a nucleic acid encoding a polypeptide of the invention as a detection tool for early diagnosis and management of pregnancy related hypertensive disorders, such as pre-eclampsia or eclampsia.

Diagnostics

The present invention features assays based on the detection of at least one of the polypeptides of the invention to diagnose pregnancy related hypertensive disorders, such as pre-eclampsia, eclampsia, or the propensity to develop such conditions. The present invention also features diagnostic assays based on the detection of at least two, at least three, at least four, or at least five or more polypeptides of the invention to diagnose pregnancy related hypertensive disorders, such as pre-eclampsia, eclampsia, or a predisposition to such conditions. Levels of any one or more of the polypeptides of the invention (either free, bound, or total levels) are measured in a subject sample and used as an indicator of a pregnancy related hypertensive disorder, such as pre-eclampsia, eclampsia, or a predisposition to such conditions. The diagnostic methods can also be combined with methods to detect levels of any additional markers of pregnancy related hypertensive disorders, such as pre-eclampsia or eclampsia, such as soluble endoglin, sFlt-1, VEGF, or PlGF. In one embodiment, a metric incorporating the levels of any one or more of the polypeptides of the invention, soluble endoglin, sFlt-1, VEGF, or PlGF, or any combination thereof, is used to determine whether a relationship between levels of at least two of the polypeptides is indicative of pre-eclampsia or eclampsia.

Standard methods may be used to measure levels of any one or more of the polypeptides of the invention in any bodily fluid, including, but not limited to, urine, blood, serum, plasma, saliva, amniotic fluid, or cerebrospinal fluid. Such methods include immunoassay, ELISA, western blotting using antibodies directed to the polypeptide of the invention and quantitative enzyme immunoassay techniques such as those described in Ong et al. (*Obstet. Gynecol.* 98:608-611, 2001) and Su et al. (*Obstet. Gynecol.,* 97:898-904, 2001). ELISA assays are the preferred method for measuring levels of a polypeptide of the invention. In preferred embodiments, the level of follistatin related protein, inhibin-A, beta fertilin, or insulin-like growth factor binding protein -5 is measured. In additional preferred embodiments, the body mass index (BMI) and gestational age of the fetus is also measured and included the diagnostic metric. For example, if the level of any of the following polypeptides: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3 is increased (e.g., 10%, 20%, 30%, 40%, 50%, 60%, 70%, 80%, 90% or more), relative to a reference sample, this is considered a positive indicator of a pregnancy related hypertensive disorder, such as pre-eclampsia or eclampsia. In another example, if the levels of any one of the following proteins: alpha defensin, ADAM-TS3, cholecystokinin precursor, interferon stimulated T-cell alpha chemoattractant precursor, and azurocidin is decreased (e.g., 10%, 20%, 30%, 40%, 50%, 60%, 70%, 80%, 90%, 95%, 96%, 97%, 98%, 99% or more), relative to a reference sample, this is considered a positive indicator of a pregnancy related hypertensive disorder, such as pre-eclampsia or eclampsia.

Metrics measuing the levels of sFlt-1, VEGF, PlGF, and/or soluble endoglin can also be used in combination with any of the diagnostic methods of the invention. For example, the PAAI (sFlt-1/VEGF+PlGF) is used, in combination with measurement of any one or more polypeptides of the invention, as an anti-angiogenic index that is diagnostic of pregnancy related hypertensive disorders, such as pre-eclampsia, eclampsia, or the propensity to develop such conditions. The PAAI (sFlt-1/VEGF+PlGF) ratio is merely one example of a useful metric that may be used as a diagnostic indicator. It is not intended to limit the invention. Another example is the following soluble endoglin anti-angiogenic index: (sFlt-1+0.25(soluble endoglin polypeptide))/PlGF. Virtually any metric that detects an alteration in the levels of any polypeptide of the invention, soluble endoglin, sFlt-1, PlGF, or VEGF, or any combination thereof, in a subject relative to a reference sample may be used as a diagnostic indicator. One example of a metric that can be used in the diagnostic methods of the invention is (sFlt1+soluble endoglin+follistatin related protein)/PlGF.

Expression levels of particular nucleic acids or polypeptides may be correlated with a particular disease state (e.g., pregnancy related hypertensive disorders, such as pre-eclampsia or eclampsia), and thus are useful in diagnosis. Oligonucleotides or longer fragments derived from a nucleic acid sequence encoding a polypeptide of the invention may be used as a probe not only to monitor expression, but also to identify subjects having a genetic variation, mutation, or polymorphism in a nucleic acid molecule, encoding a polypeptide of the invention, that is indicative of a predisposition to develop the conditions. These polymorphisms may affect nucleic acid or polypeptide expression levels or biological activity. Detection of genetic variation, mutation, or polymorphism relative to a normal, reference sample can be used as a diagnostic indicator of a pregnancy related hypertensive disorder, such as pre-eclampsia, eclampsia, or a predisposition to develop such disorders.

Such genetic alterations may be present in the promoter sequence, an open reading frame, intronic sequence, or untranslated 3' region of a gene. Information related to genetic alterations can be used to diagnose a subject as having a pregnancy related hypertensive disorder, such as pre-eclampsia, eclampsia, or a predisposition to develop such conditions. As noted throughout, specific alterations in the levels of biological activity of any polypeptide of the invention or any combination thereof, can be correlated with the likelihood of developing a pregnancy related hypertensive disorder, such as pre-eclampsia or eclampsia, or the predisposition to the same. As a result, one skilled in the art, having detected a given mutation, can then assay one or more of the biological activities of the polypeptide to determine if the mutation causes or increases the likelihood of pre-eclampsia or eclampsia.

In one embodiment, a subject having pre-eclampsia, eclampsia, or a propensity to develop such conditions will show an alteration in the expression of a nucleic acid encoding a polypeptide of the invention. Methods for detecting such alterations in nucleic acids are standard in the art and are described in Ausubel et al., supra. In one example northern blotting or real-time PCR is used to detect mRNA levels for a nucleic acid encoding any polypeptide of the invention.

In another embodiment, hybridization with PCR probes that are capable of detecting a nucleic acid molecule encoding a polypeptide of the invention, including genomic sequences, or closely related molecules, may be used to hybridize to a nucleic acid sequence derived from a subject having a pregnancy related hypertensive disorder, such as pre-eclampsia or eclampsia, or at risk of developing such conditions. The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques may be used to identify mutations indicative of a pregnancy related hypertensive disorder, such as pre-eclampsia or eclampsia, or may be used to monitor expression levels of a gene encoding a polypeptide of the invention (for example, by Northern analysis, Ausubel et al., supra).

A subject having a pregnancy related hypertensive disorder, such as pre-eclampsia, eclampsia, or a propensity to develop such conditions will show an increase relative to a reference sample or level (e.g., 10%, 20%, 30%, 40%, 50%, 60%, 70%, 80%, 90%, 95%, 96%, 97%, 98%, 99% or more) in the expression of a secreted or intracellular polypeptide or a nucleic acid encoding a secreted or intracellular polypeptide selected from the group consisting of: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-I anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta glucosidase, relative to a reference sample. In another example, a subject having a pregnancy related hypertensive disorder, such as pre-eclampsia, eclampsia, or a propensity to develop such conditions will show a decrease (e.g., 10%, 20%, 30%, 40%, 50%, 60%, 70%, 80%, 90%, 95%, 96%, 97%, 98%, 99% or more) relative to a reference sample or level in the expression of a secreted or intracellular polypeptide or a nucleic acid encoding a secreted or intracellular polypeptide selected from the group consisting of: alpha defensin, ADAM-TS3, cholecystokinin precursor, interferon stimulated T-cell alpha chemoattractant precursor, azurocidin lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11, relative to a reference sample.

A variety of protocols for measuring an alteration in the expression of such polypeptides are known, including immunological methods (such as ELISAs and RIAs), and provide a basis for diagnosing a pregnancy related hypertensive disorder, such as pre-eclampsia or eclampsia, or a risk of developing such conditions.

In one embodiment, the level of at least one polypeptide or nucleic acid encoding a polypeptide of the invention is measured in combination with the level of soluble endoglin, sFlt-1, VEGF, or PlGF polypeptide or nucleic acid, or any combination thereof. Methods for the measurement of sFlt-1, VEGF, PlGF, and soluble endoglin are described in U.S. Patent Application Publication Numbers U.S. Patent Application Publication Numbers 20040126828, 20050025762, and 20050170444; PCT Publication Numbers WO 2004/008946 and WO 2005/077007; and U.S. patent application Ser. No. 11/235,577, each of which is hereby incorporated by reference in its entirety.

In one example, the measurement of any of the nucleic acids or polypeptides described herein preferably occurs on at least two different occasions and an alteration in the levels over time is used as an indicator of a pregnancy related hypertensive disorder, such as pre-eclampsia or eclampsia, or the propensity to develop such conditions. In another example, the measurement of any of the nucleic acids or polypeptides described herein is compared to a reference sample and an alteration as compared to normal reference levels is used as an indicator of a pregnancy related hypertensive disorder, such as pre-eclampsia or eclampsia, or the propensity to develop such conditions.

The level of any polypeptide of the invention in the bodily fluids of a subject having pre-eclampsia, eclampsia, or the propensity to develop such conditions may be altered by as little as 10%, 20%, 30%, or 40%, or by as much as 50%, 60%, 70%, 80%, 90%, 95%, 96%, 97%, 98%, 99% or more relative to the level of the same polypeptide in a reference sample. The level of any polypeptide of the invention in the bodily fluids of a subject having a pregnancy related hypertensive disorder, such as pre-eclampsia or eclampsia, or the propensity to develop such conditions may be altered by as little as 10%, 20%, 30%, or 40%, or by as much as 50%, 60%, 70%, 80%, 90%, 95%, 96%, 97%, 98%, 99% or more over time from one measurement to the next.

In one embodiment, a subject sample of a bodily fluid (e.g., urine, plasma, serum, amniotic fluid, or cerebrospinal fluid) is collected early in pregnancy prior to the onset of symptoms of the pregnancy related hypertensive disorder, such as pre-eclampsia or eclampsia. In another example, the sample can be a tissue or cell collected early in pregnancy prior to the onset of symptoms of the pregnancy related hypertensive disorder. Non-limiting examples include placental tissue, placental cells, endothelial cells, and leukocytes such as monocytes. In humans, for example, maternal blood serum samples are collected from the antecubital vein of pregnant women during the first, second, or third trimesters of the pregnancy. Preferably, the assay is carried out during the first trimester, for example, at 4, 6, 8, 10, or 12 weeks, or during the second trimester, for example at 14, 16, 18, 20, 22, or 24 weeks. Such assays may also be conducted at the end of the second trimester or the third trimester, for example at 26, 28, 30, 32, 34, 36, 38, or 40 weeks. It is preferable that levels of one or more polypeptides of the invention be measured twice during this period of time. For the diagnosis of post-partum pre-eclampsia or eclampsia, the assay is carried out postpartum. For the diagnosis of a predisposition to a pregnancy related hypertensive disorder, such as pre-eclampsia or eclampsia, the assay may be carried out prior to the onset of pregnancy. In one example, for the monitoring and management of therapy, the assay is carried out after the diagnosis of pre-eclampsia but during the pregnancy.

In one particular example, a sample of bodily fluid (e.g., (blood, serum, plasma, urine, amniotic fluid, and cerebrospinal fluid) is collected during pregnancy and the levels of at least one polypeptide of the invention determined by ELISA. In another example, a sample is collected during the second trimester and early in the third trimester and in increase or decrease in the level of a polypeptide of the invention from the first sampling to the next is indicative of pre-eclampsia or eclampsia, or the propensity to develop either. In another particular example, serial blood samples can be collected during pregnancy and the levels of any one or more of the polypeptides of the invention determined by ELISA. In another example, a sample is collected during the second trimester and early in the third trimester and an alteration in the levels of any one or more of the polypeptides of the invention from the first sampling to the next is indicative of a pregnancy related hypertensive disorder, such as pre-eclampsia or eclampsia, or a predisposition thereto.

In veterinary practice, assays may be carried out at any time during the pregnancy but are preferably carried out early in pregnancy, prior to the onset of symptoms of the pregnancy related hypertensive disorder, such as pre-eclampsia or eclampsia. Given that the term of pregnancies varies widely between species, the timing of the assay will be determined by a veterinarian, but will generally correspond to the timing of assays during a human pregnancy.

The diagnostic methods described herein can be used individually or in combination with any other diagnostic method described herein for a more accurate diagnosis of the presence of, severity of, or estimated time of onset of the pregnancy related hypertensive disorder, such as pre-eclampsia or eclampsia. For example, the diagnostic methods using the nucleic acids that encode the polypeptides of the invention can be used initially and then increased expression of the polypeptide can be confirmed using standard immunological methods (e.g., western blooting or ELISA). In addition, the diagnostic methods described herein can be used in combination with any other diagnostic methods determined to be useful for the accurate diagnosis of the presence of, severity of, or estimated time of onset of the pregnancy related hypertensive disorder, such as pre-eclampsia or eclampsia. The diagnostic methods described herein can also be used to monitor and manage pregnancy related hypertensive disorders, such as pre-eclampsia or eclampsia in a subject.

Expression level of each polypeptide or nucleic acids encoding polypeptides of the invention may be considered individually, although it is within the scope of the invention to provide combinations of two or more polypeptides of the invention or nucleic acids encoding polypeptides of the invention for use in the methods and compositions of the invention to increase the confidence of the analysis. A panel comprises two or more polypeptides of the invention, or fragments thereof, two or more, 2-5, 5-10, 10-15, 15-20, 20-25 or more than 25 nucleic acid molecules, or fragments thereof or complementary nucleic acid molecules, or two or more binding molecules, such as antibodies, that recognize a polypeptide of the invention. In one embodiment, these panels of polypeptides of the invention are selected such that the polypeptides of the invention within any one panel share certain features, such as polypeptides that are shown herein to be increased in samples from pre-eclamptic women. Similarly, different panels of polypeptides of the invention may be composed of polypeptides of the invention representing different stages of a pregnancy related hypertensive disorder, for example separate panels for mild-pre-eclampsia, to severe pre-eclampsia, to eclampsia. Panels of the polypeptides of the invention can also include binding molecules (e.g., antibodies) that specifically bind sFlt-1, VEGF, PlGF, and soluble endoglin, and may further be provided on biochips, as discussed below.

Diagnostic Kits

The invention also provides for a diagnostic test kit. The diagnostic test kit includes the components or reagents required to carry out any of the diagnostic assays described above and instructions for the use of the components or reagents to diagnose a pregnancy related hypertensive disorder, such as pre-eclampsia or eclampsia, or a predisposition to a pregnancy related hypertensive disorder, such as pre-eclampsia or eclampsia. For example, a diagnostic test kit can include antibodies to any polypeptide of the invention and components required to detect, and more preferably to evaluate, binding between the antibodies and the polypeptide of the invention. Non-limiting examples of antibodies useful in the diagnostic methods and kits of the invention include human FLRG antibody, catalog number AF1288, R&D systems, Minneapolis, Minn. and human secreted frizzled related protein antibody, catalog number AF1384, R&D systems, Minneapolis, Minn. For detection, either the antibody or the polypeptide of the invention is labeled, and either the antibody or the polypeptide of the invention is substrate-bound, such that polypeptide of the invention-antibody interaction can be established by determining the amount of label attached to the substrate following binding between the antibody and the polypeptide of the invention. A conventional ELISA is a common, art-known method for detecting antibody-substrate interaction and can be provided with the kit of the invention. Polypeptides of the invention can be detected in virtually any bodily fluid including, but not limited to urine, serum, plasma, saliva, amniotic fluid, or cerebrospinal fluid. The invention also provides for a diagnostic test kit that includes a nucleic acid encoding a polypeptide of the invention that can be used to detect and determine levels of nucleic acids encoding a polypeptide of the invention. A kit that determines an alteration in the level of a polypeptide of the invention relative to a reference, such as the level present in a normal control, is useful as a diagnostic kit in the methods of the invention.

The diagnostic kits of the invention can also include antibodies or nucleic acids for the detection of soluble endoglin, sFlt-1, VEGF, or PlGF polypeptides or nucleic acids as described in U.S. Patent Application Publication Numbers 20040126828, 20050025762, and 20050170444; PCT Publication Numbers WO 2004/008946 and WO 2005/077007; and U.S. patent application Ser. No. 11/235,577.

Desirably, the kit includes any of the components needed to perform any of the diagnostic methods described above. In one embodiment of the invention, such a kit includes a solid support (e.g., a membrane or a microtiter plate) coated with a primary agent (e.g., an antibody or protein that recognizes the antigen), standard solutions of purified protein for preparation of a standard curve, a body fluid (e.g. serum or urine) control for quality testing of the analytical run, a secondary agent (e.g., a second antibody reactive with a second epitope in the antigen to be detected or an antibody or protein that recognizes the primary antibody) conjugated to a label or an enzyme such as horse radish peroxidase or otherwise labeled, a substrate solution, a stopping solution, a washing buffer and an instruction manual. The membrane can be supported on a dipstick structure where the sample is deposited on the membrane by placing the dipstick structure into the sample or the membrane can be supported in a lateral flow cassette where the sample is deposited on the membrane through an opening in the cassette. The kit can also be in an array format and can include an array of polypeptides of the invention or binding molecules that specifically bind polypeptides of the invention arranged on a biochip, such as, for example, a GeneChip™.

The diagnostic kits also generally include a label or instructions for the intended use of the kit components and a reference sample or purified proteins to be used to establish a standard curve. In one example, the kit contains instructions for the use of the kit for the diagnosis of a pregnancy related hypertensive disorder, such as pre-eclampsia or eclampsia, or the propensity to develop pre-eclampsia or eclampsia. In yet another example, the kit contains instructions for the use of the kit to monitor therapeutic treatment or dosage regimens for the treatment of pregnancy related hypertensive disorders, such as pre-eclampsia or eclampsia. It will be understood that the reference sample values will depend on the intended use of the kit. For example, the sample can be compared to a normal reference value, wherein an alteration in the levels of one or more of the polypeptides of the invention or a metric using levels of one or more of the polypeptides of the invention is indicative of a pregnancy related hypertensive disorder, such as pre-eclampsia or eclampsia, or a predisposition to pre-eclampsia or eclampsia. In another example, a kit used for therapeutic monitoring can have a reference value that is indicative of a pregnancy related hypertensive disorder, such as pre-eclampsia or eclampsia, wherein an alteration in the level of one or more of the polypeptides of the invention or a metric using levels of one or more of the polypeptides of the invention relative to the reference sample can be used to indicate therapeutic efficacy or effective dosages of therapeutic compounds.

Arrays and Biochips

The invention also includes an array comprising a panel of polypeptides of the invention. The array can be used to assay expression of one or more genes or polypeptides in the array.

It will be appreciated by one skilled in the art that the panels of polypeptides of the invention of the invention may be provided on solid supports, as a biochip. For example, polynucleotides may be coupled to an array (e.g., a biochip using GeneChip™ for hybridization analysis), to a resin (e.g., a resin which can be packed into a column for column chromatography), or a matrix (e.g., a nitrocellulose matrix for northern blot analysis). The immobilization of nucleic acid molecules complementary to nucleic acid molecules encoding any of the polypeptides of the invention, either covalently or noncovalently, permits a discrete analysis of the presence or activity of each of the nucleic acid molecules encoding the polypeptides of the invention in a sample. In an array, for example, polynucleotides complementary to each member of a panel of nucleic acid molecules encoding polypeptides of the invention may individually be attached to different, known locations on the array. The array may be hybridized with, for example, polynucleotides extracted from a bodily fluid, tissue, or cell sample from a subject. The hybridization of polynucleotides from the sample with the array at any location on the array can be detected, and thus the presence or quantity of the nucleic acids or transcripts encoding polypeptides of the invention in the sample can be ascertained. In one embodiment, an array based on a biochip is employed. Similarly, immunological analyses may be performed using protein arrays or antibody arrays that include immobilized antibodies or other binding molecules specific for polypeptides of the invention. Such protein arrays can be hybridized with a bodily fluid, tissue, or cell sample, which contains polypeptides of the invention or antibodies to polypeptides of the invention, from a subject. Additional details on examples of arrays and biochips can be found, for example, in U.S. Patent Application Publication No. 20050266409, herein incorporated by reference.

Exemplary Binding Molecules and Antibodies

Examples of antibodies and binding proteins that can be used in the diagnostic methods and kits of the invention are described below. The antibodies described below can also be used in the therapeutic methods of the invention and can be modified to increase potency or stability or to reduce reactivity to the antibodies. These examples are intended to illustrate the invention and not to limit the invention in anyway.

Follistatin Related Protein

Follistatin related protein, also known as FLRG, FSRP, FRP, FLS-1, and FSTL1, is a protein related to follistatin. Follistatin is a secreted glycoprotein that binds activin in vitro and in vivo and inhibits the biological functions of activin. Follistatin related protein also binds to activin with high affinity and is expressed in the basement membrane between the dermis and the epidermis and around blood vessels. The gene encoding follistatin related protein, FLRG, was induced during the wound healing process (Wankell et al., *J. Endocrin.* 171:385-395 (2001) and Tortoriello et al., *Endocrinology* 142:3426-3434 (2001)).

Activin and other TGFβ superfamily members, or fragments thereof, can be used as specific binding molecules to detect follistatin related protein in a biological sample. Exemplary antibodies that specifically bind follistatin related protein that can also be used to detect follistatin related protein in a biological sample include the polyclonal FSRP antibody described in Tortorielle et al., supra, and antibodies available from Abnova Corporation (e.g., catalog no. H00010468-A01) and human FLRG antibody, R&D systems (e.g., catalog nos. AF1288 and AF1694).

Inhibin A

Inhibin is a disulfide-linked, dimeric glycoprotein composed of an a-subunit and one of two β-subunits. Inhibin is a member of the TGFβ superfamily and is expressed in the adrenal cortex. One hypothesis regarding inhibin action is that inhibin binds the membrane bound serine-threonine kinase ActRII subunit, and blocks the signal generating subunit (ActRI) phosphorylation, thereby antagonizing activin activation. One example of a protein that specifically binds to inhibin A is betaglycan (Vale et al., *Ann. N. Y. Acad. Sci.* 1038:142-147 (2004). Betaglycan, or fragments thereof, can be used as specific binding molecules to detect follistatin related protein in a biological sample. Examples of antibodies, or antigen binding fragments thereof, that specifically bind inhibin A that can also be used to detect inhibin A in a biological sample include antibodies available from Abnova Corp. (e.g., catalog no. H00003624-A01), Abcam (e.g., catalog no. Ab10599, Ab724), and Genetex (e.g., catalog no. GTX10599 and GTX20724), and the antibody described in Rishi et al., *Am. J. Surg. Pathol.* 21:583-589 (1997).

Beta Fertilin

Beta fertilin, also known as fertilin beta, is a sperm protein that is a candidate molecule fro mediating the binding and fusion of the sperm and egg plasma membranes. Fertilin is a heterodimer with a beta subunit that has a region of homology to the disintegrin family of integrin ligands and an alpha subunit that has a region of homology to viral fusion peptides. Fertilin alpha and beta have also been shown to interact with the heat shock protein calmegin. (Ikawa et al., *Dev. Biol.* 240:254-261 (2001) and Evans et al., *Dev. Biol.* 187:94-106 (1997)).

Calmegin, or fragments thereof, can be used as specific binding molecules to detect beta fertilin in a biological sample. Examples of antibodies, or antigen binding fragments thereof, that specifically bind beta fertilin that can also be used to detect beta fertilin in a biological sample include the antibodies described in Ikawa et al., supra, and antibodies commercially available from Chemicon (e.g., catalog nos. MAB 19292 and 19030) and United States Biological (e.g., catalog no. A0858-070).

Insulin Like Growth Factor Binding Protein-5

Insulin like growth factor binding protein-5, also known as IGFBP-5 or ILGFBP-5, is a member of the superfamily of insulin-like growth factor binding proteins, which are cysteine-rich proteins with conserved cysteine residues clustered in the amino-terminal and the carboxy-terminal regions of the molecule. IGFBP-5 interacts with IGF-I and functions to inhibit the survival effect of IGF-I (Tonner et al., *Development* 129:4547-4557 (2002)) and modulate IGF-I ligand-receptor interactions (Tonner et al., *Adv. Exp. Med. Biol.* 480:45-53 (2000)). Additional IGFBP-5 binding proteins include plasminogen activator inhibitor-1 (Tonner et al., *J. Endocrinol.* 167:265-73 (2000)) and alphas2-casein (Tonner et al., *Adv. Exp. Med. Biol.* 480:45-53 (2000)).

IGF, plasminogen activator inhibitor-1, alpha s2-casein, or any fragments thereof, can be used as specific binding molecules to detect IGFBP-5 in a biological sample. Examples of antibodies, or antigen binding fragments thereof, that specifically bind IGFBP-5 that can also be used to detect IGFBP-5 in a biological sample include the antibodies from Diagnostic Systems Laboratories Inc. (e.g., catalog no. R00737), Alpha Diagnostic International (e.g., catalog no. IGFBP5-1s) and Abcam (e.g., catalog no. Ab4257).

Secreted Frizzled Related Protein

The secreted frizzled related proteins are a family of secreted proteins that contain an N-terminal signal peptide, a frizzled-related CRD, and a C-terminal hydrophilic region with some homology to the netrins, but lack evidence of any transmembrane domains.

The secreted frizzled related proteins appear to act as soluble modulators of Wnt signaling, presumably by competing with membrane frizzled receptors for the binding of secreted Wnt ligands.

Any Wnt family member protein, or any fragments thereof, can be used as specific binding molecules to detect secreted frizzled related protein in a biological sample. One example of an antibody that specifically binds secreted frizzled related protein and can be used to detect secreted frizzled related protein in a biological sample is the human secreted frizzled related protein antibody, (catalog no. AF1384) from R&D systems.

Screening Assays

As discussed above, the expression level of one ore more polypeptides of the invention or nucleic acids encoding a polypeptide of the invention is altered in a subject having a pregnancy related hypertensive disorder, such as pre-eclampsia or eclampsia, or a propensity to develop such conditions. Based on these discoveries, polypeptides of the invention (both intracellular and secreted) are useful for the high-throughput low-cost screening of candidate compounds to identify those that modulate the expression of a polypeptide of the invention or nucleic acid molecule encoding a polypeptide of the invention whose expression is altered in a subject having a pregnancy related hypertensive disorder, such as pre-eclampsia or eclampsia.

Any number of methods are available for carrying out screening assays to identify new candidate compounds that alter the expression of a nucleic acid molecule encoding a polypeptide of the invention. In one working example, candidate compounds are added at varying concentrations to the culture medium of cultured cells expressing a nucleic acid sequence encoding a polypeptide of the invention. Exemplary cell cultures include any mammalian, yeast, insect, or bacterial cell cultures. Preferred cell cultures include mammalian cell cultures such as trophoblasts (e.g., BEWO, JAR, and JEG cells) and HUVECs. These cells can then be used to screen for new candidate compounds. Gene expression is then measured, for example, by microarray analysis, Northern blot analysis (Ausubel et al., supra), or RT-PCR, using any appropriate fragment prepared from the nucleic acid molecule as a hybridization probe. The level of gene expression in the presence of the candidate compound is compared to the level measured in a control culture medium lacking the candidate compound. A compound considered to be useful in the invention is one that promotes a decrease in the expression of a polypeptide, or fragment thereof, or a nucleic acid molecule encoding the polypeptide, or fragment thereof, selected from the following group of polypeptides: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein -5, CD33L, cytokine receptor like factor 1, platelet derived endothelial growth factor, lysyl hydroxylase isoform 2, stanniocalcin precursor, secreted frizzled related protein, and galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta-glucosidase. Additional useful compounds are compounds that promote an increase in the expression of a polypeptide, or fragment thereof, or a nucleic acid molecule encoding the polypeptide, or fragment thereof, selected from the following group of polypeptides: alpha defensin, ADAM-TS3, cholecystokinin precursor, interferon stimulated T-cell alpha chemoattractant precursor, and azurocidin, or the level of any one of the following intracellular polypeptides, or fragments thereof, in a sample from the subject: lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11. Such compounds may be used, for example, as a therapeutic to treat pregnancy related hypertensive disorders, such as pre-eclampsia or eclampsia, in a subject.

In another working example, the effect of candidate compounds may be measured at the level of polypeptide production using the same general approach and standard immunological techniques, such as Western blotting or immunoprecipitation with an antibody specific for a polypeptide of the invention. For example, immunoassays may be used to detect or monitor the expression of at least one of the polypeptides of the invention in an organism. Polyclonal or monoclonal antibodies (produced as described above) that are capable of binding to such a polypeptide may be used in any standard immunoassay format (e.g., ELISA, western blot, or RIA assay) to measure the level of the polypeptide. In some embodiments, a compound that promotes a decrease in the expression or biological activity of a polypeptide of the invention is considered particularly useful. Again, such a molecule may be used, for example, as a therapeutic to delay, ameliorate, or treat the pregnancy related hypertensive disorder, such as pre-eclampsia or eclampsia, or the symptoms of the pregnancy related hypertensive disorder in a subject.

In yet another working example, candidate compounds may be screened to identify those that specifically bind to a polypeptide of the invention. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind a polypeptide of the invention.

In another working example, a nucleic acid encoding a polypeptide of the invention is expressed as a transcriptional or translational fusion protein with a detectable reporter, and expressed in an isolated cell (e.g., mammalian or insect cell) under the control of a heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that alters (e.g., increases or decreases) the expression of a polypeptide of the invention fused to a detectable reporter is a compound that is useful for the treatment of a pregnancy related hypertensive disorder, such as pre-eclampsia or eclampsia.

In one particular working example, a candidate compound that binds to a polypeptide of the invention may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the immobilized polypeptide of the invention is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to alter (e.g., increase or decrease) the activity of a polypeptide of the invention. Compounds isolated by this approach may also be used, for example, as therapeutics to treat a pregnancy related hypertensive disorder, such as pre-eclampsia or eclampsia, in a human subject. Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized to identify compounds or proteins that bind to a polypeptide of the invention.

Potential antagonists include organic molecules, peptides, peptide mimetics, polypeptides, nucleic acids, and antibodies that bind to a polypeptide of the invention or a nucleic acid sequence encoding a polypeptide of the invention.

DNA sequences encoding a polypeptide of the invention may also be used in the discovery and development of a therapeutic compound for the treatment of a pregnancy related hypertensive disorder, such as pre-eclampsia or eclampsia. The encoded polypeptide, upon expression, can be used as a target for the screening of drugs. Additionally, the DNA sequences encoding the amino terminal regions of the encoded polypeptide or Shine-Delgarno or other translation facilitating sequences may be isolated by standard techniques (Ausubel et al., supra).

Optionally, compounds identified in any of the above-described assays may be confirmed as useful in an assay for compounds that alter (e.g., increase or decrease) the biological activity of a polypeptide of the invention using standard assays such as those described herein.

Small molecules of the invention preferably have a molecular weight below 2,000 daltons, more preferably between 300 and 1,000 daltons, and most preferably between 400 and 700 daltons. It is preferred that these small molecules are organic molecules.

Test compounds and extracts In general, compounds capable of altering (e.g., increasing or decreasing) the activity of a polypeptide of the invention are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their molt-disrupting activity should be employed whenever possible.

When a crude extract is found to alter (e.g., increase or decrease) the activity of a polypeptide of the invention by at least 10%, 20%, 30%, 40%, 50%, 60%, 70%, 80%, 90%, or more, or to bind to a polypeptide of the invention, further fractionation of the positive lead extract is necessary to isolate chemical constituents responsible for the observed effect. Thus, the goal of the extraction, fractionation, and purification process is the careful characterization and identification of a chemical entity within the crude extract that alters (e.g., increases or decreases) the activity of a polypeptide of the invention. Methods of fractionation and purification of such heterogeneous extracts are known in the art. If desired, compounds shown to be useful as therapeutics for the treatment of a pregnancy related hypertensive disorder in a human are chemically modified according to methods known in the art.

Therapeutics

The present invention features methods and compositions for treating or preventing pregnancy related hypertensive disorders, such as pre-eclampsia or eclampsia, in a subject. We have discovered that levels of follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3 are increased in subjects having pregnancy related hypertensive disorders, such as pre-eclampsia or eclampsia, or predisposition thereto. Therefore, the invention includes methods and agents that decrease the expression levels or biological activity of any one or more of these polypeptides or nucleic acid molecules. Such agents include compounds that downregulate or inhibit the biological activity of any one or more of the above polypeptides; a purified antibody or antigen-binding fragment that specifically binds any one of the above polypeptides; antisense nucleobase oligomers; and dsRNAs targeting any of the above polypeptides. These methods are described in detail below.

We have also discovered that the levels of alpha defensin, ADAM-TS3, cholecystokinin precursor, interferon stimulated T-cell alpha chemoattractant precursor, and azurocidin are decreased in subjects having a pregnancy related hypertensive disorder, such as pre-eclampsia or eclampsia, or a predisposition to develop such conditions. Therefore, the invention also includes any methods and agents that increase the expression levels or biological activity of any one or more of these polypeptides or nucleic acid molecules. Such agents include compounds that upregulate or increase the biological activity of any one or more of the above polypeptides or purified forms of the polypeptides themselves.

These methods and agents can be combined with any additional therapies for pregnancy related hypertensive disorders such as therapeutics aimed at decreasing sFlt-1 or soluble endoglin levels or increasing VEGF or PlGF levels as described in U.S. Patent Application Publication Numbers 20040126828, 20050025762, and 20050170444; PCT Publication Numbers WO 2004/008946 and WO 2005/077007; and U.S. patent application Ser. No. 11/235,577.

In addition to the use of compounds that can increase the levels of any of the above polypeptides in a subject sample, the invention provides for the use of any chronic hypertension medications used in combination with any of the therapeutic methods described herein. Medications used for the treatment of hypertension during pregnancy include methyldopa, hydralazine hydrochloride, or labetalol. For each of these medications, modes of administration and dosages are determined by the physician and by the manufacturer's instructions.

Purified Proteins

In a preferred embodiment of the present invention, purified forms of any one or more of the following polypeptides: alpha defensin, ADAM-TS3, cholecystokinin precursor, interferon stimulated T-cell alpha chemoattractant precursor, and azurocidin are administered to the subject in order to treat or prevent pregnancy related hypertensive disorders, such as pre-eclampsia or eclampsia.

Purified alpha defensin, ADAM-TS3, cholecystokinin precursor, interferon stimulated T-cell alpha chemoattractant precursor, and azurocidin polypeptides include any polypeptide with an amino acid sequence that is homologous, more desirably, substantially identical to the amino acid sequence of alpha defensin, ADAM-TS3, cholecystokinin precursor, interferon stimulated T-cell alpha chemoattractant precursor, and azurocidin, that can induce angiogenesis or that is capable of promoting selective growth of vascular endothelial cells or umbilical vein endothelial cells.

Therapeutic Nucleic Acids

Recent work has shown that the delivery of nucleic acid molecules (e.g., DNA or RNA) capable of expressing an endothelial cell mitogen such as VEGF to the site of a blood vessel injury will induce proliferation and reendothelialization of the injured vessel. While the present invention does not relate to blood vessel injury, these general techniques for the delivery of nucleic acid to endothelial cells can be used in the present invention for the delivery of nucleic acids encoding alpha defensin, ADAM-TS3, cholecystokinin precursor, interferon stimulated T-cell alpha chemoattractant precursor, or azurocidin. These general techniques are described in U.S. Pat. Nos. 5,830,879 and 6,258,787 and are incorporated herein by reference.

In the present invention, the nucleic acid molecule may be any nucleic acid (e.g., DNA or RNA) including genomic DNA, cDNA, and mRNA, encoding any of the following: alpha defensin, ADAM-TS3, cholecystokinin precursor, interferon stimulated T-cell alpha chemoattractant precursor, or azurocidin. The nucleic acids encoding the desired protein may be obtained using routine procedures in the art, e.g. recombinant DNA, PCR amplification.

Modes for Delivering Nucleic Acids

For any of the nucleic acid applications described herein, standard methods for administering nucleic acids can be used. For example, to simplify the manipulation and handling of the nucleic acid encoding any of the following polypeptides: alpha defensin, ADAM-TS3, cholecystokinin precursor, interferon stimulated T-cell alpha chemoattractant precursor, or azurocidin; the nucleic acid is preferably inserted into a cassette where it is operably linked to a promoter. The promoter must be capable of driving expression of the polypeptide in the desired target host cell. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum. Gene Ther.* 4:151-159, 1993) and mouse mammary tumor virus (MMTV) promoters may also be used. Certain proteins can be expressed using their native promoter. Other elements that can enhance expression can also be included (e.g., enhancers or a system that results in high levels of expression such as a tat gene and tar element). The recombinant vector can be a plasmid vector such as pUC118, pBR322, or other known plasmid vectors, that includes, for example, an *E. coli* origin of replication (see, Sambrook, et al., Molecular Cloning: A Laboratory Manual, Cold Spring Harbor Laboratory press, 1989). The plasmid vector may also include a selectable marker such as the β lactamase gene for ampicillin resistance, provided that the marker polypeptide does not adversely affect the metabolism of the organism being treated. The cassette can also be bound to a nucleic acid binding moiety in a synthetic delivery system, such as the system disclosed in PCT Publication No. WO95/22618.

The nucleic acid can be introduced into the cells by any means appropriate for the vector employed. Many such methods are well known in the art (Sambrook et al., supra, and Watson et al., "Recombinant DNA", Chapter 12, 2d edition, Scientific American Books, 1992). Recombinant vectors can be transferred by methods such as calcium phosphate precipitation, electroporation, liposome-mediated transfection, gene gun, microinjection, viral capsid-mediated transfer, polybrene-mediated transfer, or protoplast fusion. For a review of the procedures for liposome preparation, targeting and delivery of contents, see Mannino and Gould-Fogerite, (*Bio Techniques,* 6:682-690, 1988), Felgner and Holm, (*Bethesda Res. Lab. Focus,* 11:21, 1989) and Maurer (*Bethesda Res. Lab. Focus,* 11:25, 1989).

Transfer of the recombinant vector (either plasmid vector or viral vectors) can be accomplished through direct injection into the amniotic fluid or intravenous delivery.

Gene delivery using adenoviral vectors or adeno-associated vectors (AAV) can also be used. Adenoviruses are present in a large number of animal species, are not very pathogenic, and can replicate equally well in dividing and quiescent cells. As a general rule, adenoviruses used for gene delivery are lacking one or more genes required for viral replication. Replication-defective recombinant adenoviral vectors used for the delivery of a nucleic acid encoding a desired protein, can be produced in accordance with art-known techniques (see Quantin et al., *Proc. Natl. Acad. Sci. USA,* 89:2581-2584, 1992; Stratford-Perricadet et al., *J. Clin. Invest.,* 90:626-630, 1992; and Rosenfeld et al., *Cell,* 68:143-155, 1992). For an example of the use of gene therapy in utero see U.S. Pat. No. 6,399,585.

Once transferred, the nucleic acid is expressed by the cells at the site of injury for a period of time sufficient to increase blood serum levels of the desired protein. Because the vectors containing the nucleic acid are not normally incorporated into the genome of the cells, expression of the protein of interest takes place for only a limited time. Typically, the protein is expressed at therapeutic levels for about two days to several weeks, preferably for about one to two weeks. Re-application of the DNA can be utilized to provide additional periods of expression of the therapeutic protein.

Therapeutic Nucleobase Oligomers that Inhibit Protein Expression

The present invention also features the use of nucleobase oligomers to downregulate expression of any of the following: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3.

In one example, the nucleobase oligomer is an antisense nucleobase oligomer. By binding to the complementary nucleic acid sequence (the sense or coding strand), antisense nucleobase oligomers are able to inhibit protein expression presumably through the enzymatic cleavage of the RNA strand by RNAse H. Preferably the antisense nucleobase oligomer is capable of reducing expression of one or more of the above polypeptides or nucleic acids encoding one or more of the above polypeptides in a cell that expresses increased levels of that protein. Preferably the decrease in protein expression is at least 10% relative to cells treated with a control nucleobase oligomer, more preferably 25%, and most preferably 50%, 60%, 70%, 80%, 90%, 95%, 96%, 97%, 98%, 99% or greater. Methods for selecting and preparing antisense nucleobase oligomers are well known in the art. For an example of the use of antisense nucleobase oligomers to downregulate VEGF expression see U.S. Pat. No. 6,410,322.

Methods for assaying levels of protein expression are also well known in the art and include western blotting, immunoprecipitation, and ELISA.

The present invention also features the use of RNA interference (RNAi) to inhibit expression of any one or more of the following: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3. RNA interference (RNAi) is a mechanism of post-transcriptional gene silencing (PTGS) in which double-stranded RNA (dsRNA) corresponding to a gene or mRNA of interest is introduced into an organism resulting in the degradation of the corresponding mRNA. In the RNAi reaction, both the sense and anti-sense strands of a dsRNA molecule are processed into small RNA fragments or segments ranging in length from 18 to 25 nucleotides, preferably 21 to 23 nucleotides (nt), and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as “guide RNAs” or “short interfering RNAs” (siRNAs). dsRNAs or siRNAs that are useful in the present invention are substantially complementary (e.g., at least 85%, 90%, 95%, 96%, 97%, 98%, 99%, or more) to at least 18, 19, 20, 21, 22, 23, 24, or 25 consecutive nucleotides of a gene encoding any one or more of the following polypeptides: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-I anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3.

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene. siRNAs can also be chemically synthesized or obtained from a company that chemically synthesizes siRNAs (e.g., Pharmacon Research Inc., Pharmacia, or ABI).

General descriptions of the specific requirements and modifications of dsRNA are described in PCT Publication No. WO01/75164. While dsRNA molecules can vary in length, it is most preferable to use siRNA molecules which are 21- to 23-nucleotide dsRNAs with characteristic 2- to 3-nucleotide 3' overhanging ends typically either (2'-deoxy) thymidine or uracil. The siRNAs typically comprise a 3' hydroxyl group. Single stranded siRNA as well as blunt ended forms of dsRNA and shRNA can also be used. In order to further enhance the stability of the RNA, the 3' overhangs can be stabilized against degradation. In one such embodiment, the RNA is stabilized by including purine nucleotides, such as adenosine or guanosine. Alternatively, substitution of pyrimidine nucleotides by modified analogs, e.g., substitution of uridine 2-nucleotide overhangs by (2'-deoxy) thymidine is tolerated and does not affect the efficiency of RNAi. The absence of a 2' hydroxyl group significantly enhances the nuclease resistance of the overhang in tissue culture medium.

Alternatively siRNA can be prepared using any of the methods set forth in PCT Publication No. WO01/75164 or using standard procedures for in vitro transcription of RNA and dsRNA annealing procedures as described in Elbashir et al. (*Genes & Dev.,* 15:188-200, 2001). siRNAs are also obtained as described in Elbashir et al. by incubation of dsRNA that corresponds to a sequence of the target gene in a cell-free Drosophila lysate from syncytial blastoderm Drosophila embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g., size exclusion chromatography), glycerol gradient centrifugation, and affinity purification with antibody can be used to isolate the 21 to 23 nt RNAs.

A variety of methods are available for transfection, or introduction, of dsRNA or oligonucleotides into mammalian cells. For example, there are several commercially available transfection reagents including but not limited to: TransIT-TKO™ (Mirus, Cat. # MIR 2150), Transmessenger™ (Qiagen, Cat. # 301525), and Oligofectamine™ (Invitrogen, Cat. # MIR 12252-011). Protocols for each transfection reagent are available from the manufacturer.

In the present invention, the dsRNA, or siRNA, is substantially complementary (e.g., 85%, 90%, 95%, 96%, 97%, 98%, 99%, or more) to at least a portion of the mRNA sequence of any one of the following proteins: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein -5, CD33L, cytokine receptor like factor 1, platelet derived endothelial growth factor, lysyl hydroxylase isoform 2, stanniocalcin precursor, secreted frizzled related protein, and galectin -3 and can reduce or inhibit the expression of the protein. Preferably, the decrease in protein expression is at least 10% relative to cells treated with a control dsRNA or siRNA, more preferably 25%, and most preferably at least 50%. Methods for assaying levels of protein expression are also well known in the art and include western blotting, immunoprecipitation, and ELISA.

In the present invention, the nucleobase oligomers used include any modification that enhances the stability or function of the nucleic acid in any way. Examples include modifications to the phosphate backbone, the internucleotide linkage, or to the sugar moiety. Examples of modifications that may be used in the nucleobase oligomers of the invention, can be found in U.S. Patent Application Publication Nos. 20030114412, paragraphs [0030] to [0046] and 20030114407, paragraphs [0036] to [0055], and 20030190659, paragraphs [0083] to [0106].

Assays for Gene and Protein Expression

The following methods can be used to evaluate protein or gene expression and determine efficacy for any of the above-mentioned methods for increasing or decreasing the expression of any one or more polypeptides of the invention.

A sample from the subject (e.g., a bodily fluid such as blood, serum, plasma, urine, amniotic fluid, and cerebrospinal fluid, a cell, or a tissue) is measured for levels of a desired polypeptide, using methods such as ELISA, western blotting, or immunoassays using specific antibodies. Methods used to measure serum levels of polypeptides include ELISA, western blotting, or immunoassays using specific antibodies. A positive result is considered an alteration of at least 20%, preferably 30%, more preferably at least 50%, 60%, 70%, 80%, 90%, 95%, 96%, 97%, 98%, 99% or more in the serum levels of a polypeptide of the invention as compared to a reference sample.

In addition, in vitro angiogenesis assays can be performed to determine if the subject's blood has converted from an anti-angiogenic state to a pro-angiogenic state. One example of such an in vitro assay for angiogenesis is the endothelial tube assay. In this assay, growth factor reduced Matrigel (7 mg/mL, Collaborative Biomedical Products, Bedford, Mass.) is placed in wells (100 μl/well) of a pre-chilled 48-well cell culture plate and is incubated at 37° C. for 25-30 minutes to allow polymerization. Human umbilical vein endothelial cells (30,000+ in 300 μl of endothelial basal medium with no serum, Clonetics, Walkersville, Md.) at passages 3-5 are treated with 10% patient serum, plated onto the Matrigel coated wells, and are incubated at 37° C. for 12-16 hours. Tube formation is then assessed through an inverted phase contrast microscope at 4× (Nikon Corporation, Tokyo, Japan) and is analyzed (tube area and total length) using the Simple PCI imaging analysis software. A positive result can be considered conversion from an anti-angiogenic state to a pro-angiogenic state using the in vitro angiogenesis assay.

Bodily fluid samples from the subject can also be measured for levels of nucleic acid encoding a polypeptide of the invention. There are several art-known methods to assay for gene expression. Some examples include the preparation of RNA from the blood samples of the subject and the use of the RNA for northern blotting, PCR based amplification, or RNAse protection assays.

Use of Antibodies for Therapeutic Treatment

The use of compounds, such as antibodies, to bind to and neutralize the activity of any one or more of the following polypeptides: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein -5, CD33L, cytokine receptor like factor 1, platelet derived endothelial growth factor, lysyl hydroxylase isoform 2, stanniocalcin precursor, secreted frizzled related protein, and galectin -3, can be used to prevent or treat pre-eclampsia or eclampsia.

The present invention provides antibodies that bind specifically to the any of the above proteins. The antibodies are used to neutralize the activity of any one or more of the above proteins. Methods for the preparation and use of antibodies for therapeutic purposes are described in several patents including U.S. Pat. Nos. 6,054,297; 5,821,337; 6,365,157; and 6,165,464 and are incorporated herein by reference. Antibodies can be polyclonal or monoclonal; monoclonal antibodies are preferred. Some examples of antibodies to some of the polypeptides of the invention are described above under "Exemplary binding molecules and antibodies."

Monoclonal antibodies, particularly those derived from rodents including mice, have been used for the treatment of various diseases; however, there are limitations to their use including the induction of a human anti-mouse immunoglobulin response that causes rapid clearance and a reduction in the efficacy of the treatment. For example, a major limitation in the clinical use of rodent monoclonal antibodies is an anti-globulin response during therapy (Miller et al., *Blood,* 62:988-995 1983; Schroff et al., *Cancer Res.,* 45:879-885, 1985).

The art has attempted to overcome this problem by constructing "chimeric" antibodies in which an animal antigen-binding variable domain is coupled to a human constant domain (U.S. Pat. No. 4,816,567; Morrison et al., *Proc. Natl. Acad. Sci. USA,* 81:6851-6855, 1984; Boulianne et al., *Nature,* 312:643-646, 1984; Neuberger et al., *Nature,* 314: 268-270, 1985). The production and use of such chimeric antibodies are described below.

A cocktail of the monoclonal antibodies of the present invention can be used as an effective treatment for pregnancy related hypertensive disorders, such as pre-eclampsia or eclampsia. The cocktail may include as few as two, three, or four different antibodies or as many as six, eight, or ten different antibodies. In addition, the antibodies of the present invention can be combined with an anti-hypertensive drug (e.g., methyldopa, hydralazine hydrochloride, or labetalol) or any other medication used to treat pregnancy related hypertensive disorders, such as pre-eclampsia or eclampsia, or the symptoms associated with pregnancy related hypertensive disorders.

Non-limiting examples of antibodies that are useful in the methods of the invention are as follows: anti-interleukin 8 (see Leong et al. *Cytokine* 16:106-119, 2001 and Mian et al., *Clin. Cancer Res.* 9:3167-3175, 2003); anti-inhibin A (Verotec Catalog No. MCA951 S, see Rishi et al. *Am. J. Surg. Pathol.* 21:582-589, 1997); and anti-VEFG-C (e.g., Alitalo et al;, U.S. Pat. No. 6,361,946).

Preparation of Antibodies

Monoclonal antibodies that specifically bind to any of the polypeptides of the invention may be produced by methods known in the art. These methods include the immunological method described by Kohler and Milstein (*Nature,* 256: 495-497, 1975) and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam, 1985), as well as by the recombinant DNA method described by Huse et al. (*Science,* 246, 1275-1281, 1989).

Monoclonal antibodies may be prepared from supernatants of cultured hybridoma cells or from ascites induced by intraperitoneal inoculation of hybridoma cells into mice. The hybridoma technique described originally by Kohler and Milstein (*Eur. J. Immunol,* 6, 511-519, 1976) has been widely applied to produce hybrid cell lines that secrete high levels of monoclonal antibodies against many specific antigens.

The route and schedule of immunization of the host animal or cultured antibody-producing cells therefrom are generally in keeping with established and conventional techniques for antibody stimulation and production. Typically, mice are used as the test model, however, any mammalian subject including human subjects or antibody producing cells therefrom can be manipulated according to the processes of this invention to serve as the basis for production of mammalian, including human, hybrid cell lines.

After immunization, immune lymphoid cells are fused with myeloma cells to generate a hybrid cell line that can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. The use of spleen cells is preferred, since they offer a more concentrated and convenient source of antibody producing cells with respect to the mouse system. The myeloma cells provide the basis for continuous propagation of the fused hybrid. Myeloma cells are tumor cells derived from plasma cells. Murine myeloma cell lines can be obtained, for example, from the American Type Culture Collection (ATCC; Manassas, Va.). Human myeloma and mouse-human heteromyeloma cell lines have also been described (Kozbor et al., *J. Immunol.,* 133:3001-3005, 1984; Brodeur et al., Monoclonal Antibody Production Techniques and Applications, Marcel Dekker, Inc., New York, pp. 51-63, 1987).

The hybrid cell lines can be maintained in vitro in cell culture media. Once the hybridoma cell line is established, it can be maintained on a variety of nutritionally adequate media such as hypoxanthine-aminopterin-thymidine (HAT) medium. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromatography, affinity chromatography, or the like.

The antibody may be prepared in any mammal, including mice, rats, rabbits, goats, and humans. The antibody may be a member of one of the following immunoglobulin classes: IgG, IgM, IgA, IgD, or IgE, and the subclasses thereof, and preferably is an IgG antibody.

While the preferred animal for producing monoclonal antibodies is mouse, the invention is not so limited; in fact, human antibodies may be used and may prove to be preferable. Such antibodies can be obtained by using human hybridomas (Cole et al., "Monoclonal Antibodies and Cancer Therapy", Alan R. Liss Inc., p. 77-96, 1985). In the present invention, techniques developed for the production of chimeric antibodies by splicing the genes from a mouse antibody molecule of appropriate antigen specificity together with genes from a human antibody molecule can be used (Morrison et al., *Proc. Natl. Acad. Sci.* 81, 6851-6855, 1984; Neuberger et al., *Nature* 312, 604-608, 1984; Takeda et al., *Nature* 314, 452-454, 1985); such antibodies are within the scope of this invention and are described below.

As another alternative to the cell fusion technique, Epstein-Barr virus (EBV) immortalized B cells are used to produce the monoclonal antibodies of the present invention (Crawford D. et al., *J. of Gen. Virol.,* 64:697-700, 1983; Kozbor and Roder, *J. Immunol.,* 4:1275-1280, 1981; Kozbor et al., *Methods in Enzymology,* 121:120-140, 1986). In general, the procedure consists of isolating Epstein-Barr virus from a suitable source, generally an infected cell line, and exposing the target antibody secreting cells to supernatants containing the virus. The cells are washed, and cultured in an appropriate cell culture medium. Subsequently, virally transformed cells present in the cell culture can be identified by the presence of the Epstein-Barr viral nuclear antigen, and transformed antibody secreting cells can be identified using standard methods known in the art. Other methods for producing monoclonal antibodies, such as recombinant DNA, are also included within the scope of the invention.

Preparation of Immunogens

Any of the polypeptides of the invention may be used alone as an immunogen, or may be attached to a carrier protein or to other objects, such as sepharose beads. Any of the proteins of the invention may be purified from cells known to express the endogenous protein such as human umbilical vein endothelial cells (trophoblasts or HUVEC; Burrows et al., *Clin. Cancer Res.* 1:1623-1634, 1995; Fonsatti et al., *Clin. Cancer Res.* 6:2037-2043, 2000). Additionally, nucleic acid molecules that encode any of the polypeptides of the invention, or portions thereof, can be inserted into known vectors for expression in host cells using standard recombinant DNA techniques. Suitable host cells for protein expression include baculovirus cells (e.g., Sf9 cells), bacterial cells (e.g., *E. coli*), and mammalian cells (e.g., NIH3T3 cells).

In addition, peptides derived from any of the polypeptides of the invention can be synthesized and used as immunogens. The methods for making antibody to peptides are well known in the art and generally require coupling the peptide to a suitable carrier molecule, such as serum albumin. Peptides can be any length, preferably 10 amino acids or greater, more preferably 25 amino acids or greater, and most preferably 40, 50, 60, 70, 80, or 100 amino acids or greater. Preferably, the amino acid sequences are at least 60%, more preferably 85%, and, most preferably 90%, 95%, 96%, 97%, 98%, 99%, or 100% identical to the sequence of any of the nucleic acid sequences encoding the polypeptides of the invention. The peptides can be commercially obtained or made using techniques well known in the art, such as, for example, the Merrifield solid-phase method (*Science,* 232:341-347, 1985). The procedure may use commercially available synthesizers such as a Biosearth 9500 automated peptide machine, with cleavage of the blocked amino acids being achieved with hydrogen fluoride, and the peptides purified by preparative HPLC using a Waters Delta Prep 3000 instrument, on a 15-20 μm Vydac C4 PrepPAK column.

Functional Equivalents of Antibodies

The invention also includes functional equivalents of the antibodies described in this specification. Functional equivalents include polypeptides with amino acid sequences substantially identical to the amino acid sequence of the variable or hypervariable regions of the antibodies of the invention. Functional equivalents have binding characteristics comparable to those of the antibodies, and include, for example, chimerized, humanized and single chain antibodies as well as fragments thereof. Methods of producing such functional equivalents are disclosed, for example, in PCT Publication No. WO93/21319; European Patent Application No. 239,400; PCT Publication No. WO89/09622; European Patent Application No. 338,745; European Patent Application No. 332424; and U.S. Pat. No. 4,816,567; each of which is herein incorporated by reference.

Chimerized antibodies preferably have constant regions derived substantially or exclusively from human antibody constant regions and variable regions derived substantially or exclusively from the sequence of the variable region from a mammal other than a human. Such humanized antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Methods for humanizing non-human antibodies are well known in the art (for reviews see Vaswani and Hamilton, *Ann Allergy Asthma Immunol.,* 81:105-119, 1998 and Carter, *Nature Reviews Cancer,* 1:118-129, 2001). Generally, a humanized antibody has one or more amino acid residues introduced into it from a source that is non-human. These non-human amino acid residues are often referred to as import residues, which are typically taken from an import variable domain. Humanization can be essentially performed following the methods known in the art (Jones et al., *Nature,* 321:522-525, 1986; Riechmann et al., *Nature,* 332:323-329, 1988; and Verhoeyen et al., *Science,* 239:1534-1536 1988), by substituting rodent CDRs or other CDR sequences for the corresponding sequences of a human antibody. Accordingly, such humanized antibodies are chimeric antibodies wherein substantially less than an intact human variable domain has been substituted by the corresponding sequence from a non-human species (see for example, U.S. Pat. No. 4,816,567). In practice, humanized antibodies are typically human antibodies in which some CDR residues and possibly some FR residues are substituted by residues from analogous sites in rodent antibodies (Presta, *Curr. Op. Struct. Biol.,* 2:593-596, 1992).

Additional methods for the preparation of humanized antibodies can be found in U.S. Pat. Nos. 5,821,337, 6,054,297, 6,639,055, and Carter, (supra) which are all incorporated herein by reference. The humanized antibody is selected from any class of immunoglobulins, including IgM, IgG, IgD, IgA and IgE, and any isotype, including $IgG_1$, $IgG_2$, $IgG_3$, and $IgG_4$. Where cytotoxic activity is not needed, such as in the present invention, the constant domain is preferably of the $IgG_2$ class. The humanized antibody may comprise sequences from more than one class or isotype, and selecting particular constant domains to optimize desired effector functions is within the ordinary skill in the art.

Human antibodies can also be produced using various techniques known in the art, including phage display libraries (Marks et al., *J. Mol. Biol.,* 222:581-597, 1991 and Winter et al. *Annu. Rev. Immunol.,* 12:433-455, 1994). The techniques of Cole et al. and Boerner et al. are also useful for the preparation of human monoclonal antibodies (Cole et al., supra; Boemer et al., *J. Immunol.,* 147: 86-95, 1991).

Suitable mammals other than a human include any mammal from which monoclonal antibodies may be made. Examples of mammals other than a human include, for example a rabbit, rat, mouse, horse, goat, or primate; a mouse is preferred.

Functional equivalents of antibodies also include single-chain antibody fragments, also known as single-chain antibodies (scFvs). Single-chain antibody fragments are recombinant polypeptides which typically bind antigens or receptors; these fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the $V_L$ and $V_H$ domains occurs once they are linked so as to maintain the target molecule binding-specificity of the whole antibody from which the single-chain antibody fragment is derived. Generally, the carboxyl terminus of the $V_L$ or $V_H$ sequence is covalently linked by such a peptide linker to the amino acid terminus of a complementary $V_L$ and $V_H$ sequence. Single-chain antibody fragments can be generated by molecular cloning, antibody phage display library or similar techniques. These proteins can be produced either in eukaryotic cells or prokaryotic cells, including bacteria.

Single-chain antibody fragments contain amino acid sequences having at least one of the variable regions or CDRs of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient.

Functional equivalents further include fragments of antibodies that have the same or comparable binding characteristics to those of the whole antibody. Such fragments may contain one or both Fab fragments or the $F(ab')_2$ fragment. Preferably the antibody fragments contain all six CDRs of the whole antibody, although fragments containing fewer than all of such regions, such as three, four or five CDRs, are also functional.

Further, the functional equivalents may be or may combine members of any one of the following immunoglobulin classes: IgG, IgM, IgA, IgD, or IgE, and the subclasses thereof.

Preparation of Functional Equivalents of Antibodies

Equivalents of antibodies are prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody.

DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the CDRs derived substantially or exclusively from the corresponding human antibody regions and DNA encoding CDRs derived substantially or exclusively from a mammal other than a human.

Suitable sources of DNA molecules that encode fragments of antibodies include cells, such as hybridomas, that express the full-length antibody. The fragments may be used by themselves as antibody equivalents, or may be recombined into equivalents, as described above.

The DNA deletions and recombinations described in this section may be carried out by known methods, such as those described in the published patent applications listed above.

Antibody Screening and Selection

Monoclonal antibodies are isolated and purified using standard art-known methods. For example, antibodies can be screened using standard art-known methods such as ELISA or western blot analysis. Non-limiting examples of such techniques are described in Examples II and III of U.S. Pat. No. 6,365,157, herein incorporated by reference.

Therapeutic Uses of Antibodies

When used in vivo for the treatment or prevention of a pregnancy related hypertensive disorder, such as pre-eclampsia or eclampsia, the antibodies of the subject invention are administered to the subject in therapeutically effective amounts. Preferably, the antibodies are administered parenterally or intravenously by continuous infusion. The dose and dosage regimen depends upon the severity of the disease, and the overall health of the subject. The amount of antibody administered is typically in the range of about 0.001 to about 10 mg/kg of subject weight, preferably 0.01 to about 5 mg/kg of subject weight.

For parenteral administration, the antibodies are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibodies typically are formulated in such vehicles at concentrations of about 1 mg/ml to 10 mg/ml.

Combination Therapies

Optionally, a therapeutic of the invention may be administered in combination with any other standard pregnancy related hypertensive disorder therapeutic; such methods are known to the skilled artisan.

Dosages and Modes of Administration

Preferably, the therapeutic compound of the invention is administered during pregnancy for the treatment or prevention of the pregnancy related hypertensive disorder, such as pre-eclampsia or eclampsia, or after pregnancy to treat postpartum pre-eclampsia or eclampsia. Techniques and dosages for administration vary depending on the type of compound (e.g., chemical compound, antibody, antisense, or nucleic acid vector) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral or local by direct injection into the amniotic fluid. Intravenous delivery by continuous infusion is the preferred method for administering the therapeutic compounds of the present invention.

The composition can be in the form of a pill, tablet, capsule, liquid, or sustained release tablet for oral administration; or a liquid for intravenous, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depends on various clinical factors including the overall health of the subject and the severity of the symptoms of the pregnancy related hypertensive disorder, such as pre-eclampsia. In general, once the pregnancy related hypertensive disorder, such as pre-eclampsia or a propensity to develop pre-eclampsia, is detected, continuous infusion of the purified protein is used to treat or prevent further progression of the condition. Treatment can be continued for a period of time ranging from 1 to 100 days, more preferably 1 to 60 days, and most preferably 1 to 20 days, or until the completion of pregnancy. Dosages vary depending on each compound and the severity of the condition and are titrated to achieve a steady-state blood serum concentration.

Subject Monitoring

The diagnostic methods described herein can also be used to monitor the pregnancy related hypertensive disorder, such as pre-eclampsia or eclampsia, during therapy or to determine the dosages of therapeutic compounds. In one example, a therapeutic compound is administered and the level of expression of a polypeptide of the invention is determined during the course of therapy.

Therapeutics that modulate the expression of any one or more nucleic acids or polypeptides of the invention are taken as particularly useful in the invention.

In one example, a therapeutic agent or method that decreases, by 10%, 20%, 30%, 40%, 50%, 60%, 70%, 80%, 90%, 95%, 96%, 97%, 98%, 99% or more, the level of any of the following polypeptides or nucleic acids encoding the polypeptides: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, galectin-3, sperminine oxidase, UDP glycosyltransferase 2 family polypeptide B28, neurotrophic tyrosine kinase receptor 2, neutral endopeptidase, CDC28 protein kinase regulatory subunit 2, and beta glucosidase during the course of therapy, is considered to be an effective therapeutic agent or an effective dosage of a therapeutic agent. In another example, a therapeutic agent or method that increases, by 10%, 20%, 30%, 40%, 50%, 60%, 70%, 80%, 90%, 95%, 96%, 97%, 98%, 99% or more, the level of any of the following polypeptides or nucleic acids encoding the polypeptides: alpha defensin, ADAM-TS3, cholecystokinin precursor, interferon stimulated T-cell alpha chemoattractant precursor, azurocidin, lanosterol synthase, calcium/calmodulin-dependent serine protein kinase, estrogen receptor-alternatively spliced transcript H, chemokine receptor 1, tyrosinase-related protein 1, hydoxy-delta-5-steroid dehydrogenase, dihydropyramidinase-like-4, and cytochrome P450-family 11 during the course of therapy, is considered to be an effective therapeutic agent or an effective dosage of a therapeutic agent.

The disease state or treatment of a subject having a pregnancy related hypertensive disorder, such as pre-eclampsia or eclampsia, or a propensity to develop such a condition, can be monitored using the methods and compositions of the invention. In one embodiment, the expression of a polypeptide of the invention present in a bodily fluid, such as urine, plasma, amniotic fluid, or CSF, is monitored. Such monitoring may be useful, for example, in assessing the efficacy of a particular drug in a subject or in assessing disease progression.

EXAMPLES

Example 1

Gene Expression Profiling of Placental Tissue from Pre-Eclamptic and Normotensive Women In order to identify novel secreted factors involved in the pathogenesis of pre-eclampsia, we performed gene expression profiling of placental tissue from 19 women with pre-eclampsia and 15 nomotensive pregnant women using Affymetrix U95A microarray chips (see Table 1).

TABLE 1

Clinical characteristics of the study patients

| | Normal (n = 15) | Pre-eclampsia (n = 19) |
|---|---|---|
| Maternal Age (years) | 35.2 | 31.9 |
| Gestational Age (wks) | 39.0 | 31.1* |
| Primiparous (%) | 19 | 81* |
| Systolic BP (mm Hg) | 107 | 167.2** |
| Diastolic BP (mm Hg) | 83 | 101.8** |
| Proteinuria (g protein/g creat) | <0.3 | 5.2** |
| Serum Uric Acid (mg/dl) | NA | 6.8 |
| Hematocrit (%) | 35.7 | 33.9 |
| Platelet Count (K/μl) | 217 | 198 |
| Serum Creatinine (mg/dl) | 0.5 | 0.6 |

Data shown are mean values.
*p < 0.05,
**p < 0.005

Data were analyzed using the computer program BADGE (Bayesian Analysis of Differential Gene Expression version 1.0) (http://genomethods.org/badge) (see Ramoni and Sebastiani, in Berthold and Hand eds. *Intelligent Data Analysis: An Introduction*, Springer, New York, N.Y. (1999)) and hierarchical clustering analysis (Eisen et al., *Proc. Natl. Acad. Sci.*, 95:14863-8 (1998)) to identify differentially expressed genes across experimental conditions (FIG. 1). The software BADGE (Bayesian Analysis of Gene Expression) v1.0 implements a Bayesian approach to identify differentially expressed genes across different experimental conditions. Cumulative distribution function (CDF) for expression ratio greater than 1.0. The genes are ranked in order of the conditional probability of increased fold expression given the expression data; the null probability value is 0.5.

Figure 2:
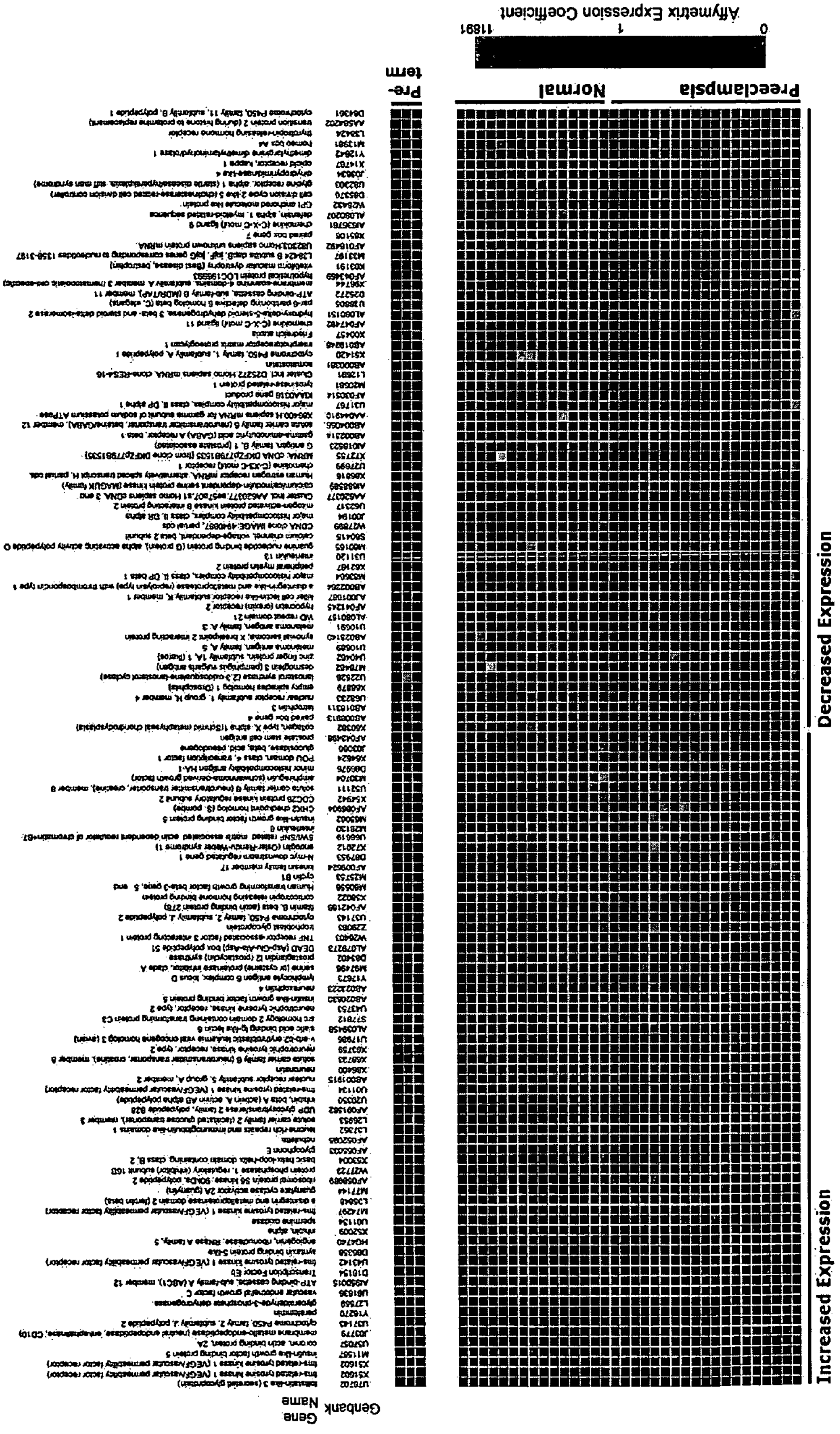
FIG. 2 is a colormap showing a predictive gene set in normal versus preeclamptic placenta based on mRNA expression using the BADGE program. Rows represent predictive genes for pre-eclampsia while columns represent expression levels for a given patient relative to the average gene expression. The expected false positive rate of 1.0% yields a predictive gene set of 127 genes, with 65 upregulated and 62 downregulated respectively. Significantly upregulated genes include soluble fms-like tyrosine kinase I and follistatin-related protein. mRNA expression profile from 3 pre-term placentas are also shown as additional controls.

A predictive gene set in normal versus pre-eclampsia placenta mRNA expression was discovered using the BADGE program. A colormap of the predictive gene set is shown in FIG. 2. Rows represent predictive genes for pre-eclampsia while columns represent expression levels for a given patient relative to the average gene expression. The expected false positive rate of 1.0% yields a predictive gene set of 127 genes, with 65 upregulated and 62 downregulated respectively (Table 2). (See FIGS. 6A-44 for amino acid and nucleic acid sequences for the polypeptides of the invention.)

TABLE 2

Summary of predictive genes

| Affy Probe | Genbank | Probability | Fold | Gene Symbol | Gene Name |
|---|---|---|---|---|---|
| 33900_at | U76702 | 0.99992 | 3.849 | FSTL3 | follistatin-like 3 (secreted glycoprotein) |
| 990_at | X51602 | 0.99990 | 3.233 | FLT1 | fms-related tyrosine kinase 1 (vascular endothelial growth factor/vascular permeability factor receptor) |
| 991_g_at | X51602 | 0.99989 | 2.727 | FLT1 | fms-related tyrosine kinase 1 (vascular endothelial growth factor/vascular permeability factor receptor) |
| 1601_s_at | M11567 | 0.99986 | 3.254 | IGFBP5 | insulin-like growth factor binding protein 5 |
| 36317_at | U57057 | 0.99982 | 3.767 | CORO2A | coronin, actin binding protein, 2A |
| 1389_at | J03779 | 0.99982 | 2.299 | MME | membrane metallo-endopeptidase (neutral endopeptidase, enkephalinase, CALLA, CD10) |
| 501_g_at | U37143 | 0.99980 | 2.293 | CYP2J2 | cytochrome P450, family 2, subfamily J, polypeptide 2 |
| 37657_at | Y16270 | 0.99979 | 3.089 | PALM | paralemmin |
| HUMGAPDH | L27559 | 0.99978 | 3.647 | GAPD | glyceraldehyde-3-phosphate dehydrogenase |
| 159_at | U61836 | 0.99969 | 3.343 | VEGFC | vascular endothelial growth factor C |
| 31754_at | AI950015 | 0.99966 | 3.737 | ABCA12 | ATP-binding cassette, sub-family A (ABC1), member 12 |

TABLE 2-continued

Summary of predictive genes

| Affy Probe | Genbank | Probability | Fold | Gene Symbol | Gene Name |
|---|---|---|---|---|---|
| 1149_at | D16154 | 0.99960 | 3.241 | — | Transcription Factor Eb |
| 1545_g_at | U43142 | 0.99959 | 2.692 | FLT1 | fms-related tyrosine kinase 1 (vascular endothelial growth factor/vascular permeability factor receptor) |
| 34129_at | D86358 | 0.99953 | 2.211 | STXBP5L | syntaxin binding protein 5-like |
| 1103_at | HG4740 | 0.99952 | 3.141 | ANG | angiogenin, ribonuclease, RNase A family, 5 |
| 255_s_at | X52009 | 0.99950 | 2.761 | INHA | inhibin, alpha |
| 1650_g_at | U01134 | 0.99948 | 2.745 | SMOX | spermine oxidase |
| 1964_g_at | M74297 | 0.99946 | 2.331 | FLT1 | fms-related tyrosine kinase 1 (vascular endothelial growth factor/vascular permeability factor receptor) |
| 32298_at | L35848 | 0.99940 | 2.894 | ADAM2 | a disintegrin and metalloproteinase domain 2 (fertilin beta) |
| 33995_at | M77144 | 0.99939 | 5.997 | GUCA2A | guanylate cyclase activator 2A (guanylin) |
| 32892_at | AF058989 | 0.99937 | 2.014 | RPS6KA2 | ribosomal protein S6 kinase, 90 kDa, polypeptide 2 |
| 41577_at | W27723 | 0.99910 | 2.361 | PPP1R16B | protein phosphatase 1, regulatory (inhibitor) subunit 16B |
| 40790_at | X53004 | 0.99903 | 2.169 | BHLHB2 | basic helix-loop-helix domain containing, class B, 2 |
| 41024_f_at | AF055033 | 0.99891 | 2.617 | GYPE | glycophorin E |
| 36426_g_at | AF052095 | 0.99879 | 1.981 | NEBL | nebulette |
| 34800_at | L37362 | 0.99868 | 2.943 | LRIG1 | leucine-rich repeats and immunoglobulin-like domains 1 |
| 36979_at | L26953 | 0.99868 | 2.389 | SLC2A3 | solute carrier family 2 (facilitated glucose transporter), member 3 |
| 31382_f_at | AF091582 | 0.99851 | 2.065 | UGT2B28 | UDP glycosyltransferase 2 family, polypeptide B28 |
| 40357_at | U20350 | 0.99831 | 3.380 | INHBA | inhibin, beta A (activin A, activin AB alpha polypeptide) |
| 1963_at | U01134 | 0.99822 | 2.714 | FLT1 | fms-related tyrosine kinase 1 (vascular endothelial growth factor/vascular permeability factor receptor) |
| 35865_at | AB001915 | 0.99815 | 2.632 | NR5A2 | nuclear receptor subfamily 5, group A, member 2 |
| 39051_at | X86400 | 0.99814 | 1.805 | NNAT | neuronatin |
| 33642_s_at | X68733 | 0.99807 | 3.236 | SLC6A8 | solute carrier family 6 (neurotransmitter transporter, creatine), member 8 |
| 33182_at | X63759 | 0.99804 | 2.698 | NTRK2 | neurotrophic tyrosine kinase, receptor, type 2 |
| 33639_g_at | U17986 | 0.99802 | 1.694 | ERBB3 | v-erb-b2 erythroblastic leukemia viral oncogene homolog 3 (avian) |
| 34483_at | AL039458 | 0.99793 | 2.234 | SIGLEC6 | sialic acid binding Ig-like lectin 6 |
| 1511_at | S77812 | 0.99793 | 1.771 | SHC3 | src homology 2 domain containing transforming protein C3 |
| 38280_s_at | U43753 | 0.99787 | 3.286 | NTRK2 | neurotrophic tyrosine kinase, receptor, type 2 |
| 41420_at | AB020630 | 0.99785 | 2.479 | IGFBP5 | insulin-like growth factor binding protein 5 |
| 34088_at | AB023223 | 0.99783 | 2.009 | NXPH4 | neurexophilin 4 |
| 36284_at | Y17673 | 0.99781 | 2.978 | LY6D | lymphocyte antigen 6 complex, locus D |
| 33825_at | M97496 | 0.99777 | 2.575 | SERPINA3 | serine (or cysteine) proteinase inhibitor, clade A (alpha-1 antiproteinase, antitrypsin), member 3 |
| 36533_at | D83402 | 0.99742 | 2.354 | PTGIS | prostaglandin I2 (prostacyclin) synthase |
| 37813_at | AL079273 | 0.99735 | 2.073 | DDX51 | DEAD (Asp-Glu-Ala-Asp) box polypeptide 51 |
| 39202_at | W26403 | 0.99731 | 1.667 | TRAF3IP1 | TNF receptor-associated factor 3 interacting protein 1 |
| 368_at | Z29083 | 0.99721 | 1.904 | TPBG | trophoblast glycoprotein |
| 500_at | U37143 | 0.99716 | 1.751 | CYP2J2 | cytochrome P450, family 2, subfamily J, polypeptide 2 |
| 38078_at | AF042166 | 0.99699 | 1.774 | FLNB | filamin B, beta (actin binding protein 278) |
| 41608_at | X58022 | 0.99693 | 2.906 | CRHBP | corticotropin releasing hormone binding protein |

TABLE 2-continued

Summary of predictive genes

| Affy Probe | Genbank | Probability | Fold | Gene Symbol | Gene Name |
|---|---|---|---|---|---|
| 1734_at | M60556 | 0.99656 | 2.200 | — | Human transforming growth factor beta-3 gene, 5 end |
| 1945_at | M25753 | 0.99644 | 1.747 | CCNB1 | cyclin B1 |
| 31990_at | AF009624 | 0.99636 | 1.496 | KIF17 | kinesin family member 17 |
| 36933_at | D87953 | 0.99618 | 2.050 | NDRG1 | N-myc downstream regulated gene 1 |
| 32562_at | X72012 | 0.99610 | 1.941 | ENG | endoglin (Osler-Rendu-Weber syndrome 1) |
| 32565_at | U66619 | 0.99606 | 2.098 | SMARCD3 | SWI/SNF related, matrix associated, actin dependent regulator of chromatin, subfamily d, member 3 |
| 1369_s_at | M28130 | 0.99601 | 3.111 | IL8 | interleukin 8 |
| 1678_g_at | M65062 | 0.99589 | 2.334 | IGFBP5 | insulin-like growth factor binding protein 5 |
| 37887_at | AF086904 | 0.99572 | 1.887 | CHEK2 | CHK2 checkpoint homolog (*S. pombe*) |
| 40690_at | X54942 | 0.99568 | 1.913 | CKS2 | CDC28 protein kinase regulatory subunit 2 |
| 40926_at | U52111 | 0.99559 | 2.068 | SLC6A8 | solute carrier family 6 (neurotransmitter transporter, creatine), member 8 |
| 34898_at | M30704 | 0.99558 | 2.179 | AREG | amphiregulin (schwannoma-derived growth factor) |
| 33748_at | D86976 | 0.99546 | 2.523 | HA-1 | minor histocompatibility antigen HA-1 |
| 35940_at | X64624 | 0.99536 | 2.086 | POU4F1 | POU domain, class 4, transcription factor 1 |
| 32632_g_at | J03060 | 0.99526 | 2.108 | GBAP | glucosidase, beta; acid, pseudogene |
| 33792_at | AF043498 | 0.99518 | 2.318 | PSCA | prostate stem cell antigen |
| 38566_at | X60382 | 0.00495 | 0.730 | COL10A1 | collagen, type X, alpha 1(Schmid metaphyseal chondrodysplasia) |
| 31740_s_at | AB008913 | 0.00488 | 0.637 | PAX4 | paired box gene 4 |
| 33359_at | AB018311 | 0.00485 | 0.547 | LPHN3 | latrophilin 3 |
| 38519_at | U68233 | 0.00476 | 0.483 | NR1H4 | nuclear receptor subfamily 1, group H, member 4 |
| 33046_f_at | X68879 | 0.00473 | 0.492 | EMX1 | empty spiracles homolog 1 (*Drosophila*) |
| 39108_at | U22526 | 0.00472 | 0.616 | LSS | lanosterol synthase (2,3-oxidosqualene-lanosterol cyclase) |
| 33693_at | M76482 | 0.00451 | 0.499 | DSG3 | desmoglein 3 (pemphigus vulgaris antigen) |
| 834_at | U40462 | 0.00436 | 0.615 | ZNFN1A1 | zinc finger protein, subfamily 1A, 1 (Ikaros) |
| 34575_f_at | U10689 | 0.00416 | 0.480 | MAGEA5 | melanoma antigen, family A, 5 |
| 33379_at | AB023140 | 0.00407 | 0.432 | SSX2IP | synovial sarcoma, X breakpoint 2 interacting protein |
| 31599_f_at | U10691 | 0.00390 | 0.420 | MAGEA3 | melanoma antigen, family A, 3 |
| 32935_at | AL080157 | 0.00389 | 0.512 | WDR21 | WD repeat domain 21 |
| 33072_at | AF041245 | 0.00361 | 0.809 | HCRTR2 | hypocretin (orexin) receptor 2 |
| 36777_at | AJ001687 | 0.00357 | 0.525 | KLRK1 | killer cell lectin-like receptor subfamily K, member 1 |
| 36269_at | AB002364 | 0.00356 | 0.538 | ADAMTS3 | a disintegrin-like and metalloprotease (reprolysin type) with thrombospondin type 1 motif, 3 |
| 38095_i_at | M83664 | 0.00351 | 0.596 | HLA-DPB1 | major histocompatibility complex, class II, DP beta 1 |
| 36272_r_at | X62167 | 0.00319 | 0.335 | PMP2 | peripheral myelin protein 2 |
| 494_at | U31120 | 0.00307 | 0.610 | IL13 | interleukin 13 |
| 34698_at | M60165 | 0.00300 | 0.522 | GNAO1 | guanine nucleotide binding protein (G protein), alpha activating activity polypeptide O |
| 39646_at | S60415 | 0.00291 | 0.414 | CACNB2 | calcium channel, voltage-dependent, beta 2 subunit |
| 36049_at | W27899 | 0.00278 | 0.497 | — | CDNA clone IMAGE: 4940887, partial cds |
| 37039_at | J00194 | 0.00277 | 0.602 | HLA-DRA | major histocompatibility complex, class II, DR alpha |
| 37588_s_at | U62317 | 0.00262 | 0.621 | MAPK8IP2 | mitogen-activated protein kinase 8 interacting protein 2 |
| 33846_at | AA620377 | 0.00260 | 0.522 | — | Cluster Incl. AA620377: ae57a07.s1 *Homo sapiens* cDNA, 3 end /clone = IMAGE-950964 |
| 36416_g_at | AI688589 | 0.00259 | 0.512 | CASK | calcium/calmodulin-dependent serine protein kinase (MAGUK family) |

TABLE 2-continued

| Summary of predictive genes | | | | | |
|---|---|---|---|---|---|
| Affy Probe | Genbank | Probability | Fold | Gene Symbol | Gene Name |
| 1298_at | X86816 | 0.00256 | 0.447 | — | Human estrogen receptor mRNA, alternatively spliced transcript H, partial cds. |
| 40646_at | U27699 | 0.00235 | 0.562 | CX3CR1 | chemokine (C—X3—C motif) receptor 1 |
| 37108_at | X72755 | 0.00229 | 0.529 | — | MRNA; cDNA DKFZp779B1535 (from clone DKFZp779B1535) |
| 32997_at | AI018523 | 0.00228 | 0.363 | GAGEB1 | G antigen, family B, 1 (prostate associated) |
| 35028_at | AB002314 | 0.00227 | 0.438 | GABRB1 | gamma-aminobutyric acid (GABA) A receptor, beta 1 |
| 40679_at | AB004066 | 0.00213 | 0.458 | SLC6A12 | solute carrier family 6 (neurotransmitter transporter, betaine/GABA), member 12 |
| 39498_at | AA044910 | 0.00213 | 0.497 | — | Cluster Incl. X86400: *H. sapiens* mRNA for gamma subunit of sodium potassium ATPase |
| 38833_at | U31767 | 0.00199 | 0.670 | HLA-DPA1 | major histocompatibility complex, class II, DP alpha 1 |
| 35031_r_at | AF030514 | 0.00183 | 0.281 | KIAA0316 | KIAA0316 gene product |
| 36911_at | M20681 | 0.00180 | 0.433 | TYRP1 | tyrosinase-related protein 1 |
| 31494_at | L12691 | 0.00175 | 0.434 | — | Cluster Incl. D25272: *Homo sapiens* mRNA, clone-RES4-16 |
| 37782_at | AB000381 | 0.00170 | 0.654 | SST | somatostatin |
| 36767_at | X51420 | 0.00164 | 0.302 | CYP1A1 | cytochrome P450, family 1, subfamily A, polypeptide 1 |
| 35539_at | AB019246 | 0.00159 | 0.386 | IMPG1 | interphotoreceptor matrix proteoglycan 1 |
| 38330_at | X00457 | 0.00159 | 0.371 | FRDA | Friedreich ataxia |
| 35061_at | AF047492 | 0.00152 | 0.272 | CXCL11 | chemokine (C—X—C motif) ligand 11 |
| 34002_at | AL080151 | 0.00139 | 0.627 | HSD3B2 | hydroxy-delta-5-steroid dehydrogenase, 3 beta- and steroid delta-isomerase 2 |
| 32017_at | U38805 | 0.00139 | 0.531 | PARD6B | par-6 partitioning defective 6 homolog beta (*C. elegans*) |
| 31398_at | D25272 | 0.00132 | 0.440 | ABCB11 | ATP-binding cassette, sub-family B (MDR/TAP), member 11 |
| 32451_at | X96744 | 0.00131 | 0.556 | MS4A3 | membrane-spanning 4-domains, subfamily A, member 3 (hematopoietic cell-specific) |
| 34045_at | AF043469 | 0.00131 | 0.503 | LOC196993 | hypothetical protein LOC196993 |
| 36428_at | K03191 | 0.00130 | 0.569 | VMD2 | vitelliform macular dystrophy (Best disease, bestrophin) |
| AFFX-DapX-3_a | M33197 | 0.00122 | 0.469 | — | L38424 B subtilis dapB, jojF, jojG genes corresponding to nucleotides 1358-3197 of L38424 |
| 31324_at | AF016492 | 0.00116 | 0.484 | — | U82303: *Homo sapiens* unknown protein mRNA |
| 32474_at | X85106 | 0.00111 | 0.644 | PAX7 | paired box gene 7 |
| 37219_at | AI636761 | 0.00098 | 0.395 | CXCL9 | chemokine (C—X—C motif) ligand 9 |
| 31506_s_at | AL080207 | 0.00097 | 0.288 | DEFA1 | defensin, alpha 1, myeloid-related sequence |
| 378_s_at | W28432 | 0.00075 | 0.529 | GML | GPI anchored molecule like protein |
| 41820_s_at | D85376 | 0.00073 | 0.570 | CDC2L5 | cell division cycle 2-like 5 (cholinesterase-related cell division controller) |
| 31310_at | U82303 | 0.00061 | 0.523 | GLRA1 | glycine receptor, alpha 1 (startle disease/hyperekplexia, stiff man syndrome) |
| 39502_at | J03634 | 0.00046 | 0.553 | DPYSL4 | dihydropyrimidinase-like 4 |
| 35024_at | X14767 | 0.00031 | 0.272 | OPRK1 | opioid receptor, kappa 1 |
| 36220_at | Y12642 | 0.00030 | 0.346 | DDAH1 | dimethylarginine dimethylaminohydrolase 1 |
| 204_at | M13981 | 0.00022 | 0.601 | HOXA4 | homeo box A4 |
| 750_at | L38424 | 0.00021 | 0.389 | TRHR | thyrotropin-releasing hormone receptor |
| 33478_at | AA584202 | 0.00009 | 0.296 | TNP2 | transition protein 2 (during histone to protamine replacement) |
| 1412_g_at | D84361 | 0.00008 | 0.560 | CYP11B1 | cytochrome P450, family 11, subfamily B, polypeptide 1 |

Figure 3:
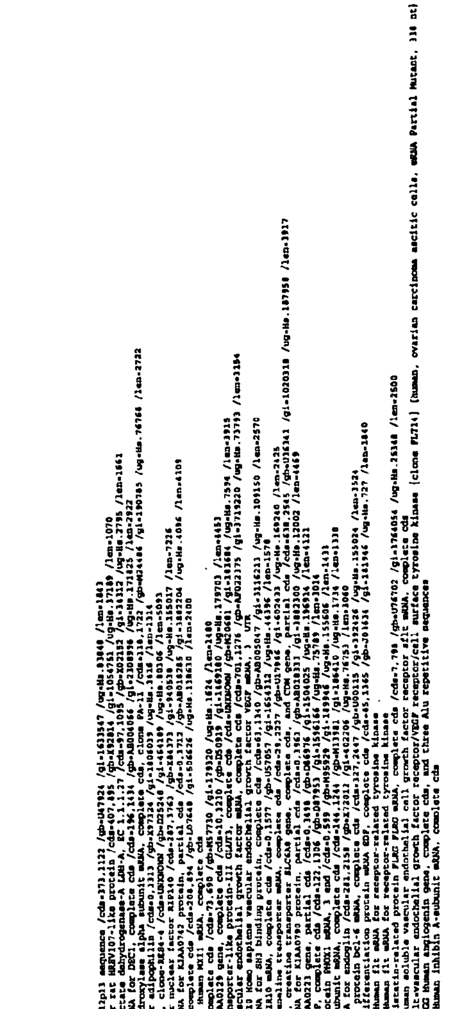
FIG. 3 shows a hierarchical clustering of the affymetrix patient data using Cluster and Treeview, (by Michael Eisen, Stanford University). The samples labeled as P are preeclamptic patients and the samples labeled as N are normal pregnant patients. The dataset was filtered from 12625 to 3564 genes using presence and expression criteria, and the resulting set was median-centered and normalized for genes and arrays. We used hierarchical clustering to analyze possible classes in genes. The cluster includes sFlt1 along with other genes confirmed in literature.

*Genes selected with a 1.0% false positive error rate for a total of 127 gene, 65 of these upregulated. Genes with no Locuslink classification are labeled with Genbank accession numbers A hierarchical clustering of the Affymetrix patient data was performed using Cluster and Treeview, (by Michael Eisen, Stanford University) (FIG. 3). The samples labeled as P are preeclamptic patients and the samples labeled as N are normal pregnant patients. The dataset was filtered from 12625 to 3564 genes using presence and expression criteria, and the resulting set was median-centered and normalized for genes and arrays. We used hierarchical clustering to analyze possible classes in genes. The above cluster includes sFlt1 along with other genes confirmed in literature.

From the predictive gene set, we found that expression of the gene for the following secreted polypeptides was upregulated in blood samples taken from women with pre-eclampsia: follistatin related protein, interleukin 8, inhibin A, VEGF-C, angiogenin, beta fertilin, hypothetical protein (#AL039458), leukocyte associated Ig-like receptor secreted protein, erythroid differentiation protein, adipogenesis inhibitory factor, corticotropin releasing factor binding protein, alpha-1 anti-chymotrypsin, insulin-like growth factor binding protein-5, CD33L, cytokine receptor like factor 1, platelet derived endothelial growth factor, lysyl hydroxylase isoform 2, stanniocalcin precursor, secreted frizzled related protein, and galectin-3. We have also discovered that expression levels of the gene for the following secreted polypeptides were decreased in blood samples taken from women with pre-eclampsia: alpha defensin, ADAM-TS3, cholecystokinin precursor, interferon stimulated T-cell alpha chemoattractant precursor, and azurocidin. In addition we also found the following intracellular polypeptides or enzymes that are increased in preeclamptic placenta sperminine oxidase, UDP glycosyltransferase 2 family polypeptide B28, neurotrophic tyrosine kinase receptor 2, neutral endopeptidase, CDC28 protein kinase regulatory subunit 2 and beta glucosidase. The following intracellular gene products/enzymes are decreased in preeclamptic placentas are: lanosterol synthase, calcium/calmodulin-dependent serine protein kinase, estrogen receptor-alternatively spliced transcript H, chemokine (CX3C motif) receptor 1, tyrosinase-related protein 1, hydoxy-delta delta-5-steroid dehydrogenase, dihydropyramidinase-like-4, and cytochrome P450-family 11.

Example 2 mRNA Expression of Flt-1 and sFlt-1 in Pre-Eclampsia

Figure 4:
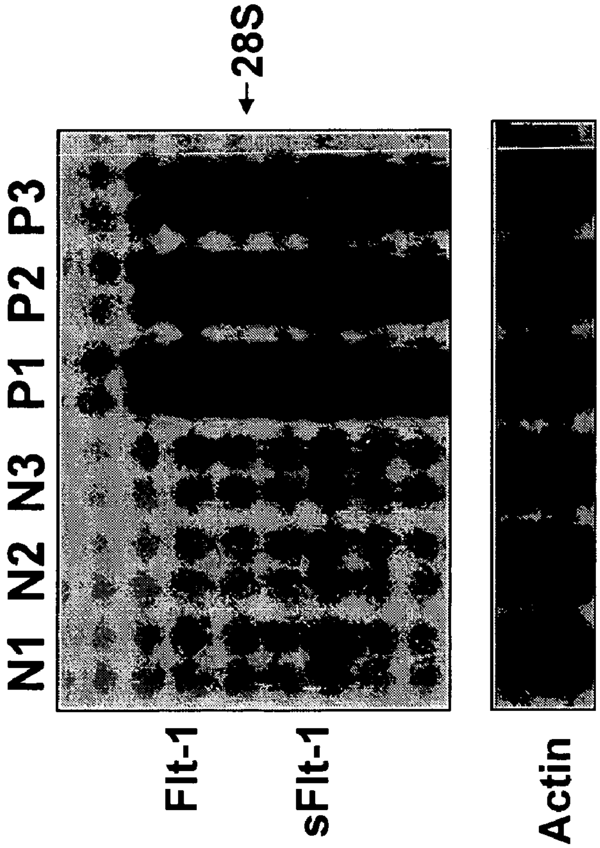
FIG. 4 is an autoradiogram showing mRNA expression of Flt-1 and sFlt-1 in pre-eclampsia. mRNA expression of placental sFlt-1 from 3 patients with pre-eclampsia (P1, P2, P3) and three normotensive term pregnancies (N1, N2, N3) were determined by northern blot analysis. The higher band (7.5 kb) is the full length Flt-1 mRNA and the lower, more abundant band (3.4 kb) is the alternatively spliced sFlt-1 mRNA. Actin is included as a control and 28S is shown as arrowhead.

As the above cluster identified sFlt1 along with other genes confirmed in the literature, we chose to confirm the ability of the array to identify predictive markers of pre-eclampsia using sFlt-1. For these experiments, mRNA expression of placental sFlt-1 from 3 patients with pre-eclampsia (P1, P2, P3) and three normotensive term pregnancies (N1, N2, N3) were determined by northern blot analysis (FIG. 4). The higher band (7.5 kb) is the full length Flt-1 mRNA and the lower, more abundant band (3.4 kb) is the alternatively spliced sFlt-1 mRNA. Actin is included as a control and 28S is shown as arrowhead. These results show the increased expression of the gene for sFlt-1 in pre-eclamptic patients and confirm the use of the predictive gene set identified by the array as markers for pre-eclampsia or eclampsia or the propensity to develop pre-eclampsia or eclampsia.

Example 3

Figure 5:
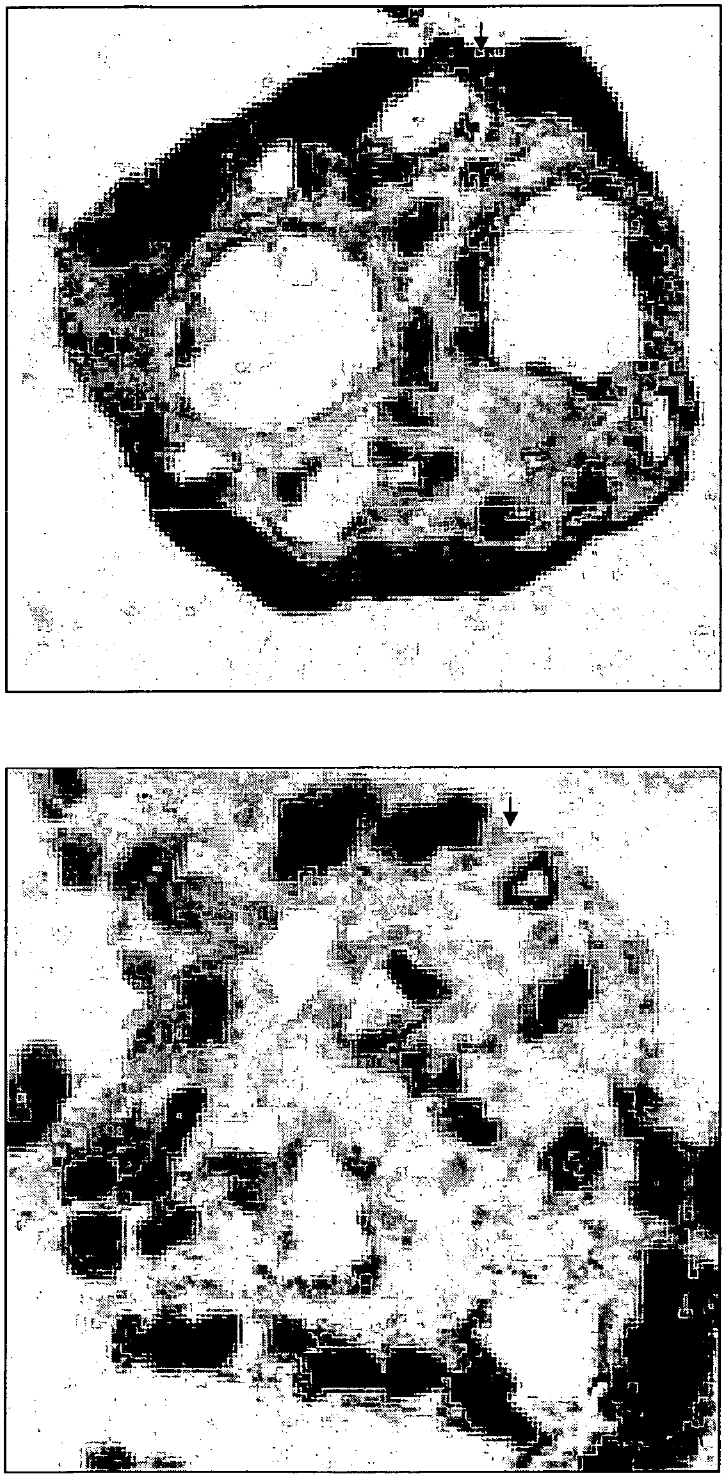
FIG. 5 is a set of images showing the immunohistochemistry of Flt-1 expression in normal and preeclamptic placentas. A monoclonal antibody against human Flt-1 was used for these experiments. The data shown here demonstrates increased expression of Flt-1 by the syncitiotrophoblasts of the preeclamptic placenta.

Immunohistochemistry Analysis of Flt-1 Expression in Normal and Pre-Eclamptic Patients In order to visualize Flt-1 expression in placental samples from normal and pre-eclamptic patients, a monoclonal antibody against human Flt-1 was used for immunohistochemistry analysis. Increased expression of Flt-1 by the syncitiotrophoblasts of the preeclamptic placenta was detected (FIG. 5), further confirming the ability of the array to identify genes that can be used as markers for pre-eclampsia or eclampsia or the propensity to develop pre-eclampsia or eclampsia.

OTHER EMBODIMENTS

The description of the specific embodiments of the invention is presented for the purposes of illustration. It is not intended to be exhaustive or to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference. Other embodiments are in the claims.

What is claimed is:

1. A method of diagnosing a subject as having, or having a predisposition to, pre-eclampsia or eclampsia, said method comprising measuring the level of insulin-like growth factor binding protein-5 in a sample from said subject, wherein said sample is a bodily fluid from said subject, and wherein a significant increase in the level of said insulin-like growth factor binding protein-5 as compared to the level in a normal reference, is a diagnostic indicator of said pre-eclampsia or eclampsia or a predisposition to said pre-eclampsia or eclampsia.

2. The method of claim 1, wherein said increase is at least 20%.

3. The method of claim 1, wherein said subject is further diagnosed as having, or having a propensity to develop, mild pre-eclampsia, severe pre-eclampsia, pre-eclampsia-associated gestational hypertension, pre-eclampsia-associated HELLP syndrome, or pre-eclampsia-associated pregnancy with a small for gestational age (SGA) infant.

4. The method of claim 1, wherein the normal reference is a bodily fluid sample previously taken from said subject.

5. The method of claim 1, further comprising measuring the level of at least one polypeptide, or fragment thereof, selected from the group consisting of soluble endoglin, sFlt-1, VEGF, and PlGF in a sample from said subject.

6. The method of claim 5, further comprising comparing the level of said soluble endoglin, sFlt-1, VEGF, or PlGF to the level of said soluble endoglin, sFlt-1, VEGF, or PlGF in a reference sample, wherein an increase in the level of said soluble endoglin; or sFlt-1, or a decrease in the level of free VEGF or free PlGF in the subject sample relative to the level of said soluble endoglin, sFlt-1, VEGF, or PlGF in the reference sample is a diagnostic indicator of pre-eclampsia or eclampsia or a predisposition to pre-eclampsia or eclampsia in said subject.

7. The method of claim 1, wherein said measuring is done using an immunological assay.

8. The method of claim 7, wherein said immunological assay is an ELISA.

9. The method of claim 1, wherein said subject is a non-pregnant human, a pregnant human, a post-partum human, or a non-human.

10. The method of claim 9, wherein said non-human is selected from the group consisting of a cow, a horse, a sheep, a pig, a goat, a dog, or a cat.

11. The method of claim 1, wherein said method is used to diagnose pre-eclampsia or eclampsia, or a predisposition to pre-eclampsia or eclampsia, at least 4 weeks prior to the onset of symptoms.

12. The method of claim 1, wherein said bodily fluid is selected from the group consisting of blood, urine, amniotic fluid, saliva, serum, plasma, and cerebrospinal fluid.

13. The method of claim 6, further comprising (a) calculating the relationship between said levels of soluble endoglin, sFlt-1, VEGF, or PlGF relative to each other in said subject sample using a metric;

(b) calculating the relationship between said levels of soluble endoglin, sFlt-1, VEGF, or PlGF relative to each other in a reference sample using the same metric as in step (a); and (c) comparing the relationship calculated in step (a) in said subject sample with the relationship calculated in step (b) in said reference sample, wherein an alteration in the relationship calculated in step (a) as compared to the relationship calculated in step (b) is a diagnostic indicator of pre-eclampsia or eclampsia or a predisposition to pre-eclampsia or eclampsia in said subject.

14. The method of claim 1, wherein said method is used to diagnose pre-eclampsia or eclampsia, or a predisposition to pre-eclampsia or eclampsia, prior to the development of at least one symptom of pre-eclampsia or eclampsia in said subject, said at least one symptom selected from the group consisting of a systolic blood pressure (BP)>140 mmHg and a diastolic BP>90 mmHg after 20 weeks gestation; new onset proteinuria; greater than 300 mg of protein in a 24-hour urine collection; and a single random urine sample having a protein/creatinine ratio greater than 0.3.

15. The method of claim 13, wherein said metric is selected from the group consisting of sFlt-1/PlGF, [sFlt-1/VEGF+PlGF], (sFlt-1+0.25(soluble endoglin polypeptide))/PlGF, and (sFlt1+soluble endoglin)/PlGF.

16. The method of claim 1, wherein said pre-eclampsia is premature pre-eclampsia.

17. A method of diagnosing a subject as having, or having a predisposition to, pre-eclampsia or eclampsia, said method comprising measuring the level of at least one polypeptide in a sample from said subject, wherein said sample is a tissue sample from said subject and wherein said at least one polypeptide is selected from the group consisting of follistatin like 3 protein (FSTL3), beta fertilin, CD33L, neurotrophic tyrosine kinase receptor 2, and beta glucosidase, and wherein a significant increase in the level of said at least one polypeptide as compared to the level in a normal reference, is a diagnostic indicator of said pre-eclampsia or eclampsia or a predisposition to said pre-eclampsia or eclampsia.

18. The method of claim 17, wherein said increase is at least 20%.

19. The method of claim 17, wherein said subject is further diagnosed as having, or having a propensity to develop, mild pre-eclampsia, severe pre-eclampsia, pre-eclampsia-associated gestational hypertension, pre-eclampsia-associated HELLP syndrome, or pre-eclampsia-associated pregnancy with a small for gestational age (SGA) infant.

20. The method of claim 17, further comprising measuring the level of at least one polypeptide, or fragment thereof, selected from the group consisting of soluble endoglin, sFlt-1, VEGF, and PlGF in a sample from said subject.

21. The method of claim 20, further comprising comparing the level of said soluble endoglin, sFlt-1, VEGF, or PlGF to the level of said soluble endoglin, sFlt-1, VEGF, or PlGF in a reference sample, wherein an increase in the level of said soluble endoglin or sFlt-1, or a decrease in the level of free VEGF or free PlGF in the reference sample is a diagnostic indicator of pre-eclampsia or eclampsia or a predisposition to pre-eclampsia or eclampsia in said subject.

22. The method of claim 17, wherein said polypeptide is follistatin like 3 protein (FSTL3).

23. The method of claim 17, wherein said subject is a non-pregnant human, a pregnant human, a post-partum human, or a non-human.

24. The method of claim 23 wherein said non-human is selected from the group consisting of a cow, a horse, a sheep, a pig, a goat, a dog, or a cat.

25. The method of claim 17, wherein said method is used to diagnose pre-eclampsia or eclampsia, or a predisposition to pre-eclampsia or eclampsia, at least 4 weeks prior to the onset of symptoms.

26. The method of claim 21, further comprising (a) calculating the relationship between said levels of soluble endoglin, sFlt-1, VEGF, or PlGF relative to each other in said subject sample using a metric;

(b) calculating the relationship between said levels of soluble endoglin, sFlt-1, VEGF, or PlGF relative to each other in a reference sample using the same metric as in step (a); and (c) comparing the relationship calculated in step (a) in said subject sample with the relationship calculated in step (b) in said reference sample, wherein an alteration in the relationship calculated in step (a) as compared to the relationship calculated in step (b) is a diagnostic indicator of pre-eclampsia or eclampsia or a predisposition to pre-eclampsia or eclampsia in said subject.

27. The method of claim 26, wherein said metric is selected from the group consisting of sFlt-1/PlGF, [sFlt-1/VEGF+PlGF], (sFlt-1+0.25(soluble endoglin polypeptide))/PlGF, and (sFlt1+soluble endoglin)/PlGF.

28. The method of claim 17, wherein said method is used to diagnose pre-eclampsia or eclampsia, or a predisposition to pre-eclampsia or eclampsia, prior to the development of at least one symptom of pre-eclampsia or eclampsia in said subject, said at least one symptom selected from the group consisting of a systolic blood pressure (BP)>140 mmHg and a diastolic BP>90 mmHg after 20 weeks gestation; new onset proteinuria; greater than 300 mg of protein in a 24-hour urine collection; and a single random urine sample having a protein/creatinine ratio greater than 0.3.

29. The method of claim 17, wherein said pre-eclampsia is premature pre-eclampsia.

* * * * *

UNITED STATES PATENT AND TRADEMARK OFFICE

CERTIFICATE OF CORRECTION

PATENT NO. : 7,955,805 B2
APPLICATION NO. : 11/300928
DATED : June 7, 2011
INVENTOR(S) : Karumanchi et al.

It is certified that error appears in the above-identified patent and that said Letters Patent is hereby corrected as shown below:

Title Page, Item (56) under OTHER PUBLICATIONS, for "Davis-Smyth et al. (1996), insert onto new line to separate from Barker et al.

Under OTHER PUBLICATIONS, in "Davis-Smyth et al. (1996), replace "Recpetor" with --Receptor--.

Title Page 2, Item (56) under OTHER PUBLICATIONS, in Krussel et al., replace "Recpetors" with --Receptors--;

Under OTHER PUBLICATIONS, in Oswald et al., replace "Mesanchymal" with --Mesenchymal--;

Under OTHER PUBLICATIONS, in Schultze-Mosgau et al., replace "Grat" with --Graft--;

Under OTHER PUBLICATIONS, in Schultze-Mosgau et al., replace "SIte" with --Site--.

Title Page 3, Item (56) under OTHER PUBLICATIONS, in Barleon et al., replace "4:143-154." with --4:143-154 (2001).--;

Under OTHER PUBLICATIONS, in Clark et al., replace "Endothelila" with --Endothelial--;

Under OTHER PUBLICATIONS, in Henry et al., replace "Admimistration" with --Administration--;

Under OTHER PUBLICATIONS, in Kendall et al. (1993), replace "Recpetor" with --Receptor--;

Signed and Sealed this
Tenth Day of January, 2012

David J. Kappos
*Director of the United States Patent and Trademark Office*

Title Page 3, Item (56) under OTHER PUBLICATIONS, in Kincaid-Smith, replace "Revisted" with --Revisited--.

Title Page 4, Item (56) under OTHER PUBLICATIONS, in Reimer et al., replace "Epxressed" with --Expressed--;

Under OTHER PUBLICATIONS, in Taylor et al. , replace "Concentyrations" with --Concentrations--;

Under OTHER PUBLICATIONS, in Taylor et al., replace "(2003." with --(2003).--.

Column 2, Line 16, replace "alpha-i" with --alpha-1--.

Column 10, Line 5, replace "alpha-I" with --alpha-1--.

Column 18, Line 33, replace "alpha-I" with --alpha-1--.

Column 28, Line 43, replace "alpha-I" with --alpha-1--.

Column 37, Line 11, Start paragraph on new line after "Test compounds and extracts.".

Column 41, Line 37, replace "alpha-I" with --alpha-1--.

Column 44, Line 31, replace "MCA951 S," with --MCA951S--.

Column 47, Line 29, replace "Boemer" with --Boerner--.

Column 223, Line 43, replace "soluble endoglin; or sFlt-1," with --soluble endoglin or sFlt-1--.